US012510533B2

(12) United States Patent
Anton et al.

(10) Patent No.: US 12,510,533 B2
(45) **Date of Patent: *Dec. 30, 2025**

(54) METHODS FOR TREATING MULTIPLE MYELOMA AND THE USE OF COMPANION BIOMARKERS FOR 4-(4-(4-(((2-(2,6-DIOXOPIPERIDIN-3-YL)-1-OXOISOINDOLIN-4-YL)OXY)METHYL) BENZYL)PIPERAZIN-1-YL)-3-FLUOROBENZONITRILE

(71) Applicant: Celgene Corporation, Summit, NJ (US)

(72) Inventors: Maria Soraya Carrancio Anton, San Diego, CA (US); Joshua Hansen, La Jolla, CA (US); Antonia Lopez-Girona, San Diego, CA (US); Gang Lu, San Diego, CA (US); Lilly L. Wong, Solana Beach, CA (US)

(73) Assignee: Celgene Corporation, Summit, NJ (US)

( * ) Notice: Subject to any disclaimer, the term of this patent is extended or adjusted under 35 U.S.C. 154(b) by 125 days.

This patent is subject to a terminal disclaimer.

(21) Appl. No.: 18/216,405

(22) Filed: Jun. 29, 2023

(65) Prior Publication Data

US 2023/0341375 A1 Oct. 26, 2023

Related U.S. Application Data

(63) Continuation of application No. 17/173,176, filed on Feb. 10, 2021, now Pat. No. 11,726,080, which is a (Continued)

(51) Int. Cl.

*G01N 33/50* (2006.01)
*A61K 31/496* (2006.01)
(Continued)

(52) U.S. Cl.

CPC ........ *G01N 33/5011* (2013.01); *A61K 31/496* (2013.01); *A61P 35/02* (2018.01); (Continued)

(58) Field of Classification Search

CPC .. A61K 31/496; A61K 45/06; G01N 2800/52; G01N 33/5011; G01N 33/57426; (Continued)

(56) References Cited

U.S. PATENT DOCUMENTS

| | | |
|---|---|---|
| 5,811,097 A | 9/1998 | Allison et al. |
| 5,814,633 A | 9/1998 | Muller et al. |

(Continued)

FOREIGN PATENT DOCUMENTS

| | | |
|---|---|---|
| WO | WO 93/18186 A1 | 9/1993 |
| WO | WO 95/21822 A1 | 8/1995 |

(Continued)

OTHER PUBLICATIONS

Anderson et al., "Thalidomide derivative CC-4047 inhibits osteoclast formation by down-regulation of PU.1," *Blood*, 107(8):3098-3105 (2006).

(Continued)

*Primary Examiner* — Savitha M Rao
(74) *Attorney, Agent, or Firm* — Jones Day

(57) ABSTRACT

A method of identifying a subject having cancer who is likely to be responsive to a treatment compound, comprising administering the treatment compound to the subject having the cancer; obtaining a sample from the subject; determining the level of a biomarker in the sample from the subject; and diagnosing the subject as being likely to be responsive to the treatment compound if the level of the biomarker in the sample of the subject changes as compared to a reference level of the biomarker; wherein the treatment compound is Compound 1, Compound 2, or Compound 3.

18 Claims, 36 Drawing Sheets

Related U.S. Application Data continuation of application No. 16/420,031, filed on May 22, 2019, now Pat. No. 10,969,381.

(60) Provisional application No. 62/737,772, filed on Sep. 27, 2018, provisional application No. 62/675,732, filed on May 23, 2018.

(51) Int. Cl.

| | |
|---|---|
| ***A61K 45/06*** | (2006.01) |
| ***A61P 35/00*** | (2006.01) |
| ***A61P 35/02*** | (2006.01) |
| ***G01N 33/574*** | (2006.01) |
| ***G01N 33/68*** | (2006.01) |

(52) U.S. Cl.

CPC ... *G01N 33/57484* (2013.01); *G01N 33/6866* (2013.01); *G01N 33/6869* (2013.01); *A61K 45/06* (2013.01); *A61P 35/00* (2018.01); *G01N 2800/52* (2013.01)

(58) Field of Classification Search

CPC ......... G01N 33/57484; G01N 33/6866; G01N 33/6869

See application file for complete search history.

(56) References Cited

U.S. PATENT DOCUMENTS

| | | | |
|---|---|---|---|
| 5,855,887 | A | 1/1999 | Allison et al. |
| 5,948,893 | A | 9/1999 | June et al. |
| 6,051,227 | A | 4/2000 | Allison et al. |
| 6,207,157 | B1 | 3/2001 | Gu et al. |
| 6,352,694 | B1 | 3/2002 | June et al. |
| 6,534,055 | B1 | 3/2003 | June et al. |
| 6,682,736 | B1 | 1/2004 | Hanson et al. |
| 6,692,964 | B1 | 2/2004 | June et al. |
| 6,887,466 | B2 | 5/2005 | June et al. |
| 6,905,681 | B1 | 6/2005 | June et al. |
| 6,927,024 | B2 | 8/2005 | Dodge et al. |
| 6,984,720 | B1 | 1/2006 | Korman et al. |
| 7,101,663 | B2 | 9/2006 | Godfrey et al. |
| 7,122,799 | B2 | 10/2006 | Hsieh et al. |
| 7,186,507 | B2 | 3/2007 | Bacallao et al. |
| 7,488,802 | B2 | 2/2009 | Collins et al. |
| 7,605,238 | B2 | 10/2009 | Korman et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 9,587,281 | B2 | 3/2017 | Thakurta et al. |
| 10,357,489 | B2 | 7/2019 | Alexander et al. |
| 10,969,381 | B2 | 4/2021 | Hansen et al. |
| 11,726,080 | B2 | 8/2023 | Anton et al. |
| 2017/0292959 | A1 | 10/2017 | Kaelin et al. |
| 2017/0362660 | A1 | 12/2017 | Thakurta et al. |
| 2018/0120291 | A1 | 5/2018 | Eltouky et al. |
| 2019/0381035 | A1 | 12/2019 | Pierce et al. |

FOREIGN PATENT DOCUMENTS

| | | | |
|---|---|---|---|
| WO | WO 2003/042402 | A2 | 5/2003 |
| WO | WO 2008/156712 | A1 | 12/2008 |
| WO | WO 2010/036959 | A2 | 4/2010 |
| WO | WO 2010/053732 | A1 | 5/2010 |
| WO | WO 2010/089411 | A2 | 8/2010 |
| WO | WO 2011/066342 | A2 | 6/2011 |
| WO | WO 2011/082400 | A2 | 7/2011 |
| WO | WO 2011/159877 | A2 | 12/2011 |
| WO | WO 2011/161699 | A2 | 12/2011 |
| WO | WO 2014/028445 | A2 | 2/2014 |
| WO | WO 2019/014100 | A1 | 1/2019 |
| WO | WO 2019/226761 | A1 | 11/2019 |
| WO | WO 2019/226770 | A1 | 11/2019 |

OTHER PUBLICATIONS

Angerer et al., "In situ hybridization to cellular RNAs," Genetic Engineering: Principles and Methods, Setlow and Hollaender Eds., Plenum Press, New York, vol. 7, pp. 43-65 (1985).

Anguille et al., "Leukemia-associated antigens and their relevance to the immunotherapy of acute myeloid leukemia," *Leukemia* 26:2186-2196 (2012).

Benboubker et al., "Lenalidomide and dexamethasone in transplant-ineligible patients with myeloma," *N. Engl. J. Med.*, 371(10):906-917 (2014).

Bjorklund et al., "Rate of CRL4(CRBN) substrate Ikaros and Aiolos degradation underlies differential activity of lenalidomide and pomalidomide in multiple myeloma cells by regulation of c-Myc and IRF4," *Blood Cancer J.*, 5:e354 (2015).

Brignone et al., "A soluble form of lymphocyte activation gene-3 (IMP321) induces activation of a large range human effector cytotoxic cells," *J. Immunol.*, 179, 4202-4211 (2007).

Bustin et al., "Real-time reverse transcription PCR (qRT-PCT) and its potential use in clinical diagnosis," *Clin. Sci.*, 109:365-379 (2005).

Chamberlain et al., "Structure of the human Cereblon-DDB1-lenalidomide complex reveals basis for responsiveness to thalidomide analogs," *Nat. Struct. Mol. Biol.*, 21(9):803-809 (2014).

Crawford et al., "Chemotherapy-induced neutropenia: risks, consequences, and new directions for its management," *Cancer*, 100(2):228-237 (2004).

Darzynkiewicz et al., "Analysis of apoptosis by cytometry using Tunel assay," *Methods*, 44(3):250-254 (2008).

Dimopoulos et al., "Lenalidomide plus dexamethasone for relapsed or refractory multiple myeloma," *N. Eng. J. Med.*, 357(21):2123-2132.

Dimopoulos et al., "Long-term follow-up on overall survival from the MM-009 and MM-010 phase III trials of lenalidomide plus dexamethasone in patients with relapsed or refractory multiple myeloma," *Leukemia*, 23(11):2147-2152 (2009).

Dumortier et al., "Ikaros regulates neutrophil differentiation," *Blood*, 101(6):2219-2226 (2003).

Durie et al., "International uniform response criteria for multiple myeloma," *Leukemia*, 20(9):1467-1473 (2006).

Engelhardt et al., "European Myeloma Network recommendations on the evaluation and treatment of newly diagnosed patients with multiple myeloma," *Haematologica*, 99(2):232-242 (2014).

Foster, "Deuterium isotope effects in the metabolism of drugs and xenobiotics: implications for drug design," *Adv. Drug Res.*, 14:1-40 (1985).

Fourcade et al., "Upregulation of Tim-3 and PD-1 expression is associated with tumor antigen-specific CD8+ T cell dysfunction in melanoma patients," *J. Exp. Med.*, 207:2175-2186 (2010).

Gall et al., "Nucleic acid hybridization in cytological preparation," *Meth. Enzymol.*, 21:470-480 (1981).

Gandhi et al., "Dexamethasone synergizes with lenalidomide to inhibit multiple myeloma tumor growth, but reduces lenalidomide-induced immunomodulation of T and NK cell function," *Curr. Cancer Drug Targets*, 10(2):155-167 (2010).

Gandhi et al., "Immunomodulatory agents lenalidomide and pomalidomide co-stimulate T cells by inducing degradation of T cell repressors Ikaros and Aiolos via modulation of the E3 ubiquitin ligase complex CRL4 (CRBN)," *Br. J. Haematol.*, 164(6):811-821 (2014).

Gandhi et al., "Immunomodulatory effects in a phase II study of lenalidomide combined with cetuximab in refractory KRAS-mutant metastatic colorectal cancer patients," *PLoS One*, 8(11):e80437 (2013).

Gatley et al., "Deuterioglucose: alteration of biodistribution by an isotope effect," *J. Nucl. Med.*, 27:388-394 (1986).

Gordon et al., "The metabolism of the abortifacient terpene, (R)-(+)-Pulegone, to a proximate toxin, menthofuran," *Drug Metabol. Dispos.*, 15(5):589-594 (1987).

Greenstein et al., "Mechanisms of glucocorticoid-mediated apoptosis in hematological malignancies," *Clin. Cancer Res.*, 8(6):1681-1694 (2002).

(56) References Cited

OTHER PUBLICATIONS

Guirguis et al., "Lenalidomide: deciphering mechanisms of action in myeloma, myelodysplastic syndrome and beyond," *Curr. Opin. Cell Biol.*, 37:61-67 (2015).
Hagnar et al., "CC-122, a pleiotropic pathway modifier, mimics an interferon response and has antitumor activity in DLBCL," *Blood*, 126(6):779-789 (2015).
Hansen et al., "Protein Degradation via CRL4CRBN Ubiquitin Ligase: Discovery and Structure-Activity Relationships of Novel Glutarimide Analogs That Promote Degradation of Aiolos and/or GSPT1," *J. Med. Chem.*, 61(2):492-503 (2018).
International Conference on Harmonization of Technical Requirements for Registration of Pharmaceuticals for Human Use, ICH Harmonized Tripartite Guideline Nonclinical Evaluation for Anticancer Pharmaceuticals S9, Oct. 29, 2009.
Ito et al., "Identification of a primary target of thalidomide teratogenicity," *Science*, 327(5971):1345-1350 (2010).
Jakubowiak, "Management strategies for relapsed/refractory multiple myeloma: Current clinical perspectives," *Semin. Hematol.*, 49(3)Suppl 1:S16-S32 (2012).
Jakubowiak, "Novel therapies for relapsed/refractory multiple myeloma: How can we improve on Salvage therapy? Introduction," *Semin. Hematol.*, 49(3)Suppl 1:S1-S2 (2012).
John et al., "The Ikaros gene family: transcriptional regulators of hematopoiesis and immunity," *Mol. Immunol.*, 48(9-10):1272-1278 (2011).
Johnson et al., "The use of molecular-based risk stratification and pharmacogenomics for outcome prediction and personalized therapeutic management of multiple myeloma," *Int. J. Hematol.*, 94:321-333 (2011).
Kallioniemi et al., "Comparative genomic hybridization for molecular cytogenetic analysis of solid tumors," Science, 258:818-821 (1992).
Kamarck "Fluorescence-activated cell sorting of hybrid and transfected cells," *Methods Enzymol.*, 151:150-165 (1987).
Keats J. Common Genetics of Myeloma Cell Lines [Internet]. Jonathan Keats Laboratory. Translational Genomics Research Institute (TGen)—Integrated Cancer Genomics Division. 2012—[cited Jan. 5, 2017]. Available from: http://www.keatslab.org/myeloma-cell-lines/common-genetics.
Kortüm et al., "Targeted sequencing of refractory myeloma reveals a high incidence of mutations in CRBN and Ras pathway genes," *Blood*, 128(9):1226-1233 (2016).
Krönke et al., Lenalidomide causes selective degradation of IKZF1 and IKZF3 in multiple myeloma cells, *Science*, 343(6168):301-305 (2014).
Kumar et al., "International Myeloma Working Group consensus criteria for response and minimal residual disease assessment in multiple myeloma," *Lancet Oncology*, 17(8):e328-e346 (2016).
Kumar et al., "Natural history of relapsed myeloma, refractory to immunomodulatory drugs and proteasome inhibitors: a multicenter IMWG study," *Leukemia*, 31(11):2443-2448 (2017).
Kumar et al., "Risk of progression and survival in multiple myeloma relapsing after therapy with IMiDs and bortezomib: a multicenter International Myeloma Working Group Study," *Leukemia*, 26(1):149-157 (2012).
Kushner et al., "Pharmacological uses and perspectives of heavy water and deuterated compounds," Can. J. Physiol. Pharmacol., 77:79-88 (1999).
Lijinsky et al., "Dose-response studies in carcinogenesis by nitroso-n-methyl-n(2-pheny)ethylamine in rats and the effects of deuterium substitution," *Fd. Chem. Toxic.*, 20:393-399 (1982).
Lijinsky et al., "Dose-response studies with nitrosoheptamethyleneimine and its α-deuterium-labeled derivative in F344 rats," *J. Nat. Cancer Inst.*, 69:1127-1133 (1982).
Lohr et al., "Genetic interrogation of circulating multiple myeloma cells at single-cell resolution," *Sci. Transl. Med.*, 8(363):363ra147 (2016).1.
Loo et al., "Development of an Fc-enhanced anti-B7-H3 monoclonal antibody with potent antitumor activity," *Clin. Cancer Res.*, 18(14):3834-3845 (2012).
Lopez-Girona et al., "Cereblon is a direct protein target for immunomodulatory and antiproliferative activities of lenalidomide and pomalidomide." *Leukemia*, 26(11):2326-2335 (2012).
Lopez-Girona et al., "Lenalidomide downregulates the cell survival factor, interferon regulatory factor-4, providing a potential mechanistic link for predicting response," *Br. J. Hematol.*, 154(3):325-336. (2011).
Lu et al., "The myeloma drug lenalidomide promotes the cereblon-dependent destruction of Ikaros proteins," *Science*, 343(6168):305-309 (2014).
Mangold et al., "Effects of deuterium labeling on azido amino acid mutagenicity in *Salmonella typhimuriu," Mutation Res.*, 308:33-42 (1994).
Matyskiela et al., "A cereblon modulator (CC-220) with improved degradation of Ikaros and Aiolos," *J. Med. Chem.*, 61(2):535-542 (2018).
Matyskiela et al., "A novel cereblon modulator recruits GSPT1 to the CRL4CRBN ubiquitin ligase," *Nature*, 535(7611):252-257 (2016).
Mishima et al., "The mutational landscape of circulating tumor cells in multiple myeloma," *Cell Rep.*, 19(1):218-224 (2017).
National Comprehensive Cancer Network (NCCN) Clinical Practice Guidelines in Oncology. Multiple Myeloma (V.3.2017). https://www.nccn.org/professionals/physician_gls/pdf/myeloma.pdf. Accessed Mar. 30, 2017.
National Comprehensive Cancer Network (NCCN). NCCN Guidelines for Multiple Myeloma. 2015. Available from URL: https://www.nccn.org/professionals/physician_gls/f_guidelines.asp.
Nijhof et al., "Current and new therapeutic strategies for relapsed and refractory multiple myeloma: an update," Drugs, 78:19-37 (2018).
Nijhof et al., "Upregulation of CD38 expression on multiple myeloma cells by all-trans retinoic acid improves the efficacy of daratumumab," *Leukemia*, 29(10):2039-2049 (2015).
Oken et al., "Toxicity and response criteria of the Eastern Cooperative Oncology Group," *Am. J. Clin. Oncol.*, 5(6):649-655 (1982).
Pal et al., "Immunomodulatory derivatives induce PU.1 down-regulation , myeloid maturation arrest, and neutropenia," *Blood*, 115(3):605-614 (2010).
Palumbo et al., "Multiple myeloma-medical progress," *N. Engl. J. Med.*, 364(11):1046-1060 (2011).
Pardoll "The blockade of immune checkpoints in cancer immunotherapy," *Nature Reviews Cancer*, 12:252-264 (2012).
Rajkumar et al., "Combination therapy with lenalidomide plus dexamethasone (Rev/Dex) for newly diagnosed myeloma," *Blood*, 106(13):4050-4053 (2005).
Rajkumar et al., "Consensus recommendations for the uniform reporting of clinical trials: report of the International Myeloma Workshop Consensus Panel 1," *Blood*, 117(18):4691-4695 (2011).
Rajkumar et al., "Lenalidomide and high dose dexamethasone versus lenalidomide plus low-dose dexamethasone as initial therapy for newly diagnosed multiple myeloma: an open-label randomized controlled trial," *Lancet Oncol.*, 11:29-37 (2010).
Richardson et al., "Pomalidomide alone or in combination with low-dose dexamethasone in relapsed and refractory multiple myeloma: a randomized phase 2 study," *Blood*, 123(12):1826-1832 (2014).
Rychak et al., "Pomalidomide in combination with dexamethasone results in synergistic anti-tumour responses in pre-clinical models of lenalidomide-resistant multiple myeloma," *Br. J. Haematol.*, 172(6):889-901 (2016).
Sakuishi et al., "Targeting Tim-3 and PD-1 pathways to reverse T cell exhaustion and restore anti-tumor immunity," *J. Exp. Med.*, 207:2187-2194 (2010).
San Miguel et al., "Pomalidomide plus low-dose dexamethasone versus high-dose dexamethasone alone for patients with relapsed and refractory multiple myeloma (MM-003): a randomised, open-label, phase 3 trial," *Lancet Oncol.*, 14(11):1055-1066 (2013).
Shaffer et al., "IRF4 addiction in multiple myeloma," *Nature*, 454(7201):226-231 (2008).
Straathof et al., "An inducible caspase 9 safety switch for T-cell therapy," *Blood*, 105(11):4247-4254 (2005).

(56) References Cited

OTHER PUBLICATIONS

Terpos et al., "Clinical implications of chromosomal abnormalities in multiple myeloma," *Leuk. Lymphoma*, 47:803-814 (2006).
Tonon, "Molecular pathogenesis of multiple myeloma," *Hematol. Oncol. Clin. North Am.*, 21:985-1006 (2007).
Wade, "Deuterium isotope effects on noncovalent interactions between molecules," *Chem. Biol. Interact.*, 117:191-217 (1999).
Weber et al., "Lenalidomide plus dexamethasone for relapsed multiple myeloma in North America," *N. Engl. J. Med.*, 357(21):2133-2142 (2007).
Wilen et al., "Strategies in optical resolutions," *Tetrahedron*, 33:2725-2736 (1977).
Wilen, Tables of Resolving Agents and Optical Resolutions, Eliel, ed., Univ. of Notre Dame Press, Notre Dame, IN, p. 268 (1972).
Zello et al., "Plasma and urine enrichments following infusion of L-[1-13C]phenylalanine and L-[ring-2H5]phenylalanine in humans: evidence for an isotope effect in renal tubular reabsorption," *Metabolism*, 43:487-491 (1994)3.
Zhou Et A., "The molecular characterization and clinical management of multiple myeloma in the post-genome era," *Leukemia* 2009;23:1941-1956.
Zhu et al., "Cereblon expression is required for the anti-myeloma activity of lenalidomide and pomalidomide," *Blood*, 118(18):4771-4779 (2011).
Zhu et al., "Immunomodulatory drugs Revlimid (lenalidomide) and CC-4047 induce apoptosis of both hematological and solid tumor cells through NK cell activation," *Cancer Immunol. Immunother.*, 57(12):1849-1859 (2008).
Zhu et al., "Molecular mechanism of action of immune-modulatory drugs thalidomide, lenalidomide and pomalidomide in multiple myeloma," *Leuk. Lymphoma*. 54:683-687 (2013).
Zonder et al., "Lenalidomide and high-dose dexamethasone compared with dexamethasone as initial therapy for multiple myeloma: a randomized Southwest Oncology Group trial (S0232)," *Blood*, 116(26):5838-5841 (2010).
Wong et al., "CC-92480, a Novel Cereblon E3 Ligase Modulator, Is Synergistic with Dexamethasone, Bortezomib, and Daratumumab in Multiple Myeloma," *Blood*, 134, Suppl. 1, p. 1815 (2019).

METHODS FOR TREATING MULTIPLE MYELOMA AND THE USE OF COMPANION BIOMARKERS FOR 4-(4-(4-(((2-(2,6-DIOXOPIPERIDIN-3-YL)-1-OXOISOINDOLIN-4-YL)OXY)METHYL)BENZYL)PIPERAZIN-1-YL)-3-FLUOROBENZONITRILE

This application is a continuation application of U.S. application Ser. No. 17/173,176, filed Feb. 10, 2021, which is a continuation application of U.S. application Ser. No. 16/420,031, filed May 22, 2019, now U.S. Pat. No. 10,969,381, which claims the benefit of U.S. Provisional Application No. 62/675,732, filed May 23, 2018, and U.S. Provisional Application No. 62/737,772 filed Sep. 27, 2018, each of which are herein incorporated by reference in their entirety.

1. FIELD

Provided herein, in some embodiments, are methods of using certain biomarkers, such as CRBN, Aiolos (IKZF3), Ikaros (IKZF1), zinc finger protein 91 (ZFP91), c-Myc, interferon regulatory factor 4 (IRF4), tumor immunity markers (soluble CD25, cytokines; tumor-infiltrating lymphocytes (TILs); T-cell activation, T-cell receptor clonality), circulating tumor cells (CTCs), soluble BCMA (sBCMA), apoptosis markers (cleaved-Caspase-1, cleaved-Caspase-7, cleaved-Caspase-3, cleaved PARP, survivin, BCL-2 like protein 11 (BIM), TUNEL, free light chain (FLC)), and cell cycle markers (p21, p27, pRb1) in predicting and monitoring clinical sensitivity and therapeutic response to 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, and methods for treating, preventing or managing multiple myeloma using such. Also described herein is 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof for use in methods for treating, preventing or managing multiple myeloma. Also provided herein, in certain embodiments, are methods of identifying a patient likely to be responsive, predicting the responsiveness of a patient, determining the dosage, or determining the efficacy of a compound in treating diseases.

2. BACKGROUND

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin, except in some patients (estimated at 1% to 5%) whose myeloma cells do not secrete these proteins (termed non-secretory myeloma). M-protein, short for monoclonal protein, also known as paraprotein, is a particularly abnormal protein produced by the myeloma plasma cells and can be found in the blood or urine of almost all patients with multiple myeloma, except for patients who have non-secretory myeloma or whose myeloma cells produce immunoglobulin light chains with heavy chain.

Skeletal symptoms, including bone pain, are among the most clinically significant symptoms of multiple myeloma. Malignant plasma cells release osteoclast stimulating factors (including IL-1, IL-6 and TNF) that cause calcium to be leached from bones, thereby causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Current multiple myeloma therapy may involve one or more of surgery, stem cell transplantation, chemotherapy, immune therapy, and/or radiation treatment to eradicate multiple myeloma cells in a patient. All of the current therapy approaches pose significant drawbacks for the patient.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in some patients with multiple myeloma, even after these patients have achieved complete response (CR), and may eventually cause relapse of the disease.

There exists a significant need for safe and effective compounds and methods for treating, preventing and managing multiple myeloma, including for patients whose multiple myeloma is newly diagnosed or refractory to standard treatments, while reducing or avoiding the toxicities and/or side effects associated with the conventional therapies.

3. SUMMARY OF THE INVENTION

In one aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker; wherein the treatment compound is Compound 1:

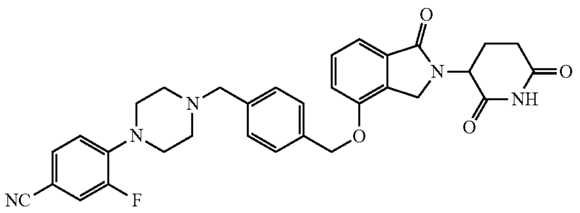

or an enantiomer, mixture of enantiomers, tautomer, isotopolog, or pharmaceutically acceptable salt thereof.

In another aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker; wherein the treatment compound is Compound 2:

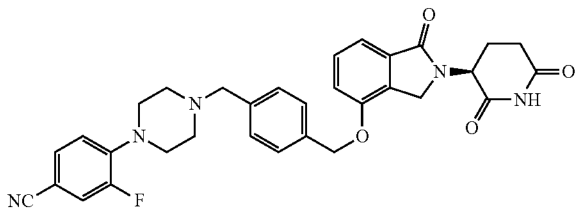

or a tautomer, isotopolog, or pharmaceutically acceptable salt thereof.

In yet another aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker; wherein the treatment compound is Compound 3:

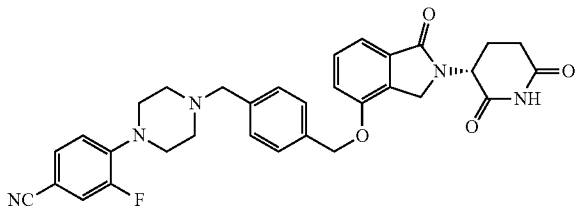

or a tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker; wherein the treatment compound is Compound 1:

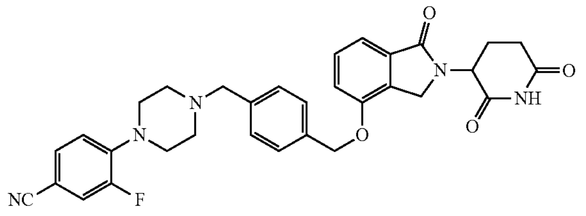

or an enantiomer, mixture of enantiomers, tautomer, isotopolog, or pharmaceutically acceptable salt thereof.

In another embodiment, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker; wherein the treatment compound is Compound 2:

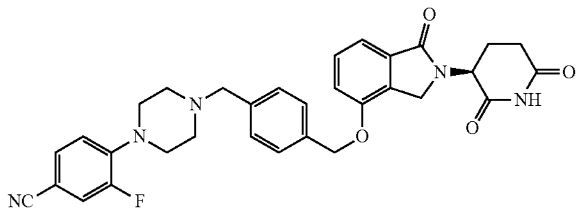 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In yet another embodiment, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker; wherein the treatment compound is Compound 3:

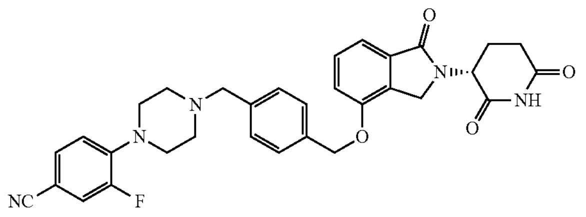

or a tautomer, isotopolog, or pharmaceutically acceptable salt thereof.

In some embodiments, provided herein are methods of identifying a subject having cancer who is likely to be responsive to a treatment compound, wherein the level of the biomarker in the sample is higher than the reference level of the biomarker. In other embodiments, provided herein are methods of identifying a subject having cancer who is likely to be responsive to a treatment compound, wherein the level of the biomarker in the sample is lower than the reference level of the biomarker In some embodiments, provided herein is a method of treating cancer, comprising:

(a) obtaining a sample from a subject having the cancer;

(b) determining the level of a biomarker in the sample;

(c) diagnosing the subject as being likely to be responsive to the treatment compound if the level of the biomarker in the sample is different from a reference level of the biomarker; and (d) administering a therapeutically effective amount of the treatment compound to the subject diagnosed as being likely to be responsive to the treatment compound;

wherein the treatment compound is Compound 1:

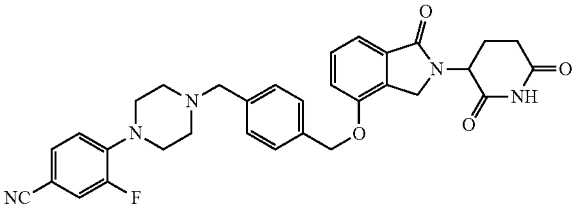

or an enantiomer, mixture of enantiomers, tautomer, isotopolog, or pharmaceutically acceptable salt thereof.

In another embodiment, provided herein is a method of treating cancer, comprising:

(a) obtaining a sample from a subject having the cancer;

(b) determining the level of a biomarker in the sample;

(c) diagnosing the subject as being likely to be responsive to the treatment compound if the level of the biomarker in the sample is different from a reference level of the biomarker; and (d) administering a therapeutically effective amount of the treatment compound to the subject diagnosed as being likely to be responsive to the treatment compound;

wherein the treatment compound is Compound 2:

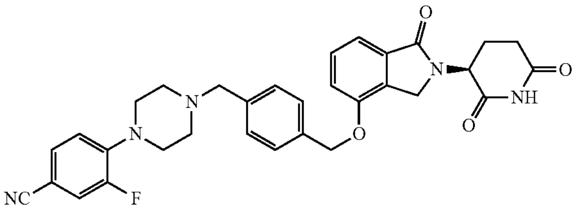

or a tautomer, isotopolog, or pharmaceutically acceptable salt thereof.

In yet another embodiment, provided herein is a method of treating cancer, comprising:

(a) obtaining a sample from a subject having the cancer;

(b) determining the level of a biomarker in the sample;

(c) diagnosing the subject as being likely to be responsive to the treatment compound if the level of the biomarker in the sample is different from a reference level of the biomarker; and (d) administering a therapeutically effective amount of the treatment compound to the subject diagnosed as being likely to be responsive to the treatment compound;

wherein the treatment compound is Compound 3:

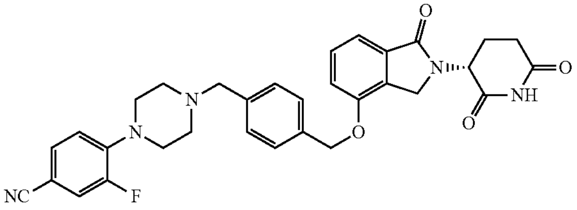

or a tautomer, isotopolog, or pharmaceutically acceptable salt thereof.

In some embodiments, provided herein are methods of treating cancer, wherein the level of the biomarker in the sample is higher than the reference level of the biomarker. In other embodiments, provided herein are methods of treating cancer, wherein the level of the biomarker in the sample is lower than the reference level of the biomarker. Also provided herein are Compound 1, Compound 2 and/or Compound 3 for use in a method for treating cancer as described above.

In some embodiments, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from the level of the biomarker obtained from a reference sample;

wherein the treatment compound is Compound 1:

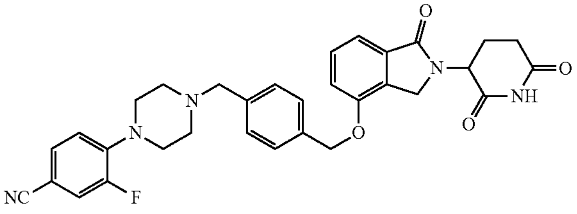

or an enantiomer, mixture of enantiomers, tautomer, isotopolog, or pharmaceutically acceptable salt thereof.

In another embodiment, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from the level of the biomarker obtained from a reference sample;

wherein the treatment compound is Compound 2:

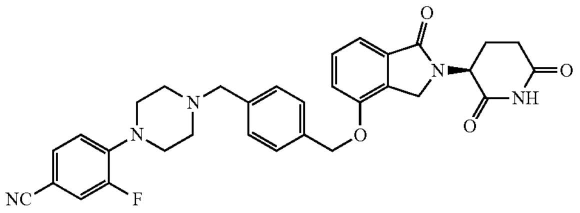

or a tautomer, isotopolog, or pharmaceutically acceptable salt thereof.

In yet another embodiment, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from the level of the biomarker obtained from a reference sample;

wherein the treatment compound is Compound 3:

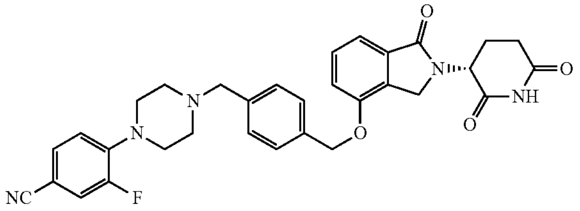

or a tautomer, isotopolog, or pharmaceutically acceptable salt thereof.

In another aspect, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from the level of the biomarker obtained from a reference sample;

wherein the treatment compound is Compound 1:

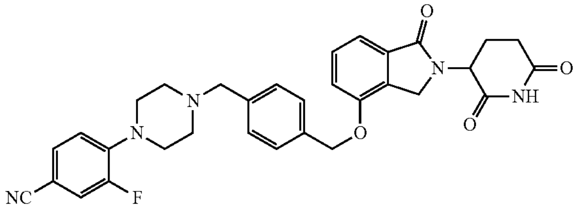

or an enantiomer, mixture of enantiomers, tautomer, isotopolog, or pharmaceutically acceptable salt thereof.

In another embodiment, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from the level of the biomarker obtained from a reference sample;

wherein the treatment compound is Compound 2:

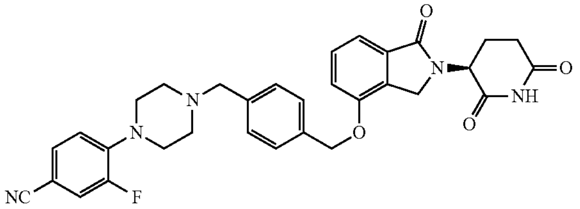

or a tautomer, isotopolog, or pharmaceutically acceptable salt thereof.

In yet another embodiment, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from the level of the biomarker obtained from a reference sample;

wherein the treatment compound is Compound 3:

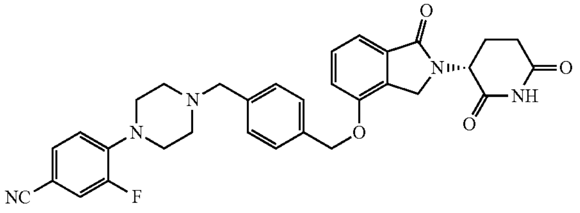

or a tautomer, isotopolog, or pharmaceutically acceptable salt thereof.

In some embodiments, provided herein are methods of predicting the responsiveness of a subject having or suspected of having cancer to a treatment compound, wherein the level of the biomarker in the sample is higher than the reference level of the biomarker. In other embodiments, provided herein are methods of predicting the responsiveness of a subject having or suspected of having cancer to a treatment compound, wherein the level of the biomarker in the sample is lower than the reference level of the biomarker In another aspect, provided herein is a method of monitoring the efficacy of a treatment compound in treating cancer in a subject, comprising:

(a) administering the treatment compound to the subject;

(b) obtaining a sample from the subject;

(c) determining the level of a biomarker in the sample; and (d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 1:

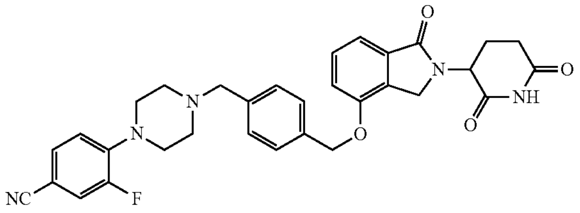

or an enantiomer, mixture of enantiomers, tautomer, isotopolog, or pharmaceutically acceptable salt thereof.

In some embodiments, provided herein is a method of monitoring the efficacy of a treatment compound in treating cancer in a subject, comprising:

(a) administering the treatment compound to the subject;

(b) obtaining a sample from the subject;

(c) determining the level of a biomarker in the sample; and (d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 2:

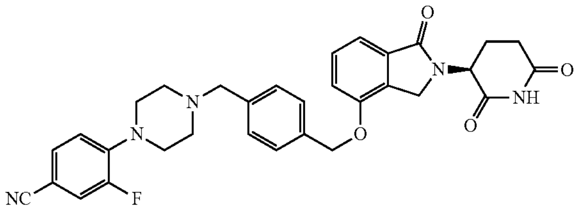

or a tautomer, isotopolog, or pharmaceutically acceptable salt thereof.

In another embodiment, provided herein is a method of monitoring the efficacy of a treatment compound in treating cancer in a subject, comprising:

(a) administering the treatment compound to the subject;

(b) obtaining a sample from the subject;

(c) determining the level of a biomarker in the sample; and (d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 3:

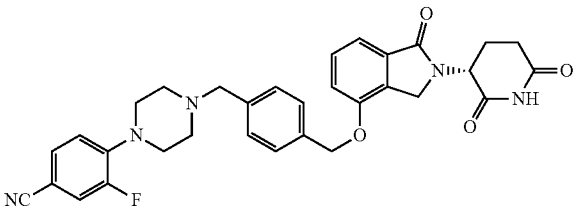

or a tautomer, isotopolog, or pharmaceutically acceptable salt thereof.

In some embodiments, provided herein are methods of monitoring the efficacy of a treatment compound in treating cancer in a subject, wherein an increased level of the biomarker as compared to the reference level is indicative of the efficacy of the treatment compound in treating the cancer in the subject. In some embodiments, provided herein are methods of monitoring the efficacy of a treatment compound in treating cancer in a subject, wherein a decreased level of the biomarker as compared to the reference level is indicative of the efficacy of the treatment compound in treating the cancer in the subject.

In some embodiments, the methods of identifying a subject having cancer who is likely to respond to a treatment compound further comprises administering a therapeutically effective amount of the treatment compound to the subject diagnosed as being likely to be responsive to the treatment compound. In additional embodiments, the methods of predicting the responsiveness of a subject having or suspected of having cancer to a treatment compound, further comprises administering a therapeutically effective amount of the treatment compound to the subject diagnosed as being likely to be responsive to the treatment compound.

In some embodiments of any one of the methods provided herein, the reference sample is obtained from the subject prior to administering the treatment compound to the subject, and wherein the reference sample is from the same source as the sample.

In some embodiments of any one of the methods provided herein, the reference sample is obtained from a healthy subject not having the cancer, and wherein the reference sample is from the same source as the sample.

In some embodiments of any one of the methods provided herein, the reference sample is obtained from a subject receiving an anti-cancer compound that is not said treatment compound, and wherein the reference sample is from the same source as the sample. In specific embodiments, the reference sample is obtained from a subject receiving an anti-cancer compound that is not the treatment compound, wherein the reference sample is from the same source as the sample, and the anti-cancer compound is selected from the group comprising lenalidomide, pomalidomide, or a derivative thereof.

In some embodiments of the methods provided herein, the cancer is multiple myeloma (MM). In some specific embodiments, the MM is relapsed, refractory, or resistant to conventional therapy. In one embodiment, the MM is lenalidomide-resistant MM. In another embodiment, the MM is pomalidomide-resistant MM. In some embodiments, the MM is newly diagnosed MM. In some embodiments, the MM is transplant-eligible MM. In other embodiments, the MM is non-transplant-eligible MM.

In certain embodiments of the methods provided herein, the biomarker is cereblon (CRBN). In some embodiments of the methods provided herein, the biomarker is a CRBN-associated protein.

In some embodiments of the methods provided herein, the biomarker has a function in an apoptosis pathway. In yet other embodiments of the methods provided herein, the biomarker has a function in a cell cycle pathway. In some embodiments of the methods provided herein, the biomarker has a function in T-cell activation. In some embodiments of the methods provided herein, the biomarker is circulating tumor cells (CTCs).

In some embodiments of the methods provided herein, the biomarker is tumor-infiltrating lymphocytes (TILs).

In some specific embodiments, the biomarker is a CRBN-associated protein and is selected from the group consisting of IKZF1, IKZF3, ZFP91, c-MYC, and IRF4. In some specific embodiments, the biomarker is IKZF1. In another embodiment, the biomarker is IKZF3. In yet another embodiment, the biomarker is ZFP91. In still another embodiment, the biomarker is c-MYC. In certain embodiments, the biomarker is IRF4.

In other embodiments, the biomarker has a function in apoptosis and is selected from the group consisting of cleaved Caspase-1 (c-Caspase-1), cleaved Caspase-3 (c-Caspase-3), cleaved Caspase-7 (c-Caspase-7), cleaved PARP, survivin, BIM BCL-2 like protein 11 (BIM), and serum free light chain. In certain embodiments, the biomarker is cleaved Caspase-3 (c-Caspase-3). In some embodiments, the biomarker is cleaved Caspase-1 (c-Caspase-1). In still other embodiments, the biomarker is cleaved Caspase-7 (c-Caspase-7). In another embodiment, the biomarker is cleaved PARP. In yet another embodiment, the biomarker is survivin. In some embodiments, the biomarker is survivin. In other embodiments, the biomarker is BCL-2 like protein 11 (BIM). In certain embodiments, the biomarker is serum free light chain (sFLC).

In yet other embodiments, the biomarker has a function in apoptosis and is measured by terminal deoxynucleotidyl transferase dUTP nick end labeling (TUNEL). In certain embodiments, the biomarker has a function in apoptosis and is measured by Annexin-V and 7-AAD. In still other embodiments, the biomarker has a function in apoptosis and is measured by Annexin-V and propidium iodide (PI).

In other embodiments of the methods provided herein, the biomarker has a function in cell cycle is selected from the group consisting of cyclin-dependent kinase inhibitor 1 (p21), cyclin-dependent kinase inhibitor 1B (p27), and retinoblastoma protein (pRb1). In some embodiments, the biomarker is p21. In certain embodiments, the biomarker is p27. In yet another embodiment, the biomarker is pRb1.

In some embodiments of the methods provided herein, the biomarker has a function in T-cell activation and is selected from the group consisting of interleukin-2 (IL-2), tumor necrosis factor alpha (TNFα), interferon gamma (IFNγ), and T-cell receptor (TCR) clonality. In other specific embodiments, the biomarker is IL-2. In still other embodiments, the biomarker is TNFα. In certain embodiments, the biomarker is IFNγ. In some embodiments, the biomarker is T-cell receptor (TCR) clonality. In a specific embodiment, the biomarker is T-cell receptor (TCR) clonality and the biomarker is measured by DNA sequencing of the TCR. In some specific embodiments, the biomarker has a function in T-cell activation and the level of the biomarker is measured by histology.

In some embodiments of the methods provided herein, the level of the biomarker is higher than a reference level.

In yet other embodiments of the methods provided herein, the level of the biomarker is lower than a reference level.

In some embodiments, provided herein is a method of identifying a subject with multiple myeloma that is relapsed, refractory, or resistant to conventional therapy who is likely to be responsive to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 1:

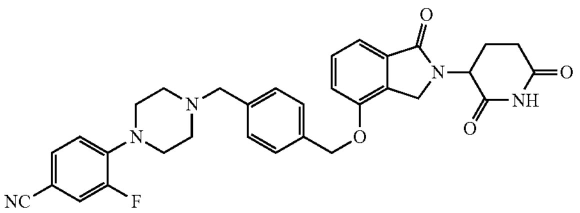

or an enantiomer, mixture of enantiomers, tautomer, isotopolog, or pharmaceutically acceptable salt thereof.

In another embodiment, provided herein is a method of identifying a subject with multiple myeloma that is relapsed, refractory, or resistant to conventional therapy who is likely to be responsive to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 2:

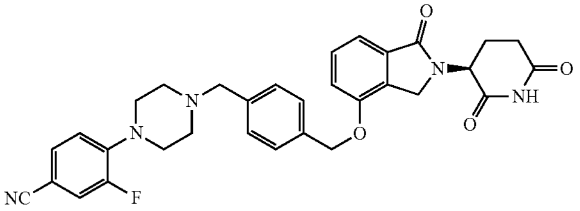 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In yet another embodiment, provided herein is a method of identifying a subject with multiple myeloma that is relapsed, refractory, or resistant to conventional therapy who is likely to be responsive to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 3:

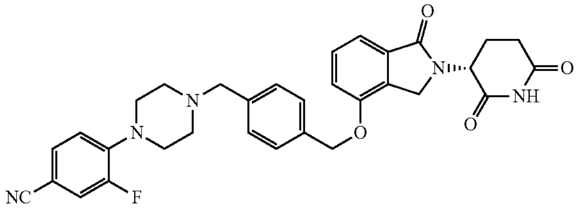

or a tautomer, isotopolog, or pharmaceutically acceptable salt thereof.

In some embodiments, provided herein is a method of predicting the responsiveness of a subject having multiple myeloma to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 1:

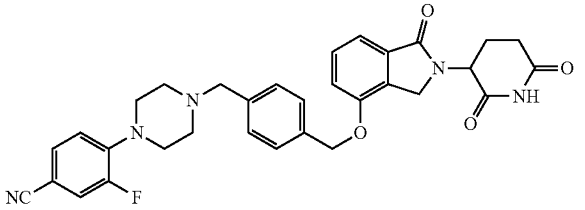

or an enantiomer, mixture of enantiomers, tautomer, isotopolog, or pharmaceutically acceptable salt thereof.

In another embodiment, provided herein is a method of predicting the responsiveness of a subject having multiple myeloma to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 2:

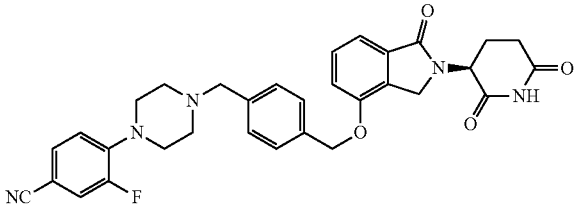

or a tautomer, isotopolog, or pharmaceutically acceptable salt thereof.

In yet another embodiment, provided herein is a method of predicting the responsiveness of a subject having multiple myeloma to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 3:

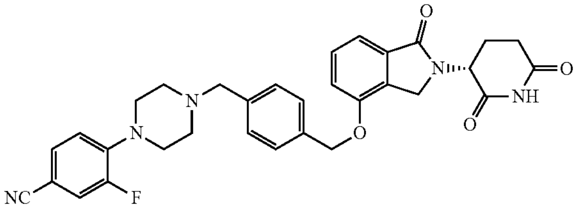

or a tautomer, isotopolog, or pharmaceutically acceptable salt thereof.

In specific embodiments of the methods of predicting the responsiveness of a subject having multiple myeloma to a treatment compound, the biomarker is CRBN. In certain embodiments of the methods of predicting the responsiveness of a subject having multiple myeloma to a treatment compound the methods comprise diagnosing the subject as being likely to be responsive to the treatment compound if the level of the biomarker in the sample is detected and lower than the reference sample. In some embodiments of the methods of predicting the responsiveness of a subject having multiple myeloma to a treatment compound the methods comprise diagnosing the subject as being likely to be responsive to the treatment compound if the biomarker in the sample is detectable. In some specific embodiments, the MM is relapsed, refractory, or resistant to conventional therapy. In one embodiment, the MM is lenalidomide-resistant MM. In another embodiment, the MM is pomalidomide-resistant MM.

In some embodiments of any one of the methods provided herein, the level of the biomarker is measured by determining the protein level of the biomarker. In other embodiments of any one of the methods provided herein, the level of the biomarker is measured by determining the mRNA level of the biomarker. In yet further embodiments of any one of the methods provided herein, the level of the biomarker is measured by determining the cDNA level of the biomarker. In certain embodiments of any one of the methods provided herein, the biomarker is determined by DNA sequencing. In other embodiments of any one of the methods provided herein, the biomarker is determined by RNA-sequencing (RNA-seq).

In some embodiments, the level of the biomarker is measured by determining the protein level of the biomarker, comprising contacting proteins within the sample with a first antibody that immunospecifically binds to the biomarker protein. In other embodiments, the level of the biomarker is measured by determining the protein level of the biomarker, comprising contacting proteins within the sample with a first antibody that immunospecifically binds to the biomarker protein, further comprising:

(a) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody;

(b) detecting the presence of the second antibody bound to the biomarker protein; and (c) determining the amount of the biomarker protein based on the amount of detectable label in the second antibody.

In yet another embodiment, the level of the biomarker is measured by determining the protein level of the biomarker, comprising contacting proteins within the sample with a first antibody that immunospecifically binds to the biomarker protein, further comprising:

(a) contacting the first antibody bound to the biomarker protein with a second antibody with a detectable label, wherein the second antibody immunospecifically binds to the first antibody;

(b) detecting the presence of the second antibody bound to the first antibody; and (c) determining the amount of the biomarker protein based on the amount of detectable label in the second antibody.

In certain embodiments, provided herein is a method of determining or adjusting a dosage for treating a subject having multiple myeloma with a treatment compound comprising:

(a) administering a dosage of the treatment compound to the subject;

(b) obtaining one or more samples from the subject at different time points; and (c) determining the level of a biomarker in the one or more samples, and thereby determining if the dosage is appropriate or needs an adjustment;

wherein the treatment compound is a compound of Compound 1:

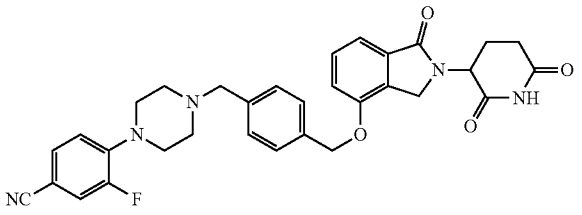

or an enantiomer, mixture of enantiomers, tautomer, isotopolog, or pharmaceutically acceptable salt thereof.

In another embodiment, provided herein is a method of determining or adjusting a dosage for treating a subject having multiple myeloma with a treatment compound comprising:

(a) administering a dosage of the treatment compound to the subject;

(b) obtaining one or more samples from the subject at different time points; and (c) determining the level of a biomarker in the one or more samples, and thereby determining if the dosage is appropriate or needs an adjustment;

wherein the treatment compound is a compound of Compound 2:

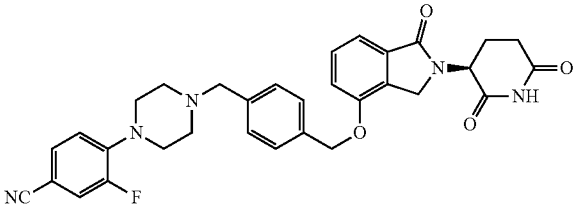

or a tautomer, isotopolog, or pharmaceutically acceptable salt thereof.

In yet another embodiment, provided herein is a method of determining or adjusting a dosage for treating a subject having multiple myeloma with a treatment compound comprising:

(a) administering a dosage of the treatment compound to the subject;

(b) obtaining one or more samples from the subject at different time points; and (c) determining the level of a biomarker in the one or more samples, and thereby determining if the dosage is appropriate or needs an adjustment;

wherein the treatment compound is a compound of Compound 3:

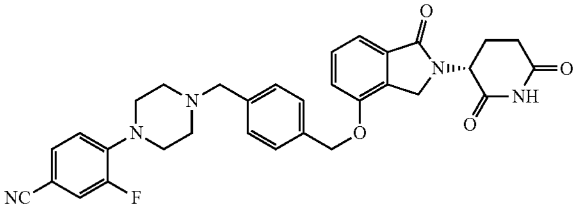

or a tautomer, isotopolog, or pharmaceutically acceptable salt thereof.

In some embodiments of the methods of determining or adjusting a dosage for treating a subject having multiple myeloma with a treatment compound, the biomarker is selected from the group consisting of IKZF1, and IKZF3. In some specific embodiments of the methods of determining or adjusting a dosage for treating a subject having multiple myeloma with a treatment compound, the biomarker is IKZF1. In yet another specific embodiment of the methods of determining or adjusting a dosage for treating a subject having multiple myeloma with a treatment compound the biomarker is IKZF3.

In some embodiments, the methods of treating cancer, further comprises administering a therapeutically effective amount of a second active agent or a support care therapy. In certain embodiments, the methods of identifying a subject having cancer who is likely to respond to a treatment compound further comprises administering a therapeutically effective amount of the treatment compound to the subject diagnosed as being likely to be responsive to the treatment compound, and also further comprises administering a therapeutically effective amount of a second active agent or a support care therapy. In additional embodiments, the methods of predicting the responsiveness of a subject having or suspected of having cancer to a treatment compound, further comprises administering a therapeutically effective amount of the treatment compound to the subject diagnosed as being likely to be responsive to the treatment compound, and also further comprises administering a therapeutically effective amount of a second active agent or a support care therapy. In specific embodiments, the second active agent is selected from the group comprising large molecules, small molecules, or cell therapies, and the second active agent is optionally selected from a group comprising of melphalan, vincristine, cyclophosphamide, etoposide, doxorubicin, bendamustine, a proteasome inhibitor, a histone deacetylase inhibitor, a BET inhibitor, a BCL2 inhibitor, an MCL-1 inhibitor, a corticosteroid, dexamethasone, an antibody, a checkpoint inhibitor, and CAR cells.

In some embodiments provided herein, the Compounds provided herein may be used in any method for treating, preventing and/or monitoring any of the diseases provided herein.

4. BRIEF DESCRIPTION OF THE FIGURES

FIG. 1 illustrates that Compound 2 and Compound 3 degraded Aiolos protein in a time and concentration dependent manner. DF15 cells expressing Enhanced ProLabel (ePL)-tagged Aiolos were incubated with Compound 2 (triangle) or Compound 3 (square) for 45 minutes, 90 minutes, or 3 hours at the indicated concentrations. Cell extracts were then generated and the amount of Aiolos-ePL protein was determined by ePL luminescence assay.

FIG. 2 illustrates that Compound 2 degraded Aiolos and Ikaros, even in pomalidomide resistant cells, and synergizes with dexamethasone to degrade IRF4 and c-MYC. Pomalidomide-sensitive (OPM2) or resistant (OPM2-P1) cells were treated with vehicle control (DMSO), pomalidomide, or Compound 2 either alone or in combination with 10 or 100 nM dexamethasone for 72 hours. $CRL4^{CRBN}$ E3 ubiquitin ligase substrates Aiolos and Ikaros, and their downstream effectors c-Myc and IRF4 were measured. Tubulin is a loading control.

FIG. 3 illustrates that Compound 2 degraded Aiolos and Ikaros, even in pomalidomide resistant cells, and synergizes with dexamethasone to induce apoptosis. Pomalidomide-sensitive (OPM2) or resistant (OPM2-P1) cells were treated with vehicle control (DMSO), pomalidomide, or Compound 2 either alone or in combination with 10 or 100 nM dexamethasone for 72 hours. $CRL4^{CRBN}$ E3 ubiquitin ligase substrates Aiolos and Ikaros, and induction of apoptotic pathway proteins BIM, cleaved PARP, cleaved caspase-3, and cleaved caspase-7 were measured. Tubulin is a loading control.

FIG. 4 illustrates that Compound 2 induced the degradation of Ikaros, Aiolos, ZFP91, c-Myc, and IRF4, which correlates with induction of the apoptotic protein cleaved-Caspase 3, and the cell cycle arrest protein p21. Immunoblot analysis of OPM2 parental cells incubated with Compound 2 at the indicated concentrations is shown. Actin is a loading control.

FIG. 5A illustrates that CRBN is required for Compound 2 mediated degradation of Ikaros and Aiolos. Shown are Cereblon, Ikaros, and Aiolos immunoblots of extracts from DF15R and DF15R-human $CRBN^{WT}$ cells that were incubated with DMSO, pomalidomide, or Compound 2 at 0.1 μM for 4 hours. Tubulin is a loading control.

FIG. 5B illustrates that Ikaros is required for Compound 2 mediated downregulation of c-Myc and IRF4, as well as induction of apoptosis. Shown are immunoblots of extracts from wild-type OPM2 cells or OPM2 cells overexpressing stabilized Ikaros-, Aiolos-, or ZFP91-mutants. Cells were incubated with DMSO, or the indicated concentration Compound 2 for five days.

FIG. 6A and FIG. 6B illustrate that Compound 2 degraded Ikaros and Aiolos in a concentration dependent manner, which induced apoptosis and cell cycle arrest in pomalidomide-resistant multiple myeloma cells. Shown is immunoblot analysis of pomalidomide-resistant MM cells (H929-1051) incubated with Compound 2 for (FIG. 6A) 4 hours or (FIG. 6B) 72 hours.

FIG. 7A and FIG. 7B illustrate that Compound 2 induces prolonged degradation of Aiolos and Ikaros. Aiolos and Ikaros degradation as a percentage of dimethyl sulfoxide (DMSO) control in (FIG. 7A) H929-1051 and (FIG. 7B) OPM2-P10 cell models after a one-time continuous exposure to Compound 2 is shown. These data are from a single experiment with one sample per data point.

FIG. 8 illustrates that Compound 2 induced prolonged degradation of Aiolos and Ikaros after 15 minutes of exposure. Compound 2 was incubated for 15 minutes with H929-1051 cells and degradation of Aiolos (left panel) and Ikaros (right panel) was measured. The data are from a single experiment with one sample per data point. The y-axis represents the amount of Aiolos or Ikaros expressed as a percentage of the level of the corresponding protein in the dimethyl sulfoxide (DMSO) control; the x-axis shows time in hours.

FIG. 9 illustrates that recovery of Aiolos levels post-washout from 6 hour exposure to Compound 2 required nearly 160 hours. Compound 2 was incubated for 6 hours with H929-1051 cells and degradation of Aiolos was measured. These data are from a single experiment with one sample per data point. The vertical dotted blue line divides the data into Compound 2 on-treatment (left of the vertical line) and post-washout segments (right of the vertical line). Results are presented for Aiolos levels in OPM2-P10 cells (left) and H929-1051 cells (right) for a total of 160 hours including and following a 6-hour incubation with 0.01 (red) or 0.1 μM Compound 2 (blue).

FIG. 10 illustrates that continuous, but not transient, exposure to Compound 2 induced apoptosis in multiple myeloma cells. Apoptosis induction by Compound 2 treatment in a lenalidomide-resistant MM cell model (H929-1051 [top row] and a pomalidomide-resistant MM cell model OPM2-P10 [bottom row]) is presented. These data are from a single experiment with one sample per data point.

FIG. 11A and FIG. 11B illustrate that Compound 2, but not pomalidomide, exhibit antiproliferative activity in lenalidomide- and pomalidomide-resistant multiple myeloma cells lines, including those with low CRBN protein levels. Anti-proliferative effects on human multiple myeloma cell lines of acquired resistance with low CRBN are shown. Cell lines were treated with (FIG. 11A) Pomalidomide, or (FIG. 11B) Compound 2 for 5 days and $IC_{50}$ values were assessed using an ATP determination assay (CellTiter-Glo). Percent control was calculated by subtracting the background and normalizing to the DMSO control (100% of control).

FIG. 12 illustrates that dexamethasone (DEX)+Compound 2 induces apoptosis. Induction of apoptosis after 72 hr treatment with dexamethasone alone or in combination with Compound 2, lenalidomide or pomalidomide in a lenalidomide-resistant multiple myeloma cell line (H929-1051) was measured using Caspase-Glo 3/7.

FIG. 13 illustrates that short daily Compound 2 exposures, for up to three days, induces Ikaros degradation in CD34+ cells. Ikaros degradation following short daily exposure to Compound 2 was measured by flow cytometry. CD34+ cells derived from healthy donor bone marrow were exposed to Compound 2 for 2, 4, and 6 hours starting on Day 14 for 1 (Day 14), 2 (Day 15), or 3 (Day 16) consecutive days. Percentage of Ikaros content (normalized to the DMSO control) is presented. At the end of the exposure period, Compound 2 was removed and cells were incubated in the absence of Compound 2 (recovery period). Ikaros was measured by flow cytometry during recovery on Days 19, 21, and 23. Data are presented as the mean of results for two donors.

FIG. 14 illustrates the degradation and recovery of Ikaros following three consecutive days of 6-hour exposures to Compound 2. CD34+ bone marrow-derived cells from healthy donors were exposed to Compound 2 on each of three consecutive days starting on Day 10 for 6 hours. Percentage of Ikaros inhibition compared with DMSO is shown. Cultures were incubated in the absence of Compound 2 from Day 13 through Day 22. Ikaros was measured by flow cytometry after completion of each exposure and every other day during recovery.

FIG. 15 illustrates the degradation and recovery of Ikaros following five consecutive days of 6-hour exposures to Compound 2CD34+ bone marrow-derived cells were exposed to Compound 2 on each of five consecutive days, starting on Day 10. Percentage of Ikaros inhibition compared to DMSO control is presented. Cultures were incubated in the absence of Compound 2 from Day 15 through Day 22. Ikaros was measured by flow cytometry after the completion of each exposure (Days 10 to 14) and every other day during recovery (Day 17, 20, and 22).

FIG. 16A and FIG. 16B illustrate the treatment scheme, and correlation between Ikaros inhibition (dotted line) and neutrophil differentiation (solid line) after exposure to Compound 2. (FIG. 16A) $CD34^+$ bone marrow-derived cells from healthy donors were cultured ex vivo and stimulated to develop into Stage IV mature neutrophils. (FIG. 16B) The cultures were exposed to different concentrations of Compound 2 for 6 hours on each of three days (Day 10, 11, and 12) and then cultured without further exposure to Compound 2 until Day 22. Percentage of Ikaros inhibition compared with DMSO control (circle) following 1 nM (square), 10 nM (upward triangle), and 100 nM (downward triangle) of Compound 2 exposure is shown on the right y-axis (dashed lines). The percentage of Stage IV cells is shown on the left y-axis (solid lines). The shaded area represents the 3 days with exposures to Compound 2.

FIG. 17A and FIG. 17B illustrate that Compound 2 directly activated human Peripheral Blood Mononuclear Cells (PBMCs) to lyse K562 erythromyelocytic leukemia cells in a concentration-dependent manner. (FIG. 17A) Representative fluorescence-activated cell sorting plots of K562 cells co-cultured with human PBMCs that had been preincubated with Compound 2 or DMSO. (FIG. 17B) Apoptosis response in K562 cells after co-culture with Compound 2 treated PBMCs. Apoptosis was measured by PI and Annexin V staining in K562 cells after 24 hour of co-culture with PBMCs that were treated with Compound 2 for 72 hours. Data are presented as mean with error bars representing standard error of the mean.

FIG. 18A and FIG. 18B illustrate that immune cells are directly activated by Compound 2 to lyse lenalidomide-sensitive and lenalidomide-resistant multiple myeloma cell lines. (FIG. 18A) Apoptosis response in NCI-H929 cells after 24-hour co-culture with PBMCs pretreated with Compound 2. (FIG. 18B) Apoptosis response in H929-1051 cells after 24-hour co-culture with PBMCs pretreated with Compound 2.

FIG. 19A-FIG. 19D illustrate that compound-primed immune cells show enhanced tumor cell killing when multiple myeloma cells are pretreated with lenalidomide, pomalidomide, or Compound 2 prior to co-culture. Compound-primed immune cells show enhanced tumor cell killing in co-culture model (right) in (FIG. 19A) H929 cells, (FIG. 19B) H929-1051, (FIG. 19C) OPM2, and (FIG. 19D) OPM2 P10 cells, compared to the MM single cultures (left), and little effect on PBMC viability (middle).

FIG. 20 illustrates that Compound 2 demonstrates greater potency for induction of Interleukin-2 production from anti-CD3 antibody bead-stimulated PBMCs than lenalidomide or pomalidomide at 72 hours. Induction of Interleukin-2 (IL-2) production from anti-CD3 antibody bead-stimulated PBMCs after treatment with Compound 2, lenalidomide (LEN), or pomalidomide (POM) for 72 hours.

FIG. 21A-FIG. 21C illustrate that Compound 2 is a potent inducer of effector cytokines. Measurement of effector cytokine induction upon treatment with Compound 2, pomalidomide (POM), or lenalidomide (LEN) for 24 hours. (FIG. 21A) IL-2, (FIG. 21B) IFN-γ, and (FIG. 21C) TNF-α. Data shown are an average from three or four donors and are represented as fold change over DMSO control; error bars represent standard error of the mean (SEM).

FIG. 22A-FIG. 22C illustrate that Compound 2 induces degradation of Ikaros in CD4+ T cells. Measurement of Ikaros degradation in CD4+ T-cells after treatment with Compound 2 (diamond), lenalidomide (LEN; circle), or pomalidomide (POM; square) for (FIG. 22A) 24 hours, (FIG. 22B) 48 hours, or (FIG. 22C) 72 hours. Data shown are an average from two donors and are represented as MFI normalized to DMSO control.

FIG. 23A-FIG. 23C illustrate that dexamethasone (DEX) in combination with Compound 2 reduces Interleukin-2 (IL-2) production from anti-CD3 antibody-stimulated PBMCs. Interleukin-2 production from anti-CD3 antibody-stimulated PBMCs after (FIG. 23A) lenalidomide (LEN) alone or with dexamethasone, (FIG. 23B) pomalidomide (POM) alone or with dexamethasone, or (FIG. 23C) Compound 2 alone or with dexamethasone.

(FIG. 26A) Aiolos, (FIG. 26B) Ikaros, (FIG. 26C) ZFP91, (FIG. 26D) c-Myc, and (FIG. 26E) IRF4.

5. DETAILED DESCRIPTION OF THE INVENTION

Figure 1:
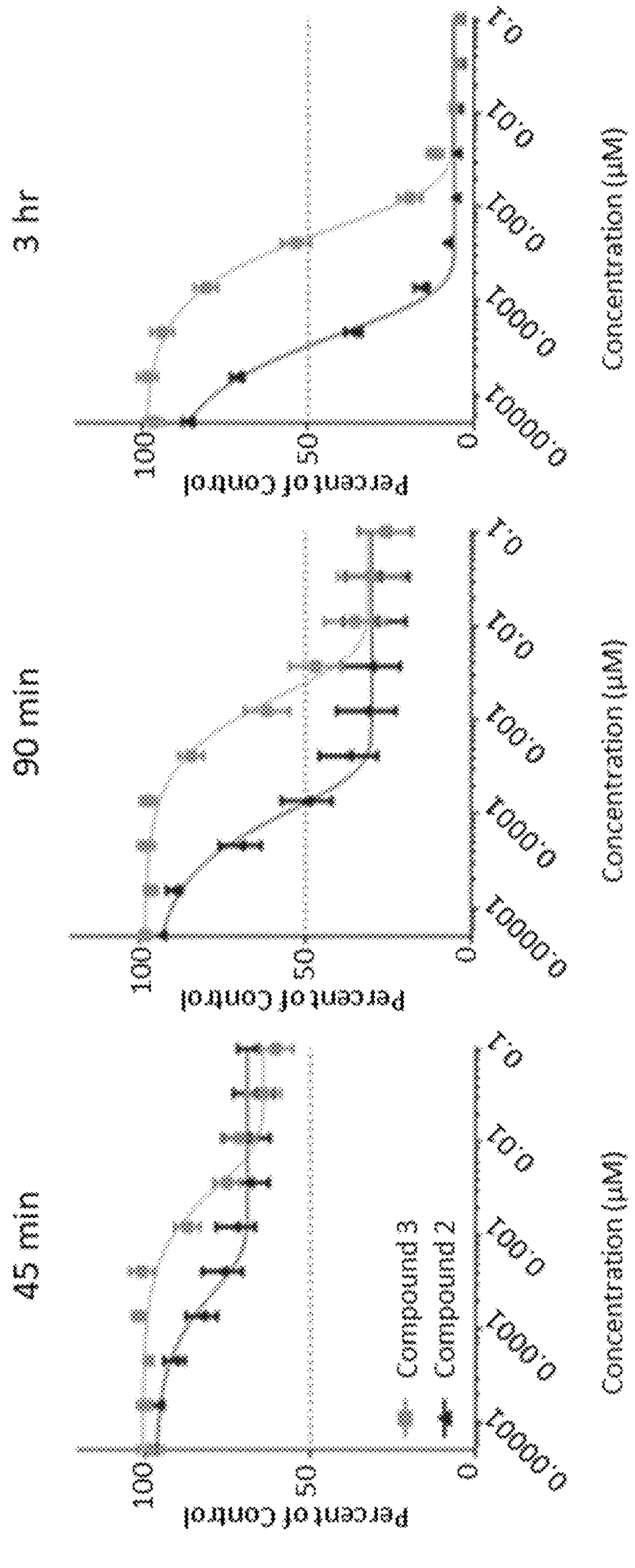

The methods provided herein are based, in part, on the discovery that a changed level, e.g., an increased level and/or a decreased level, of certain molecules (e.g., mRNAs, cDNAs, or proteins) or malignant cells (e.g., circulating tumor cells (CTCs)) in a biological sample can be used to predict responsiveness of a subject having or suspected to have MM to a treatment compound (e.g., Compound 1, Compound 2, Compound 3, or an enantiomer, a mixture of enantiomers, tautomer, isotopolog or pharmaceutically acceptable salt thereof).

5.1 Definitions

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

In general, the technical teaching of one embodiment can be combined with that disclosed in any other embodiments provided herein.

As used herein, the term "cancer" includes, but is not limited to, solid cancer and blood borne cancer. The terms "cancer" and "cancerous" refer to or describe the physiological condition in mammals that is typically characterized by unregulated cell growth. A cancer can be a cancer of the hematopoietic and lymphoid tissue. A hematopoietic malignancy refers to a cancer that affects the blood, bone marrow, lymph, and lymphatic system.

As used herein "multiple myeloma" refers to hematological conditions characterized by malignant plasma cells and includes the following disorders: monoclonal gammopathy of undetermined significance (MGUS); low risk, intermediate risk, and high risk multiple myeloma; newly diagnosed multiple myeloma (including low risk, intermediate risk, and high risk newly diagnosed multiple myeloma); transplant eligible and transplant ineligible multiple myeloma; smoldering (indolent) multiple myeloma (including low risk, intermediate risk, and high risk smouldering multiple myeloma); active multiple myeloma; solitary plasmacytoma; extramedullary plasmacytoma; plasma cell leukemia; central nervous system multiple myeloma; light chain myeloma; non-secretory myeloma; Immunoglobulin D myeloma; and Immunoglobulin E myeloma; and multiple myeloma characterized by genetic abnormalities, such as Cyclin D translocations (for example, t(411;14)(q13;q32); t(6;14)(p21;32); t(12;14)(p13;q32)) or t(6,20)); MMSET translocations (for example, t(4;14)(p16;q32)); MAF translocations (for example, t(14;16)(q32;q32); t(20;22); t(16;22)(q11;q13); or t(14;20)(q32;q11)); or other chromosome factors (for example, deletion of 17p13, or chromosome 13; del(17/17p), nonhyperdiploidy, and gain(1q)).

As used herein and unless otherwise indicated, the terms "treat," "treating" and "treatment" refer to alleviating or reducing the severity of a symptom associated with the disease or condition being treated, for example, multiple myeloma.

The term "prevention" includes the inhibition of a symptom of the particular disease or disorder, for example multiple myeloma. In some embodiments, patients with familial history of multiple myeloma are candidates for preventive regimens. Generally, the term "preventing" refers to administration of the drug prior to the onset of symptoms, particularly to patients at risk of multiple myeloma.

As used herein and unless otherwise indicated, the term "managing" encompasses preventing the recurrence of the particular disease or disorder, such as multiple myeloma, in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" or "patient" is an animal, typically a mammal, including a human, such as a human patient.

As described herein, the term "healthy subject" is any individual that does not have multiple myeloma. In some embodiments, the "healthy subject" has no pre-existing medical conditions.

As used herein, and unless otherwise specified, the terms "therapeutically effective amount" and "effective amount" of a compound refer to an amount sufficient to provide a therapeutic benefit in the treatment, prevention and/or management of a disease, for example multiple myeloma, or to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The term "responsiveness" or "responsive" when used in reference to a treatment refers to the degree of effectiveness of the treatment in lessening or decreasing the symptoms of a disease, e.g., MM, being treated. For example, the term "increased responsiveness" when used in reference to a treatment of a cell or a subject refers to an increase in the effectiveness in lessening or decreasing the symptoms of the disease compared to a reference treatment (e.g., of the same cell or subject, or of a different cell or subject) when measured using any methods known in the art. In certain embodiments, the increase in the effectiveness is at least about 5%, at least about 10%, at least about 20%, at least about 30%, at least about 40%, or at least about 50%.

The term "sensitivity" or "sensitive" when made in reference to treatment with compound is a relative term that refers to the degree of effectiveness of the compound in lessening or decreasing the progress of a tumor or the disease being treated. For example, the term "increased sensitivity" when used in reference to treatment of a cell or tumor in connection with a compound refers to an increase of, at least about 5%, or more, in the effectiveness of the tumor treatment.

The term "refractory" or "resistant" refers to a circumstance where patients, even after intensive treatment, have residual cancer cells (e.g., multiple myeloma cells) in their lymphatic system, blood, and/or blood forming tissues (e.g., marrow). In the context of multiple myeloma, the term "refractory or resistant" refers to a circumstance where patients, even after intensive treatment, have residual myeloma cells and/or reduced normal cells in the marrow. It is understood that a refractory disease is a disease that is nonresponsive on therapy (failure to achieve minimal response or development of progressive disease), or progresses within approximately 60 days of last dose.

The term "relapsed" refers to a situation where patients who have had a remission of cancer after therapy have a return of cancer cells (e.g., multiple myeloma cells) in their lymphatic system, blood, and/or blood forming tissues (e.g. marrow) and a decrease in normal blood cells.

An improvement in the cancer or cancer-related disease can be characterized as a complete (CR) or partial response (PR). "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about 10%, about 20%, about 30%, about 40%, about 50%, about 60%, about 70%, about 80%, or about 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

In the context of a cancer, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates will be computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response≥partial response (PR), according to the IMWG Uniform Response Criteria. In one embodiment, duration of response (DoR) is the time from achieving a response until relapse or disease progression. In one embodiment, DoR is the time from achieving a response≥partial response (PR) until relapse or disease progression. In one embodiment, DoR is the time from the first documentation of a response until to the first documentation of progressive disease or death. In one embodiment, DoR is the time from the first documentation of a response≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In the context of multiple myeloma, response may be assessed using the International Myeloma Working Group (IMWG) consensus criteria for response and minimal residual disease assessment (Rajkumar et al., *Blood,* 2011, 117(18):4691-5; Kumar et al., *Lancet Oncol.,* 2016, 17(8): e328-e346). The criteria can be summarized as follows (with further details available in *Lancet Oncol.,* 2016, 17(8):e328-e346).

| Response Criteria | |
|---|---|
| MWG MRD criteria (requires a complete response as defined below) | |
| Sustained MRD-negative | MRD negativity in the marrow (NGF or NGS, or both) and by imaging as defined below, confirmed minimum of 1 year apart. Subsequent evaluations can be used to further specify the duration of negativity (eg, MRD-negative at 5 years) |
| Flow MRD-negative | Absence of phenotypically aberrant clonal plasma cells by NGF on bone marrow aspirates using the EuroFlow standard operation procedure for MRD detection in multiple myeloma (or validated equivalent method) with a minimum sensitivity of 1 in $10^5$ nucleated cells or higher |
| Sequencing MRD-negative | Absence of clonal plasma cells by NGS on bone marrow aspirate in which presence of a clone is defined as less than two identical sequencing reads obtained after DNA sequencing of bone marrow aspirates using the LymphoSIGHT platform (or validated equivalent method) with a minimum sensitivity of 1 in $10^5$ nucleated cells or higher |

-continued

| Response Criteria | |
|---|---|
| Imaging plus MRD-negative | MRD negativity as defined by NGF or NGS plus disappearance of every area of increased tracer uptake found at baseline or a preceding PET/CT or decrease to less mediastinal blood pool SUV or decrease to less than that of surrounding normal tissue |
| | Standard IMWG response criteria |
| Stringent complete response | Complete response as defined below plus normal FLC ratio and absence of clonal cells in bone marrow biopsy by immunohistochemistry (κ/λ ratio ≤4:1 or ≥1:2 for κ and λ patients, respectively, after counting ≥100 plasma cells) |
| Complete response | Negative immunofixation on the serum and urine and disappearance of any soft tissue plasmacytomas and <5% plasma cells in bone marrow aspirates |
| Very good partial response | Serum and urine M-protein detectable by immunofixation but not on electrophoresis or ≥90% reduction in serum M-protein plus urine M-protein level <100 mg per 24 h |
| Partial response | ≥50% reduction of serum M-protein plus reduction in 24 h urinary M-protein by ≥90% or to <200 mg per 24 h;<br>If the serum and urine M-protein are unmeasurable, a ≥50% decrease in the difference between involved and uninvolved FLC levels is required in place of the M-protein criteria;<br>If serum and urine M-protein are unmeasurable, and serum-free light assay is also unmeasurable, ≥50% reduction in plasma cells is required in place of M-protein, provided baseline bone marrow plasma-cell percentage was ≥30%.<br>In addition to these criteria, if present at baseline, a ≥50% reduction in the size (SPD) of soft tissue plasmacytomas is also required |
| Minimal response | ≥25% but ≤49% reduction of serum M-protein and reduction in 24-h urine M-protein by 50-89%. In addition to the above listed criteria, if present at baseline, a ≥50% reduction in the size (SPD) of soft tissue plasmacytomas is also required |
| Stable disease | Not recommended for use as an indicator of response; stability of disease is best described by providing the time-to-progression estimates. Not meeting criteria for complete response, very good partial response, partial response, minimal response, or progressive disease |
| Progressive disease | Any one or more of the following criteria:<br>Increase of 25% from lowest confirmed response value in one or more of the following criteria:<br>Serum M-protein (absolute increase must be ≥0.5 g/dL);<br>Serum M-protein increase ≥1 g/dL, if the lowest M component was ≥5 g/dL;<br>Urine M-protein (absolute increase must be ≥200 mg/24 h);<br>In patients without measurable serum and urine M-protein levels, the difference between involved and uninvolved FLC levels (absolute increase must be >10 mg/dL);<br>In patients without measurable serum and urine M-protein levels and without measurable involved FLC levels, bone marrow plasma-cell percentage irrespective of baseline status (absolute increase must be ≥10%);<br>Appearance of a new lesion(s), ≥50% increase from nadir in SPD of >1 lesion, or ≥50% increase in the longest diameter of a previous lesion >1 cm in short axis;<br>≥50% increase in circulating plasma cells (minimum of 200 cells per μL) if this is the only measure of disease |
| Clinical relapse | Clinical relapse requires one or more of the following criteria:<br>Direct indicators of increasing disease and/or end organ dysfunction (CRAB features) related to the underlying clonal plasma-cell proliferative disorder. It is not used in calculation of time to progression or progression-free survival but is listed as something that can be reported optionally or for use in clinical practice;<br>Development of new soft tissue plasmacytomas or bone lesions (osteoporotic fractures do not constitute progression);<br>Definite increase in the size of existing plasmacytomas or bone lesions. A definite increase is defined as a 50% (and ≥1 cm) increase as measured serially by the SPD of the measurable lesion;<br>Hypercalcaemia (>11 mg/dL);<br>Decrease in haemoglobin of ≥2 g/dL not related to therapy or other non-myeloma-related conditions;<br>Rise in serum creatinine by 2 mg/dL or more from the start of the therapy and attributable to myeloma;<br>Hyperviscosity related to serum paraprotein |

-continued

| Response Criteria | |
|---|---|
| Relapse from complete response (to be used only if the end point is disease-free survival) | Any one or more of the following criteria: Reappearance of serum or urine M-protein by immunofixation or electrophoresis; Development of ≥5% plasma cells in the bone marrow; Appearance of any other sign of progression (ie, new plasmacytoma, lytic bone lesion, or hypercalcaemia see above) |
| Relapse from MRD negative (to be used only if the end point is disease-free survival) | Any one or more of the following criteria: Loss of MRD negative state (evidence of clonal plasma cells on NGF or NGS, or positive imaging study for recurrence of myeloma); Reappearance of serum or urine M-protein by immunofixation or electrophoresis; Development of ≥5% clonal plasma cells in the bone marrow; Appearance of any other sign of progression (ie, new plasmacytoma, lytic bone lesion, or hypercalcaemia) |

RD = minimal residual disease.
NGF = next-generation flow.
NGS = next-generation sequencing.
FLC = free light chain.
M-protein = myeloma protein.
SPD = sum of the products of the maximal perpendicular diameters of measured lesions.
CRAB features = calcium elevation, renal failure, anaemia, lytic bone lesions.
FCM = flow cytometry.
SUVmax = maximum standardised uptake value.
$^{18}$F-FDGPET = $^{18}$F-fluorodeoxyglucose PET.

As used herein, "induction therapy" refers to the first treatment given for a disease, or the first treatment given with the intent of inducing complete remission in a disease, such as cancer. When used by itself, induction therapy is the one accepted as the best available treatment. If residual cancer is detected, patients are treated with another chemotherapy course, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

As used herein, the term "reference level" is intended to mean a control level of a biomarker used to evaluate a test level of the biomarker in a sample from an individual. A reference level can be a normal reference level in a sample from a normal subject or a disease reference level from a disease-state subject. A normal reference level is an amount of expression of a biomarker in a non-diseased subject or subjects. A disease-state reference level is an amount of expression of a biomarker in a subject with a positive diagnosis for the disease or condition. A reference level also can be a stage-specific reference level. A stage-specific reference level refers to a level of a biomarker characteristic of a given stage of progression of a disease or condition. A reference level can also be an amount of expression of a biomarker prior to treatment, or at a different time during treatment. For example, a reference level can be the amount of expression of a biomarker in the bone marrow prior to treatment. In another example, a reference level may be the expression of a biomarker in the blood at some point during or after treatment.

The terms "likely" or "likelihood" generally refer to an increase in the probability of an event. The term "likely" when used in reference to the responsiveness of a patient generally contemplates an increased probability that the patient will be responsive to a treatment compound. The term "likely" when used in reference to the responsiveness of a patient can also generally mean the increase of biomarkers, such as mRNA or protein expression, that may evidence an increase in the probability that the patient will be responsive to a treatment compound.

The terms "predict" or "predicting," as used herein, generally mean to determine or tell in advance. When used to "predict" the responsiveness of a treatment, for example, the term "predicting" can mean that the likelihood of responding, or not responding, to the cancer treatment can be determined at the outset, before the treatment has begun, or before the treatment period has progressed substantially.

The terms "monitor" or "monitoring," as used herein, generally refer to the overseeing, supervision, regulation, watching, tracking, or surveillance of an activity. For example, the term "monitoring the effectiveness of a compound" refers to tracking the effectiveness in treating cancer in a patient or in a tumor cell culture. Similarly, the term "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

As used herein, the terms "T-cell activation" and "activated T-cell" is intended to mean cellular activation of resting naïve T-cells into effector T-cells that are capable of inducing tumor cell death. T-cell activation can be initiated by the interaction of the T-cell receptor (TCR)/CD3 complex with an antigen. An exemplarity activated T cell exhibits cell responses that include, but are not limited to, cell proliferation, cytokine secretion, and/or effector function. In the context of the present application, T-cell activation may be induced by treatment with Compound 1, Compound 2, or Compound 3.

As used herein, there term "T-cell activation associated cytokine" refers to any of the numerous factors that are secreted by activated T-cell, or whose secretion increases in activated T-cells, relative to resting naïve T-cells. Non-limiting examples of T-cell activation associated cytokines include IL-2, IFNγ, and TNFα.

The term "regulate" as used herein refers to controlling the activity of a molecule or biological function, such as enhancing or diminishing the activity or function.

A "biological marker" or "biomarker" is a substance whose detection indicates a particular biological state, such as, for example, the presence of cancer. Exemplary biomarkers can be determined individually. It is understood that several biomarkers can be measured simultaneously. A person of ordinary skill would understand that a "biomarker" indicates a change in the level of mRNA expression that may correlate with the response to a treatment, or patient's likelihood of responding to a treatment. The biomarker can be a nucleic acid, such as mRNA or cDNA. The biomarker can also be a protein. A specific example of a biomarker is one or more tumor cells that are circulating in the peripheral blood (i.e., circulating tumor cells, CTCs). A biomarker can also be the changing of the structure or sequence of a gene, resulting in a variant form that is caused by the alteration of single base units in DNA, or the deletion, insertion, or rearrangement of larger sections of genes or chromosomes.

An additional exemplary "biomarker" is one that indicates a change in the level of polypeptide or protein expression that may correlate with the response to a treatment, or patient's likelihood of responding to a treatment. The biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

The terms "polypeptide" and "protein," as used interchangeably herein, refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

The term "antibody," "immunoglobulin," or "Ig" as used interchangeably herein, encompasses fully assembled antibodies and antibody fragments that retain the ability to specifically bind to the antigen. Antibodies provided herein include, but are not limited to, synthetic antibodies, monoclonal antibodies, polyclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to CRBN antigen (e.g., one or more complementarity determining regions (CDRs) of an anti-CRBN antibody). Immunoglobulins can be composed of heavy chains and light chains. The antibodies provided herein can be of any class (e.g., IgG, IgE, IgM, IgD, and IgA) or any subclass (e.g., $IgG_1$, $IgG_2$, $IgG_3$, $IgG_4$, $IgA_1$, and $IgA_2$) of immunoglobulin molecule. In some embodiments, the anti-CRBN antibodies are fully human, such as fully human monoclonal CRBN antibodies. In certain embodiments, antibodies provided herein are IgG antibodies, or a subclass thereof (e.g., human IgG1 or IgG4). In other embodiments, the antibodies provided herein include immunoglobulin molecules and immunologically active portions of immunoglobulin molecules, i.e., antigen binding domains or molecules that contain an antigen-binding site that immunospecifically binds to Aiolos, Ikaros, c-MYC, IRF4, Caspase-3, BCMA, free kappa light chains, or free lambda light chains.

The terms "immunoglobulin light chain" or "light chain" refers to the small polypeptide subunit of an antibody. The light chain can be a lambda light chain or a kappa light chain. When the light chain is attached to a heavy chain, the light chains are termed "bound light chains". When the light chains are not attached to the heavy chain, they are termed "free light chains (FLC)". When the free light chains can be detected in the serum or plasma of a patient, they are termed "serum free light chains" or "plasma free light chains." It is further understood that "serum free light chains" can also be termed "soluble free light chains." It is understood by a person of average skill in the art that the amount of free light chain in the serum or plasma is proportional to the amount of disease burden, where the disease is multiple myeloma. It is also understood that the levels of free light chain, or the ratio of free light kappa to free light lambda can be used for the monitoring or diagnosis of myeloma. For example, a decrease in abnormally high levels of free light chain kappa to free light chain lambda in the serum of a patient with multiple myeloma that is being treated with Compound 2, can be used to monitor the efficacy of treatment with Compound 2. Similarly, an increase in free light chains in a patient being treated with a different compound, such as lenalidomide, can indicate resistance to treatment and can serve as a predictor of response to Compound 1, Compound 2, or Compound 3.

The terms "antigen binding domain," "antigen binding region," "antigen binding fragment," and similar terms refer to the portion of an antibody that comprises the amino acid residues that interact with an antigen and confer on the binding agent its specificity and affinity for the antigen (e.g., the CDR). The antigen binding region can be derived from any animal species, such as rodents (e.g., rabbit, rat, or hamster) and humans. In some embodiments, the antigen binding region is of human origin.

The term "epitope" as used herein refers to a localized region on the surface of an antigen that is capable of binding to one or more antigen binding regions of an antibody, that has antigenic or immunogenic activity in an animal, such as a mammal (e.g., a human), and that is capable of eliciting an immune response. An epitope having immunogenic activity is a portion of a polypeptide that elicits an antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic.

Epitopes usually consist of chemically active surface groupings of molecules, such as amino acids or sugar side chains, and have specific three dimensional structural characteristics as well as specific charge characteristics. A region of a polypeptide contributing to an epitope may be contiguous amino acids of the polypeptide, or the epitope may come together from two or more non-contiguous regions of the polypeptide. The epitope may or may not be a three-dimensional surface feature of the antigen.

The terms "cereblon" or "CRBN" and similar terms refers to the polypeptides ("polypeptides," "peptides," and "proteins" are used interchangeably herein) comprising the amino acid sequence of any CRBN, such as a human CRBN protein (e.g., human CRBN isoform 1, GenBank Accession No. NP_057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants), splice variants, fragments, derivatives, substitution variant, deletion variant, insertion variant, fusion polypeptides, and interspecies homologs, which, in certain embodiments, retain CRBN activity and/or are sufficient to generate an anti-CRBN immune response.

As used herein, the term "cereblon-associated protein" or "CAP" refers to a protein that interacts with or binds to cereblon (CRBN) directly or indirectly. For example, the term refers to any protein that directly binds to cereblon, as well as any protein that is an indirect downstream effector of CRBN pathways. An exemplary CAP is a substrate of CRBN, for example, a protein substrate of the E3 ubiquitin ligase complex involving CRBN, such as IKZF1, IKZF3, ZFP91, or the downstream effector proteins thereof, such as c-Myc, or IRF4.

As used herein, the term "cereblon modulator compound" refers to compound that binds to CRBN and alters it activity or substrate specificity. For example, binding of a cereblon modulator compound can increase the degradation of IKZF1, IKZF3, ZFP91, IRF4, or c-MYC. Exemplary cereblon modulator compounds can be, but are not limited to, lenalidomide, pomalidomide, or a similar compound.

As used herein, the term "mutation" refers to any changing of the structure of a gene, resulting in a variant (also called "mutant") form. Mutations in a gene may be caused by the alternation of single base in DNA, or the deletion, insertion, or rearrangement of larger sections of genes or chromosomes. In some embodiments, the mutation can affect the function or the resulting protein. For example, a mutation in a single nucleotide of DNA (i.e. point mutation) in the coding region of a protein can result in a codon that codes for a different amino acid (i.e. missense mutation). This different amino acid can alter the structure of the protein, such that a compound or its derivatives cannot bind and/or inhibit the protein The term "T-cell receptor (TCR) clonality" refers to the somatic alteration of the germline configuration of the T-cell receptor genes to a unique configuration, in order to permit development of a clone of T cells with a T-cell receptor specific to a given antigen. The T-cell receptor genes (alpha, beta, delta, and gamma) can be somatically rearranged to produce heterodimeric cell surface T-cell receptors. The somatic TCR-gene rearrangements can result in expansion of diverse clones (polyclonal), or monoclonal expansion of a T-cell population with a single TCR-rearrangement pattern. The TCR clonality can be determined by standard molecular biology techniques such as PCR, Southern blotting, or sequencing of the TCR (e.g. next-generation sequencing).

The term "soluble" refers to forms of a biological molecule that are in the extracellular space (e.g. serum) and not on the surface of a cell. The term "soluble B-cell maturation antigen," "soluble BCMA (sBCMA)," "soluble CD25," or "soluble IL-2 receptor (sIL-2R)" refer to soluble proteins that are a released form of the proteins and are present in the sera.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a biomarker molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition. An mRNA from a patient sample can be "upregulated" when treated with a drug, as compared to a non-treated control. This upregulation can be, for example, an increase of about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control mRNA level. Alternatively, an mRNA can be "downregulated", or expressed at a lower level, in response to administration of certain compounds or other agents. A downregulated mRNA can be, for example, present at a level of about 99%, about 95%, about 90%, about 80%, about 70%, about 60%, about 50%, about 40%, about 30%, about 20%, about 10%, about 1%, or less of the comparative control mRNA level.

Similarly, the level of a polypeptide or protein biomarker from a patient sample can be increased when treated with a drug, as compared to a non-treated control. This increase can be about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control protein level. Alternatively, the level of a protein biomarker can be decreased in response to administration of certain compounds or other agents. This decrease can be, for example, present at a level of about 99%, about 95%, about 90%, about 80%, about 70%, about 60%, about 50%, about 40%, about 30%, about 20%, about 10%, about 1%, or less of the comparative control level of a polypeptide or protein.

In addition, the level of CTCs from a patient sample can be decreased in response to administration of certain compounds or other agents. This decrease can be, for example, present at a level of about 99%, about 95%, about 90%, about 80%, about 70%, about 60%, about 50%, about 40%, about 30%, about 20%, about 10%, about 1%, or less of the comparative control level of CTCs.

The DNA sequence of the TCR, or the TCR clonality, can also be increased when treated with a drug, as compared to a non-treated control. The somatic TCR-gene rearrangements can result in expansion of diverse clones (polyclonal), or monoclonal expansion of a T-cell population with a single TCR-rearrangement pattern. This increase in specific clones can be about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control TCR clonality.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g., if they produce a given or detectable level of signal in a hybridization assay. Portions of polynucleotides are complementary to each other if they follow conventional base-pairing rules, e.g., A pairs with T (or U) and G pairs with C, although small regions (e.g., fewer than about 3 bases) of mismatch, insertion, or deleted sequence may be present.

"Sequence identity" or "identity" in the context of two nucleic acid sequences refers to the residues in the two sequences that are the same when aligned for maximum correspondence over a specified comparison window, and can take into consideration of additions, deletions, and substitutions.

The term "substantial identity" or "homologous" in their various grammatical forms in the context of polynucleotides generally means that a polynucleotide comprises a sequence that has a desired identity, for example, at least 60% identity, at least 70% identity, at least 80% identity, at least 90% identity, and at least 95% identity, compared to a reference sequence. Another indication that nucleotide sequences are substantially identical is if two molecules hybridize to each other under stringent conditions.

The terms "isolated" and "purified" refer to isolation of a substance (such as mRNA, DNA, or protein) such that the substance comprises a substantial portion of the sample in which it resides, i.e., greater than the portion of the substance that is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

As used herein, the term "bound" indicates direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and embodiments where the attachment is indirect.

The term "sample" as used herein relates to a material or mixture of materials, typically, although not necessarily, in fluid form, containing one or more components of interest.

"Biological sample" as used herein refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include, but are not limited to, whole blood, partially purified blood, PBMC, tissue biopsies, including bone marrow core biopsy, bone marrow aspirate, isolated bone marrow mononuclear cells, circulating tumor cells and the like.

The term "circulating tumor cell (CTC)" as used herein refers to multiple myeloma cells detected in the peripheral blood that have shed off from the tumor cells in the bone marrow. In some embodiments, CTCs can serve as a biomarker for response and prognosis. In other embodiments, the mutational landscape of CTCs in MM can be a biomarker.

The term "analyte" as used herein refers to a known or unknown component of a sample.

The term "capture agent" as used herein refers to an agent that binds an mRNA or protein through an interaction that is sufficient to permit the agent to bind and to concentrate the mRNA or protein from a heterogeneous mixture.

The term "probe" as used herein refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "nucleic acid probe" or "oligonucleotide probe" refers to a nucleic acid capable of binding to a target nucleic acid of complementary sequence, such as the mRNA biomarkers provided herein, usually through complementary base pairing by forming hydrogen bond. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with tags, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term "stringent assay conditions" generally refers to the combination of hybridization and wash conditions.

A "label" or "detectable moiety" in reference to a nucleic acid refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently through a linker or a chemical bond, or noncovalently through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The term "polymerase chain reaction" or "PCR" as used herein generally refers to a procedure wherein small amounts of a nucleic acid, RNA and/or DNA, are amplified as described, for example, in U.S. Pat. No. 4,683,195. Generally, sequence information from the ends or beyond of the region of interest needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 1987, 51:263-273; *PCR Technology* (Stockton Press, NY, Erlich, ed., 1989).

The term "cycle number" or "$C_T$" when used herein in reference to PCR methods, refers to the PCR cycle number at which the fluorescence level passes a given set threshold level. The $C_T$ measurement can be used, for example, to approximate levels of mRNA in an original sample. The $C_T$ measurement is often used in terms of "$dC_T$" or the "difference in the $C_T$" score, when the $C_T$ of one nucleic acid is subtracted from the $C_T$ of another nucleic acid.

As used herein, the terms "compound" and "treatment compound" are used interchangeably, and include Compound 1, Compound 2, Compound 3, or an enantiomer, a mixture of enantiomers, tautomer, isotopolog or pharmaceutically acceptable salt thereof.

"Tautomer" as used herein refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

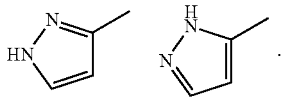

As used herein and unless otherwise indicated, the term "pharmaceutically acceptable salt" includes, but is not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

Unless specifically stated otherwise, where a compound may assume alternative tautomeric, regioisomeric and/or stereoisomeric forms, all alternative isomers are intended to be encompassed within the scope of the claimed subject matter. For example, where a compound can have one of two tautomeric forms, it is intended that both tautomers be encompassed herein.

Thus, the compounds provided herein may be enantiomerically pure, or be stereoisomeric or diastereomeric mixtures. As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. A stereomerically pure compound as used herein comprises greater than about 80% by weight of one stereoisomer of the compound, more preferably greater than about 90% by weight of one stereoisomer of the compound, even more preferably greater than about 95% by weight of one stereoisomer of the compound, and most preferably greater than about 97% by weight of one stereoisomer of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. As used herein, stereoisomeric or diastereomeric mixtures means a composition that comprises more than one stereoisomer of a compound. A typical stereomeric mixture of a compound comprises about 50% by weight of one stereoisomer of the compound and about 50% by weight of other stereoisomers of the compound, or comprises greater than about 50% by weight of one stereoisomer of the compound and less than about 50% by weight of other stereoisomers of the compound, or comprises greater than about 45% by weight of one stereoisomer of the compound and less than about 55% by weight of the other stereoisomers of the compound, or comprises greater than about 40% by weight of one stereoisomer of the compound and less than about 60% by weight of the other stereoisomers of the compound, or comprises greater than about 35% by weight of one stereoisomer of the compound and less than about 65% by weight of the other stereoisomers of the compound.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

In the description herein, if there is any discrepancy between a chemical name and chemical structure, the structure controls.

It should also be noted compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopolog" or "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologs of the compounds, for example, the isotopologs are deuterium, carbon-13, or nitrogen-15 enriched compounds. In some embodiments, isotopologs provided herein are deuterium enriched compounds. In some embodiments, isotopologs provided herein are deuterium enriched compounds, where the deuteration occurs on the chiral center. In some embodiments, provided herein are isotopologs of the compounds of Compound 1, where deuteration occurs on the chiral center. In some embodiments, provided herein are isotopologs of Compound 2, where deuteration occurs on the chiral center. In some embodiments, provided herein are isotopologs of Compound 3, where deuteration occurs on the chiral center.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As described herein, the term "second active agent" refers to any additional treatment that is biologically active. It is understood that the second active agent can be a hematopoietic growth factor, cytokine, anti-cancer agent, antibiotic, cox-2 inhibitor, immunomodulatory agent, immunosuppressive agent, corticosteroid, therapeutic antibody that specifically binds to a cancer antigen or a pharmacologically active mutant, or derivative thereof.

The term "supportive care agent" refers to any substance that treats, prevents or manages an adverse effect from treatment with Compound 1, Compound 2 or Compound 3, or an enantiomer or a mixture of enantiomers, tautomers, isotopolog or a pharmaceutically acceptable salt thereof. It is understood that the term "support care therapy" is refers to any therapeutic agent that is mainly directed to sustaining the strength and/or comfort of the patient. Exemplary support care therapies include, but are not limited to, therapies for pain control, intravenous fluids, and electrolyte support, such as isotonic saline, glucose saline, or balanced crystalloid solutions.

The term "biological therapy" refers to administration of biological therapeutics such as cord blood, stem cells, growth factors and the like.

The terms "co-administration" and "in combination with" include the administration of one or more therapeutic agents (for example, a compound provided herein and another anti-multiple myeloma agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

As used herein, the terms "immunospecifically binds," "immunospecifically recognizes," "specifically binds," and "specifically recognizes" are analogous terms in the context of antibodies and refer to molecules that bind to an antigen/epitope as such binding is understood by one skilled in the art. Antibodies that specifically bind to a target structure, or subunit thereof, do not cross-react with biological molecules that are outside the target structure family. In some embodiments, an antibody or antibody fragment binds to a selected antigen with a specific affinity of greater than $10^{-7}$ M, $10^{-8}$ M, $10^{-9}$ M, $10^{-10}$ M, or $10^{-11}$ M, between $10^{-8}$ M and $10^{-11}$ M, between $10^{-9}$ M and $10^{-10}$ M, or between $10^{-10}$ M and $10^{-11}$ M. For example, a molecule (e.g., an antibody) that specifically binds to an antigen may bind to other peptides or polypeptides, generally with lower affinity as determined by, e.g., immunoassays, or other assays known in the art. In a specific embodiment, molecules that specifically bind to an antigen do not cross react with other proteins.

As described herein, the term "detectable label" refers to the attachment of a specific tag to an antibody to aid in the detection or isolation/purification of a protein. Examples of types of labels include, but are not limited to, a radioisotope, a fluorophore (e.g., fluorescein isothiocyanate (FITC), phycoerythrin (PE)), chemiluminescence, enzyme reporters, and element particles (e.g., gold particles). Detection can be direct or indirect. Optical methods include microscopy (both confocal and non-confocal), imaging methods and non-imaging methods. Electrochemical methods include voltammetry and amperometry methods. Radio frequency methods include multipolar resonance spectroscopy.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning: A Laboratory Manual* (2d ed. 1989); Glover, ed., *DNA Cloning*, Volumes I and II (1985); Gait, ed., *Oligonucleotide Synthesis* (1984); Hames & Higgins, eds., *Nucleic Acid Hybridization* (1984); Hames & Higgins, eds., *Transcription and Translation* (1984); Freshney, ed., *Animal Cell Culture: Immobilized Cells and Enzymes* (IRL Press, 1986); *Immunochemical Methods in Cell and Molecular Biology* (Academic Press, London); Scopes, *Protein Purification: Principles and Practice* (Springer Verlag, N.Y., 2d ed. 1987); and Weir & Blackwell, eds., *Handbook of Experimental Immunology*, Volumes I-IV (1986).

5.2 Biomarkers and Methods of Use Thereof

The methods provided herein are based, in part, on the finding that detectable increase or decrease in certain biomarkers upon compound treatment are observed in subjects with MM, who are responsive to a given treatment, e.g., a compound, such as Compound 1, Compound 2, or Compound 3, or an enantiomer, a mixture of enantiomers, tautomer, isotopolog or pharmaceutically acceptable salt thereof as described in Section 5.7 below, and that the levels of these biomarkers may be used for predicting the responsiveness of the subjects to the treatment. In some embodiments, the levels of biomarkers can be predictive of response to Compound 1, Compound 2, or Compound 3. In some embodiments, the compound is as described herein. In certain embodiments, the compound is Compound 1, Compound 2, or Compound 3. In one embodiment, the compound is Compound 1. In another embodiment, the compound is Compound 2. In yet another embodiment, the compound is Compound 3.

According to one aspect, the invention is directed to Compound 1, Compound 2 or Compound 3 for use in a method of treating, preventing and/or managing the diseases as provided herein.

As described in the Examples in Section 6, and shown in the figures, the levels of certain proteins, molecules, mRNAs, or cell composition change in response to treatment with Compound 1, Compound 2, or Compound 3. These biomarkers include CRBN, IKZF1, IKZF3, ZFP91, c-Myc, IRF4, Caspase-1, Caspase-3, Caspase-7, PARP, survivin, Bcl-2 like protein 11 (BIM), serum free light chain (sFLC), p21, p27, pRb1, IL-2, TNFα, IFNγ, tumor infiltrating lymphocytes (TILs), T-cell antigen receptor (TCR) clonality, and circulating tumor cells (CTCs). In addition, the Examples and figures show that the expression of certain proteins change after treatment with Compound 1, Compound 2, or Compound 3, and can serve as biomarkers for predicting response to treatment and/or selecting patients likely to respond to treatment with Compound 1, Compound 2, or Compound 3. These biomarkers include CRBN. Thus, in some embodiments, the biomarker provided herein is selected from the group consisting of CRBN, IKZF1, IKZF3, ZFP91, c-Myc, IRF4, Caspase-1, Caspase-3, Caspase-7, PARP, survivin, Bcl-2 like protein 11 (BIM), serum free light chain (sFLC), p21, p27, pRb1, IL-2, TNFα, IFNγ, tumor infiltrating lymphocytes (TILs), T-cell antigen receptor (TCR) clonality, and circulating tumor cells (CTCs). Each of the biomarkers provided herein includes various isoforms, phosphorylated forms, cleaved forms, modified forms, and splicing variants thereof. For example, Caspase-3 includes the cleaved form of Caspase-3, Caspase-1 includes cleaved Caspase-1, Caspase-7 includes cleaved Caspase-7, PARP includes cleaved PARP, and pRb1 includes phosphorylated pRb1. Thus, in some embodiments, the levels of the isoforms, phosphorylated forms, cleaved forms, modified forms, and/or splicing variants of these biomarkers increase or decrease in response to the compound treatment, and thus these isoforms, phosphorylated forms, cleaved forms, modified forms, and/or splicing variants of the biomarkers can be used to predict a patient's response.

IKAROS Family Zinc Finger 1 (IKZF1, also known as Ikaros) and IKAROS Family Zinc Finger 3 (IKZF3, also known as Aiolos) are hematopoietic-specific transcription factors involved in the regulation of lymphocyte development. The expression of IKZF1 and IKZF3 are restricted to the fetal and adult hemo-lymphopoietic system, and function as regulators of lymphocyte differentiation. Regulation of gene expression involves Ikaros homodimers, Ikaros/Aiolos heterodimers, and Aiolos homodimers. Multiple isoforms of human Ikaros and Aiolos have been found in both normal and leukaemic B cells. Non-DNA-binding isoforms are largely found in the cytoplasm, and are thought to function as dominant-negative factors. Overexpression of some dominant-negative isoforms has been associated with B-cell malignancies, such as acute lymphoblastic leukemia (ALL).

Caspase-1, -3, and -7 are members of the caspase family. Caspase-3 cleaves and activates Caspase-7, as well as Caspase-6, and -9. Cleavage of Caspase 7 occurs upon cell death stimuli and induces apoptosis. Caspase-3 itself is processed by Caspase-8, -9, and -10. The effector caspases, Caspase-3, -6, and -7 proteolytically degrade a host of intracellular proteins to carry out cell apoptosis. Caspase-3 has virtually no activity until it is cleaved by an initiator caspase after apoptotic signaling events have occurred. Similarly, Pro-Caspase-1 is converted to an active Caspase-1 upon cleavage, and Caspase-1 is also involved in some forms of apoptosis. In addition, poly(ADP-ribose) polymerase (PARP) can be cleaved by caspases. For example, PARP is known to be cleaved by Caspase-3 during apoptosis. PARP is a family of proteins involved in regulating various important cellular processes such as differentiation, proliferation, and tumor transformation. PARP also regulates the molecular events involved in cell recovery from DNA damage. Caspase activation can be inhibited by survivin, thereby preventing apoptosis. Another protein involved in promoting apoptosis is Bcl-2 like protein 11 (BIM). Apoptosis can also be promoted by serum free light chain (sFLC). Thus, in some embodiments cleaved-Caspase-1 (c-Caspase-1), cleaved-Caspase-3 (c-Caspase-3), cleaved-Caspase-7 (c-Caspase-7), cleaved PARP, survivin, BIM, and serum free light chain (sFLC) are biomarkers that are indicative of apoptosis.

In certain embodiments of the various methods provided herein, the biomarker is a protein that is directly or indirectly affected by cereblon (CRBN), for example through protein-protein interactions (e.g., certain CRBN substrates or downstream effectors thereof), or through various cellular pathways (e.g., signal transduction pathways). In specific embodiments, the biomarker is a CRBN-associated protein (CAP). In some embodiments, the biomarker is mRNA of a protein that is directly or indirectly affected by CRBN. In other embodiments, the biomarker is cDNA of a protein that is directly or indirectly affected by CRBN. At least two isoforms of the protein CRBN exist, which are 442 and 441 amino acids long, respectively.

Figure 4:
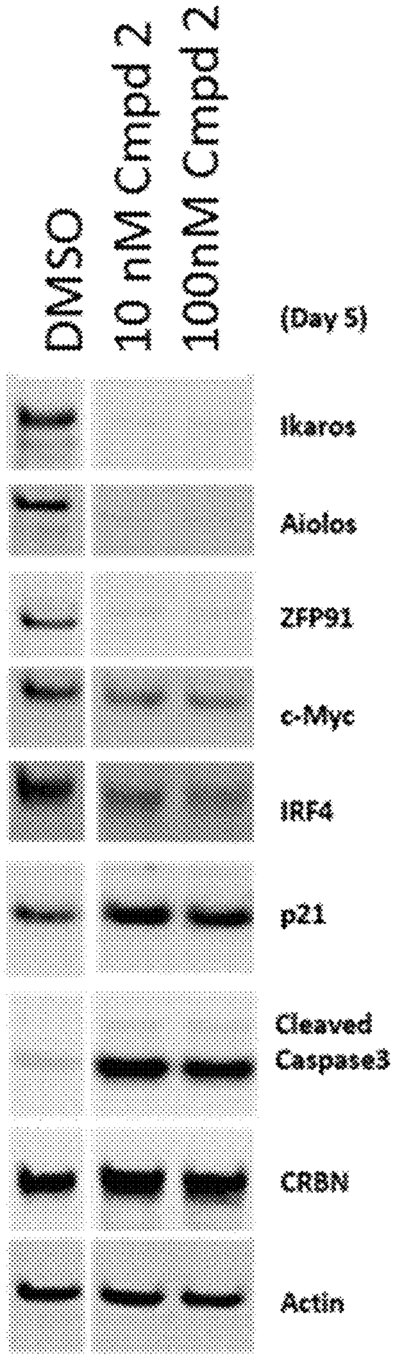

As described in the Examples, treatment with Compounds 1-3 decrease the levels of Aiolos, Ikaros, ZFP91, c-Myc, and IRF4 (e.g., FIG. 4). Therefore, detecting the level of CRBN-associated proteins can be instrumental in monitoring the efficacy, predicting response, identifying a subject having cancer who is likely to be responsive, treating cancer, identifying a subject having multiple myeloma who is likely to be response to a treatment compound, and determining or adjusting a dose for treating a subject having multiple myeloma with a treatment compound. Therefore, in some embodiments, the biomarker is a CRBN-associated protein and the treatment compound is Compound 1. In other embodiments, the biomarker is a CRBN-associated protein and the treatment compound is Compound 2. In still other embodiments, in some embodiments, the biomarker is a CRBN-associated protein and the treatment compound is Compound 3. In certain embodiments, the biomarker is a CRBN-associated protein selected from the group consisting of Aiolos, Ikaros, ZFP91, c-Myc, and IRF4. In certain specific embodiments, the biomarker is a CRBN-associated protein selected from the group consisting of Aiolos, Ikaros, ZFP91, c-Myc, and IRF4, and the treatment compound is Compound 1. In certain specific embodiments, the biomarker is a CRBN-associated protein selected from the group consisting of Aiolos, Ikaros, ZFP91, c-Myc, and IRF4, and the treatment compound is Compound 2. In certain specific embodiments, the biomarker is a CRBN-associated protein selected from the group consisting of Aiolos, Ikaros, ZFP91, c-Myc, and IRF4, and the treatment compound is Compound 3.

In some embodiments, the biomarker is an IKAROS Family member zinc-finger transcription factor, such as IKZF1 or IKZF3. In a specific embodiment, the biomarker is IKZF1 and the treatment compound is Compound 1. In another specific embodiment, the biomarker is IKZF1 and the treatment compound is Compound 2. In another specific embodiment, the biomarker is IKZF1 and the treatment compound is Compound 3. In a specific embodiment, the biomarker is IKZF3 and the treatment compound is Compound 1. In another specific embodiment, the biomarker is IKZF3 and the treatment compound is Compound 2. In another specific embodiment, the biomarker is IKZF3 and the treatment compound is Compound 3. In a specific embodiment, the biomarker is ZFP91 and the treatment compound is Compound 1. In another specific embodiment, the biomarker is I ZFP91 and the treatment compound is Compound 2. In another specific embodiment, the biomarker is ZFP91 and the treatment compound is Compound 3. In yet another specific embodiment, the biomarker is c-Myc and the treatment compound is Compound 1. In another specific embodiment, the biomarker is c-Myc and the treatment compound is Compound 2. In another specific embodiment, the biomarker is c-Myc and the treatment compound is Compound 3. In another specific embodiment, the biomarker is IRF4 and the treatment compound is Compound 1. In another specific embodiment, the biomarker is IRF4 and the treatment compound is Compound 2. In another specific embodiment, the biomarker is IRF4 and the treatment compound is Compound 3. In other embodiments, the biomarker is a binding partner of, downstream effector thereof, or a factor in a cellular pathway affected by IKZF1, IKZF3, ZFP91, c-Myc, or IRF4.

As described in the Examples, the levels of the proteins in the apoptosis pathway, such as Caspase-1, Caspase-3, Caspase-7, PARP, survivin, BIM, and sFLC change with treatment Compounds 1-3. For example, treatment with Compounds 1-3 can increase the levels of c-Caspase-3, c-Caspase-1, c-Caspase-7, cleaved-PARP, BIM, and sFLC in multiple myeloma cells, thereby indicating apoptosis. Treatment with Compounds 1-3 can also decrease the levels of survivin, thereby indicating apoptosis. Detecting apoptosis can be instrumental in monitoring the efficacy, predicting response, identifying a subject having cancer who is likely to be responsive, treating cancer, identifying a subject having multiple myeloma who is likely to be response to a treatment compound, and determining or adjusting a dose for treating a subject having multiple myeloma with a treatment compound. Therefore, in some embodiments the biomarker has a function in an apoptosis pathway. In certain embodiments, the biomarker has a function in the apoptosis pathway and the treatment compound is Compound 1. In certain embodiments, the biomarker has a function in the apoptosis pathway and the treatment compound is Compound 2. In certain embodiments, the biomarker has a function in the apoptosis pathway and the treatment compound is Compound 3.

In specific embodiments, the biomarker has a function in an apoptosis pathway and is selected from the group consisting of cleaved caspase 1 (c-caspase 1), cleaved caspase 3 (c-caspase 3), cleaved caspase 7 (c-caspase 7), cleaved PARP, survivin, BIM BCL-2 like protein 11 (BIM), and serum free light chain. Thus, in some embodiments, the biomarker has a function in an apoptosis pathway and is selected from the group consisting of cleaved caspase 1 (c-caspase 1), cleaved caspase 3 (c-caspase 3), cleaved caspase 7 (c-caspase 7), cleaved PARP, survivin, BIM BCL-2 like protein 11 (BIM), and serum free light chain, and the treatment compound is Compound 1. In some embodiments, the biomarker has a function in an apoptosis pathway and is selected from the group consisting of cleaved caspase 1 (c-caspase 1), cleaved caspase 3 (c-caspase 3), cleaved caspase 7 (c-caspase 7), cleaved PARP, survivin, BIM BCL-2 like protein 11 (BIM), and serum free light chain, and the treatment compound is Compound 2. In some embodiments, the biomarker has a function in an apoptosis pathway and is selected from the group consisting of cleaved caspase 1 (c-caspase 1), cleaved caspase 3 (c-caspase 3), cleaved caspase 7 (c-caspase 7), cleaved PARP, survivin, BIM BCL-2 like protein 11 (BIM), and serum free light chain, and the treatment compound is Compound 3. In specific embodiments, the levels of Caspase-3, including cleaved-Caspase-3, are a biomarker and the treatment compound is Compound 1. In some embodiments, the levels of Caspase-3, including cleaved-Caspase-3, are a biomarker and the treatment compound is Compound 2. In some embodiments, the levels of Caspase-3, including cleaved-Caspase-3, are a biomarker and the treatment compound is Compound 3. In some embodiments, the levels of Caspase-1, including cleaved-Caspase-1, are a biomarker and the treatment compound is Compound 1. In some embodiments, the levels of Caspase-1, including cleaved-Caspase-1, are a biomarker and the treatment compound is Compound 2. In some embodiments, the levels of Caspase-1, including cleaved-Caspase-1, are a biomarker and the treatment compound is Compound 3. In some embodiments, the levels of Caspase-7, including cleaved-Caspase-7, are a biomarker and the treatment compound is Compound 1. In some embodiments, the levels of Caspase-7, including cleaved-Caspase-7, are a biomarker and the treatment compound is Compound 2. In some embodiments, the levels of Caspase-7, including cleaved-Caspase-7, are a biomarker and the treatment compound is Compound 3. In some embodiments, the levels of PARP, including cleaved-PARP, are a biomarker and the treatment compound is Compound 1. In some embodiments, the levels of PARP, including cleaved-PARP, are a biomarker and the treatment compound is Compound 2. In some embodiments, the levels of PARP, including cleaved-PARP, are a biomarker and the treatment compound is Compound 3. In some embodiments, the levels of survivin are a biomarker and the treatment compound is Compound 1. In some embodiments, the levels of survivin are a biomarker and the treatment compound is Compound 2. In some embodiments, the levels of survivin are a biomarker and the treatment compound is Compound 3. In some embodiments, the levels of BIM are a biomarker and the treatment compound is Compound 1. In some embodiments, the levels of BIM are a biomarker and the treatment compound is Compound 2. In some embodiments, the levels of BIM are a biomarker and the treatment compound is Compound 3. In addition, changes in the levels of serum free light chain (sFLC), and CTCs change with treatment Compounds 1-3. For example, treatment with Compounds 1-3 can decrease the amount of sFLC detected in the blood or serum/plasma. Therefore, in some embodiments, sFLC is a biomarker and the treatment compound is Compound 1. In some embodiments, sFLC is a biomarker and the treatment compound is Compound 2. In some embodiments, sFLC is a biomarker and the treatment compound is Compound 3. Similarly, treatment with Compounds 1-3 can decrease the amount of CTCs that are detected in the peripheral blood. Therefore, in some embodiments, the levels of CTC in the peripheral blood are a biomarker and the treatment compound is Compound 1. In some embodiments, the levels of CTC in the peripheral blood are a biomarker and the treatment compound is Compound 2. In some embodiments, the levels of CTC in the peripheral blood are a biomarker and the treatment compound is Compound 3. Treatment with Compounds 1-3 can also decrease the amount of soluble BCMA (sBCMA) that are detected in the serum from multiple myeloma patients. Therefore, in some embodiments, the levels of sBCMA are a biomarker and the treatment compound is Compound 1. In some embodiments, the levels of sBCMA are a biomarker and the treatment compound is Compound 2. In some embodiments, the levels of sBCMA are a biomarker and the treatment compound is Compound 3.

Terminal deoxynucleotidyl transferase dUTP nick end labeling (TUNEL) is a method for detecting DNA fragmentation by labeling the 3'-hydroxyl termini in the double-strand DNA breaks generated during apoptosis. It is a common method known in the art (Darzynkiewicz et al., *Methods,* 2008, 44(3): 250-254). Thus, in some embodiments, the biomarker is the detection of apoptosis by TUNEL and the treatment compound is Compound 1. In some embodiments, the biomarker is the detection of apoptosis by TUNEL and the treatment compound is Compound 2. In some embodiments, the biomarker is the detection of apoptosis by TUNEL and the treatment compound is Compound 3.

Apoptosis can also be measured by Annexin-V and 7-AAD or Annexin-V and propidium iodide (PI). Annexin V (or Annexin A5) is a member of the annexin family of intracellular proteins that binds to phosphatidylserine (PS) in a calcium-dependent manner. PS is normally only found on the intracellular leaflet of the plasma membrane in healthy cells, but during early apoptosis, membrane asymmetry is lost and PS translocates to the external leaflet. Fluorochrome-labeled Annexin V can then be used to specifically target and identify apoptotic cells. Annexin V binding alone cannot differentiate between apoptotic and necrotic cells. To help distinguish between the necrotic and apoptotic cells 7-amino-actinomycin D (7-AAD) or PI solution can be used. Early apoptotic cells will exclude 7-AAD and PI, while late stage apoptotic cells and necrotic cells will stain positively, due to the passage of these dyes into the nucleus where they bind to DNA. Thus, in some embodiments, the biomarker is the detection of apoptosis by Annexin V/7-AAD and the treatment compound is Compound 1. In some embodiments, the biomarker is the detection of apoptosis by Annexin V/7-AAD and the treatment compound is Compound 2. In some embodiments, the biomarker is the detection of apoptosis by Annexin V/7-AAD and the treatment compound is Compound 3. In other embodiments, the biomarker is the detection of apoptosis by Annexin V/PI and the treatment compound is Compound 1. In yet another embodiment, the biomarker is the detection of apoptosis by Annexin V/PI and the treatment compound is Compound 2. In some embodiments, the biomarker is the detection of apoptosis by Annexin V/PI and the treatment compound is Compound 3.

In some embodiments, detecting modulation of the immune response can be instrumental in monitoring the efficacy, predicting response, identifying a subject having cancer who is likely to be responsive, treating cancer, identifying a subject having multiple myeloma who is likely to be responsive to a treatment compound, and determining or adjusting a dose for treating a subject having multiple myeloma with a treatment compound. For example, the Examples in Section 6 below describe enhanced T-cell mediated tumor cell lysis in a co-culture model (Example 11), activation of effector T cells (Example 12), the activation and proliferation of T-cells (Example 16) with treatment Compounds 1-3. Therefore, in some embodiments, T-cell activation can be a biomarker for treatment with Compound 1. In some embodiments, T-cell activation can be a biomarker for treatment with Compound 2. In some embodiments, T-cell activation can be a biomarker for treatment with Compound 3.

In some specific embodiments, T-cell activation can be a biomarker for treatment with a treatment compound, and the biomarker is selected from the group consisting of interleukin-2 (IL-2), tumor necrosis factor alpha (TNFα), interferon gamma (IFNγ), and T-cell receptor (TCR) clonality. For example, in some embodiments the biomarker is T-cell receptor (TCR) clonality after treatment with Compounds 1-3. In some specific embodiments, TCR clonality can be a biomarker and the treatment compound is Compound 1. In some specific embodiments, TCR clonality can be a biomarker and the treatment compound is Compound 2. In some specific embodiments, TCR clonality can be a biomarker and the treatment compound is Compound 3.

Further, the release of cytokines is centrally important to many aspects of T cell function. For example, IL-2 is a potent T cell growth factor that is essential for the long-term proliferation of activated T cells. Secretion of other cytokines, such as TNFα and IFNγ, can facilitate the effector T-cell function in killing tumor cells. Therefore, detecting cytokines can indicate T-cell activation. In some embodiments, the biomarker has a function in T-cell activation, the biomarker is IL-2, and the treatment compound is Compound 1. In some embodiments, the biomarker has a function in T-cell activation, the biomarker is IL-2, and the treatment compound is Compound 2. In some embodiments, the biomarker has a function in T-cell activation, the biomarker is IL-2, and the treatment compound is Compound 3. In other embodiments, the biomarker has a function in T-cell activation, the biomarker is TNFα, and the treatment compound is Compound 1. In some embodiments, the biomarker has a function in T-cell activation, the biomarker is TNFα, and the treatment compound is Compound 2. In some embodiments, the biomarker has a function in T-cell activation, the biomarker is TNFα, and the treatment compound is Compound 3. In yet another embodiment, the biomarker has a function in T-cell activation, the biomarker is IFNγ, and the treatment compound is Compound 1. In some embodiments, the biomarker has a function in T-cell activation, the biomarker is IFNγ, and the treatment compound is Compound 2. In some embodiments, the biomarker has a function in T-cell activation, the biomarker is IFNγ, and the treatment compound is Compound 3.

Circulating tumor cells (CTCs) are prognostic in multiple myeloma and characterization of CTCs, including identifying relevant mutations, from peripheral blood can indicate disease burden, and may predict response to treatment (Mishima et al., Cell Rep., 2017, 19(1):218-224; Lohr et al., Sci Transl Med., 2016, 8(363):363ra147). Therefore, in some embodiments, CTCs in the peripheral blood can be a biomarker and the treatment compound is Compound 1, Compound 2, or Compound 3. In some specific embodiments, CTCs in the peripheral blood can be a biomarker and the treatment compound is Compound 1. In some specific embodiments, CTCs in the peripheral blood can be a biomarker and the treatment compound is Compound 2. In some specific embodiments, CTCs in the peripheral blood can be a biomarker and the treatment compound is Compound 3. In other embodiments, the mutational profile of CTCs can be a biomarker for predicting response to treatment with Compound 1, Compound 2, or Compound 3. In some specific embodiments, the mutational profile of CTCs can be a biomarker and the treatment compound is Compound 1. In some specific embodiments, the mutational profile of CTCs can be a biomarker and the treatment compound is Compound 2. In some specific embodiments, the mutational profile of CTCs can be a biomarker and the treatment compound is Compound 3.

Inhibiting the progression of the cell cycle in a cancer cell can be an effective means of preventing the progression of a cancer. As described in Example 6, Compound 2 can induce G1 cell cycle arrest and apoptosis in multiple myeloma cells. Detecting members of the cell cycle pathway can be instrumental in monitoring the efficacy, predicting response, identifying a subject having cancer who is likely to be responsive, treating cancer, identifying a subject having multiple myeloma who is likely to be response to a treatment compound, and determining or adjusting a dose for treating a subject having multiple myeloma with a treatment compound. Therefore, in some embodiments, the biomarker has a function in a cell cycle pathway. In certain specific embodiments, the biomarker has a function in a cell cycle pathway and the treatment compound is Compound 1. In other specific embodiments, the biomarker has a function in a cell cycle pathway and the treatment compound is Compound 2. In still other embodiments, the biomarker has a function in a cell cycle pathway and the treatment compound is Compound 3.

In certain embodiments, the biomarker has a function in a cell cycle pathway, and is selected from the group consisting of cyclin-dependent kinase inhibitor 1 (p21), cyclin-dependent kinase inhibitor 1B (p27), and retinoblastoma protein (pRb1). In some embodiments, the biomarker is selected from the group consisting of cyclin-dependent kinase inhibitor 1 (p21), cyclin-dependent kinase inhibitor 1B (p27), and retinoblastoma protein (pRb1), and the treatment compound is Compound 1. In other embodiments, the biomarker is selected from the group consisting of cyclin-dependent kinase inhibitor 1 (p21), cyclin-dependent kinase inhibitor 1B (p27), and retinoblastoma protein (pRb1), and the treatment compound is Compound 2. In still other embodiments, the biomarker is selected from the group consisting of cyclin-dependent kinase inhibitor 1 (p21), cyclin-dependent kinase inhibitor 1B (p27), and retinoblastoma protein (pRb1), and the treatment compound is Compound 3. In specific embodiments, the biomarker is p21 and the treatment compound is Compound 1. In other embodiments, the biomarker is p21, and the treatment compound is Compound 2. In still other embodiments, the biomarker is p21, and the treatment compound is Compound 3. In certain embodiments, the biomarker is p27 and the treatment compound is Compound 1. In other embodiments, the biomarker is p27, and the treatment compound is Compound 2. In still other embodiments, the biomarker is p27, and the treatment compound is Compound 3. In specific embodiments, the biomarker is pRb1 and the treatment compound is Compound 1. In other embodiments, the biomarker is pRb1, and the treatment compound is Compound 2. In still other embodiments, the biomarker is pRb1, and the treatment compound is Compound 3.

As described in the Examples in Section 6, the treatment compounds can inhibit proliferation of multiple myeloma cells with acquired resistance to cereblon modulators, such as lenalidomide and pomalidomide, even if the cells have reduced, but detectable, levels of CRBN (Example 8). Therefore, in some embodiments, reduced levels of CRBN is a biomarker for diagnosing the subject as being likely to be responsive to the treatment compound and the treatment compound is Compound 1. In other embodiments, reduced levels of CRBN is a biomarker for diagnosing the subject as being likely to be responsive to the treatment compound and the treatment compound is Compound 2. In yet another embodiment, reduced levels of CRBN is a biomarker for diagnosing the subject as being likely to be responsive to the treatment compound and the treatment compound is Compound 3. In some embodiments of the methods of predicting the responsiveness of a subject having multiple myeloma to a treatment compound the methods comprise diagnosing the subject as being likely to be responsive to the treatment compound if the biomarker in the sample is detectable. In some specific embodiments, the MM is relapsed, refractory, or resistant to conventional therapy. In one embodiment, the MM is lenalidomide-resistant MM. In another embodiment, the MM is pomalidomide-resistant MM.

Biomarkers can also be useful for determining or adjusting dosage for treating a subject having multiple myeloma with a treatment compound. For example, detecting an increase in a biomarker, such as IKZF1, after treatment with a treatment compound can indicate that a subject requires more frequent dosing, or treatment for an extended period. Therefore, in some embodiments, the biomarker is for determining or adjusting dosage for treating a subject having multiple myeloma with a treatment compound and is selected from the group consisting of IKZF1 and IKZF3. In specific embodiments, the biomarker is selected from the group consisting of IKZF1 and IKZF3, and the treatment compound is Compound 1. In another specific embodiment, the biomarker is selected from the group consisting of IKZF1 and IKZF3, and the treatment compound is Compound 2. In yet another specific embodiment, the biomarker is selected from the group consisting of IKZF1 and IKZF3, and the treatment compound is Compound 3. In certain embodiments, the biomarker is IKZF1 and the treatment compound is Compound 1. In certain embodiments, the biomarker is IKZF1 and the treatment compound is Compound 2. In certain embodiments, the biomarker is IKZF1 and the treatment compound is Compound 3. In some embodiments, the biomarker is IKZF3 and the treatment compound is Compound 1. In other embodiments, the biomarker is IKZF3 and the treatment compound is Compound 2. In still other embodiments, the biomarker is IKZF3 and the treatment compound is Compound 3.

In some embodiments, the biomarker measured comprises one biomarker. In some embodiments, the biomarker measured comprises one or more biomarker. In certain embodiments, the biomarkers measured comprise two biomarkers. In some embodiments, the biomarker measured comprises two or more biomarker. In other embodiments, the biomarkers measured comprise three biomarkers. In some embodiments, the biomarker measured comprises three or more biomarker. In certain embodiments, the biomarkers measured comprise four biomarkers. In some embodiments, the biomarker measured comprises four or more biomarker. In some embodiments, the biomarkers measured comprise five biomarkers. In some embodiments, the biomarker measured comprises five or more biomarker. In other embodiments, the biomarkers measured comprise six biomarkers. In some embodiments, the biomarker measured comprises six or more biomarker. In yet other embodiments, the biomarkers measured comprise seven biomarkers. In some embodiments, the biomarker measured comprises seven or more biomarker. In certain embodiments, the biomarkers measured comprise eight biomarkers. In some embodiments, the biomarker measured comprises eight or more biomarker. In other embodiments, the biomarkers measured comprise nine biomarkers. In some embodiments, the biomarker measured comprises nine or more biomarker. In another embodiment, the biomarkers measured comprise ten or more biomarkers.

Also provided herein are methods for the treatment or management of cancer using a biomarker, e.g., Aiolos, Ikaros, CRBN, ZFP91, c-MYC, IRF4, c-Caspase 1, c-Caspase-3, c-Caspase 7, cleaved-PARP, survivin, BIM, sFLC, p21, p27, pRB1, soluble BCMA, CTCs, TILs, IL-2, IFNγ, TNFα, or TCR clonality, as a predictive or prognostic factor for the compounds provided herein. In certain embodiments, provided herein are methods for screening or identifying multiple myeloma patients for treatment with a compound using the level of one or more biomarkers provided herein, e.g., Aiolos, Ikaros, CRBN, ZFP91, c-MYC, IRF4, c-Caspase 1, c-Caspase-3, c-Caspase 7, cleaved-PARP, survivin, BIM, sFLC, p21, p27, pRB1, soluble BCMA, CTCs, TILs, IL-2, IFNγ, TNFα, or TCR clonality, as a predictive or prognostic factor. In some embodiments, provided herein are methods for selecting patients having a higher response rate to therapy with a compound provided herein, using a biomarker (e.g., Aiolos, Ikaros, CRBN, ZFP91, c-MYC, IRF4, c-Caspase 1, c-Caspase-3, c-Caspase 7, cleaved-PARP, survivin, BIM, sFLC, p21, p27, pRB1, soluble BCMA, CTCs, TILs, IL-2, IFNγ, TNFα, or TCR clonality) level as a predictive or prognostic factor. In certain embodiments, the treatment compound is Compound 1, Compound 2, or Compound 3. In one embodiment, the treatment compound is Compound 1. In another embodiment, the compound is Compound 2. In another embodiment, the treatment compound is Compound 3.

In one aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker; wherein the treatment compound is Compound 1:

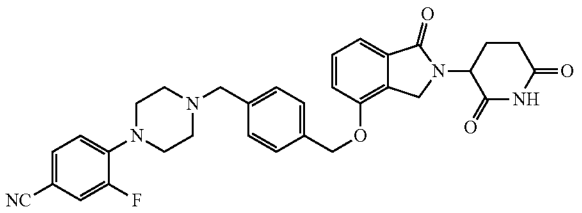

or an enantiomer, mixture of enantiomers, tautomer, isotopolog, or pharmaceutically acceptable salt thereof.

In another aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker; wherein the treatment compound is Compound 2:

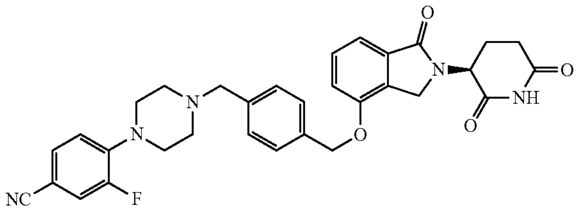

or a tautomer, isotopolog, or pharmaceutically acceptable salt thereof.

In another aspect, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample; and (d) diagnosing the subject as being likely to be responsive to the treatment compound if the level of the biomarker in the sample is different from a reference level of the biomarker; wherein the treatment compound is Compound 3:

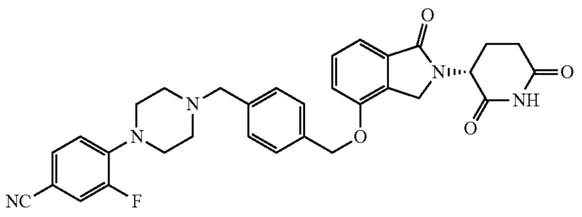

or a tautomer, isotopolog, or pharmaceutically acceptable salt thereof.

In another aspect of the invention the method of identifying a subject having cancer who is likely to be responsive to a treatment compound, which has been administered to the subject, comprising:

(a) determining the level of a biomarker in a sample obtained from the subject; and (b) diagnosing the subject as being likely to be responsive to the treatment compound if the level of the biomarker in the sample is different from a reference level of the biomarker; wherein the treatment compound is Compound 1, Compound 2 or Compound 3 or an enantiomer, mixture of enantiomers, tautomer, isotopolog, or pharmaceutically acceptable salt thereof.

In another aspect, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker; wherein the treatment compound is Compound 1:

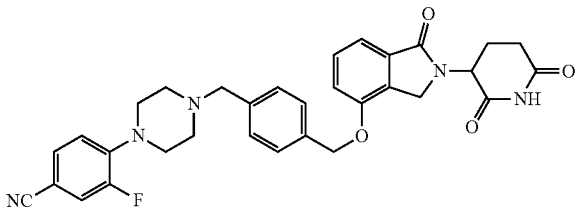

or an enantiomer, mixture of enantiomers, tautomer, isotopolog, or pharmaceutically acceptable salt thereof.

In another aspect, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker; wherein the treatment compound is Compound 2:

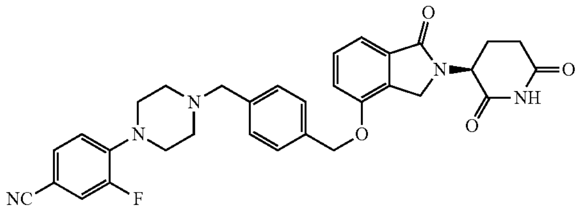

or a tautomer, isotopolog, or pharmaceutically acceptable salt thereof.

In another aspect, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from a reference level of the biomarker; wherein the treatment compound is Compound 3:

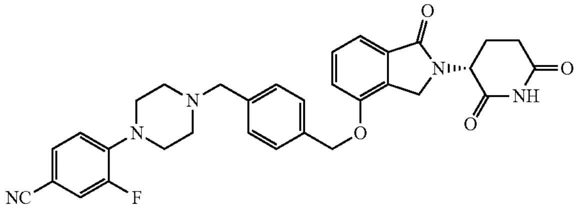

or a tautomer, isotopolog, or pharmaceutically acceptable salt thereof.

In another aspect, provided herein is a method of identifying a subject having cancer who is likely to be responsive to a treatment compound, comprising:

(a) administering the treatment compound to a sample obtained from the subject;

(c) determining the level of a biomarker in the sample; and (d) diagnosing the subject as being likely to be responsive to the treatment compound if the level of the biomarker in the sample is different from a reference level of the biomarker; wherein the treatment compound is Compound 1, Compound 2 or Compound 3 or an enantiomer, mixture of enantiomers, tautomer, isotopolog, or pharmaceutically acceptable salt thereof.

In another aspect, when a subject is diagnosed as being likely to be responsive to a treatment compound, the methods provided herein further comprise administering a therapeutically effective amount of the treatment compound to the subject.

Thus, in some embodiments, provided herein is a method of treating cancer, comprising:

(a) obtaining a sample from a subject having the cancer;

(b) determining the level of a biomarker in the sample;

(c) diagnosing the subject as being likely to be responsive to a treatment compound if the level of the biomarker in the sample is different from a reference level of the biomarker; and (d) administering a therapeutically effective amount of the treatment compound to the subject; wherein the treatment compound is Compound 1:

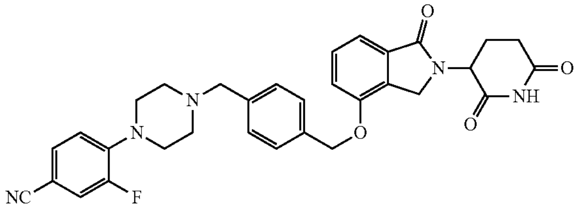

or an enantiomer, mixture of enantiomers, tautomer, isotopolog, or pharmaceutically acceptable salt thereof.

In some embodiments, provided herein is a method of treating cancer, comprising:

(a) obtaining a sample from a subject having the cancer;

(b) determining the level of a biomarker in the sample;

(c) diagnosing the subject as being likely to be responsive to a treatment compound if the level of the biomarker in the sample is different from a reference level of the biomarker; and (d) administering a therapeutically effective amount of the treatment compound to the subject; wherein the treatment compound is Compound 2:

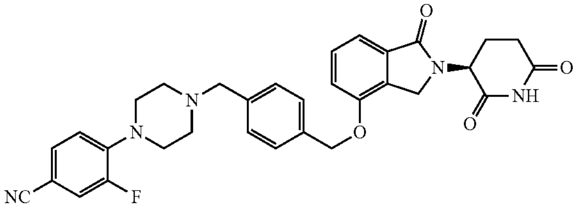

or a tautomer, isotopolog, or pharmaceutically acceptable salt thereof.

In some embodiments, provided herein is a method of treating cancer, comprising:

(a) obtaining a sample from a subject having the cancer;

(b) determining the level of a biomarker in the sample;

(c) diagnosing the subject as being likely to be responsive to a treatment compound if the level of the biomarker in the sample is different from a reference level of the biomarker; and (d) administering a therapeutically effective amount of the treatment compound to the subject; wherein the treatment compound is Compound 3:

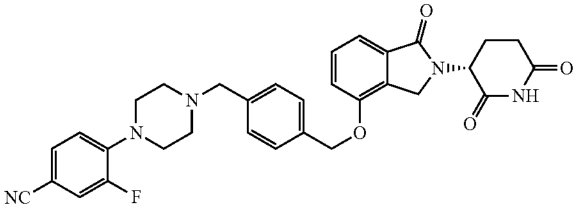

or a tautomer, isotopolog, or pharmaceutically acceptable salt.

In some embodiments, provided herein is Compound 1, Compound 2 or Compound 3 or an enantiomer, mixture of enantiomers, tautomer, isotopolog, or pharmaceutically acceptable salt thereof for use in a method of treating cancer, comprising:

(a) obtaining a sample from a subject having the cancer;

(b) determining the level of a biomarker in the sample;

(c) diagnosing the subject as being likely to be responsive to a treatment compound if the level of the biomarker in the sample is different from a reference level of the biomarker; and (d) administering a therapeutically effective amount of the treatment compound to the subject.

In some embodiments of the various methods provided herein, the method comprises or further comprises a step of administering a treatment compound. In other embodiments, provided herein are methods for selectively treating a patient selected using the methods provided herein.

One embodiment of the methods provided herein comprises treating the multiple myeloma patient that is selected based on the biomarkers described herein, comprising administering to a patient Compound 1, or an enantiomer, mixture of enantiomers, tautomer, isotopolog, or pharmaceutically acceptable salt thereof.

Another embodiment of the methods provided herein further comprises a method of treating the multiple myeloma patient that is selected based on the level of the biomarkers described herein, comprising administering to a patient Compound 2, or a tautomer, isotopolog, or pharmaceutically acceptable salt thereof.

In yet another embodiment of the methods provided herein further comprises a method of treating the multiple myeloma patient that is selected based on the level of the biomarkers described herein, comprising administering to a patient Compound 3, or a tautomer, isotopolog, or pharmaceutically acceptable salt thereof.

Another embodiment of the methods provided herein further comprises a method of preventing multiple myeloma in a patient selected based on the level of the biomarkers described herein, which comprises administering to a patient a compound provided herein, e.g., Compound 1, Compound 2 or Compound 3, or an enantiomer, mixture of enantiomers, tautomer, isotopolog, or pharmaceutically acceptable salt thereof.

In yet another embodiment of the methods provided herein further comprises a method of managing multiple myeloma based on the level of the biomarkers described herein, which comprises administering to a patient a compound provided herein, e.g., Compound 1, Compound 2 or Compound 3, or an enantiomer, mixture of enantiomers, tautomer, isotopolog, or pharmaceutically acceptable salt thereof.

One embodiment of the methods provided herein, further comprises methods for inducing a therapeutic response assessed with the International Uniform Response Criteria for Multiple Myeloma (IURC) (see Durie B G, et al., *Leukemia,* 2006, 20(9):1467-73) of a patient based on the level of the biomarkers described herein, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to a patient having multiple myeloma. In another embodiment, provided herein are methods for achieving a stringent complete response, complete response, or very good partial response, as determined by the International Uniform Response Criteria for Multiple Myeloma (IURC) in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in overall survival, progression-free survival, event-free survival, time to progression, or disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in overall survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in progression-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in event-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in time to progression in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma. In another embodiment, provided herein are methods for achieving an increase in disease-free survival in a patient, comprising administering an effective amount of a compound described herein, e.g., Compound 1, Compound 2 or Compound 3, or an enantiomer, mixture of enantiomers, tautomer, isotopolog, or pharmaceutically acceptable salt thereof, to patient having multiple myeloma.

Also provided herein are methods further comprising treating patients who have been previously treated for multiple myeloma but are non-responsive to standard therapies, as well as those who have not previously been treated. Further encompassed are methods of treating patients who have undergone surgery in an attempt to treat multiple myeloma, as well as those who have not. Also provided herein are methods of treating patients who have been previously undergone transplant therapy, as well as those who have not.

Some embodiments of the methods provided herein further comprise treatment of multiple myeloma that is relapsed, refractory or resistant. The methods provided herein include prevention of multiple myeloma that is relapsed, refractory or resistant. The methods provided herein include management of multiple myeloma that is relapsed, refractory or resistant. In some such embodiments, the myeloma is primary, secondary, tertiary, quadruply or quintuply relapsed multiple myeloma. In one embodiment, the methods provided herein reduce, maintain or eliminate minimal residual disease (MRD). In one embodiment, methods provided herein encompass treating, preventing or managing various types of multiple myeloma, such as monoclonal gammopathy of undetermined significance (MGUS), low risk, intermediate risk, and high risk multiple myeloma, newly diagnosed multiple myeloma (including low risk, intermediate risk, and high risk newly diagnosed multiple myeloma), transplant eligible and transplant ineligible multiple myeloma, smoldering (indolent) multiple myeloma (including low risk, intermediate risk, and high risk smouldering multiple myeloma), active multiple myeloma, solitary plasmacytoma, extramedullary plasmacytoma, plasma cell leukemia, central nervous system multiple myeloma, light chain myeloma, non-secretory myeloma, Immunoglobulin D myeloma, and Immunoglobulin E myeloma, by administering a therapeutically effective amount of a compound described herein. In another embodiment, methods provided herein encompass treating, preventing or managing multiple myeloma characterized by genetic abnormalities, such as Cyclin D translocations (for example, t(411;14)(q13;q32); t(6;14)(p21;32); t(12;14)(p13;q32); or t(6;20)); MMSET translocations (for example, t(4;14)(p16;q32));

MAF translocations (for example, t(14;16)(q32;q32); t(20; 22); t(16; 22)(q11;q13); or t(14;20)(q32;q11)); or other chromosome factors (for example, deletion of 17p13, or chromosome 13; del(17/17p), nonhyperdiploidy, and gain (1q)), by administering a therapeutically effective amount of a compound described herein. In one embodiment, the methods comprise administering a therapeutically effective amount of Compound 1, or an enantiomer, mixture of enantiomers, tautomer, isotopolog, or pharmaceutically acceptable salt thereof. In another embodiment, the methods comprise administering a therapeutically effective amount of Compound 2, or a tautomer, isotopolog, or pharmaceutically acceptable salt thereof. In another embodiment, the methods comprise administering a therapeutically effective amount of Compound 3, or a tautomer, isotopolog, or pharmaceutically acceptable salt thereof.

In one embodiment, the high risk multiple myeloma is multiple myeloma that is relapsed within 12 months of first treatment. In yet another embodiment, the high risk multiple myeloma is multiple myeloma that is characterized by genetic abnormalities, for example, one or more of del(17/17p and t(14;16)(q32;q32).

In some such embodiments, the multiple myeloma is transplant eligible newly diagnosed multiple myeloma. In another embodiment, the multiple myeloma is transplant ineligible newly diagnosed multiple myeloma. In yet other embodiments, the multiple myeloma is characterized by early progression (for example less than 12 months) following initial treatment. In still other embodiments, the multiple myeloma is characterized by early progression (for example less than 12 months) following autologous stem cell transplant. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, and pomalidomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, and pomalidomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, and pomalidomide), and one other active agent, as described herein.

Certain embodiments of the methods provided herein further comprise methods of treating, preventing, and/or managing multiple myeloma, including relapsed/refractory multiple myeloma in patients with impaired renal function or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof to a patient having relapsed/refractory multiple myeloma with impaired renal function.

Certain embodiments of the methods provided herein further comprise methods of treating, preventing, and/or managing multiple myeloma, including relapsed or refractory multiple myeloma in frail patients or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof to a frail patient having multiple myeloma. In some such embodiments, the frail patient is characterized by ineligibility for induction therapy, or intolerance to dexamethasone treatment. In some such embodiment the frail patient is elderly, for example, older than 65 years old.

In certain embodiments, a therapeutically or prophylactically effective amount of the compound is from about from about 0.01 to about 25 mg per day, from about 0.01 to about 10 mg per day, from about 0.01 to about 5 mg per day, from about 0.01 to about 2 mg per day, from about 0.01 to about 1 mg per day, from about 0.01 to about 0.5 mg per day, from about 0.01 to about 0.25 mg per day, from about 0.1 to about 25 mg per day, from about 0.1 to about 10 mg per day, from about 0.1 to about 5 mg per day, from about 0.1 to about 2 mg per day, from about 0.1 to about 1 mg per day, from about 0.1 to about 0.5 mg per day, from about 0.1 to about 0.25 mg per day, from about 0.5 to about 25 mg per day, from about 0.5 to about 10 mg per day, from about 0.5 to about 5 mg per day, from about 0.5 to about 2 mg per day, from about 0.5 to about 1 mg per day, from about 1 to about 25 mg per day, from about 1 to about 10 mg per day, from about 1 to about 5 mg per day, from about 1 to about 2.5 mg per day, or from about 1 to about 2 mg per day. In one embodiment, a therapeutically or prophylactically effective amount of Compound 1, Compound 2 or Compound 3 is from about 0.1 mg per day to about 0.4 mg per day.

In certain embodiments, the therapeutically or prophylactically effective amount is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 15, about 20, or about 25 mg per day. In some such embodiments, the therapeutically or prophylactically effective amount is about 0.1, about 0.2, about 0.3, about 0.4, about 0.5, about 0.6 or about 0.7 mg per day.

In one embodiment, the recommended daily dose range of Compound 1, Compound 2 or Compound 3, or an enantiomer, mixture of enantiomers, tautomer, isotopolog, or pharmaceutically acceptable salt thereof, for the conditions described herein lie within the range of from about 0.1 mg to about 25 mg per day, preferably given as a single once-a-day dose, or in divided doses throughout a day. In other embodiments, the dosage ranges from about 0.1 to about 10 mg per day. Specific doses per day include 0.1, 0.2, 0.3, 0.4, 0.5, 1, 2, 3, 4, 5, 6, 7, 8, 9, 10, 11, 12, 13, 14, 15, 16, 17, 18, 19, 20, 21, 22, 23, 24, or 25 mg per day. More specific doses per day include 0.1, 0.2, 0.3, 0.4, or 0.5 mg per day.

In a specific embodiment, the recommended starting dosage may be 0.1, 0.2, 0.3, 0.4, 0.5, 1, 2, 3, 4, 5, 10, 15, 20, or 25 mg per day. In another embodiment, the recommended starting dosage may be 0.1, 0.2, 0.3, 0.4, or 0.5, mg per day. The dose may be escalated to 1, 2, 3, 4, or 5 mg per day.

In certain embodiments, the therapeutically or prophylactically effective amount is from about 0.001 to about 5 mg/kg/day, from about 0.001 to about 4 mg/kg/day, from about 0.001 to about 3 mg/kg/day, from about 0.001 to about 2 mg/kg/day, from about 0.001 to about 1 mg/kg/day, from about 0.001 to about 0.05 mg/kg/day, from about 0.001 to about 0.04 mg/kg/day, from about 0.001 to about 0.03 mg/kg/day, from about 0.001 to about 0.02 mg/kg/day, from about 0.001 to about 0.01 mg/kg/day, or from about 0.001 to about 0.005 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the patient to be treated with one of the methods provided herein has not been treated with multiple myeloma therapy prior to the administration of Compound 1, Compound 2 or Compound 3 provided herein, or an enantiomer, mixture of enantiomers, tautomer, isotopolog, or pharmaceutically acceptable salt thereof. In certain embodiments, the patient to be treated with one of the methods provided herein has been treated with multiple myeloma therapy prior to the administration of Compound 1, Compound 2 or Compound 3 provided herein or an enantiomer, mixture of enantiomers, tautomer, isotopolog, or pharmaceutically acceptable salt thereof. In certain embodiments, the patient to be treated with one of the methods provided herein has developed drug resistance to the anti-multiple myeloma therapy. In some such embodiments, the patient has developed resistance to one, two, or three anti-multiple myeloma therapies, wherein the therapies are selected from a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, and pomalidomide).

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old. In one embodiment, the subject is an elderly multiple myeloma subject, such as a subject older than 65 years old. In one embodiment, the subject is an elderly multiple myeloma subject, such as a subject older than 75 years old.

Depending on the state of the disease to be treated and the subject's condition, Compound 1 or compound 2 provided herein, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Compound 1, Compound 2 or Compound 3 provided herein, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, Compound 2 or Compound 3 provided herein, or an enantiomer, mixture of enantiomers, tautomer, isotopolog, or pharmaceutically acceptable salt thereof, is administered orally. In another embodiment, the compound of Compound 1, Compound 2 or Compound 3 provided herein, or an enantiomer, mixture of enantiomers, tautomer, isotopolog, or pharmaceutically acceptable salt thereof, is administered parenterally. In yet another embodiment, the compound of Compound 1, Compound 2 or Compound 3 provided herein, or an enantiomer, mixture of enantiomers, tautomer, isotopolog, or pharmaceutically acceptable salt thereof, is administered intravenously.

Compound 1, Compound 2 or Compound 3 provided herein, or an enantiomer, mixture of enantiomers, tautomer, isotopolog, or pharmaceutically acceptable salt thereof, can be delivered as a single dose such as, e.g., a single bolus injection, or oral tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MM scan and other commonly accepted evaluation modalities.

Compound 1, Compound 2 or Compound 3 provided herein, or an enantiomer, mixture of enantiomers, tautomer, isotopolog, or pharmaceutically acceptable salt thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, Compound 2 or Compound 3 provided herein, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound 1, Compound 2 or Compound 3 provided herein, or an enantiomer, mixture of enantiomers, tautomer, isotopolog, or pharmaceutically acceptable salt thereof, is administered once a day. In another embodiment, Compound 1, Compound 2 or Compound 3 provided herein, or an enantiomer, mixture of enantiomers, tautomer, isotopolog, or pharmaceutically acceptable salt thereof, is administered twice a day. In yet another embodiment, Compound 1, Compound 2 or Compound 3 provided herein, or an enantiomer, mixture of enantiomers, tautomer, isotopolog, or pharmaceutically acceptable salt thereof, is administered three times a day. In still another embodiment, Compound 1, Compound 2 or Compound 3 provided herein, or an enantiomer, mixture of enantiomers, tautomer, isotopolog, or pharmaceutically acceptable salt thereof, is administered four times a day.

In one embodiment, a therapeutically effective amount of Compound 1, Compound 2 or Compound 3 is administered in a treatment cycle which includes an administration period of up to 20 days followed by a rest period. In one embodiment, a therapeutically effective amount of Compound 1, Compound 2 or Compound 3 is administered in a treatment cycle which includes an administration period of up to 15 days followed by a rest period. In one embodiment, a therapeutically effective amount of Compound 1, Compound 2 or Compound 3 is administered in a treatment cycle which includes an administration period of up to 10 days followed by a rest period. In one embodiment, a therapeutically effective amount of Compound 1, Compound 2 or Compound 3 is administered in a treatment cycle which includes an administration period of up to 7 days followed by a rest period. In one embodiment, a therapeutically effective amount of Compound 1, Compound 2 or Compound 3 is administered in a treatment cycle which includes an administration period of up to 5 days followed by a rest period. In one embodiment, a therapeutically effective amount of Compound 1, Compound 2 or Compound 3 is administered in a treatment cycle which includes an administration period of up to 4 days followed by a rest period. In one embodiment, a therapeutically effective amount of Compound 1, Compound 2 or Compound 3 is administered in a treatment cycle which includes an administration period of up to 3 days followed by a rest period.

In one embodiment, the treatment cycle includes an administration period of up to 14 days followed by a rest period. In one embodiment, the treatment cycle includes an administration period of up to 10 days followed by a rest period. In one embodiment, the treatment cycle includes an administration period of up to 7 days followed by a rest period. In one embodiment, the treatment cycle includes an administration period of up to 5 days followed by a rest period. In one embodiment, the treatment cycle includes an administration period of up to 4 days followed by a rest period. In one embodiment, the treatment cycle includes an administration period of up to 3 days followed by a rest period.

In one embodiment, the rest period is from about 2 days up to about 11 days. In one embodiment, the rest period is from about 2 days up to about 10 days. In one embodiment, the rest period is about 2 days. In one embodiment, the rest period is about 3 days. In one embodiment, the rest period is about 4 days. In one embodiment, the rest period is about 5 days. In one embodiment, the rest period is about 6 days. In another embodiment, the rest period is about 7 days. In another embodiment, the rest period is about 8 days. In another embodiment, the rest period is about 9 days. In another embodiment, the rest period is about 10 days. In another embodiment, the rest period is about 11 days.

In one embodiment, the treatment cycle includes an administration period of up to 15 days followed by a rest period from about 2 days up to about 10 days. In one embodiment, the treatment cycle includes an administration period of up to 10 days followed by a rest period from about 2 days up to about 10 days. In one embodiment, the treatment cycle includes an administration period of up to 7 days followed by a rest period from about 2 days up to about 10 days. In one embodiment, the treatment cycle includes an administration period of up to 5 days followed by a rest period from about 2 days up to about 10 days. In one embodiment, the treatment cycle includes an administration period of up to 3 days followed by a rest period from about 10 days up to about 15 days. In one embodiment, the treatment cycle includes an administration period of up to 3 days followed by a rest period from about 3 days up to about 15 days.

In one embodiment, the treatment cycle includes an administration period of up to 15 days followed by a rest period of 7 days. In one embodiment, the treatment cycle includes an administration period of up to 10 days followed by a rest period of 5 days. In one embodiment, the treatment cycle includes an administration period of up to 10 days followed by a rest period of 4 days. In one embodiment, the treatment cycle includes an administration period of up to 10 days followed by a rest period of 3 days. In one embodiment, the treatment cycle includes an administration period of up to 10 days followed by a rest period of 2 days. In one embodiment, the treatment cycle includes an administration period of up to 7 days followed by a rest period of 7 days. In one embodiment, the treatment cycle includes an administration period of up to 5 days followed by a rest period of 5 days. In one embodiment, the treatment cycle includes an administration period of up to 3 days followed by a rest period of 11 days. In another embodiment, the treatment cycle includes an administration period of up to 5 days followed by a rest period of 9 days. In another embodiment, the treatment cycle includes an administration period of up to 5 days followed by a rest period of 2 days. In another embodiment, the treatment cycle includes an administration period of up to 3 days followed by a rest period of 4 days.

In one embodiment, the treatment cycle includes an administration of a therapeutically effective amount of Compound 1, Compound 2 or Compound 3 on days 1 to 5 of a 28 day cycle. In another embodiment, the treatment cycle includes an administration of Compound 1, Compound 2 or Compound 3 on days 1 to 10 of a 28 day cycle. In one embodiment, the treatment cycle includes an administration of a therapeutically effective amount of Compound 1, Compound 2 or Compound 3 on days 1 to 21 of a 28 day cycle. In another embodiment, the treatment cycle includes an administration of a therapeutically effective amount of Compound 1, Compound 2 or Compound 3 on days 1 to 5 of a 7 day cycle. In another embodiment, the treatment cycle includes an administration of a therapeutically effective amount of Compound 1, Compound 2 or Compound 3 on days 1 to 7 of a 7 day cycle. In one embodiment, the treatment cycle includes an administration of a therapeutically effective amount of Compound 1, Compound 2 or Compound 3 on days 1 to 10 and days 15 to 24 of a 28 day cycle. In one embodiment, the treatment cycle includes an administration of a therapeutically effective amount of Compound 1, Compound 2 or Compound 3 on days 1 to 3 and days 15 to 18 of a 28 day cycle. In one embodiment, the treatment cycle includes an administration of a therapeutically effective amount of Compound 1, Compound 2 or Compound 3 on days 1 to 7 and days 15 to 21 of a 28 day cycle. In one embodiment, the treatment cycle includes an administration of a therapeutically effective amount of Compound 1, Compound 2 or Compound 3 on days 1 to 5 and days 15 to 19 of a 28 day cycle. In one embodiment, the treatment cycle includes an administration of a therapeutically effective amount of Compound 1, Compound 2 or Compound 3 on days 1 to 3 and days 15 to 17 of a 28 day cycle.

In one embodiment, the treatment cycle includes an administration of a therapeutically effective amount of Compound 1, Compound 2 or Compound 3 on days 1 to 14 of a 21 day cycle. In another embodiment, the treatment cycle includes an administration of Compound 1, Compound 2 or Compound 3 on days 1 to 4 and 8 to 11 of a 21 day cycle. In one embodiment, the treatment cycle includes an administration of a therapeutically effective amount of Compound 1, Compound 2 or Compound 3 on days 1 to 5 and 8 to 12 of a 21 day cycle. In another embodiment, the treatment cycle includes an administration of a therapeutically effective amount of Compound 1, Compound 2 or Compound 3 on days 1 to 5 and 11 to 15 of a 21 day cycle. In another embodiment, the treatment cycle includes an administration of a therapeutically effective amount of Compound 1, Compound 2 or Compound 3 on days 1 to 5, 8 to 12 and 15 to 19 of a 21 day cycle. In another embodiment, the treatment cycle includes an administration of a therapeutically effective amount of Compound 1, Compound 2 or Compound 3 on days 1 to 4, 8 to 11 and 15 to 18 of a 21 day cycle. In another embodiment, the treatment cycle includes an administration of a therapeutically effective amount of Compound 1, Compound 2 or Compound 3 on days 1 to 4, 8 to 10 and 15 to 17 of a 21 day cycle. In another embodiment, the treatment cycle includes an administration of a therapeutically effective amount of Compound 1, Compound 2 or Compound 3 on days 1 to 3, and 8 to 11 of a 21 day cycle. In another embodiment, the treatment cycle includes an administration of a therapeutically effective amount of Compound 1, Compound 2 or Compound 3 on days 1 to 3 and 11 to 13 of a 21 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In some embodiments, a therapeutically effective amount of Compound 1, Compound 2 or Compound 3 is administered for 1 to 13 cycles of 28 days (e.g. about 1 year). In certain instances, the cycling therapy is not limited to the number of cycles, and the therapy is continued until disease progression. Cycles can in certain instances include varying the duration of administration periods and/or rest periods described herein.

In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day, administered once per day. In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, or 0.8 mg/day, administered once per day. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 of a 28 day cycle. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 and 15 to 24 of a 28 day cycle. In some such embodiments, the treatment cycle includes administering Compound 1, Compound 2 or Compound 3 once a day at a dosage amount of about 0.1 mg on days 1 to 10 and 15 to 24 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 19 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 17 of a 28 day cycle. In other embodiments, the treatment cycle includes administering Compound 1, Compound 2 or Compound 3 twice a day at a dosage amount of about 0.2 mg on days 1 to 3 and 15 to 17 of a 28 day cycle. In one such embodiment, the compound is administered on days 1 to 3 (morning and evening), day 14 (evening only), days 15 and 16 (morning and evening), and day 17 (morning only) in Cycle 1.

In some embodiments, provided herein is a method of identifying a subject with multiple myeloma that is relapsed, refractory, or resistant to conventional therapy who is likely to be responsive to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 1:

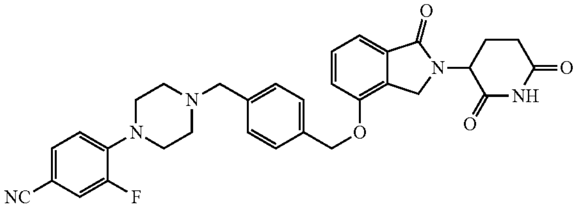

or an enantiomer, mixture of enantiomers, tautomer, isotopolog, or pharmaceutically acceptable salt thereof.

In another embodiment, provided herein is a method of identifying a subject with multiple myeloma that is relapsed, refractory, or resistant to conventional therapy who is likely to be responsive to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 2:

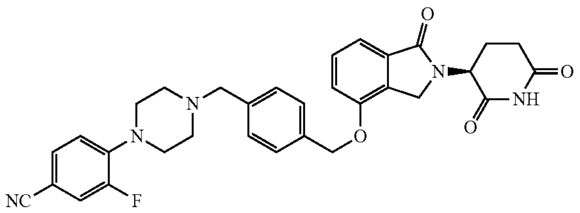

or a tautomer, isotopolog, or pharmaceutically acceptable salt thereof.

In yet another embodiment, provided herein is a method of identifying a subject with multiple myeloma that is relapsed, refractory, or resistant to conventional therapy who is likely to be responsive to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 3:

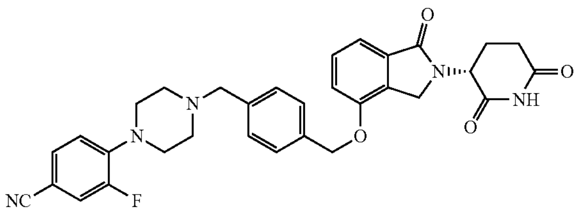

or a tautomer, isotopolog, or pharmaceutically acceptable salt thereof.

In some embodiments, provided herein is a method of identifying a subject with multiple myeloma that is relapsed, refractory, or resistant to conventional therapy who is likely to be responsive to a treatment compound, comprising:

(a) determining the level of a biomarker in a sample obtained from the subject; and (c) diagnosing the subject as being likely to be responsive to the treatment compound if the level of the biomarker in the sample is lower than a reference level of the biomarker;

wherein the treatment compound is a compound of Compound 1, Compound 2 or Compound 3 or a tautomer, isotopolog, or pharmaceutically acceptable salt thereof.

In another aspect, provided herein is a method of predicting the responsiveness of a subject having multiple myeloma to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 1:

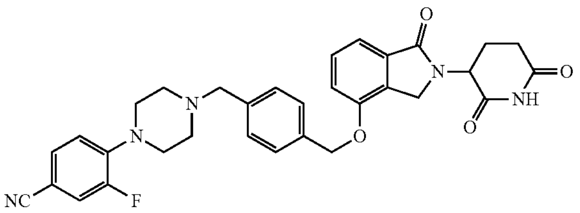

or an enantiomer, mixture of enantiomers, tautomer, isotopolog, or pharmaceutically acceptable salt thereof.

In another embodiment, provided herein is a method of predicting the responsiveness of a subject having multiple myeloma to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 2:

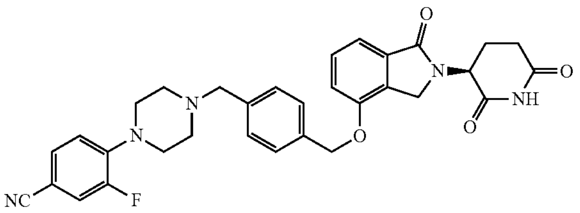

or a tautomer, isotopolog, or pharmaceutically acceptable salt thereof.

In yet another embodiment, a method of predicting the responsiveness of a subject having multiple myeloma to a treatment compound, comprising:

(a) obtaining a sample from a subject;

(b) determining the level of a biomarker in the sample; and (c) diagnosing the subject as being likely to be responsive to the treatment compound if the level of the biomarker in the sample is lower than a reference level of the biomarker;

wherein the treatment compound is a compound of Compound 3:

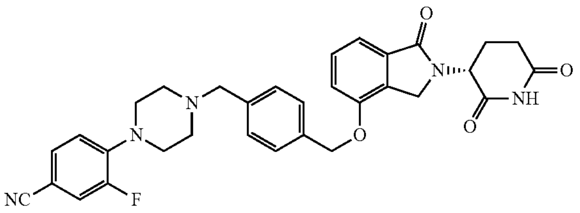

or a tautomer, isotopolog, or pharmaceutically acceptable salt thereof.

In another aspect, provided herein is a method of predicting the responsiveness of a subject having multiple myeloma to a treatment compound, comprising:

(a) determining the level of a biomarker in a sample obtained from a subject; and (c) diagnosing the subject as being likely to be responsive to the treatment compound if the level of the biomarker in the sample is lower than a reference level of the biomarker;

wherein the treatment compound is a compound of Compound 1, Compound 2 or Compound 3 or a tautomer, isotopolog, or pharmaceutically acceptable salt thereof.

It is understood that the dosing regimen can be adjusted to a patient's response, or lack thereof, according to the level of a biomarker. For example, the dosage can be adjusted if a patient is neutropenic or if the patient does not respond. Therefore, in some embodiments, provided herein is a method of determining or adjusting a dosage for treating a subject having multiple myeloma with a treatment compound comprising:

(a) administering a dosage of the treatment compound to the subject;

(b) obtaining one or more samples from the subject at different time points;

(c) determining the level of a biomarker in the one or more samples, and thereby determining if the dosage is appropriate or needs an adjustment;

wherein the treatment compound is a compound of Compound 1:

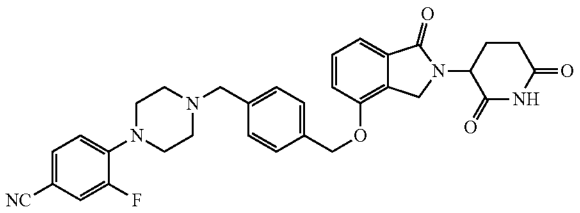

or an enantiomer, mixture of enantiomers, tautomer, isotopolog, or pharmaceutically acceptable salt thereof.

In another embodiment, provided herein is a method of determining or adjusting a dosage for treating a subject having multiple myeloma with a treatment compound comprising:

(a) administering a dosage of the treatment compound to the subject;

(b) obtaining one or more samples from the subject at different time points;

(c) determining the level of a biomarker in the one or more samples, and thereby determining if the dosage is appropriate or needs an adjustment; wherein the treatment compound is a compound of Compound 2:

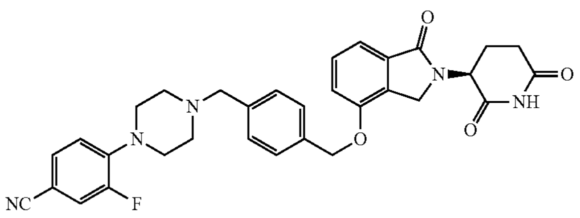

or a tautomer, isotopolog, or pharmaceutically acceptable salt thereof.

In yet another embodiment, provided herein is a method of determining or adjusting a dosage for treating a subject having multiple myeloma with a treatment compound comprising:

(a) administering a dosage of the treatment compound to the subject;

(b) obtaining one or more samples from the subject at different time points;

(c) determining the level of a biomarker in the one or more samples, and thereby determining if the dosage is appropriate or needs an adjustment wherein the treatment compound is a compound of Compound 3:

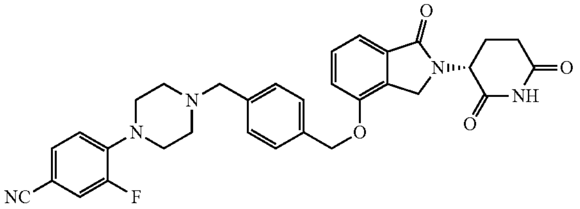

or a tautomer, isotopolog, or pharmaceutically acceptable salt thereof.

In yet another embodiment, provided herein is a method of determining or adjusting a dosage for treating a subject having multiple myeloma with a treatment compound, wherein the compound has been administered to the subject, comprising:

(a) determining the level of a biomarker in one or more samples obtained from the subject, and thereby determining if the dosage is appropriate or needs an adjustment wherein the treatment compound is a compound of Compound 1, Compound 2 or Compound 3 or a tautomer, isotopolog, or pharmaceutically acceptable salt thereof.

In some embodiments, the different time points can include a reference sample obtained prior to treatment with a treatment compound, and one or more samples obtained from the subject at different times during treatment with a treatment compound. In other embodiments, the different time points can include a reference sample obtained during treatment, and one or more samples taken at a later time during treatment with a treatment compound. In yet another embodiment, the different time points can include a reference sample taken prior to treatment, and a sample taken after treatment.

Also provided herein are methods for predicting or monitoring the responsiveness of a patient to a treatment compound, or efficacy of a treatment compound, using a biomarker (e.g., Aiolos, Ikaros, CRBN, ZFP91, c-MYC, IRF4, c-Caspase 1, c-Caspase-3, c-Caspase 7, cleaved-PARP, survivin, BIM, sFLC, p21, p27, pRB1, soluble BCMA, CTCs, TILs, IL-2, IFNγ, TNFα, or TCR clonality). In certain embodiments, provided herein are methods for predicting the responsiveness of a subject having or suspected of having cancer (e.g., multiple myeloma), to a treatment compound, using a predictive or prognostic factor, such as Aiolos, Ikaros, CRBN, ZFP91, c-MYC, IRF4, c-Caspase 1, c-Caspase-3, c-Caspase 7, cleaved-PARP, survivin, BIM, sFLC, p21, p27, pRB1, soluble BCMA, CTCs, TILs, IL-2, IFNγ, TNFα, or TCR clonality. In some embodiments, provided herein are methods for monitoring the efficacy of a treatment of cancer (e.g., multiple myeloma) in a subject with a treatment compound using a biomarker (e.g., Aiolos, Ikaros, CRBN, ZFP91, c-MYC, IRF4, c-Caspase 1, c-Caspase-3, c-Caspase 7, cleaved-PARP, survivin, BIM, sFLC, p21, p27, pRB1, soluble BCMA, CTCs, TILs, IL-2, IFNγ, TNFα, or TCR clonality) level as a predictive or prognostic factor. In certain embodiments, the treatment compound is Compound 1, Compound 2, or Compound 3. In one embodiment, the treatment compound is Compound 1. In another embodiment, the compound is Compound 2. In another embodiment, the treatment compound is Compound 3.

Thus, in some aspects, provided herein is a method of predicting the responsiveness of a subject having or suspected of having cancer to a treatment compound, comprising:

(a) administering the treatment compound to the subject;
(b) obtaining a sample from the subject;
(c) determining the level of a biomarker in the sample; and
(d) diagnosing the subject as being likely to be responsive to the treatment compound if the level of the biomarker in the sample is different from the level of the biomarker obtained from a reference sample; wherein the treatment compound is Compound 1:

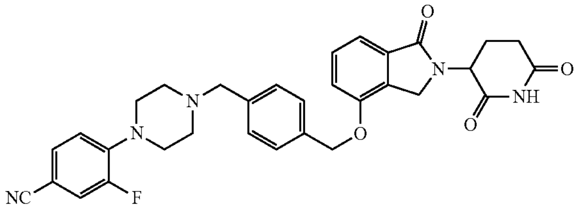

or an enantiomer, a mixture of enantiomers, tautomer, isotopolog, pharmaceutically acceptable salt, or a polymorph thereof.

In another aspect, provided herein is a method of predicting the responsiveness of a subject having or suspected of having cancer to a treatment compound, comprising:

(a) administering the treatment compound to the subject;
(b) obtaining a sample from the subject;
(c) determining the level of a biomarker in the sample; and
(d) diagnosing the subject as being likely to be responsive to the treatment compound if the level of the biomarker in the sample is different from the level of the biomarker obtained from a reference sample; wherein the treatment compound is Compound 2:

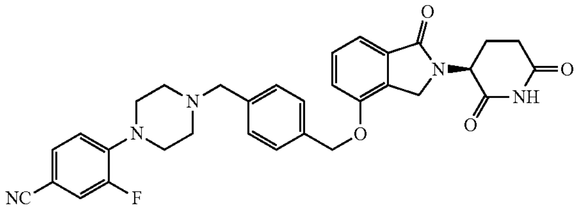

or a tautomer, isotopolog, or pharmaceutically acceptable salt thereof.

In yet another aspect, provided herein is a method of predicting the responsiveness of a subject having or suspected of having cancer to a treatment compound, comprising:

(a) administering the treatment compound to the subject;
(b) obtaining a sample from the subject;
(c) determining the level of a biomarker in the sample; and
(d) diagnosing the subject as being likely to be responsive to the treatment compound if the level of the biomarker in the sample is different from the level of the biomarker obtained from a reference sample; wherein the treatment compound is Compound 3:

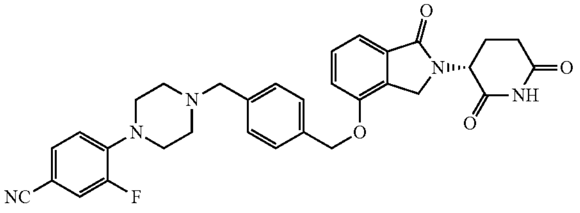

or a tautomer, isotopolog, or a pharmaceutically acceptable salt thereof.

In another aspect, provided herein is a method of predicting the responsiveness of a subject having or suspected of having cancer to a treatment compound, which has been administered to the subject, comprising:

(a) determining the level of a biomarker in a sample obtained from the subject; and
(b) diagnosing the subject as being likely to be responsive to the treatment compound if the level of the biomarker in the sample is different from the level of the biomarker obtained from a reference sample; wherein the treatment compound is Compound 1, Compound 2 or Compound 3 or a tautomer, isotopolog, or a pharmaceutically acceptable salt thereof.

In yet another aspect, provided herein is a method of predicting the responsiveness of a subject having or suspected of having cancer to a treatment compound, comprising:

(a) obtaining a sample from the subject;
(b) administering the treatment compound to the sample;
(c) determining the level of a biomarker in the sample; and
(d) diagnosing the subject as being likely to be responsive to the treatment compound if the level of the biomarker in the sample is different from the level of the biomarker obtained from a reference sample; wherein the treatment compound is Compound 1:

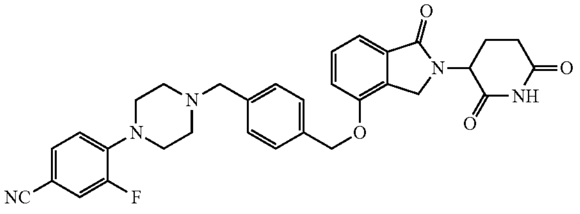

or an enantiomer, a mixture of enantiomers, tautomer, isotopolog, pharmaceutically acceptable salt, or a polymorph thereof.

In yet another aspect, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from the level of the biomarker obtained from a reference sample; wherein the treatment compound is Compound 2:

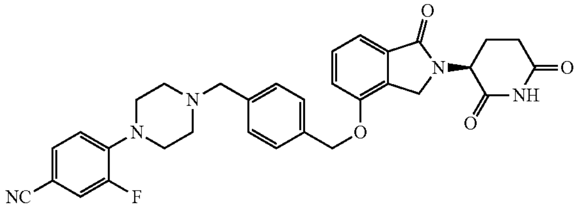

or a tautomer, isotopolog, pharmaceutically acceptable salt, or a polymorph thereof.

In yet another aspect, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample; and (d) diagnosing the subject as being likely to be responsive to the treatment compound if the level of the biomarker in the sample is different from the level of the biomarker obtained from a reference sample; wherein the treatment compound is Compound 3:

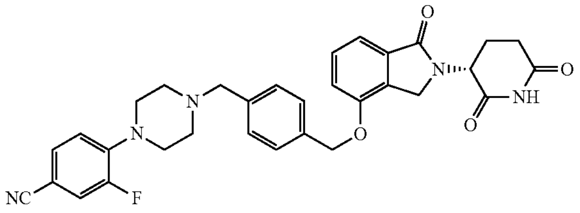

or a tautomer, isotopolog, pharmaceutically acceptable salt, or a polymorph thereof.

In yet another aspect, provided herein is a method of predicting the responsiveness of a subject having or suspected of having cancer to a treatment compound, comprising:

(a) administering the treatment compound to a sample obtained from the subject;

(b) determining the level of a biomarker in the sample; and (c) diagnosing the subject as being likely to be responsive to the treatment compound if the level of the biomarker in the sample is different from the level of the biomarker obtained from a reference sample; wherein the treatment compound is Compound 1, Compound 2 or Compound 3 or a tautomer, isotopolog, pharmaceutically acceptable salt, or a polymorph thereof.

In some embodiments of the various methods provided herein, the level of the biomarker in the sample is higher than the level of the biomarker obtained from the reference sample. In other embodiments of the various methods provided herein, the level of the biomarker in the sample is lower than the level of the biomarker obtained from the reference sample.

In yet another aspect, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample; and (d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 1:

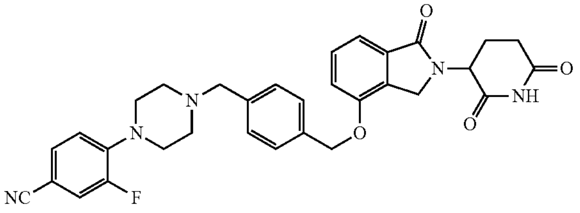

or an enantiomer, a mixture of enantiomers, tautomer, isotopolog, pharmaceutically acceptable salt, or a polymorph thereof.

In yet another aspect, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample; and (d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 2:

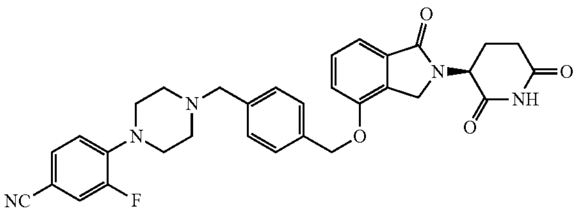

or a tautomer, isotopolog, pharmaceutically acceptable salt, or a polymorph thereof.

In yet another aspect, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample; and (d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 3:

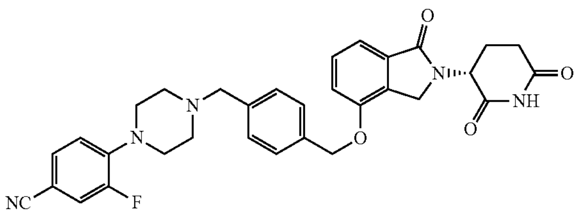

or a tautomer, isotopolog, pharmaceutically acceptable salt, or a polymorph thereof.

In yet another aspect, provided herein is a method of monitoring the efficacy of a treatment of cancer in a subject with a treatment compound, which has been administered to the subject, comprising:

(a) determining the level of a biomarker in a sample obtained from the subject; and (b) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 1, Compound 2 or Compound 3 or a tautomer, isotopolog, pharmaceutically acceptable salt, or a polymorph thereof.

In some embodiments, an increased level as compared to the reference level is indicative of the efficacy of the treatment compound in treating the cancer in the subject. For example, an increase in c-Caspase-3, c-Caspase 1, c-Caspase 7, cleaved-PARP, BIM, TUNEL, Annexin-V/7-AAD, Annexin-V/PI, p21, p27, free light chain, IL-2, TNFα, IFNγ, or TCR clonality, relative to a reference, is indicative of the efficacy of the treatment compound in treating the multiple myeloma in the subject. In other embodiments, a decreased level as compared to the reference level is indicative of the efficacy of the treatment compound in treating the cancer in the subject. For example, a decrease in Aiolos (IKZF3), Ikaros (IKZF1), CTC, ZFP91, c-MYC, IRF4, phospho-Rb1, relative to a reference, is indicative of the efficacy of the treatment compound in treating the multiple myeloma in the subject.

It is understood that the level of a biomarker will be relative to the reference level. Therefore, in some embodiments, decreased level as compared to the reference level is indicative of the efficacy of the treatment compound in treating the cancer in the subject. For example, an decrease in c-Caspase-3, c-Caspase 1, c-Caspase 7, cleaved-PARP, BIM, TUNEL, Annexin-V/7-AAD, Annexin-V/PI, p21, p27, free light chain, IL-2, TNFα, IFNγ, or TCR clonality from a healthy patient, relative to a reference from a multiple myeloma patient, is indicative of the efficacy of the treatment compound in treating the multiple myeloma in the subject. In other embodiments, an increased level as compared to the reference level is indicative of the efficacy of the treatment compound in treating the cancer in the subject. For example, an increase in Aiolos (IKZF3), Ikaros (IKZF1), CTC, ZFP91, c-MYC, IRF4, phospho-Rb1 from a healthy patient, relative to a reference from a multiple myeloma patient, is indicative of the efficacy of the treatment compound in treating the multiple myeloma in the subject.

As discussed elsewhere herein, encompassed herein is a method of reducing, treating and/or preventing adverse or undesired effects associated with conventional therapy including, but not limited to, surgery, chemotherapy, radiation therapy, biological therapy and immunotherapy. A compound provided herein, e.g., Compound 1, Compound 2 or Compound 3, or an enantiomer, mixture of enantiomers, tautomer, isotopolog, or pharmaceutically acceptable salt thereof, and other active ingredient can be administered to a patient identified using the biomarkers described herein prior to, during, or after the occurrence of the adverse effect associated with conventional therapy.

Compound 1, Compound 2 or Compound 3 provided herein, or an enantiomer, mixture of enantiomers, tautomer, isotopolog, or pharmaceutically acceptable salt thereof, can also be combined or used in combination with other therapeutic agents useful in the treatment and/or prevention of multiple myeloma described herein.

In some embodiments of the various methods provided herein, the method comprises administering to a patient Compound 1, Compound 2 or Compound 3, or an enantiomer, mixture of enantiomers, tautomer, isotopolog, or pharmaceutically acceptable salt thereof, in combination with one or more second active agents, and optionally in combination with radiation therapy, blood transfusions, or surgery.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, e.g., Compound 1, Compound 2 or Compound 3, or an enantiomer, mixture of enantiomers, tautomer, isotopolog, or pharmaceutically acceptable salt thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein, as is quadruple therapy. In one embodiment, the second therapy is dexamethasone.

Administration of Compound 1, Compound 2 or Compound 3, or an enantiomer, mixture of enantiomers, tautomer, isotopolog, or pharmaceutically acceptable salt thereof, and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of Compound 1, Compound 2 or Compound 3, or an enantiomer, mixture of enantiomers, tautomer, isotopolog, or pharmaceutically acceptable salt thereof, is independent of the route of administration of a second therapy. In one embodiment, Compound 1, Compound 2 or Compound 3, or an enantiomer, mixture of enantiomers, tautomer, isotopolog, or pharmaceutically acceptable salt thereof, is administered orally. In another embodiment, Compound 1, Compound 2 or Compound 3 is administered intravenously. Thus, in accordance with these embodiments, Compound 1, Compound 2 or Compound 3, or an enantiomer, mixture of enantiomers, tautomer, isotopolog, or pharmaceutically acceptable salt thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound 1, Compound 2 or Compound 3, or an enantiomer, mixture of enantiomers, tautomer, isotopolog, or pharmaceutically acceptable salt thereof, and a second therapy are administered by the same mode of administration, orally or by IV. In another embodiment, Compound 1, Compound 2 or Compound 3, or an enantiomer, mixture of enantiomers, tautomer, isotopolog, or pharmaceutically acceptable salt thereof, is administered by one mode of administration, e.g., by IV, whereas the second agent (an anti-multiple myeloma agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of multiple myeloma being treated or managed, the severity and stage of disease, and the amount of Compound 1, Compound 2 or Compound 3, or an enantiomer, mixture of enantiomers, tautomer, isotopolog, or pharmaceutically acceptable salt thereof, provided herein and any optional additional active agents concurrently administered to the patient.

One or more second active ingredients or agents can be used together with Compound 1, Compound 2 or Compound 3 in the methods and compositions provided herein. Second active agents can be large molecules (e.g., proteins), small molecules (e.g., synthetic inorganic, organometallic, or organic molecules), or cell therapies (e.g., CAR cells).

Examples of second active agents that can be used in the methods and compositions described herein include one or more of melphalan, vincristine, cyclophosphamide, etoposide, doxorubicin, bendamustine, a proteasome inhibitor (for example, bortezomib, carfilzomib, ixazomib, oprozomib or marizomib), a histone deacetylase inhibitor (for example, panobinostat, ACY241), a BET inhibitor (for example, GSK525762A, OTX015, BMS-986158, TEN-010, CPI-0610, INCB54329, BAY1238097, FT-1101, C90010, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, EP11313 and EP11336), a BCL2 inhibitor (for example, venetoclax or navitoclax), an MCL-1 inhibitor (for example, AZD5991, AMG176, MIK665, S64315, or S63845), a corticosteroid (for example, prednisone), dexamethasone; an antibody (for example, a CS1 antibody, such as elotuzumab; a CD38 antibody, such as daratumumab isatuximab; or a BCMA antibody or antibody-conjugate, such as GSK2857916 or BI 836909), a checkpoint inhibitor (as described herein), or CAR cells (as described herein).

In one embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is dexamethasone.

In some embodiments, the dexamethasone is administered at a 4 mg dose on days 1 and 8 of a 21 day cycle. In some other embodiments, the dexamethasone is administered at a 4 mg dose on days 1, 4, 8 and 11 of a 21 day cycle. In some embodiments, the dexamethasone is administered at a 4 mg dose on days 1, 8, and 15 of a 28 day cycle. In some other embodiments, the dexamethasone is administered at a 4 mg dose on days 1, 4, 8, 11, 15 and 18 of a 28 day cycle. In some embodiments, the dexamethasone is administered at a 4 mg dose on days 1, 8, 15, and 22 of a 28 day cycle. In one such embodiment, the dexamethasone is administered at a 4 mg dose on days 1, 10, 15, and 22 of Cycle 1. In some embodiments, the dexamethasone is administered at a 4 mg dose on days 1, 3, 15, and 17 of a 28 day cycle. In one such embodiment, the dexamethasone is administered at a 4 mg dose on days 1, 3, 14, and 17 of Cycle 1.

In some other embodiments, the dexamethasone is administered at an 8 mg dose on days 1 and 8 of a 21 day cycle. In some other embodiments, the dexamethasone is administered at an 8 mg dose on days 1, 4, 8 and 11 of a 21 day cycle. In some embodiments, the dexamethasone is administered at an 8 mg dose on days 1, 8, and 15 of a 28 day cycle. In some other embodiments, the dexamethasone is administered at an 8 mg dose on days 1, 4, 8, 11, 15 and 18 of a 28 day cycle. In some embodiments, the dexamethasone is administered at an 8 mg dose on days 1, 8, 15, and 22 of a 28 day cycle. In one such embodiment, the dexamethasone is administered at an 8 mg dose on days 1, 10, 15, and 22 of Cycle 1. In some embodiments, the dexamethasone is administered at an 8 mg dose on days 1, 3, 15, and 17 of a 28 day cycle. In one such embodiment, the dexamethasone is administered at an 8 mg dose on days 1, 3, 14, and 17 of Cycle 1.

In some embodiments, the dexamethasone is administered at a 10 mg dose on days 1 and 8 of a 21 day cycle. In some other embodiments, the dexamethasone is administered at a 10 mg dose on days 1, 4, 8 and 11 of a 21 day cycle. In some embodiments, the dexamethasone is administered at a 10 mg dose on days 1, 8, and 15 of a 28 day cycle. In some other embodiments, the dexamethasone is administered at a 10 mg dose on days 1, 4, 8, 11, 15 and 18 of a 28 day cycle. In some embodiments, the dexamethasone is administered at a 10 mg dose on days 1, 8, 15, and 22 of a 28 day cycle. In one such embodiment, the dexamethasone is administered at a 10 mg dose on days 1, 10, 15, and 22 of Cycle 1. In some embodiments, the dexamethasone is administered at a 10 mg dose on days 1, 3, 15, and 17 of a 28 day cycle. In one such embodiment, the dexamethasone is administered at a 10 mg dose on days 1, 3, 14, and 17 of Cycle 1.

In some embodiments, the dexamethasone is administered at a 20 mg dose on days 1 and 8 of a 21 day cycle. In some other embodiments, the dexamethasone is administered at a 20 mg dose on days 1, 4, 8 and 11 of a 21 day cycle. In some embodiments, the dexamethasone is administered at a 20 mg dose on days 1, 8, and 15 of a 28 day cycle. In some other embodiments, the dexamethasone is administered at a 20 mg dose on days 1, 4, 8, 11, 15 and 18 of a 28 day cycle. In some embodiments, the dexamethasone is administered at a 20 mg dose on days 1, 8, 15, and 22 of a 28 day cycle. In one such embodiment, the dexamethasone is administered at a 20 mg dose on days 1, 10, 15, and 22 of Cycle 1. In some embodiments, the dexamethasone is administered at a 20 mg dose on days 1, 3, 15, and 17 of a 28 day cycle. In one such embodiment, the dexamethasone is administered at a 20 mg dose on days 1, 3, 14, and 17 of Cycle 1.

In some embodiments, the dexamethasone is administered at a 40 mg dose on days 1 and 8 of a 21 day cycle. In some other embodiments, the dexamethasone is administered at a 40 mg dose on days 1, 4, 8 and 11 of a 21 day cycle. In some embodiments, the dexamethasone is administered at a 40 mg dose on days 1, 8, and 15 of a 28 day cycle. In one such embodiment, the dexamethasone is administered at a 40 mg dose on days 1, 10, 15, and 22 of Cycle 1. In some other embodiments, the dexamethasone is administered at a 40 mg dose on days 1, 4, 8, 11, 15 and 18 of a 28 day cycle. In other such embodiments, the dexamethasone is administered at a 40 mg dose on days 1, 8, 15, and 22 of a 28 day cycle. In other such embodiments, the dexamethasone is administered at a 40 mg dose on days 1, 3, 15, and 17 of a 28 day cycle. In one such embodiment, the dexamethasone is administered at a 40 mg dose on days 1, 3, 14, and 17 of Cycle 1.

In another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is bortezomib. In yet another embodiment, the second active agent used together with Compound 1, Compound 2 or Compound 3, or an enantiomer, mixture of enantiomers, tautomer, isotopolog, or pharmaceutically acceptable salt thereof, in the methods and compositions described herein is daratumumab. In some such embodiments, the methods additionally comprise administration of dexamethasone. In some embodiments, the methods comprise administration of Compound 1, Compound 2 or Compound 3, or an enantiomer, mixture of enantiomers, tautomer, isotopolog, or pharmaceutically acceptable salt thereof, with a proteasome inhibitor as described herein, a CD38 inhibitor as described herein and a corticosteroid as described herein.

In certain embodiments, Compound 1, Compound 2 or Compound 3, or an enantiomer, mixture of enantiomers, tautomer, isotopolog, or pharmaceutically acceptable salt thereof, is administered in combination with checkpoint inhibitors. In one embodiment, one checkpoint inhibitor is used in combination with Compound 1, or a tautomer, isotopolog, or pharmaceutically acceptable salt thereof, in connection with the methods provided herein. In another embodiment, two checkpoint inhibitors are used in combination with Compound 1, or a tautomer, isotopolog, or pharmaceutically acceptable salt thereof, in connection with the methods provided herein. In yet another embodiment, three or more checkpoint inhibitors are used in combination with Compound 1, Compound 2 or Compound 3, or an enantiomer, mixture of enantiomers, tautomer, isotopolog, or pharmaceutically acceptable salt thereof, in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, *Nature Reviews Cancer,* 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., *J. Immunol.,* 2007, 179, 4202-4211). In another embodiment, the LAG-3 inhibitor is BMS-986016.

In one embodiment, the checkpoint inhibitor is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., *Clin. Cancer Res.,* 2012, 3834).

In one embodiment, the checkpoint inhibitors is a TIM3 (T-cell immunoglobulin domain and mucin domain 3) inhibitor (Fourcade et al., *J. Exp. Med.,* 2010, 207, 2175-86; Sakuishi et al., *J. Exp. Med.,* 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In certain embodiments, Compound 1, Compound 2 or Compound 3 can be used in combination with one or more immune cells expressing one or more chimeric antigen receptors (CARs) on their surface (e.g., a modified immune cell). Generally, CARs comprise an extracellular domain from a first protein (e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin $\alpha v\beta 3$ (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ES0-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, C0-029, FGF-5, G250, Ga733 (EpCAM), HTgp-175, M344, MA-50, MG7-Ag, MOV18, NB\70K, NY-C0-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al., *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, a Fe receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or WIC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., Blood 1 05(11):4247-4254 (2005). In certain embodiments, Compound 1, compound 2 or Compound 3 as provided herein is administered to patients with various types or stages of multiple myeloma in combination with chimeric antigen receptor (CAR) T-cells. In certain embodiments the CAR T cell in the combination targets B cell maturation antigen (BCMA), and in more specific embodiments, the CAR T cell is bb2121 or bb21217. In some embodiments, the CAR T cell is JCARH125.

In some embodiments of the various methods provided herein, the reference sample is obtained from the subject prior to administering the treatment compound to the subject, and the control sample is from the same source as the sample. In other embodiments of the various methods provided herein, the reference sample is obtained from a healthy subject not having cancer, and the control sample is from the same source as the sample.

In some embodiments of the various methods provided herein, the cancer is a blood borne cancer. In certain embodiments, the blood borne cancer is metastatic. In some embodiments of the various methods provided herein, the cancer is multiple myeloma.

In some embodiments, methods provided herein encompass treating, preventing, or managing various types of cancers. In some embodiments, methods provided herein encompass treating, or preventing various types of cancers. In some embodiments, methods provided herein encompass treating various types of cancers, such as the cancers provided herein. In one embodiment, methods provided herein encompass treating, preventing, or managing multiple myeloma by administering a therapeutically effective amount of Compound 1, or enantiomer, mixture of enantiomers, tautomer, isotopolog, or pharmaceutically acceptable salt thereof. In one embodiment, methods provided herein encompass treating, preventing, or managing multiple myeloma by administering a therapeutically effective amount of Compound 2, or a tautomer, isotopolog, or pharmaceutically acceptable salt thereof. In one embodiment, methods provided herein encompass treating, preventing, or managing multiple myeloma by administering a therapeutically effective amount of Compound 3, or a tautomer, isotopolog, or pharmaceutically acceptable salt thereof.

In certain embodiments, provided herein are method of treating, preventing, or managing cancer in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, or managing MM, including relapsed/refractory MM in patients with impaired renal function or a symptom thereof, comprising administering a therapeutically effective amount of Compound 1, Compound 2, or Compound 3, or an enantiomer, mixture of enantiomers, tautomer, isotopolog, or pharmaceutically acceptable salt thereof, to a patient having relapsed/refractory MM with impaired renal function alone or in combination with a second active agent. In some embodiments, the methods comprise the step of administering to the subject a compound provided herein, or an enantiomer, mixture of enantiomers, tautomer, isotopolog, or pharmaceutically acceptable salt thereof, in combination with a second active agent in amounts effective to treat, prevent, or manage relapsed/refractory MM in patients with impaired renal function. In certain embodiments, the compound is Compound 1. In certain embodiments, the compound is Compound 2. In certain embodiments, the compound is Compound 3.

In some embodiments, the level of the biomarker decreases with the compound treatment. In some embodiments, the biomarker is selected from the group consisting of CRBN, IKZF1, IKZF3, CTC, soluble BCMA, survivin, serum free light chain, ZFP91, c-MYC, IRF4, pRB1, and the level of the biomarker decreases as compared to a reference level prior to treatment with a treatment compound.

In other embodiments, the level of the biomarker increases with the compound treatment. In some embodiments, the biomarker is selected from the group consisting of Caspase 1, Caspase-3, Caspase 7, PARP, IFNγ, TNFα, IL2, p21, p27, BIM, and TCR clonality and the level of the biomarker increases as compared to a reference level prior to treatment with a treatment compound.

In certain embodiments of the various methods provided herein, the biomarker is a protein that is directly or indirectly affected by CRBN, for example through protein-protein interactions (e.g., certain CRBN substrates or downstream effectors thereof), or through various cellular pathways (e.g., signal transduction pathways). In specific embodiments, the biomarker is a CRBN-associated protein (CAP). In some embodiments, the biomarker is mRNA of a protein that is directly or indirectly affected by CRBN. In other embodiments, the biomarker is cDNA of a protein that is directly or indirectly affected by CRBN.

Thus, in some embodiments, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is Compound 1:

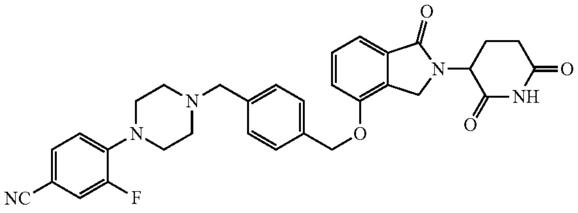

or an enantiomer, mixture of enantiomers, tautomer, isotopolog, or pharmaceutically acceptable salt thereof.

In another embodiment, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is Compound 2:

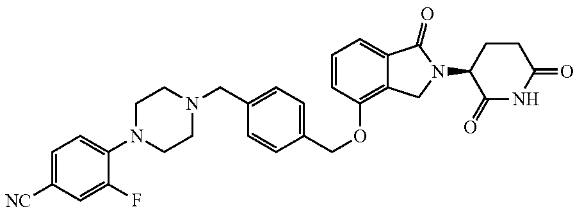

or a tautomer, isotopolog, or pharmaceutically acceptable salt thereof.

In yet another embodiment, provided herein is a method of identifying a subject having cancer who is likely to be responsive to a treatment compound, comprising:

(a) administering the treatment compound to the subject;

(b) obtaining a sample from the subject;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is Compound 3:

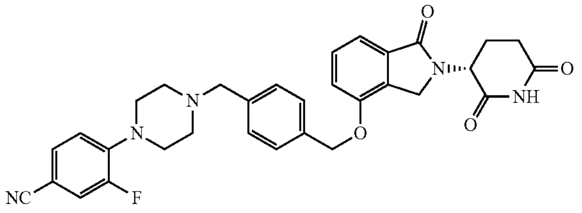

or a tautomer, isotopolog, or pharmaceutically acceptable salt thereof.

In another embodiment, provided herein is a method of identifying a subject having cancer who is likely to be responsive to a treatment compound, which has been administered to the subject, comprising:

(a) determining the level of a biomarker in a sample obtained from the subject, wherein the biomarker is a CAP; and (b) diagnosing the subject as being likely to be responsive to the treatment compound if the level of the biomarker in the sample is different from a reference level of the biomarker;

wherein the treatment compound is Compound 1, Compound 2 or Compound 3 or a tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is Compound 1:

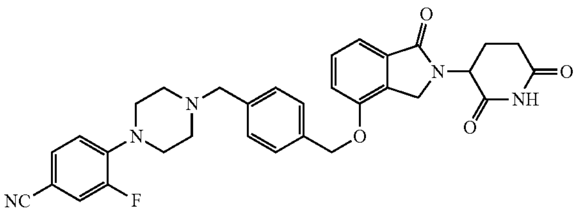

or an enantiomer, mixture of enantiomers, tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is Compound 2:

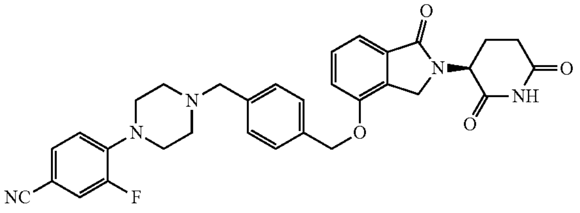 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level of a biomarker in the sample, wherein the biomarker is a CAP; and (d) diagnosing the subject as being likely to be responsive to the treatment compound if the level of the biomarker in the sample is different from a reference level of the biomarker;

wherein the treatment compound is Compound 3:

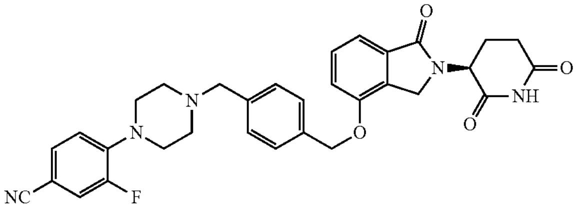

or a tautomer, isotopolog, or pharmaceutically acceptable salt thereof.

In some embodiments, provided herein is a method of identifying a subject having cancer who is likely to be responsive to a treatment compound, comprising:

(a) administering the treatment compound to a sample obtained from the subject;
(b) determining the level of a biomarker in the sample, wherein the biomarker is a CAP; and
(c) diagnosing the subject as being likely to be responsive to the treatment compound if the level of the biomarker in the sample is different from a reference level of the biomarker;

wherein the treatment compound is Compound 1, Compound 2 or Compound 3 or a tautomer, isotopolog, or pharmaceutically acceptable salt thereof.

In some embodiments, provided herein is a method of treating cancer, comprising:

(a) obtaining a sample from a subject having the cancer;
(b) determining the level of a biomarker in the sample, wherein the biomarker is a CAP;
(c) diagnosing the subject as being likely to be responsive to a treatment compound if the level of the biomarker in the sample is different from a reference level of the biomarker; and
(d) administering a therapeutically effective amount of the treatment compound to the subject; wherein the treatment compound is Compound 1:

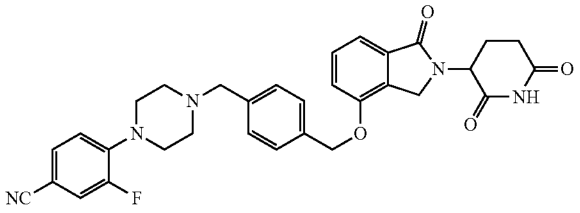

or an enantiomer, mixture of enantiomers, tautomer, isotopolog, or pharmaceutically acceptable salt thereof.

In some embodiments, provided herein is a method of treating cancer, comprising:

(a) obtaining a sample from a subject having the cancer;
(b) determining the level of a biomarker in the sample, wherein the biomarker is a CAP;
(c) diagnosing the subject as being likely to be responsive to a treatment compound if the level of the biomarker in the sample is different from a reference level of the biomarker; and
(d) administering a therapeutically effective amount of the treatment compound to the subject; wherein the treatment compound is Compound 2:

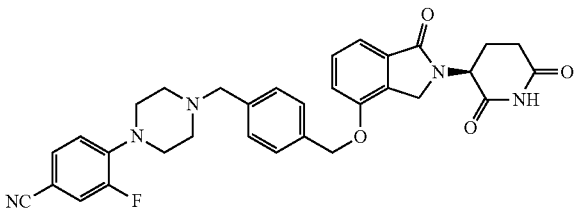

or a tautomer, isotopolog, or pharmaceutically acceptable salt thereof.

In some embodiments, provided herein is a method of treating cancer, comprising:

(a) obtaining a sample from a subject having the cancer;
(b) determining the level of a biomarker in the sample, wherein the biomarker is a CAP;
(c) diagnosing the subject as being likely to be responsive to a treatment compound if the level of the biomarker in the sample is different from a reference level of the biomarker; and
(d) administering a therapeutically effective amount of the treatment compound to the subject; wherein the treatment compound is Compound 3:

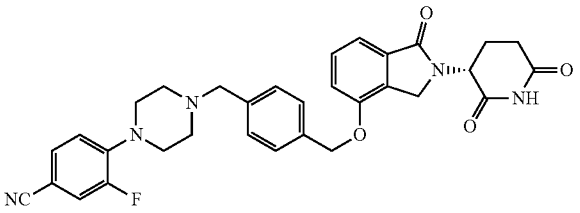

or a tautomer, isotopolog, or pharmaceutically acceptable salt thereof.

In some embodiments, provided herein is Compound 1, Compound 2 or Compound 3 for use in a method of treating cancer, comprising:

(a) obtaining a sample from a subject having the cancer;
(b) determining the level of a biomarker in the sample, wherein the biomarker is a CAP;
(c) diagnosing the subject as being likely to be responsive to a treatment compound if the level of the biomarker in the sample is different from a reference level of the biomarker; and
(d) administering a therapeutically effective amount of the treatment compound to the subject; wherein the treatment compound is Compound 1, Compound 2 or Compound 3 or a tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to the subject;
(b) obtaining a sample from the subject;
(c) determining the level of a biomarker in the sample, wherein the biomarker is a CAP;
(d) diagnosing the subject as being likely to be responsive to the treatment compound if the level of the biomarker in the sample is different from the level of the biomarker obtained from a reference sample; wherein the treatment compound is Compound 1:

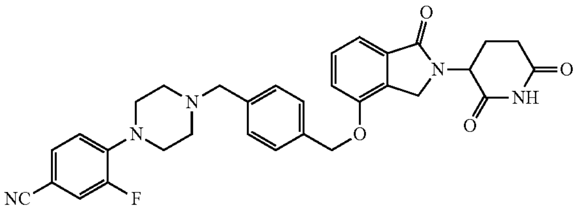

or an enantiomer, mixture of enantiomers, tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample, wherein the biomarker is a CAP;

(d) diagnosing the subject as being likely to be responsive to the treatment compound if the level of the biomarker in the sample is different from the level of the biomarker obtained from a reference sample; wherein the treatment compound is Compound 2:

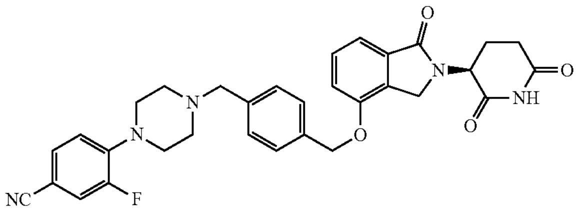

or a tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample, wherein the biomarker is a CAP;

(d) diagnosing the subject as being likely to be responsive to the treatment compound if the level of the biomarker in the sample is different from the level of the biomarker obtained from a reference sample; wherein the treatment compound is Compound 3:

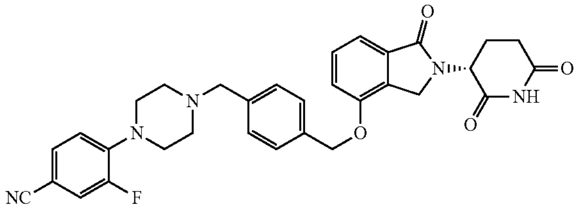

or a tautomer, isotopolog, or pharmaceutically acceptable salt thereof.

In some embodiments, provided herein is a method of predicting the responsiveness of a subject having or suspected of having cancer to a treatment compound, which has been administered to the subject, comprising:

(a) determining the level of a biomarker in a sample, obtained from the subject, wherein the biomarker is a CAP;

(d) diagnosing the subject as being likely to be responsive to the treatment compound if the level of the biomarker in the sample is different from the level of the biomarker obtained from a reference sample; wherein the treatment compound is Compound 1, Compound 3 or Compound 3 or a tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample, wherein the biomarker is a CAP;

(d) diagnosing the subject as being likely to be responsive to the treatment compound if the level of the biomarker in the sample is different from the level of the biomarker obtained from a reference sample; wherein the treatment compound is Compound 1:

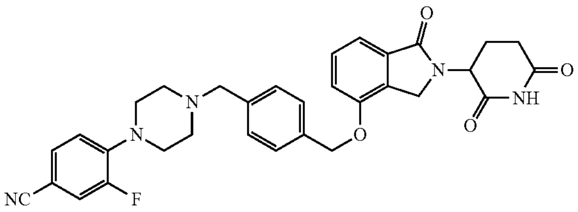

or an enantiomer, mixture of enantiomers, tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample, wherein the biomarker is a CAP;

(d) diagnosing the subject as being likely to be responsive to the treatment compound if the level of the biomarker in the sample is different from the level of the biomarker obtained from a reference sample; wherein the treatment compound is Compound 2:

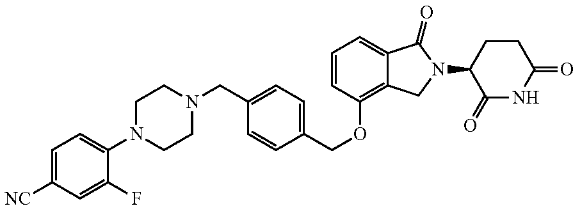

or a tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;

(b) administering the treatment compound to the sample;

(c) determining the level of a biomarker in the sample, wherein the biomarker is a CAP;

(d) diagnosing the subject as being likely to be responsive to the treatment compound if the level of the biomarker in the sample is different from the level of the biomarker obtained from a reference sample; wherein the treatment compound is Compound 3:

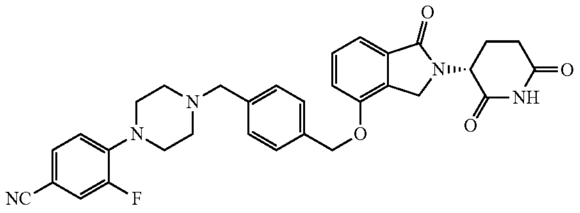

or a tautomer, isotopolog, or pharmaceutically acceptable salt thereof.

In some embodiments, provided herein is a method of predicting the responsiveness of a subject having or suspected of having cancer to a treatment compound, which has been administered to the subject, comprising:

(a) determining the level of a biomarker in a sample obtained from the subject, wherein the biomarker is a CAP;

(d) diagnosing the subject as being likely to be responsive to the treatment compound if the level of the biomarker in the sample is different from the level of the biomarker obtained from a reference sample; wherein the treatment compound is Compound 1, Compound 2 or Compound 3 or a tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample, wherein the biomarker is a CAP;

(d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 1:

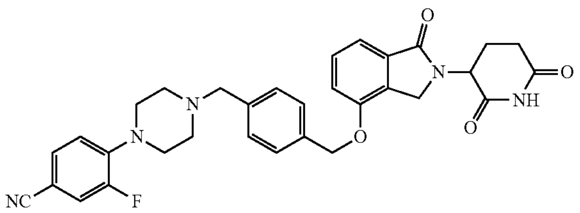

or an enantiomer, mixture of enantiomers, tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample, wherein the biomarker is a CAP;

(d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 2:

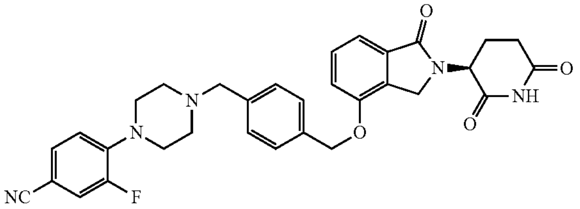 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of a biomarker in the sample, wherein the biomarker is a CAP;

(d) comparing the level of the biomarker in the sample with the level of the biomarker obtained from a reference sample, wherein a change in the biomarker level is indicative of the efficacy of the treatment compound in treating the cancer in the subject;

wherein the treatment compound is Compound 3:

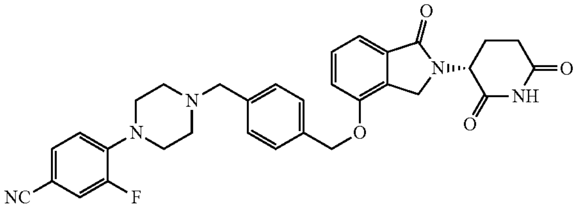

or a tautomer, isotopolog, or pharmaceutically acceptable salt thereof.

In some embodiments, provided herein is a method of monitoring the efficacy of a treatment of cancer in a subject with a treatment compound, which has been administered to the subject, comprising:

(a) determining the level of a biomarker in a sample obtained from the subject, wherein the biomarker is a CAP;

(b) comparing the level of the biomarker in the sample with the level of the biomarker obtained from a reference sample, wherein a change in the biomarker level is indicative of the efficacy of the treatment compound in treating the cancer in the subject; wherein the treatment compound is Compound 1, Compound 2 or Compound 3 or a tautomer, isotopolog, or pharmaceutically acceptable salt thereof.

In some embodiments, the biomarker is a CAP selected from the group consisting of IKZF1, IKZF3, ZFP91, c-MYC, and IRF4. In some embodiments, the biomarker is an Ikaros family member, such as IKZF1 or IKZF3. In a specific embodiment, the biomarker is IKZF1. In another specific embodiment, the biomarker is IKZF3. In a specific embodiment, the biomarker is ZFP91. In some embodiments, the biomarker is a binding partner of, downstream effector of, or a factor in a cellular pathway impacted IKZF1, and IKZF3. For example, in some embodiments, the biomarker is a binding partner of, downstream effector of, or a factor in a cellular pathway impacted by IKZF1, or IKZF3. In a specific embodiment, the biomarker is a downstream effector of IKZF1, such as IRF4. In a specific embodiment, the biomarker is a downstream effector of IKZF3, such as IRF4. In a specific embodiment, the biomarker is a downstream effector of IKZF1, such as c-MYC. In a specific embodiment, the biomarker is a downstream effector of IKZF3, such as c-MYC.

As shown in the Examples, the level of a biomarker, such CRBN, IKZF1, IKZF3, CTC, soluble BCMA, survivin, serum free light chain, ZFP91, c-MYC, IRF4, pRB1, decreases as compared to a reference in response to Compound 1, Compound 2, or Compound 3 treatment. Accordingly, in some embodiments, the biomarker is selected from the group consisting of CRBN, IKZF1, IKZF3, CTC, soluble BCMA, survivin, serum free light chain, ZFP91, c-MYC, IRF4, and pRB1, and the level of the biomarker decreases in response to the Compound 1, Compound 2, or Compound 3 treatment. Thus, in some embodiments of the various methods provided herein, the biomarker is CRBN, IKZF1, IKZF3, CTC, soluble BCMA, TIL, survivin, serum free light chain, ZFP91, c-MYC, IRF4, pRB1, or a protein (or a factor) impacted thereby, and wherein the level of the biomarker is lower than a reference level.

Thus, in some embodiments, provided herein is a method of identifying a subject having cancer who is likely to be responsive to a treatment compound, comprising:

(a) administering the treatment compound to the subject;
(b) obtaining a sample from the subject;
(c) determining the level CRBN, IKZF1, IKZF3, CTC, SBCMA, TIL, survivin, serum free light chain, ZFP91, c-MYC, IRF4, or pRB1 in the sample; and
(d) diagnosing the subject as being likely to be responsive to the treatment compound if the level CRBN, IKZF1, IKZF3, CTC, SBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1:

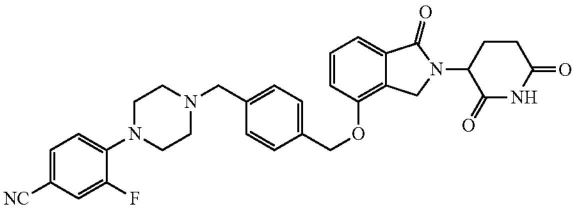

or an enantiomer, mixture of enantiomers, tautomer, isotopolog, or pharmaceutically acceptable salt thereof.

In another embodiment, provided herein is a method of identifying a subject having cancer who is likely to be responsive to a treatment compound, comprising:

(a) administering the treatment compound to the subject;
(b) obtaining a sample from the subject;
(c) determining the level CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 2:

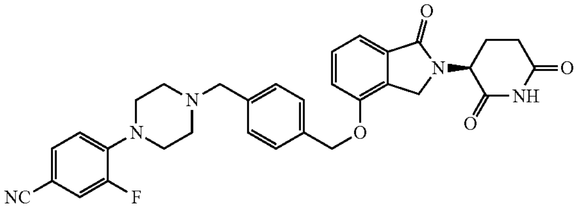

or a tautomer, isotopolog, or pharmaceutically acceptable salt thereof.

In yet another embodiment, provided herein is a method of identifying a subject having cancer who is likely to be responsive to a treatment compound, comprising:

(a) administering the treatment compound to the subject;
(b) obtaining a sample from the subject;
(c) determining the level CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 3:

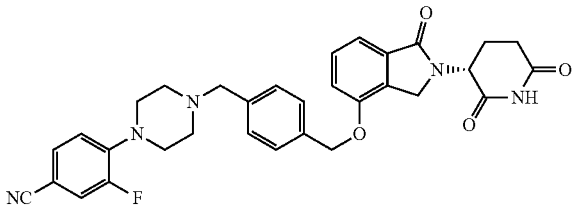 [SMILES: N#Cc1ccc(N2CCN(Cc3ccc(COc4cccc5c4CN([C@@H]4CCC(=O)NC4=O)C5=O)cc3)CC2)c(F)c1]

or a tautomer, isotopolog, or pharmaceutically acceptable salt thereof.

In another embodiment, provided herein is a method of identifying a subject having cancer who is likely to be responsive to a treatment compound, which has been administered to the subject, comprising:

(a) determining the level CRBN, IKZF1, IKZF3, CTC, sBCMA, TIL, survivin, serum free light chain, ZFP91, c-MYC, IRF4, or pRB1 in a sample obtained from the subject; and
(b) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1, Compound 2 or Compound 3 or a tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level CRBN, IKZF1, IKZF3, CTC, sBCMA, TIL, survivin, serum free light chain, ZFP91, c-MYC, IRF4, or pRB1 in the sample; and (d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1:

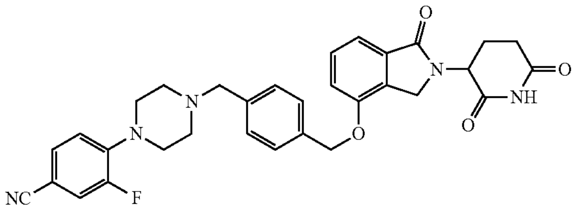

or an enantiomer, mixture of enantiomers, tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level CRBN, IKZF1, IKZF3, CTC, sBCMA, TIL, survivin, serum free light chain, ZFP91, c-MYC, IRF4, or pRB1 in the sample; and (d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 2:

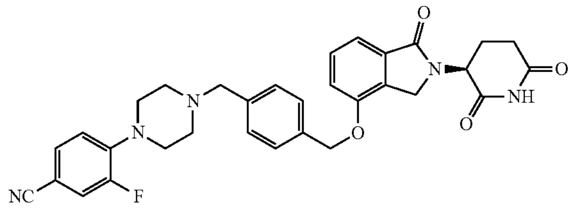

or tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level CRBN, IKZF1, IKZF3, CTC, sBCMA, TIL, survivin, serum free light chain, ZFP91, c-MYC, IRF4, or pRB1 in the sample; and (d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 3:

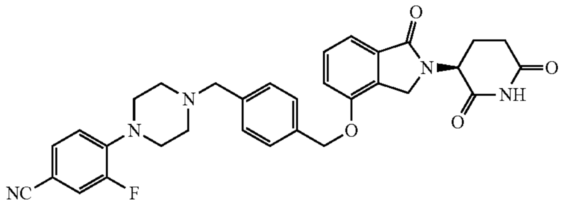

or a tautomer, isotopolog, or pharmaceutically acceptable salt thereof.

In some embodiments, provided herein is a method of identifying a subject having cancer who is likely to be responsive to a treatment compound, comprising:

(a) administering the treatment compound to a sample obtained from the subject;

(b) determining the level CRBN, IKZF1, IKZF3, CTC, sBCMA, TIL, survivin, serum free light chain, ZFP91, c-MYC, IRF4, or pRB1 in the sample; and (c) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1, Compound 2 or Compound 3 or a tautomer, isotopolog, or pharmaceutically acceptable salt thereof.

In some embodiments, provided herein is a method of treating cancer, comprising:

(a) obtaining a sample from a subject having the cancer;

(b) determining the level CRBN, IKZF1, IKZF3, CTC, sBCMA, TIL, survivin, serum free light chain, ZFP91, c-MYC, IRF4, or pRB1 in the sample;

(c) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; and (d) administering a therapeutically effective amount of the treatment compound to the subject; wherein the treatment compound is Compound 1:

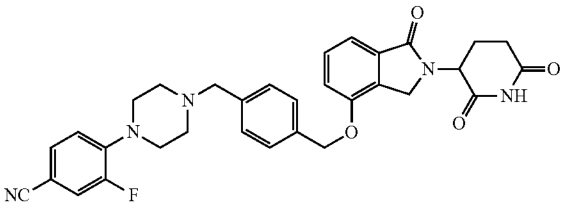

or an enantiomer, mixture of enantiomers, tautomer, isotopolog, or pharmaceutically acceptable salt thereof.

In some embodiments, provided herein is a method of treating cancer, comprising:

(a) obtaining a sample from a subject having the cancer;
(b) determining the level CRBN, IKZF1, IKZF3, CTC, sBCMA, TIL, survivin, serum free light chain, ZFP91, c-MYC, IRF4, or pRB1 in the sample;
(c) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; and
(d) administering a therapeutically effective amount of the treatment compound to the subject; wherein the treatment compound is Compound 2:

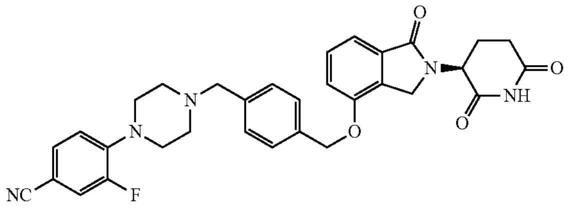 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of treating cancer, comprising:
(a) obtaining a sample from a subject having the cancer;
(b) determining the level CRBN, IKZF1, IKZF3, CTC, sBCMA, TIL, survivin, serum free light chain, ZFP91, c-MYC, IRF4, or pRB1 in the sample;
(c) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; and
(d) administering a therapeutically effective amount of the treatment compound to the subject; wherein the treatment compound is Compound 3:

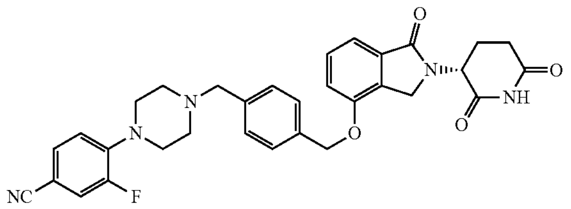

or a tautomer, isotopolog, or pharmaceutically acceptable salt thereof.

In some embodiments, provided herein is Compound 1, Compound 2 or Compound 3 for use in a method of treating cancer, comprising:
(a) obtaining a sample from a subject having the cancer;
(b) determining the level CRBN, IKZF1, IKZF3, CTC, sBCMA, TIL, survivin, serum free light chain, ZFP91, c-MYC, IRF4, or pRB1 in the sample;
(c) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; and
(d) administering a therapeutically effective amount of the treatment compound to the subject.

In some embodiments, provided herein is a method of predicting the responsiveness of a subject having or suspected of having cancer to a treatment compound, comprising:
(a) administering the treatment compound to the subject;
(b) obtaining a sample from the subject;
(c) determining the level of a biomarker in the sample, wherein the biomarker is CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1:

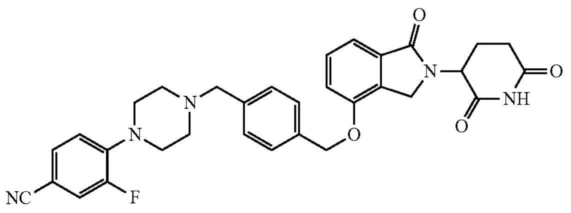

or an enantiomer, mixture of enantiomers, tautomer, isotopolog, or pharmaceutically acceptable salt thereof.

In some embodiments, provided herein is a method of predicting the responsiveness of a subject having or suspected of having cancer to a treatment compound, comprising:
(a) administering the treatment compound to the subject;
(b) obtaining a sample from the subject;
(c) determining the level of a biomarker in the sample, wherein the biomarker is CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 2:

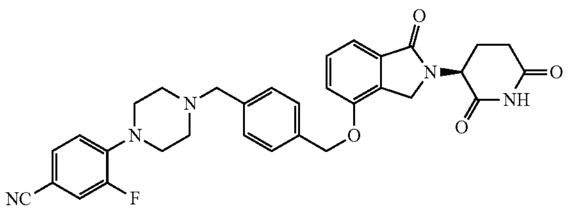

or a tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to the subject;
(b) obtaining a sample from the subject;
(c) determining the level of a biomarker in the sample, wherein the biomarker is CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 3:

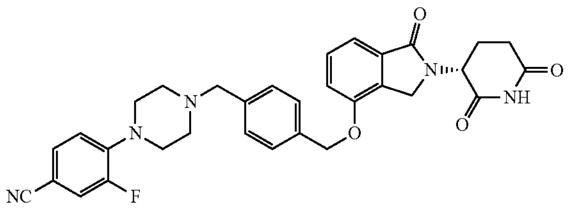 [SMILES: N#Cc1ccc(N2CCN(Cc3ccc(COc4cccc5c4CN([C@@H]4CCC(=O)NC4=O)C5=O)cc3)CC2)c(F)c1]

or a tautomer, isotopolog, or pharmaceutically acceptable salt thereof.

In some embodiments, provided herein is a method of predicting the responsiveness of a subject having or suspected of having cancer to a treatment compound, which has been administered to the subject, comprising:

(a) determining the level of a biomarker in a sample obtained from the subject, wherein the biomarker is CRBN, IKZF1, IKZF3, CTC, sBCMA, TIL, survivin, serum free light chain, ZFP91, c-MYC, IRF4, or pRB1 in the sample; and
(b) diagnosing the subject as being likely to be responsive to the treatment compound if the level CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1, Compound 2 or Compound 3 or a tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;
(b) administering the treatment compound to the sample;
(c) determining the level of CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level of CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1:

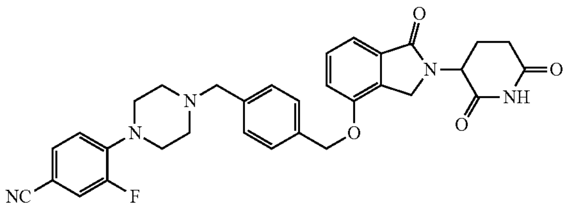

or an enantiomer, mixture of enantiomers, tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;
(b) administering the treatment compound to the sample;
(c) determining the level of CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level of CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 2:

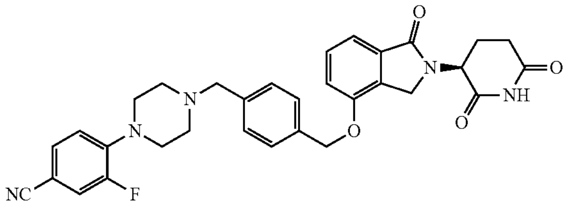

or a tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;
(b) administering the treatment compound to the sample;
(c) determining the level of CRBN, IKZF1, IKZF3, CTC, sBCMA, TIL, survivin, serum free light chain, ZFP91, c-MYC, IRF4, or pRB1 in the sample; and
(d) diagnosing the subject as being likely to be responsive to the treatment compound if the level of CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 3:

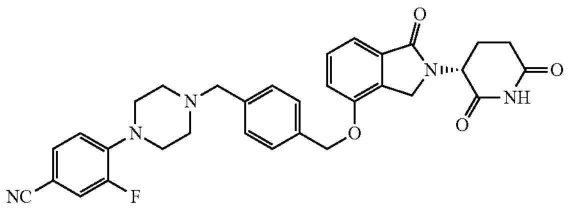

or a tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to a sample obtained from the subject;

(b) determining the level of CRBN, IKZF1, IKZF3, CTC, sBCMA, TIL, survivin, serum free light chain, ZFP91, c-MYC, IRF4, or pRB1 in the sample; and (c) diagnosing the subject as being likely to be responsive to the treatment compound if the level of CRBN, IKZF1, IKZF3, CTC, sBCMA, TIL, survivin, serum free light chain, ZFP91, c-MYC, IRF4, or pRB1 in the sample is lower than the level of CRBN, IKZF1, IKZF3, CTC, sBCMA, TIL, survivin, serum free light chain, ZFP91, c-MYC, IRF4, or pRB1 in a reference sample; wherein the treatment compound is Compound 1, Compound 2 or Compound 3 or a tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of CRBN, IKZF1, IKZF3, CTC, sBCMA, TIL, survivin, serum free light chain, ZFP91, c-MYC, IRF4, or pRB1 in the sample; and (d) comparing the level of CRBN, IKZF1, IKZF3, CTC, sBCMA, TIL, survivin, serum free light chain, ZFP91, c-MYC, IRF4, or pRB1 in the sample with the level of CRBN, IKZF1, IKZF3, CTC, sBCMA, TIL, survivin, serum free light chain, ZFP91, c-MYC, IRF4, or pRB1 obtained from a reference sample, wherein a decrease in the level as compared to the reference level is indicative of the efficacy of the treatment compound in treating the cancer in the subject; wherein the treatment compound is Compound 1:

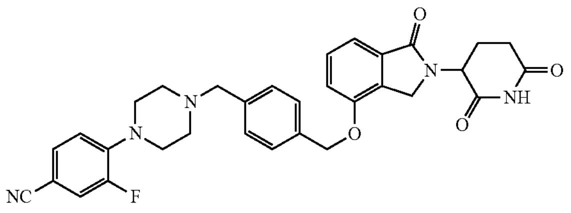

or an enantiomer, mixture of enantiomers, tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of CRBN, IKZF1, IKZF3, CTC, sBCMA, TIL, survivin, serum free light chain, ZFP91, c-MYC, IRF4, or pRB1 in the sample; and (d) comparing the level of CRBN, IKZF1, IKZF3, CTC, sBCMA, TIL, survivin, serum free light chain, ZFP91, c-MYC, IRF4, or pRB1 in the sample with the level of CRBN, IKZF1, IKZF3, CTC, sBCMA, TIL, survivin, serum free light chain, ZFP91, c-MYC, IRF4, or pRB1 obtained from a reference sample, wherein a decrease in the level as compared to the reference level is indicative of the efficacy of the treatment compound in treating the cancer in the subject; wherein the treatment compound is Compound 2:

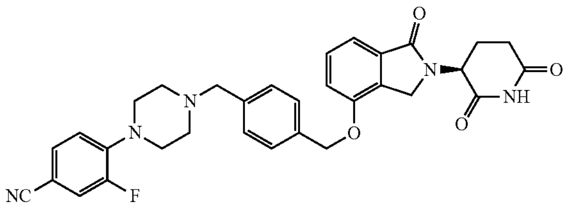

or a tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of CRBN, IKZF1, IKZF3, CTC, sBCMA, TIL, survivin, serum free light chain, ZFP91, c-MYC, IRF4, or pRB1 in the sample; and (d) comparing the level of CRBN, IKZF1, IKZF3, CTC, sBCMA, TIL, survivin, serum free light chain, ZFP91, c-MYC, IRF4, or pRB1 in the sample with the level of CRBN, IKZF1, IKZF3, CTC, sBCMA, TIL, survivin, serum free light chain, ZFP91, c-MYC, IRF4, or pRB1 obtained from a reference sample, wherein a decrease in the level as compared to the reference level is indicative of the efficacy of the treatment compound in treating the cancer in the subject; wherein the treatment compound is Compound 3:

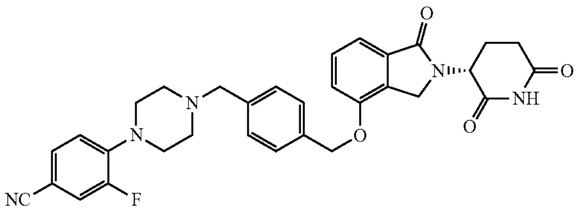

or a tautomer, isotopolog, or pharmaceutically acceptable salt thereof.

In some embodiments, provided herein is a method of monitoring the efficacy of a treatment of cancer in a subject with a treatment compound, which has been administered to the subject, comprising:

(a) determining the level of CRBN, IKZF1, IKZF3, CTC, sBCMA, TIL, survivin, serum free light chain, ZFP91, c-MYC, IRF4, or pRB1 in a sample obtained from the subject;

and (b) comparing the level of CRBN, IKZF1, IKZF3, CTC, sBCMA, TIL, survivin, serum free light chain, ZFP91, c-MYC, IRF4, or pRB1 in the sample with the level of CRBN, IKZF1, IKZF3, CTC, sBCMA, TIL, survivin, serum free light chain, ZFP91, c-MYC, IRF4, or pRB1 obtained from a reference sample, wherein a decrease in the level as compared to the reference level is indicative of the efficacy of the treatment compound in treating the cancer in the subject; wherein the treatment compound is Compound 2, Compound 2 or Compound 3 or a tautomer, isotopolog, or pharmaceutically acceptable salt thereof.

In specific embodiments of the methods described herein, the reference sample is a sample prior to treatment with the treatment compound.

In a specific embodiment, the biomarker is CRBN, and the cancer is multiple myeloma (MM). In a specific embodiment, the biomarker is CRBN, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is IKZF1, and the cancer is multiple myeloma (MM). In a specific embodiment, the biomarker is IKZF1, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is IKZF3, and the cancer is multiple myeloma (MM). In a specific embodiment, the biomarker is IKZF3, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is CTC, and the cancer is multiple myeloma (MM). In a specific embodiment, the biomarker is CTC, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is TIL, and the cancer is multiple myeloma (MM). In a specific embodiment, the biomarker is TIL, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is survivin, and the cancer is multiple myeloma (MM). In a specific embodiment, the biomarker is survivin, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is serum free light chain, and the cancer is multiple myeloma (MM). In a specific embodiment, the biomarker is serum free light chain, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is ZFP91, and the cancer is multiple myeloma (MM). In a specific embodiment, the biomarker is ZFP91, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is c-MYC, and the cancer is multiple myeloma (MM). In a specific embodiment, the biomarker is c-MYC, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is IRF4, and the cancer is multiple myeloma (MM). In a specific embodiment, the biomarker is IRF4, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In a specific embodiment, the biomarker is pRB1, and the cancer is multiple myeloma (MM). In a specific embodiment, the biomarker is pRB1, and the treatment compound is Compound 1, Compound 2, or Compound 3. In a specific embodiment, the treatment compound is Compound 1. In another specific embodiment, the treatment compound is Compound 2. In yet another specific embodiment, the treatment compound is Compound 3.

In some embodiments, the biomarker has a function in apoptosis. In certain embodiments, the biomarker provided herein has a function in cell cycle. In other embodiments, the biomarker provided herein has a function in T-cell activation.

In some embodiments, provided herein is a method of identifying a subject with multiple myeloma that is relapsed, refractory, or resistant to conventional therapy who is likely to be responsive to a treatment compound, comprising:

(a) obtaining a sample comprising a cancer cell from a subject;

(b) detecting the level of CRBN in the sample; and (c) diagnosing the subject as being likely to be responsive to the treatment compound if the level of CRBN in the sample is detectable and lower than a reference level of CRBN;

wherein the treatment compound is a compound of Compound 1:

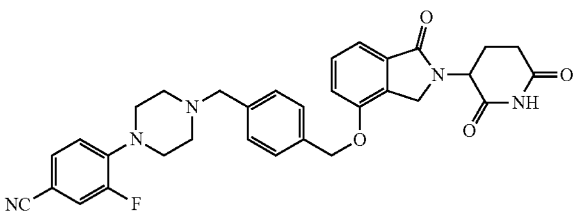 [SMILES: N#Cc1ccc(N2CCN(Cc3ccc(COc4cccc5c4CN(C4CCC(=O)NC4=O)C5=O)cc3)CC2)c(F)c1]

or an enantiomer, mixture of enantiomers, tautomer, isotopolog, or pharmaceutically acceptable salt thereof.

In another embodiment, provided herein is a method of identifying a subject with multiple myeloma that is relapsed, refractory, or resistant to conventional therapy who is likely to be responsive to a treatment compound, comprising:

(a) obtaining a sample comprising a cancer cell from a subject;

(b) detecting the level of CRBN in the sample; and (c) diagnosing the subject as being likely to be responsive to the treatment compound if the level of CRBN in the sample is detectable and lower than a reference level of CRBN;

wherein the treatment compound is a compound of Compound 2:

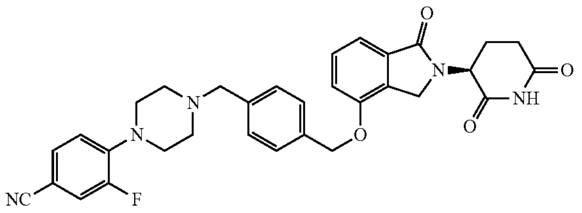

or a tautomer, isotopolog, or pharmaceutically acceptable salt thereof.

In yet another embodiment, provided herein is a method of identifying a subject with multiple myeloma that is relapsed, refractory, or resistant to conventional therapy who is likely to be responsive to a treatment compound, comprising:

(a) obtaining a sample comprising a cancer cell from a subject;

(b) detecting the level of CRBN in the sample; and (c) diagnosing the subject as being likely to be responsive to the treatment compound if the level of CRBN in the sample is detectable and lower than a reference level of CRBN;

wherein the treatment compound is a compound of Compound 3:

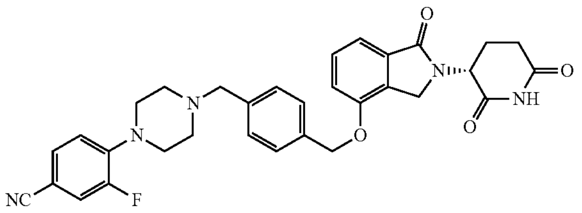 [SMILES: N#Cc1ccc(N2CCN(Cc3ccc(COc4cccc5c4CN([C@@H]4CCC(=O)NC4=O)C5=O)cc3)CC2)c(F)c1]

or a tautomer, isotopolog, or pharmaceutically acceptable salt thereof.

In some embodiments, provided herein is a method of identifying a subject with multiple myeloma that is relapsed, refractory, or resistant to conventional therapy who is likely to be responsive to a treatment compound, comprising:

(a) detecting the level of CRBN in a sample obtained from a subject; and (b) diagnosing the subject as being likely to be responsive to the treatment compound if the level of CRBN in the sample is detectable and lower than a reference level of CRBN;

wherein the treatment compound is a compound of Compound 1, Compound 2 or Compound 3 or a tautomer, isotopolog, or pharmaceutically acceptable salt thereof.

In another aspect, provided herein is a method of predicting the responsiveness of a subject having multiple myeloma to a treatment compound, comprising:

(a) obtaining a sample comprising a cancer cell from a subject;

(b) detecting the level of CRBN in the sample; and (c) diagnosing the subject as being likely to be responsive to the treatment compound if the level of CRBN in the sample is detectable and lower than a reference level of CRBN;

wherein the treatment compound is a compound of Compound 1:

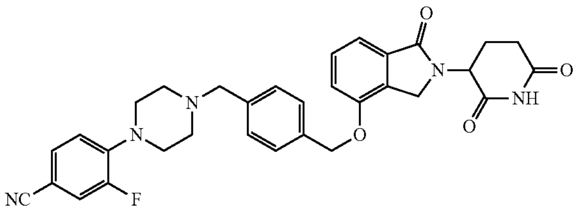 [SMILES: N#Cc1ccc(N2CCN(Cc3ccc(COc4cccc5c4CN(C4CCC(=O)NC4=O)C5=O)cc3)CC2)c(F)c1]

or an enantiomer, mixture of enantiomers, tautomer, isotopolog, or pharmaceutically acceptable salt thereof.

In another embodiment, provided herein is a method of predicting the responsiveness of a subject having multiple myeloma to a treatment compound, comprising:

(a) obtaining a sample comprising a cancer cell from a subject;

(b) detecting the level of CRBN in the sample; and (c) diagnosing the subject as being likely to be responsive to the treatment compound if the level of CRBN in the sample is detectable and lower than a reference level of CRBN;

wherein the treatment compound is a compound of Compound 2:

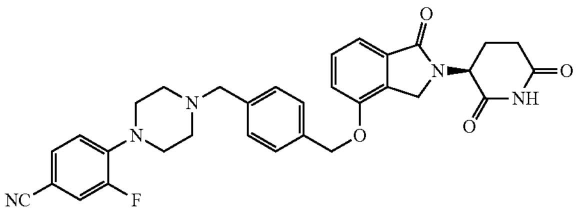 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In yet another embodiment, provided herein is a method of predicting the responsiveness of a subject having multiple myeloma to a treatment compound, comprising:

(a) obtaining a sample comprising a cancer cell from a subject;

(b) detecting the level of CRBN in the sample; and (c) diagnosing the subject as being likely to be responsive to the treatment compound if the level of CRBN in the sample is detectable and lower than a reference level of CRBN;

wherein the treatment compound is a compound of Compound 3:

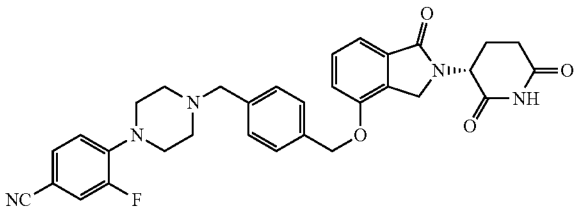 [SMILES: N#Cc1ccc(N2CCN(Cc3ccc(COc4cccc5c4CN([C@@H]4CCC(=O)NC4=O)C5=O)cc3)CC2)c(F)c1]

or a tautomer, isotopolog, or pharmaceutically acceptable salt thereof.

In another embodiment, provided herein is a method of predicting the responsiveness of a subject having multiple myeloma to a treatment compound, comprising:

(a) detecting the level of CRBN in a sample obtained from the subject; and (b) diagnosing the subject as being likely to be responsive to the treatment compound if the level of CRBN in the sample is detectable and lower than a reference level of CRBN;

wherein the treatment compound is a compound of Compound 1, Compound 2 or Compound 3 or a tautomer, isotopolog, or pharmaceutically acceptable salt thereof.

Thus, in some embodiments, provided herein is a method of detecting CRBN levels in a cancer cell and diagnosing the subject as being likely to be responsive to the treatment compound if the level of CRBN in the sample is detectable and lower than a reference level of CRBN. In some embodiments the MM is relapsed, refractory, or resistant to conventional therapy. In one embodiment, the MM is lenalidomide-resistant MM. In another embodiment, the MM is pomalidomide-resistant MM. As described in the Examples in Section 6, Compound 2 also has immunomodulatory properties in PBMCs, and CD4+ and CD8+ T-cells. Therefore, in one embodiment of the methods provided herein, CRBN is not detectable in the cancer cell and CRBN is detectable in the immune cell, and the patient is responsive to Compound 1. In another embodiment of the methods provided herein, CRBN is not detectable in the cancer cell and CRBN is detectable in the immune cell, and the patient is responsive to Compound 2. In yet another embodiment of the methods provided herein, CRBN is not detectable in the cancer cell and CRBN is detectable in the immune cell, and the patient is responsive to Compound 1.

In another aspect, provided herein is a method of determining or adjusting a dosage for treating a subject having multiple myeloma with a treatment compound comprising:

(a) administering a dosage of the treatment compound to the subject;

(b) obtaining one or more samples from the subject at different time points;

(c) determining the level of IKZF1, IKZF3, or both in the one or more samples, and thereby determining if the dosage is appropriate or needs an adjustment; wherein the treatment compound is a compound of Compound 1:

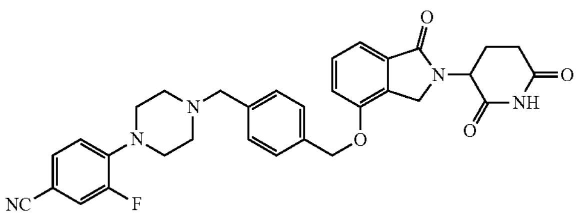 [SMILES: N#Cc1ccc(N2CCN(Cc3ccc(COc4cccc5c4CN(C4CCC(=O)NC4=O)C5=O)cc3)CC2)c(F)c1]

or an enantiomer, mixture of enantiomers, tautomer, isotopolog, or pharmaceutically acceptable salt thereof.

In another embodiment, provided herein is a method of determining or adjusting a dosage for treating a subject having multiple myeloma with a treatment compound comprising:

(a) administering a dosage of the treatment compound to the subject;

(b) obtaining one or more samples from the subject at different time points;

(c) determining the level of IKZF1, IKZF3, or both in the one or more samples, and thereby determining if the dosage is appropriate or needs an adjustment; wherein the treatment compound is a compound of Compound 2:

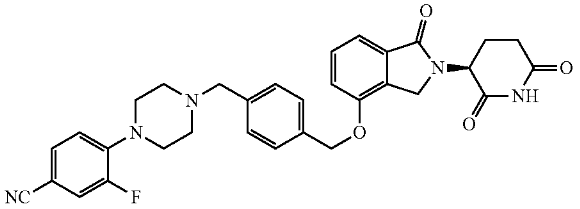

or a tautomer, isotopolog, or pharmaceutically acceptable salt thereof.

In yet another embodiment, provided herein is a method of determining or adjusting a dosage for treating a subject having multiple myeloma with a treatment compound comprising:

(a) administering a dosage of the treatment compound to the subject;

(b) obtaining one or more samples from the subject at different time points;

(c) determining the level of IKZF1, IKZF3, or both in the one or more samples, and thereby determining if the dosage is appropriate or needs an adjustment wherein the treatment compound is a compound of Compound 3:

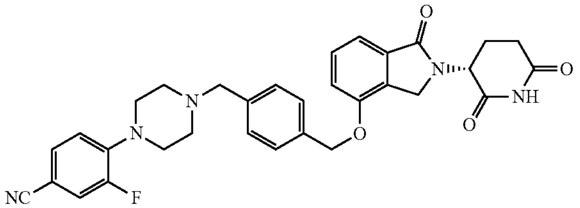 [SMILES: N#Cc1ccc(N2CCN(Cc3ccc(COc4cccc5c4CN([C@@H]4CCC(=O)NC4=O)C5=O)cc3)CC2)c(F)c1]

or a tautomer, isotopolog, or pharmaceutically acceptable salt thereof.

In another embodiment, provided herein is a method of determining or adjusting a dosage for treating a subject having multiple myeloma with a treatment compound, which has been administered to the subject, comprising:

(a) determining the level of IKZF1, IKZF3, or both in one or more samples obtained from the subject, and thereby determining if the dosage is appropriate or needs an adjustment; wherein the treatment compound is a compound of Compound 1, Compound 2 or Compound 3 or a tautomer, isotopolog, or pharmaceutically acceptable salt thereof.

In some other specific embodiments, the level of the biomarker increases with the compound treatment. In some embodiments, the biomarker is selected from the group consisting of Caspase 1, Caspase-3, Caspase 7, PARP, IFNγ, TNFα, IL2, p21, p27, BIM, and TCR clonality and the level of the biomarker increases as compared to the level in a reference sample prior to treatment with a treatment compound. In some embodiments, the biomarker has a function in apoptosis, and the level of the biomarker increases as compared to the level in a reference sample prior to treatment with a treatment compound. In other embodiments, the biomarker has a function in T-cell activation and the level of the biomarker increases as compared to the level in a reference sample prior to treatment with a treatment compound.

Thus, in some embodiments, provided herein is a method of identifying a subject having cancer who is likely to be responsive to a treatment compound, comprising:

(a) administering the treatment compound to the subject;

(b) obtaining a sample from the subject;

(c) determining the level Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1:

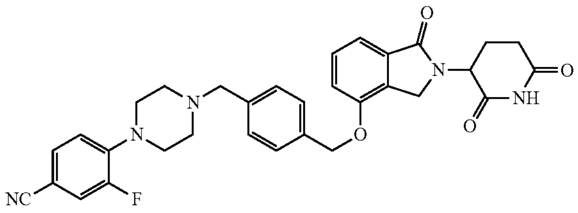

or an enantiomer, mixture of enantiomers, tautomer, isotopolog, or pharmaceutically acceptable salt thereof.

In another embodiment, provided herein is a method of identifying a subject having cancer who is likely to be responsive to a treatment compound, comprising:

(a) administering the treatment compound to the subject;

(b) obtaining a sample from the subject;

(c) determining the level Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 2:

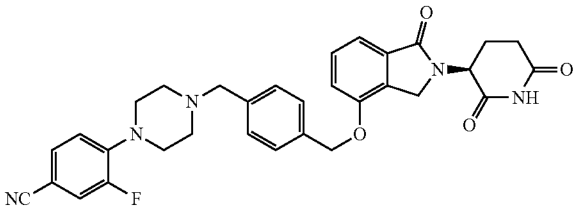

or a tautomer, isotopolog, or pharmaceutically acceptable salt thereof.

In yet another embodiment, provided herein is a method of identifying a subject having cancer who is likely to be responsive to a treatment compound, comprising:

(a) administering the treatment compound to the subject;

(b) obtaining a sample from the subject;

(c) determining the level Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 3:

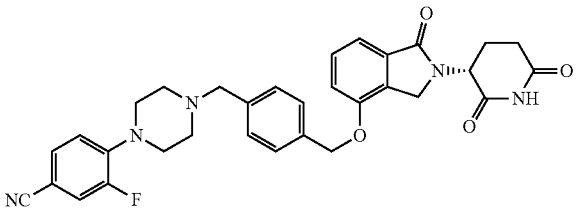

or a tautomer, isotopolog, or pharmaceutically acceptable salt thereof.

In another embodiment, provided herein is a method of identifying a subject having cancer who is likely to be responsive to a treatment compound, which has been administered to the subject, comprising:

(a) determining the level Caspase 1, Caspase-3, Caspase 7, PARP, IFNγ, TNFα, IL2, p21, p27, BIM, or TCR clonality in a sample obtained from the subject; and (b) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1, Compound 2 or Compound 3 or a tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1:

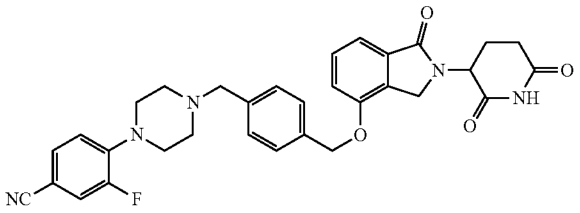

or an enantiomer, mixture of enantiomers, tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 2:

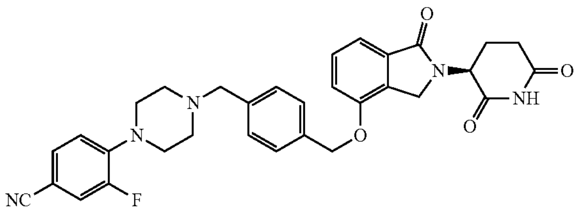 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of identifying a subject having cancer who is likely to be responsive to a treatment compound, comprising:

(a) obtaining a sample from the subject;

(b) administering the treatment compound to the sample;

(c) determining the level Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 3:

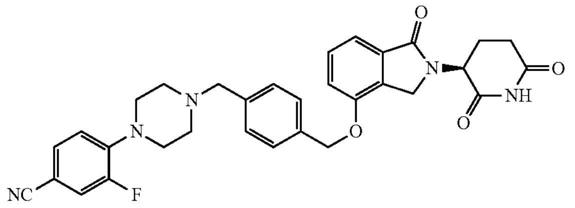

or a tautomer, isotopolog, or pharmaceutically acceptable salt thereof.

In some embodiments, provided herein is a method of identifying a subject having cancer who is likely to be responsive to a treatment compound, comprising:

(a) administering the treatment compound to a sample obtained from the subject;

(c) determining the level Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1, Compound 2 or Compound 3 or a tautomer, isotopolog, or pharmaceutically acceptable salt thereof.

In some embodiments, provided herein is a method of treating cancer, comprising:

(a) obtaining a sample from a subject having the cancer;

(b) determining the level of Caspase 1, Caspase-3, Caspase 7, PARP, IFNγ, TNFα, IL2, p21, p27, BIM, or TCR clonality in the sample;

(c) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; and (d) administering a therapeutically effective amount of the treatment compound to the subject; wherein the treatment compound is Compound 1:

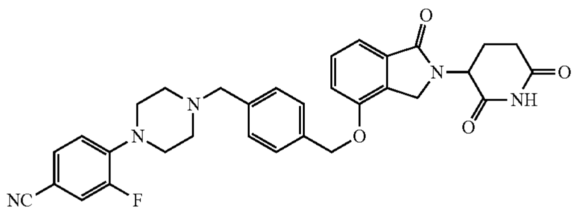 [SMILES: N#Cc1ccc(N2CCN(Cc3ccc(COc4cccc5c4CN(C4CCC(=O)NC4=O)C5=O)cc3)CC2)c(F)c1]

or an enantiomer, mixture of enantiomers, tautomer, isotopolog, or pharmaceutically acceptable salt thereof.

In some embodiments, provided herein is a method of treating cancer, comprising:

(a) obtaining a sample from a subject having the cancer;

(b) determining the level of Caspase 1, Caspase-3, Caspase 7, PARP, IFNγ, TNFα, IL2, p21, p27, BIM, or TCR clonality in the sample;

(c) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; and (d) administering a therapeutically effective amount of the treatment compound to the subject; wherein the treatment compound is Compound 2:

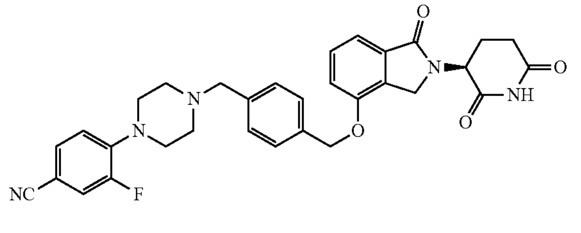 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of treating cancer, comprising:

(a) obtaining a sample from a subject having the cancer;

(b) determining the level of Caspase 1, Caspase-3, Caspase 7, PARP, IFNγ, TNFα, IL2, p21, p27, BIM, or TCR clonality in the sample;

(c) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; and (d) administering a therapeutically effective amount of the treatment compound to the subject; wherein the treatment compound is Compound 3:

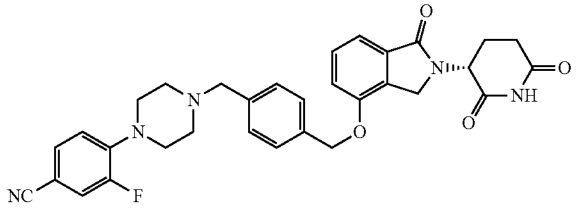

or a tautomer, isotopolog, or pharmaceutically acceptable salt thereof.

In some embodiments, provided herein is Compound 1, Compound 2 or Compound 3 or a tautomer, isotopolog, or pharmaceutically acceptable salt thereof for use in a method of treating cancer, comprising:

(a) obtaining a sample from a subject having the cancer;

(b) determining the level of Caspase 1, Caspase-3, Caspase 7, PARP, IFNγ, TNFα, IL2, p21, p27, BIM, or TCR clonality in the sample;

(c) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; and (d) administering a therapeutically effective amount of the treatment compound to the subject.

In some embodiments, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample, wherein the biomarker is Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level of Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1:

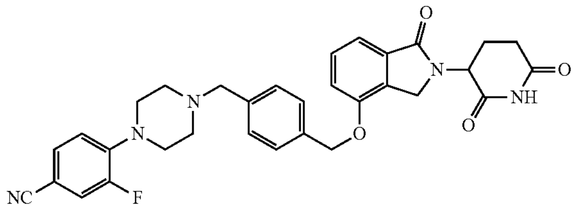

or an enantiomer, mixture of enantiomers, tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample, wherein the biomarker is Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level of Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 2:

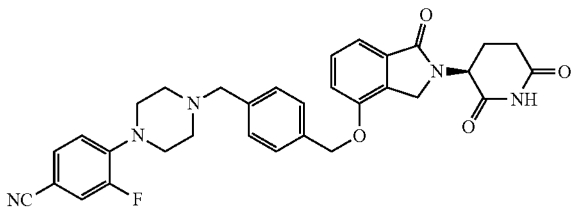 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to the subject;

(b) obtaining a sample from the subject;

(c) determining the level of a biomarker in the sample, wherein the biomarker is Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 3:

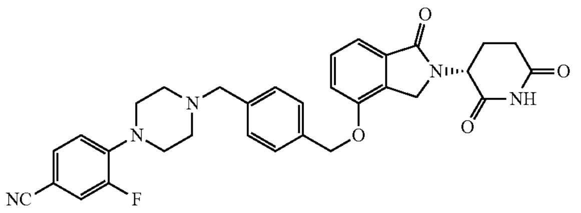

or a tautomer, isotopolog, or pharmaceutically acceptable salt thereof.

In some embodiments, provided herein is a method of predicting the responsiveness of a subject having or suspected of having cancer to a treatment compound, which has been administered to the subject, comprising:

(a) determining the level of a biomarker in a sample obtained from the subject, wherein the biomarker is Caspase 1, Caspase-3, Caspase 7, PARP, IFNγ, TNFα, IL2, p21, p27, BIM, or TCR clonality in the sample; and (b) diagnosing the subject as being likely to be responsive to the treatment compound if the level Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1, Compound 2 or Compound 3 or a tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;

(b) administering the treatment compound to the sample;

(c) determining the level of Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level of Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1:

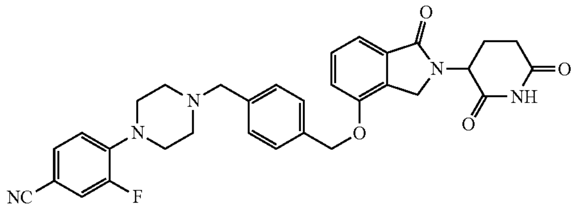 [SMILES: N#Cc1ccc(N2CCN(Cc3ccc(COc4cccc5c4CN(C4CCC(=O)NC4=O)C5=O)cc3)CC2)c(F)c1]

or an enantiomer, mixture of enantiomers, tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;

(b) administering the treatment compound to the sample;

(c) determining the level of Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level of Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 2:

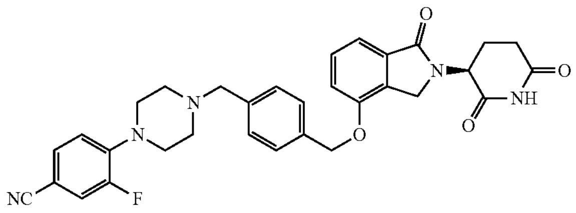 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of predicting the responsiveness of a subject having or suspected of having cancer to a treatment compound, comprising:

(a) obtaining a sample from the subject;

(b) administering the treatment compound to the sample;

(c) determining the level of Caspase 1, Caspase-3, Caspase 7, PARP, IFNγ, TNFα, IL2, p21, p27, BIM, or TCR clonality in the sample; and (d) diagnosing the subject as being likely to be responsive to the treatment compound if the level of Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 3:

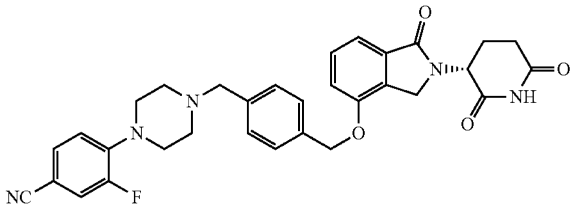

or a tautomer, isotopolog, or pharmaceutically acceptable salt thereof.

In some embodiments, provided herein is a method of predicting the responsiveness of a subject having or suspected of having cancer to a treatment compound, comprising:

(a) administering the treatment compound to a sample obtained from the subject;

(b) determining the level of Caspase 1, Caspase-3, Caspase 7, PARP, IFNγ, TNFα, IL2, p21, p27, BIM, or TCR clonality in the sample; and (c) diagnosing the subject as being likely to be responsive to the treatment compound if the level of Caspase 1, Caspase-3, Caspase 7, PARP, IFNγ, TNFα, IL2, p21, p27, BIM, or TCR clonality in the sample is higher than the level of Caspase 1, Caspase-3, Caspase 7, PARP, IFNγ, TNFα, IL2, p21, p27, BIM, or TCR clonality in a reference sample; wherein the treatment compound is Compound 1, Compound 2 or Compound 3 or a tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of Caspase 1, Caspase-3, Caspase 7, PARP, IFNγ, TNFα, IL2, p21, p27, BIM, or TCR clonality in the sample; and (d) comparing the level of Caspase 1, Caspase-3, Caspase 7, PARP, IFNγ, TNFα, IL2, p21, p27, BIM, or TCR clonality in the sample with the level of Caspase 1, Caspase-3, Caspase 7, PARP, IFNγ, TNFα, IL2, p21, p27, BIM, or TCR clonality obtained from a reference sample, wherein an increase in the level as compared to the reference level is indicative of the efficacy of the treatment compound in treating the cancer in the subject; wherein the treatment compound is Compound 1:

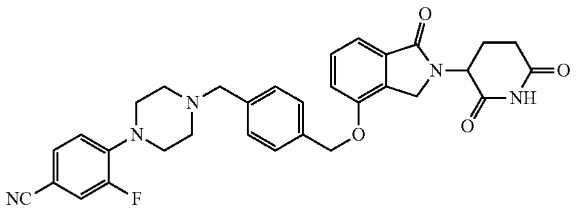

or an enantiomer, mixture of enantiomers, tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of Caspase 1, Caspase-3, Caspase 7, PARP, IFNγ, TNFα, IL2, p21, p27, BIM, or TCR clonality in the sample; and (d) comparing the level of Caspase 1, Caspase-3, Caspase 7, PARP, IFNγ, TNFα, IL2, p21, p27, BIM, or TCR clonality in the sample with the level of Caspase 1, Caspase-3, Caspase 7, PARP, IFNγ, TNFα, IL2, p21, p27, BIM, or TCR clonality obtained from a reference sample, wherein an increase in the level as compared to the reference level is indicative of the efficacy of the treatment compound in treating the cancer in the subject; wherein the treatment compound is Compound 2:

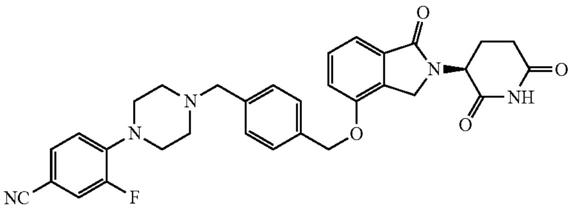 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments, provided herein is a method of monitoring the efficacy of a treatment of cancer in a subject with a treatment compound, comprising:

(a) administering the treatment compound to the subject;

(b) obtaining a sample from the subject;

(c) determining the level of Caspase 1, Caspase-3, Caspase 7, PARP, IFNγ, TNFα, IL2, p21, p27, BIM, or TCR clonality in the sample; and (d) comparing the level of Caspase 1, Caspase-3, Caspase 7, PARP, IFNγ, TNFα, IL2, p21, p27, BIM, or TCR clonality in the sample with the level of Caspase 1, Caspase-3, Caspase 7, PARP, IFNγ, TNFα, IL2, p21, p27, BIM, or TCR clonality obtained from a reference sample, wherein an increase in the level as compared to the reference level is indicative of the efficacy of the treatment compound in treating the cancer in the subject; wherein the treatment compound is Compound 3:

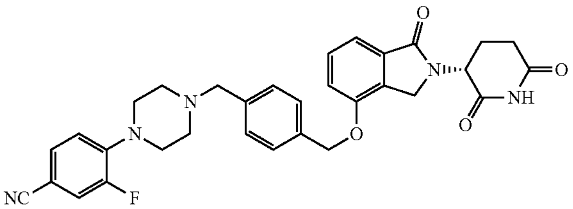

or a tautomer, isotopolog, or pharmaceutically acceptable salt thereof.

In some embodiments, provided herein is a method of monitoring the efficacy of a treatment of cancer in a subject with a treatment compound, which has been administered to the subject, comprising:

(a) determining the level of Caspase 1, Caspase-3, Caspase 7, PARP, IFNγ, TNFα, IL2, p21, p27, BIM, or TCR clonality in a sample obtained from the subject; and (b) comparing the level of Caspase 1, Caspase-3, Caspase 7, PARP, IFNγ, TNFα, IL2, p21, p27, BIM, or TCR clonality in the sample with the level of Caspase 1, Caspase-3, Caspase 7, PARP, IFNγ, TNFα, IL2, p21, p27, BIM, or TCR clonality obtained from a reference sample, wherein an increase in the level as compared to the reference level is indicative of the efficacy of the treatment compound in treating the cancer in the subject; wherein the treatment compound is Compound 1, Compound 2 or Compound 3 or a tautomer, isotopolog, or pharmaceutically acceptable salt thereof.

In specific embodiments of the methods described herein, the reference sample is a sample prior to treatment with the treatment compound.

In some embodiments of the various methods provided herein, the level of the biomarkers is measured by determining the protein level of the biomarker.

In other embodiments of the various methods provided herein, the level of the biomarkers is measured by determining the mRNA level of the biomarker.

In yet other embodiments of the various methods provided herein, the level of the biomarkers is measured by determining the cDNA level of the biomarker.

In some embodiments of the various methods provided herein, the treatment compound is a compound described in Section 5.7 below.

In some embodiments, the treatment compound is Compound 1, and the cancer is MM. In some embodiments, the treatment compound is Compound 2, and the cancer is MM. In other embodiments, the treatment compound is Compound 3, and the cancer is MM.

In some embodiments, the responsiveness of a patient or a subject, or the efficacy of a treatment is determined by the overall survival (OS), complete remission rate (CRR), objective response rate (ORR), time to progression, relapse free survival (RFS), progression-free survival (PFS) event-free survival, duration of remission, duration of response, and/or time to remission/response of a patient having a cancer. In one embodiment, the cancer is a hematological cancer. In certain embodiments, the ORR includes all responses of complete remission (CR) (i.e., morphologic leukemia-free state, morphologic CR, cytogenetic CR, molecular CR, and morphologic CR with incomplete blood recovery), and partial remission.

In other embodiments, the various methods provided herein are for increasing the overall survival (OS), complete remission rate (CRR), objective response rate (ORR), time to progression, relapse free survival (RFS), progression-free survival (PFS) event-free survival, duration of remission, duration of response, and/or time to remission/response of a patient having a cancer, for example, a hematological cancer.

In other embodiments provided herein is Compound 1, Compound 2 or Compound 3 for use in any of the methods provided herein.

5.3 Methods of Detecting and Quantifying Biomarkers

In certain embodiments, provided herein are methods of detecting and quantifying the protein level of biomarker, such as CRBN, a protein that is directly or indirectly affected by CRBN, or a protein that indicates a pharmacodynamic (PD) response (e.g., soluble BCMA) to Compound 1, Compound 2, or Compound 3, from a biological sample, comprising contacting proteins within the sample with a first antibody that immunospecifically binds to the biomarker protein. In some embodiments, the methods provided herein further comprise (i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody; (ii) detecting the presence of the second antibody bound to the biomarker protein; and (iii) determining the amount of the biomarker protein based on the amount of detectable label in the second antibody. In other embodiments, the methods provided herein further comprise (i) contacting the biomarker protein bound to the first antibody with a second antibody with a detectable label, wherein the second antibody immunospecifically binds to the first antibody; (ii) detecting the presence of the second antibody bound to the first antibody; and (iii) determining the amount of the biomarker protein based on the amount of detectable label in the second antibody.

In some embodiments of the various methods provided herein, the method comprises using dual staining immunohistochemistry to determine the level of a biomarker, such as CRBN or a protein that is directly or indirectly affected by CRBN. In a dual staining immunohistochemistry assay, a biomarker provided herein and another cancer biomarker are simultaneously detected using a first labeled antibody targeting a biomarker provided herein and a second labeled antibody targeting a cancer biomarker. Such assay can improve the specificity, accuracy, and sensitivity for detecting and measuring a biomarker provided herein. In some embodiments, the cancer biomarker is an MM biomarker.

In some embodiments of the various methods provided herein, the method comprises sequencing DNA. For example, in some embodiments the provided herein are methods of identifying a subject having multiple myeloma who is likely to be responsive to a treatment compound, as well as methods of predicting the responsiveness of a subject having multiple myeloma to a treatment compound. Patients that are resistant to initial treatment with a cereblon modulator compound can have a mutation in CRBN. Importantly, as shown in the Examples, cells that are resistant to cereblon modulators, such as lenalidomide or pomalidomide, can still be sensitive to Compound 1, Compound 2, or Compound 3. Therefore, in some embodiments, the method comprises sequencing the DNA of CRBN for mutations to identify a subject having multiple myeloma who is likely to be responsive to a treatment compound, wherein the treatment compound is Compound 1. In some embodiments, the method comprises sequencing the DNA of CRBN for mutations to identify a subject having multiple myeloma who is likely to be responsive to a treatment compound, wherein the treatment compound is Compound 2. In some embodiments, the method comprises sequencing the DNA of CRBN for mutations to identify a subject having multiple myeloma who is likely to be responsive to a treatment compound, wherein the treatment compound is Compound 3. In other embodiments, the method comprises sequencing the DNA of CRBN for mutations to predict the responsiveness of a subject having multiple myeloma to a treatment compound, wherein the treatment compound is Compound 1. In other embodiments, the method comprises sequencing the DNA of CRBN for mutations to predict the responsiveness of a subject having multiple myeloma to a treatment compound, wherein the treatment compound is Compound 2. In other embodiments, the method comprises sequencing the DNA of CRBN for mutations to predict the responsiveness of a subject having multiple myeloma to a treatment compound, wherein the treatment compound is Compound 3.

In some embodiments, the methods provided herein are for detecting T-cell activation. In some embodiments, the DNA of the TCR can be sequenced after treatment with Compound 1, Compound 2, or Compound 3. Activation of T-cells can result in the clonal expansion of a population of T-cells with a specific gene rearrangement of their TCR. The rearrangements can be determined by DNA sequencing. Therefore, in some embodiments of the various methods provided herein, the method biomarker is TCR clonality, and TCR clonality is measured by DNA sequencing of the TCR.

Thus, in some embodiments, the method provided herein comprises (i) contacting proteins within a sample with a first antibody that immunospecifically binds to a biomarker provided herein, the first antibody being coupled with a first detectable label; (ii) contacting the proteins within the sample with a second antibody that immunospecifically binds to a cancer biomarker, the second antibody being coupled with a second detectable label; (iii) detecting the presence of the first antibody and the second antibody bound to the proteins; and (iv) determining the level of the biomarker provided herein based on the amount of detectable label in the first antibody, and determining the level of the cancer biomarker based on the amount of detectable label in the second antibody. In some embodiments, the cancer biomarker is an MM biomarker.

In certain embodiments, provided herein are methods of detecting and quantifying the protein level of a biomarker, such as Aiolos or Ikaros, or any other biomarker provided herein, from a biological sample, comprising (i) contacting the biomarker protein with a first antibody; (ii) contacting the biomarker protein bound to the first antibody with a second antibody with a detectable label, wherein the second antibody immunospecifically binds to the first antibody; (iii) detecting the presence of the second antibody bound in a complex with the biomarker protein; and (iv) determining the amount of the biomarker protein based on the amount of detectable label in the second antibody using flow cytometry (e.g. FACS). It is further understood that the detection and quantification of the biomarker protein level, such as Aiolos or Ikaros, can be performed in cancer cells and non-cancer cells (e.g., CD3+ T cells). For example, Aiolos and/or Ikaros expression can be measured by flow cytometry in CD3+ T cells before, during, and/or after treatment with Compound 1, Compound 2, or Compound 3. In some embodiments, the cancer biomarker is an MM biomarker. In some embodiments, the biomarker is CTC.

In certain embodiments, provided herein are methods of evaluating the biomarker expression, such as CRBN, Aiolos, Ikaros, ZFP91, c-Myc, IRF4, c-Caspase-3, as well as TILs, from a biological sample, comprising (i) collecting bone marrow aspirate samples before, during, and/or after treatment with Compound 1, Compound 2, or Compound 3; (ii) generating clots from each sample; (iii) fixing the clots, for example, in formalin; (iv) embedding the clot paraffin, or cryo-embedding media (e.g., OCT); (v) sectioning the embedded samples for immunostaining; (vi) performing immunohistochemistry (IHC) on the sections; (vii) visualizing the stained samples by microscopy; and (viii) evaluating the biomarker expression.

In certain embodiments, provided herein are methods of detecting and quantifying tumor-infiltrating lymphocytes (TILs) as a biomarker from a biological sample, comprising; (i) staining a histology specimen with hematoxylin and eosin (H&E); (ii) visualizing TILs using light microscope; (iii) detecting TILs based on morphology and staining; (iv) determining the level of the TILs based on the amount of lymphocyte staining inside (i.e. infiltrating) the tumor.

In certain embodiments, provided herein are methods of detecting and quantifying the RNA (e.g., mRNA, total RNA, or small RNA) level of a biomarker, such as CRBN or a biomarker provided herein, from a biological sample, comprising: (a) obtaining RNA from the sample; (b) contacting the RNA with a primer that specifically binds to a sequence in the RNA to generate a first DNA molecule having a sequence complementary to said RNA (i.e. cDNA); (c) amplifying the cDNA corresponding to a segment of a gene encoding the biomarker; and (d) determining the RNA level of the biomarker based on the amount of the amplified DNA. In some embodiments, provided herein are methods of sequencing the RNA (RNA-seq) of a biomarker from a biological sample, comprising: (a) isolating RNA from a sample; (b) depleting ribosomal RNA (rRNA), enriching for RNA with 3' polyadenylated (poly(A)) tails, both, or neither; (c) reverse transcribing the RNA into cDNA; and (d) sequencing the cDNA. In some embodiments, the biomarker (s) are evaluated in combination with other biomarker(s) provided herein, such as Aiolos, Ikaros, CRBN, ZFP91, c-MYC, IRF4, c-Caspase 1, c-Caspase-3, c-Caspase 7, cleaved-PARP, survivin, BIM, sFLC, p21, p27, pRB1, soluble BCMA, CTCs, TILs, IL-2, IFNγ, TNFα, and TCR clonality.

In certain embodiments, provided herein are methods of detecting and quantifying one or more biomarkers that have a function in apoptosis. It is well-known to those skilled in the art that there are various methods to detect apoptosis. One method involves the detection of DNA fragmentation, which is a hallmark of apoptosis. Terminal deoxynucleotidyl transferase dUTP nick end labeling (TUNEL) is an established method for detecting DNA fragments. Therefore, in certain embodiments of the various methods provided herein, the biomarker has a function in apoptosis and the level of the biomarker is measured by terminal deoxynucleotidyl transferase dUTP nick end labeling (TUNEL).

One of the earlier events of apoptosis includes translocation of membrane phosphatidylserine (PS) from the inner side of the plasma membrane to the surface. Annexin V, a Ca2+-dependent phospholipid-binding protein, has high affinity for PS, and fluorochrome-labeled Annexin V can be used for the detection of exposed PS using flow cytometry. The use of fluorescent intercalating agents that bind to DNA can further facilitate the discrimination between early apoptotic cells, and late stage apoptotic cells. Cells that are early stage apoptotic cells will exclude the fluorescent intercalating agents, such as 7-amino-actinomycin D (7-AAD) and propidium iodide (PI), whereas late stage apoptotic cells will stain positively, due to the passage of these dyes into the nucleus where they bind to DNA. 7-AAD and PI have a high DNA binding constant and are efficiently excluded by intact cells. Thus, in some embodiments of the various methods provided herein, the biomarker has a function in apoptosis and the level of the biomarker is measured by Annexin-V and 7-AAD. In other embodiments of the various methods provided herein, the biomarker has a function in apoptosis and the level of the biomarker is measured by Annexin-V and propidium iodide (PI).

In certain embodiments of the various methods provided herein, the two or more of the steps are performed sequentially. In other embodiments of the methods provided herein, two or more of steps are performed in parallel (e.g., at the same time).

Exemplary assays provided herein for the methods of detecting and quantifying the protein level of a biomarker, such as Aiolos, Ikaros, CRBN, c-MYC, IRF4, cleaved-Caspase-3, soluble BCMA (sBCMA), soluble FLC (sFLC), activated T-cell-associated cytokines, or a combination thereof, are immunoassays, such as western blot analysis, enzyme-linked immunosorbent assay (ELISA) (e.g., a sandwich ELISA), immunohistochemistry (IHC), and fluorescence-activated cell sorting (FACS). By way of example, in some embodiments, serum samples can be collected before, during, and/or after treatment with Compound 1, Compound 2, or Compound 3, and sBCMA can be measured by ELISA. An exemplary assays provided herein for the methods of detecting and quantifying the RNA level of a biomarker, such as Aiolos, Ikaros, CRBN, c-MYC, IRF4, activated T-cell-associated cytokines, or a combination thereof, are reverse transcription polymerase chain reaction (RT-PCR), e.g., quantitative RT-PCR (qRT-PCR), and RNA-Seq.

5.4. Subjects, Samples, and Types of Cells

In certain embodiments, the various methods provided herein use samples (e.g., biological samples) from subjects or individuals (e.g., patients). The subject can be a patient, such as, a patient with a cancer (e.g., multiple myeloma). The subject can be a mammal, for example, a human. The subject can be male or female, and can be an adult, a child, or an infant. Samples can be analyzed at a time during an active phase of a cancer (e.g., MM), or when the cancer (e.g., MM) is inactive. In certain embodiments, more than one sample from a subject can be obtained.

In certain embodiments, the sample used in the methods provided herein comprises body fluids from a subject. Non-limiting examples of body fluids include blood (e.g., whole blood), blood plasma, amniotic fluid, aqueous humor, bile, bone marrow, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids (including cerebrospinal fluid surrounding the brain and the spinal cord), synovial fluid, intracellular fluid (the fluid inside cells), and vitreous humour (the fluid in the eyeball). In some embodiments, the sample is a blood sample. The blood sample can be obtained using conventional techniques as described in, e.g., Innis et al., eds., *PCR Protocols* (Academic Press, 1990). White blood cells can be separated from blood samples using conventional techniques or commercially available kits, e.g., RosetteSep kit (Stein Cell Technologies, Vancouver, Canada). Sub-populations of white blood cells, e.g., mononuclear cells, B cells, T cells, monocytes, granulocytes, or lymphocytes, can be further isolated using conventional techniques, e.g., magnetically activated cell sorting (MACS) (Miltenyi Biotec, Auburn, California) or fluorescently activated cell sorting (FACS) (Becton Dickinson, San Jose, California).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 6.0, about 7.0, about 8.0, about 9.0, or about 10.0 mL.

In some embodiments, the blood sample is drawn into a TruCulture tube containing anti-CD3 antibody for an ex vivo T-cell activation assay.

In some embodiments, the bone marrow sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 6.0, about 7.0, about 8.0, about 9.0, or about 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In some embodiments, the sample is obtained from the subject after receiving treatment with a therapy other than Compound 1, Compound 2, or Compound 3, and prior to the subject receiving a treatment with Compound 1, Compound 2, or Compound 3. In a specific embodiment, the sample is obtained from the subject after the disease has relapsed or the patient is refractory to a therapy other than Compound 1, Compound 2, or Compound 3. In another embodiment, the sample is obtained from the subject during the subject receiving a treatment for the disease or disorder. In another embodiment, the sample is obtained from the subject after the subject receiving a treatment for the disease or disorder. In various embodiments, the treatment comprises administering a compound (e.g., Compound 1, Compound 2, or Compound 3) to the subject.

In certain embodiments, the sample used in the methods provided herein comprises a plurality of cells, such as cancer (e.g., MM) cells. Such cells can include any type of cells, e.g., stem cells, blood cells (e.g., peripheral blood mononuclear cells (PBMC)), lymphocytes, B cells, T cells, monocytes, granulocytes, immune cells, or cancer cells.

Specific cell populations can be obtained using a combination of commercially available antibodies (e.g., antibodies from Quest Diagnostic (San Juan Capistrano, California) or Dako (Denmark)).

In certain embodiments, the cells in the methods provided herein are PBMC. In certain embodiments, the sample used in the methods provided herein is from a disease tissue, e.g., from an individual having cancer (e.g., MM).

In certain embodiments, cell lines are used as disease models for evaluating effects of compounds, studying mechanisms of action, or establishing reference levels of biomarkers, etc. In some embodiments, the cells used in the methods provided herein are from a cancer (e.g., MM) cell line. In one embodiment, the MM cell line is DF15 cell line. In another embodiment, the MM cell line is the DF15 cell line made resistant to lenalidomide and pomalidomide (DF15R). In another embodiment, the MM cell line is NCI-H929. In another embodiment, the MM cell line is NCI-H929 made resistant to lenalidomide (NCI-H929-1051). In another embodiment, the MM cell line is NCI-H929 made resistant to pomalidomide (NCI-H929-P01). In another embodiment, the MM cell line is OPM2. In another embodiment, the MM cell line is the OPM2 cell line made resistant to 100 nM of pomalidomide (OPM2-P01). In another embodiment, the MM cell line is the OPM2 cell line made resistant to 1 μM of pomalidomide (OPM2-P1). In another embodiment, the MM cell line is the OPM2 cell line made resistant to 10 μM of pomalidomide (OPM2-P10).

In certain embodiments, the methods provided herein are useful for detecting gene rearrangement in cells from an individual. In some embodiments, the methods provided herein are useful for detecting TCR gene rearrangement after treatment with Compound 1, Compound 2, or Compound 3. In certain embodiments, the number of cells used in the methods provided herein can range from a single cell to about $10^9$ cells. In some embodiments, the number of cells used in the methods provided herein is about $1\times10^4$, about $5\times10^4$, about $1\times10^5$, about $5\times10^5$, about $1\times10^6$, about $5\times10^6$, about $1\times10^7$, about $5\times10^7$, about $1\times10^8$, about $5\times10^8$, or about $1\times10^9$.

The number and type of cells collected from a subject can be monitored, for example, by measuring changes in cell surface markers using standard cell detection techniques such as flow cytometry, cell sorting, immunocytochemistry (e.g., staining with tissue specific or cell-marker specific antibodies), fluorescence activated cell sorting (FACS), magnetic activated cell sorting (MACS), evaluation of hematoxylin and eosin (H&E)-stained tumor sections, examination of the morphology of cells using light or confocal microscopy, and/or by measuring changes in gene expression using techniques well known in the art, such as PCR and gene expression profiling. These techniques can be used, too, to identify cells that are positive for one or more particular markers.

In certain embodiments, subsets of cells are used in the methods provided herein. Methods of sorting and isolating specific populations of cells are well known in the art and can be based on cell size, morphology, H&E staining, intracellular markers, or extracellular markers. Such methods include, but are not limited to, flow cytometry, flow sorting, FACS, bead based separation such as magnetic cell sorting, size-based separation (e.g., a sieve, an array of obstacles, or a filter), H&E staining, sorting in a microfluidics device, antibody-based separation, sedimentation, affinity adsorption, affinity extraction, density gradient centrifugation, laser capture microdissection, etc. Fluorescence activated cell sorting (FACS) is a well-known method for separating particles, including cells, based on the fluorescent properties of the particles (Kamarch, *Methods Enzymol.* 1987, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one embodiment, DNA, RNA (e.g., mRNA), or protein is purified from a sample, and the presence or absence of a biomarker is measured by analyzing the DNA or RNA sequence, gene expression, or protein expression. In certain embodiments, the presence or absence of a biomarker is measured by Next-Generation Sequencing (NGS), RNA sequencing (RNA-seq), fluorescence in situ hybridization (FISH), quantitative real-time PCR (qRT-PCR), microarray, flow cytometry, immunohistochemistry, or immunofluorescence. In other embodiments, the presence or absence of a biomarker is measured by ELISA or other similar methods known in the art.

5.5 Methods of Detecting mRNA Levels in a Sample

Several methods of analyzing, detecting, or quantitating mRNA levels are known in the art. Exemplary methods include, but are not limited to, northern blots, RNA-seq, ribonuclease protection assays, PCR-based methods, and the like. The mRNA sequence of a biomarker (e.g., the mRNA of CRBN or a protein that is directly or indirectly affected by CRBN, or a fragment thereof) can be used to prepare a probe that is at least partially complementary to the mRNA sequence. The probe can then be used to detect the mRNA in a sample, using any suitable assay, such as PCR-based methods, northern blotting, a dipstick assay, and the like.

In other embodiments, a nucleic acid assay for testing for compound activity in a biological sample can be prepared. An assay typically contains a solid support and at least one nucleic acid contacting the support, where the nucleic acid corresponds to at least a portion of an mRNA that has altered expression during a compound treatment in a patient, such as the mRNA of a biomarker (e.g., CRBN or a protein that is directly or indirectly affected by CRBN). The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of mRNA in a sample. For example, an assay may be in the form of a dipstick, a membrane, a chip, a disk, a test strip, a filter, a microsphere, a slide, a multi-well plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film, a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.). See, e.g., Ausubel et al., *Short Protocols in Molecular Biology* (Wiley & Sons, 3rd ed. 1995); Sambrook et al., *Molecular Cloning: A Laboratory Manual* (Cold Spring Harbor, N.Y., 3rd ed. 2001). In some embodiments, the sample is labeled with fluorescent label. Exemplary fluorescent dyes include, but are not limited to, xanthene dyes, fluorescein dyes (e.g., fluorescein isothiocyanate (FITC), 6-carboxyfluorescein (FAM), 6 carboxy-2',4',7',4,7-hexachlorofluorescein (HEX), 6-carboxy-4',5'-dichloro-2',7'-dimethoxyfluorescein (JOE)), rhodamine dyes (e.g., rhodamine 110 (R110), N,N,N',N'-tetramethyl-6-carboxyrhodamine (TAMRA), 6-carboxy-X-rhodamine (ROX), 5-carboxyrhodamine 6G (R6G5 or G5), 6-carboxyrhodamine 6G (R6G6 or G6)), cyanine dyes (e.g., Cy3, Cy5 and Cy7), Alexa dyes (e.g., Alexa-fluor-555), coumarin, Diethylaminocoumarin, umbelliferone, benzimide dyes (e.g., Hoechst 33258), phenanthridine dyes (e.g., Texas Red), ethidium dyes, acridine dyes, carbazole dyes, phenoxazine dyes, porphyrin dyes, polymethine dyes, BODIPY dyes, quinoline dyes, Pyrene, Fluorescein Chlorotriazinyl, eosin dyes, Tetramethylrhodamine, Lissamine, Napthofluorescein, and the like.

In some embodiments, the mRNA sequences comprise at least one mRNA of a biomarker provided herein. In some embodiments, the biomarker is selected from the group consisting of mRNA of CRBN, IKZF1, IKZF3, ZFP91, c-MYC, IRF4, p21, p27, pRb1, Caspase-1, Caspase-3, Caspase-7, PARP, survivin, BIM, IL-2, TNFα, IFNγ, or a fragment thereof.

In one embodiment, the biomarker is selected from the group consisting of the mRNA of CRBN, IKZF1, IKZF3, ZFP91, c-MYC, IRF4, p21, p27, pRb1, Caspase-1, Caspase-3, Caspase-7, PARP, survivin, BIM, IL-2, TNFα, IFNγ, or a fragment thereof. In one embodiment, the mRNA is CRBN mRNA. In another embodiment, the mRNA is IKZF1 mRNA. In yet another embodiment, the mRNA is IKZF3 mRNA. In another embodiment, the mRNA is c-MYC mRNA. In still another embodiment, the mRNA is IRF4 mRNA. In some embodiments, the mRNA is ZFP91. In some embodiments, the mRNA is p21. In some embodiments, the mRNA is p27. In some embodiments, the mRNA is pRb1. In some embodiments, the mRNA is Caspase-1. In some embodiments, the mRNA is Caspase-3. In some embodiments, the mRNA is Caspase-7. In some embodiments, the mRNA is PARP. In some embodiments, the mRNA is survivin. In some embodiments, the mRNA is BIM. In some embodiments, the mRNA is IL-2. In some embodiments, the mRNA is TNFα. In some embodiments, the mRNA is IFNγ. The nucleic acids may be present in specific, addressable locations on a solid support, each corresponding to at least a portion of mRNA sequences that are differentially expressed upon treatment of a compound in a cell or a patient.

In some embodiments, the biomarker is the plurality of mRNA sequences that are differentially expressed upon treatment with a compound in a cell or patient, relative to treatment with a control. In some embodiments the biomarker is the plurality of mRNA sequences that are differentially expressed between two different cell populations upon treatment with a compound. In some embodiments, the biomarker is the plurality of mRNA sequences that are differentially expressed between CD138+ cells and CD138− cells in response to treatment with Compound 1, Compound 2, or Compound 3.

A typical mRNA assay method can contain the steps of 1) obtaining surface-bound subject probes; 2) hybridizing a population of mRNAs to the surface-bound probes under conditions sufficient to provide for specific binding; (3) post-hybridization washing to remove nucleic acids not specifically bound to the surface-bound probes; and (4) detecting the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g., under conditions sufficient to provide for specific binding of target mRNAs in the sample to the probes) are described in Kallioniemi et al., *Science* 1992, 258:818-821 and International Patent Application Publication No. WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al., *Meth. Enzymol.* 1981, 21:470-480; Angerer et al., *Genetic Engineering: Principles and Methods*, Vol 7, pgs 43-65 (Plenum Press, New York, Setlow and Hollaender, eds. 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to detect the expression of CRBN or a protein that is directly or indirectly affected by CRBN. Examples of PCR methods can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, quantitative Reverse Transcription-PCR (qRT-PCR) can be used for both the detection and quantification of RNA targets (Bustin et al., *Clin. Sci.* 2005, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, qRT-PCR gives quantitative results. An additional advantage of qRT-PCR is the relative ease and convenience of use. Instruments for qRT-PCR, such as the Applied Biosystems 7500, are available commercially, so are the reagents, such as TaqMan® Sequence Detection Chemistry. For example, TaqMan® Gene Expression Assays can be used, following the manufacturer's instructions. These kits are pre-formulated gene expression assays for rapid, reliable detection and quantification of human, mouse, and rat mRNA transcripts. An exemplary qRT-PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the $C_T$), the data can be analyzed, for example, using 7500 Real-Time PCR System Sequence Detection software vs. using the comparative $C_T$ relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

In some embodiments, the expression of mRNA is determined by sequencing the RNA (RNA-Seq). Techniques for RNA-Seq are well known to one skilled in the art and methods are described in Waern et al., *Methods Mol Biol.,* 2011, 759:125-132; Wilhelm et al., *Nature Protocols,* 2010, 5(2):255-66; and Hoeijmakers et al., *Methods Mol Biol.,* 2013, 923:221-39. Briefly, a typical RNA-seq method can contain the step of (1) isolating RNA; (2) depleting ribosomal RNA; (3) cDNA synthesis; and (4) sequencing cDNA by Next-Gen sequencing.

5.6 Methods of Detecting Polypeptide or Protein Levels in a Sample

Several protein detection and quantification methods can be used to measure the level of a biomarker, such as CRBN or a protein that is directly or indirectly affected by CRBN, such as Aiolos and Ikaros. Any suitable protein quantification method can be used. In some embodiments, antibody-based methods are used. Exemplary methods that can be used include, but are not limited to, immunoblotting (Western blot), ELISA, immunohistochemistry, flow cytometry, fluorescence-activated cell sorting (FACS), cytometry bead array, mass spectroscopy, and the like. Several types of ELISA are commonly used, including direct ELISA, indirect ELISA, and sandwich ELISA.

In some embodiments, the biomarker is selected from the group consisting of the proteins of CRBN, IKZF1, IKZF3, ZFP91, c-MYC, IRF4, p21, p27, pRb1, Caspase-1, Caspase-3, Caspase-7, PARP, survivin, BIM, IL-2, TNFα, IFNγ, soluble BCMA, free lambda light chain, and free kappa light chain. In certain embodiments, the biomarker is a protein that is directly or indirectly affected by CRBN. In certain embodiments, the biomarker is CRBN protein. In a specific embodiment, the biomarker is CRBN and it is detected by IHC. In another specific embodiment, the biomarker is CRBN, Aiolos, Ikaros, ZFP91, c-Myc, IRF4, c-Caspase-3, and/or TILs, and is measured by IHC. In some embodiments, the biomarker is selected from a group consisting of IKZF1, IKZF3, ZFP91, c-MYC, IRF4. In some embodiments, the biomarker is selected from a group consisting of Aiolos and Ikaros, and is detected by FACS. In some embodiments, the biomarker is selected from a group consisting of Aiolos and Ikaros, and is detected by ELISA. In some embodiments, the biomarker is selected from a group consisting of Caspase-1, Caspase-3, Caspase-7, PARP, survivin, BIM, free lambda light chain, and free kappa light chain. In some embodiments, the biomarker is selected from a group consisting of free lambda light chain, and free kappa light chain. In a specific embodiment, the biomarker is Aiolos. In a specific embodiment, the biomarker is Ikaros. In a specific embodiment, the biomarker is c-MYC. In a specific embodiment, the biomarker is IRF4. In a specific embodiment, the biomarker is cleaved-Caspase-3. In another specific embodiment, the biomarker is ZFP91. In yet another specific embodiment, the biomarker is p21. In some embodiments, the biomarker is p27. In some embodiments, the biomarker is p27. In some embodiments, the biomarker is pRb1. In some embodiments, the biomarker is Caspase-1. In some embodiments, the biomarker is Caspase-3. In some embodiments, the biomarker is Caspase-7. In some embodiments, the biomarker is PARP. In some embodiments, the biomarker is survivin. In some embodiments, the biomarker is BIM. In some embodiments, the biomarker is IL-2. In some embodiments, the biomarker is p27. In some embodiments, the biomarker is TNFα. In some embodiments, the biomarker is IFNγ. In some embodiments, the biomarker is soluble BCMA. In some embodiments, the biomarker is free lambda light chain, and free kappa light chain. In a specific embodiment, the biomarker is free lambda light chain. In a specific embodiment, the biomarker is free kappa light chain.

5.7 Compounds

In some embodiments of the various methods provided herein, the compound is 4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1):

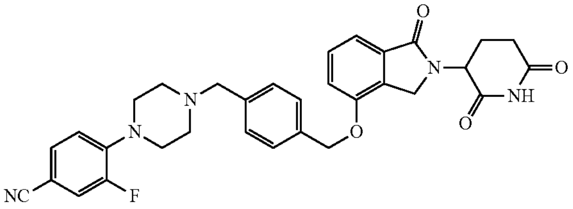 [SMILES: N#Cc1ccc(N2CCN(Cc3ccc(COc4cccc5c4CN(C4CCC(=O)NC4=O)C5=O)cc3)CC2)c(F)c1]

or an enantiomer or a mixture of enantiomers, tautomer, isotopolog or pharmaceutically acceptable salt thereof.

In some embodiments of the various methods provided herein, the compound is (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 2):

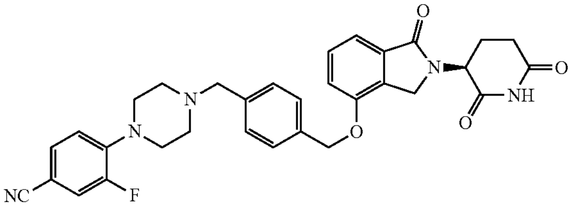 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof.

In some embodiments of the various methods provided herein, the compound is (R)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 3):

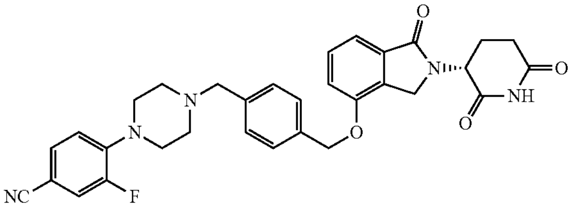

or a tautomer, isotopolog or pharmaceutically acceptable salt thereof.

The various compounds provided herein may contain chiral centers, and can exist as mixtures of enantiomers (e.g., racemic mixtures) or mixtures of diastereomers. The methods provided herein encompass the use of stereomerically pure forms of such compounds as well as mixtures of those forms. For example, mixtures comprising equal or unequal amounts of the enantiomers of a particular compound may be used in methods provided herein. These isomers may be asymmetrically synthesized or resolved using standard techniques, such as chiral columns or chiral resolving agents. See, Jacques et al., *Enantiomers, Racemates and Resolutions* (Wiley-Interscience, New York, 1981); Wilen et al., *Tetrahedron* 1977, 33:2725-2736; Eliel, *Stereochemistry of Carbon Compounds* (McGraw-Hill, N Y, 1962); Wilen, *Tables of Resolving Agents and Optical Resolutions*, p. 268 (Eliel, ed., Univ. of Notre Dame Press, Notre Dame, IN, 1972).

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.,* 20: 393 (1982); Lijinsky et. al., *J. Nat. Cancer Inst.,* 69: 1127 (1982); Mangold et. al., *Mutation Res.* 308: 33 (1994); Gordon et. al., *Drug Metab. Dispos.,* 15: 589 (1987); Zello et. al., *Metabolism,* 43: 487 (1994); Gately et. al., *J. Nucl. Med.,* 27: 388 (1986); Wade D, *Chem. Biol. Interact.* 117: 191 (1999).

Without being limited by any particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. As a result, these drugs often require the administration of multiple or high daily doses.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

Standard physiological, pharmacological and biochemical procedures are available for testing the compounds to identify those that possess the desired anti-proliferative activity.

Such assays include, for example, biochemical assays such as binding assays, radioactivity incorporation assays, as well as a variety of cell based assays. The compounds provided herein can be prepared by methods known to one of skill in the art and following procedures similar to those described in the Examples section herein and routine modifications thereof.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

5.8 Pharmaceutical Compositions

The pharmaceutical compositions provided herein contain therapeutically effective amounts of one or more of compounds provided herein and optionally a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of multiple myeloma.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

5.9 Kits

In one aspect, provided herein is a kit for identifying a subject having cancer who is likely to be responsive to a treatment compound, comprising a means for detecting the level of a biomarker in a sample that has been treated with the treatment compound, wherein the treatment compound is Compound 1:

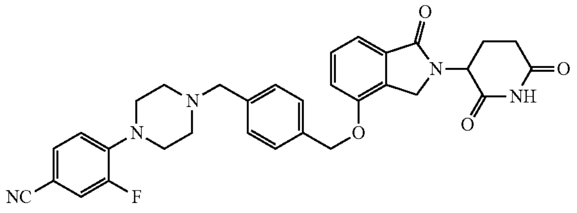

or an enantiomer, a mixture of enantiomers, tautomer, isotopolog or pharmaceutically acceptable salt thereof.

In one aspect, provided herein is a kit for identifying a subject having cancer who is likely to be responsive to a treatment compound, comprising a means for detecting the level of a biomarker in a sample that has been treated with the treatment compound, wherein the treatment compound is Compound 2:

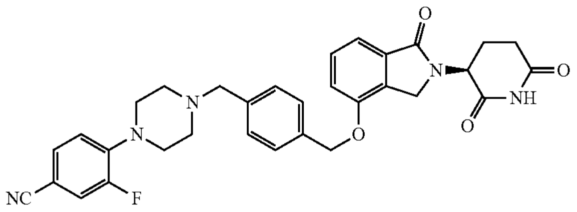 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog or pharmaceutically acceptable salt thereof.

In one aspect, provided herein is a kit for identifying a subject having cancer who is likely to be responsive to a treatment compound, comprising a means for detecting the level of a biomarker in a sample that has been treated with the treatment compound, wherein the treatment compound is Compound 3:

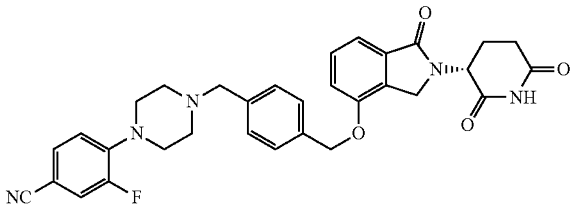

or a tautomer, isotopolog or pharmaceutically acceptable salt thereof.

In another aspect, provided herein is a kit for treating cancer, comprising a means for detecting the level of a biomarker in a sample that has been treated with a treatment compound, wherein the treatment compound is Compound 1:

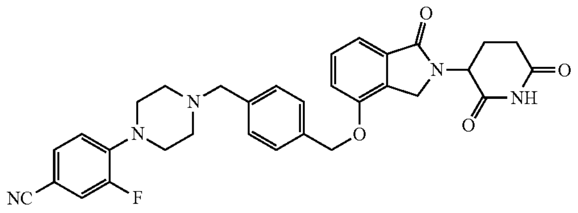

or an enantiomer, a mixture of enantiomers, tautomer, isotopolog or pharmaceutically acceptable salt thereof.

In another aspect, provided herein is a kit for treating cancer, comprising a means for detecting the level of a biomarker in a sample that has been treated with a treatment compound, wherein the treatment compound is Compound 2:

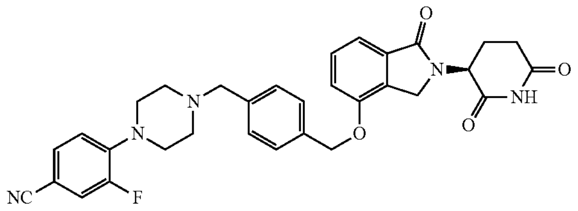 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog or pharmaceutically acceptable salt thereof.

In another aspect, provided herein is a kit for treating cancer, comprising a means for detecting the level of a biomarker in a sample that has been treated with a treatment compound, wherein the treatment compound is Compound 3:

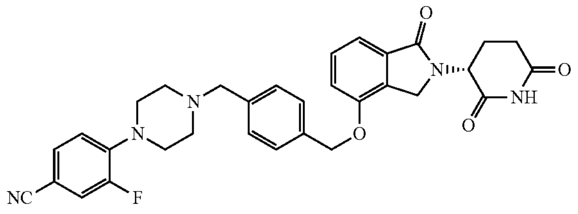

or a tautomer, isotopolog or pharmaceutically acceptable salt thereof.

In yet another aspect, provided herein is a kit for predicting the responsiveness of a subject having or suspected of having cancer to a treatment compound, comprising a means for detecting the level of a biomarker in a sample that has been treated with the treatment compound, wherein the treatment compound is Compound 1:

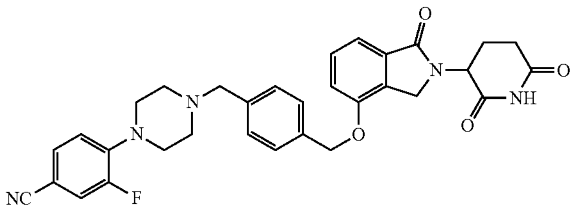

or an enantiomer, a mixture of enantiomers, tautomer, isotopolog or pharmaceutically acceptable salt thereof.

In yet another aspect, provided herein is a kit for predicting the responsiveness of a subject having or suspected of having cancer to a treatment compound, comprising a means for detecting the level of a biomarker in a sample that has been treated with the treatment compound, wherein the treatment compound is Compound 2:

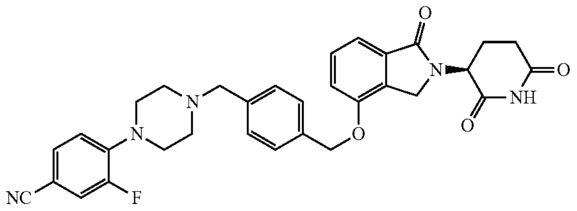 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog or pharmaceutically acceptable salt thereof.

In yet another aspect, provided herein is a kit for predicting the responsiveness of a subject having or suspected of having cancer to a treatment compound, comprising a means for detecting the level of a biomarker in a sample that has been treated with the treatment compound, wherein the treatment compound is Compound 3:

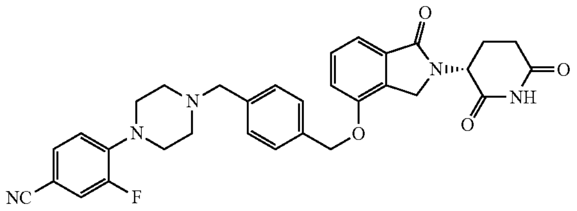

or a tautomer, isotopolog or pharmaceutically acceptable salt thereof.

In yet another aspect, provided herein is a kit for monitoring the efficacy of a treatment compound in treating cancer in a subject, comprising a means for detecting the level of a biomarker in a sample that has been treated with the treatment compound, wherein the treatment compound is Compound 1:

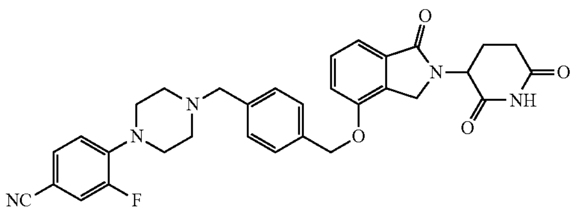

or an enantiomer, a mixture of enantiomers, tautomer, isotopolog or pharmaceutically acceptable salt thereof.

In yet another aspect, provided herein is a kit for monitoring the efficacy of a treatment compound in treating cancer in a subject, comprising a means for detecting the level of a biomarker in a sample that has been treated with the treatment compound, wherein the treatment compound is Compound 2:

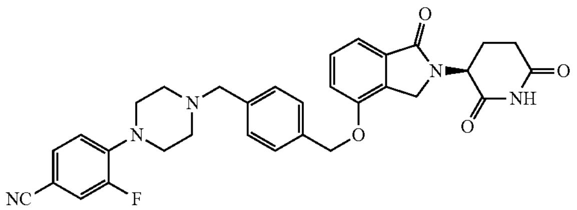 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog or pharmaceutically acceptable salt thereof.

In yet another aspect, provided herein is a kit for monitoring the efficacy of a treatment compound in treating cancer in a subject, comprising a means for detecting the level of a biomarker in a sample that has been treated with the treatment compound, wherein the treatment compound is Compound 3:

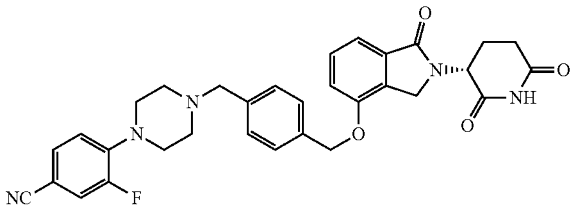

or a tautomer, isotopolog or pharmaceutically acceptable salt thereof.

In yet another aspect, provided herein is a kit for identifying a subject having multiple myeloma who is likely to be responsive to a treatment compound, comprising a means for detecting the level of a biomarker in a sample that has been treated with the treatment compound, wherein the treatment compound is Compound 1:

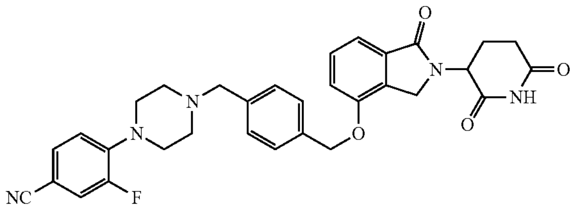

or an enantiomer, a mixture of enantiomers, tautomer, isotopolog or pharmaceutically acceptable salt thereof.

In yet another aspect, provided herein is a kit for identifying a subject having multiple myeloma who is likely to be responsive to a treatment compound, comprising a means for detecting the level of a biomarker in a sample that has been treated with the treatment compound, wherein the treatment compound is Compound 2:

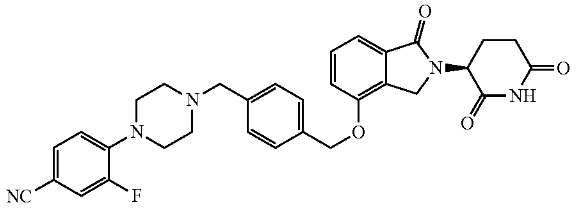

or a tautomer, isotopolog or pharmaceutically acceptable salt thereof.

In yet another aspect, provided herein is a kit for identifying a subject having multiple myeloma who is likely to be responsive to a treatment compound, comprising a means for detecting the level of a biomarker in a sample that has been treated with the treatment compound, wherein the treatment compound is Compound 3:

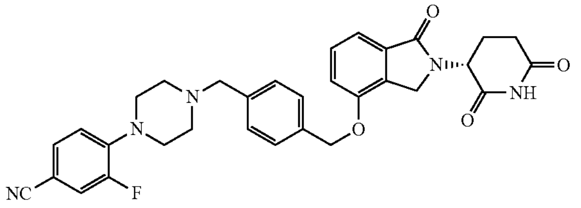 [SMILES: N#Cc1ccc(N2CCN(Cc3ccc(COc4cccc5c4CN([C@@H]4CCC(=O)NC4=O)C5=O)cc3)CC2)c(F)c1]

or a tautomer, isotopolog or pharmaceutically acceptable salt thereof.

In certain embodiments, the biomarker detected by various kits provided herein is CRBN. In certain embodiments, the biomarker detected by various kits provided herein is a CRBN associated protein (CAP). In some embodiments, the biomarker comprises one CAP. In other embodiments, the biomarker comprises two CAPs. In yet other embodiments, the biomarker comprises three CAPs. In still other embodiments, the biomarker comprises four. In other embodiments, the biomarker comprises five or more CAPs.

In certain embodiments, the biomarker detected by various kits provided herein is a CAP selected from the group consisting of IKZF1, IKZF3, ZFP91, c-MYC, IRF4. In some embodiments, the biomarker is selected from the group consisting of IKZF1 and IKZF3. In some embodiments, the biomarker is IKZF1. In certain embodiments, the biomarker is IKZF3. In other embodiments, the biomarker is ZFP91. In yet another embodiment, the biomarker is c-MYC. In other embodiments, the biomarker is IRF4.

In certain embodiments, the biomarker detected by various kits provided herein has a function in apoptosis. In certain embodiments, the biomarker detected by various kits provided herein has a function in apoptosis and is selected from the group consisting of CTC, Caspase-1, Caspase-3, Caspase-7, PARP, BIM, survivin, serum free lambda light chain, and serum free kappa light chain. In certain embodiments, the biomarker detected by various kits provided herein has a function in apoptosis and is selected from the group consisting of serum free lambda light chain, and serum free kappa light chain. In certain embodiments, the biomarker detected by various kits provided herein is CTC. In certain embodiments, the biomarker detected by various kits provided herein is Caspase-3. In certain embodiments, the biomarker detected by various kits provided herein is Caspase-7. In certain embodiments, the biomarker detected by various kits provided herein is survivin. In certain embodiments, the biomarker detected by various kits provided herein is BIM. In certain embodiments, the biomarker detected by various kits provided herein is Caspase-1. In certain embodiments, the biomarker detected by various kits provided herein is PARP. In certain embodiments, the biomarker detected by various kits provided herein is serum free lambda light chain. In certain embodiments, the biomarker detected by various kits provided herein is serum free kappa light chain.

In certain embodiments, the biomarker detected by various kits provided herein has a function in cell cycle. In certain embodiments, the biomarker detected by various kits provided herein has a function in cell cycle and is selected from the group consisting of p21, p27, and pRb1. In certain embodiments, the biomarker detected by various kits provided herein is p21. In certain embodiments, the biomarker detected by various kits provided herein is p27. In certain embodiments, the biomarker detected by various kits provided herein is pRb1.

In yet other embodiments, the biomarker detected by various kits provided herein is associated with T-cell activation. In certain embodiments, the biomarker detected by various kits provided herein is associated with T-cell activation and is selected from the group consisting of the T-cell activation associated cytokines IL-2, TNFα, and IFNγ.

In certain embodiments of various kits provided herein, the sample is obtained from a tumor biopsy, a node biopsy, a liquid biopsy (e.g. blood), or a biopsy from the bone marrow.

In some embodiments of various kits provided herein, the cancer is blood cancer. In certain embodiments, the blood cancer is selected from the group consisting of multiple myeloma. In certain embodiments, the multiple myeloma is relapsed, refractory or resistant to conventional therapy.

In certain embodiments, provided herein is a kit for detecting the mRNA level of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises reagents to generate cDNA from the mRNA. In certain embodiments, the kit further comprises reagents to sequence the cDNA generated from the mRNA. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multi-well plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an organ, an organelle, a biological fluid, a blood sample, a urine sample, or a skin sample.

In another embodiment, the kit comprises a solid support, nucleic acids attached to the support, where the nucleic acids are complementary to at least 20, 50, 100, 200, 350, or more bases of mRNA, and a means for detecting the expression of the mRNA in a biological sample.

In a specific embodiment, the pharmaceutical or assay kit comprises, in a container, a compound or a pharmaceutical composition thereof, and further comprises, in one or more containers, components for isolating RNA. In another specific embodiment, the pharmaceutical or assay kit comprises, in a container, a compound or a pharmaceutical composition, and further comprises, in one or more containers, components for conducting RT-PCR, qRT-PCR, deep sequencing, or microarray In certain embodiments, the kits provided herein employ means for detecting the expression of a biomarker by quantitative real-time PCR (qRT-PCR), microarray, flow cytometry, FACS, FISH, DNA sequencing, RNA sequencing, hematoxylin and eosin (H&E) staining, immunohistochemistry, or immunofluorescence. In other embodiments, the expression of the biomarker is measured by ELISA-based methodologies or other similar methods known in the art.

In another specific embodiment, the pharmaceutical or assay kit comprises, in a container, a compound or a pharmaceutical composition thereof, and further comprises, in one or more containers, components for isolating protein. In another specific embodiment, the pharmaceutical or assay kit comprises, in a container, a compound or a pharmaceutical composition, and further comprises, in one or more containers, components for conducting flow cytometry or ELISA.

In another aspect, provided herein are kits for measuring biomarkers that supply the materials necessary to measure the abundance of one or more gene products of the biomarkers or a subset of the biomarkers (e.g., one, two, three, four, five, or more biomarkers) provided herein. Such kits may comprise materials and reagents required for measuring DNA, RNA, protein, or cell populations. In some embodiments, such kits include microarrays, wherein the microarray is comprised of oligonucleotides and/or DNA and/or RNA fragments which hybridize to one or more gene products of the biomarkers or a subset of the biomarkers provided herein, or any combination thereof. In some embodiments, such kits may include primers for PCR of either the RNA product or the cDNA copy of the RNA product of the biomarkers or a subset of the biomarkers, or both. In some embodiments, such kits may include primers for PCR as well as probes for qPCR. In some embodiments, such kits may include multiple primers and multiple probes, wherein some of the probes have different fluorophores so as to permit simultaneously measuring multiple gene products of the biomarkers or a subset of the biomarkers provided herein. In some embodiments, such kits may further include materials and reagents for creating cDNA from RNA. In some embodiments, such kits may include antibodies specific for the protein products of the biomarkers or a subset of the biomarkers provided herein. Such kits may additionally comprise materials and reagents for isolating RNA and/or proteins from a biological sample. In addition, such kits may include materials and reagents for synthesizing cDNA from RNA isolated from a biological sample. In some embodiments, such kits may include a computer program product embedded on computer readable media for predicting whether a patient is clinically sensitive to a compound. In some embodiments, the kits may include a computer program product embedded on a computer readable media along with instructions.

In some embodiments, such kits measure the expression of one or more nucleic acid products of the biomarkers or a subset of the biomarkers provided herein. In accordance with this embodiment, the kits may comprise materials and reagents that are necessary for measuring the expression of particular nucleic acid products of the biomarkers or a subset of the biomarkers provided herein. For example, a microarray or RT-PCR kit may be produced for a specific condition and contain only those reagents and materials necessary for measuring the levels of specific RNA transcript products of the biomarkers or a subset of the biomarkers provided herein, to predict whether a hematological cancer in a patient is clinically sensitive to a compound. Alternatively, in some embodiments, the kits can comprise materials and reagents necessary for measuring the expression of particular nucleic acid products of genes other than the biomarkers provided herein. For example, in certain embodiments, the kits comprise materials and reagents necessary for measuring the expression levels of 1, 2, 3, 4, 5, 6, 7, 8, 9, 10, 15, 20, 25, 30, 35, 40, 45, 50, or more of the genes of the biomarkers provided herein, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than the biomarkers provided herein. In other embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the biomarkers provided herein, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not the biomarkers provided herein. In certain embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not the biomarkers provided herein.

For nucleic acid microarray kits, the kits generally comprise probes attached to a solid support surface. In one such embodiment, probes can be either oligonucleotides or longer probes including probes ranging from 150 nucleotides to 800 nucleotides in length. The probes may be labeled with a detectable label. In a specific embodiment, the probes are specific for one or more of the gene products of the biomarkers provided herein. The microarray kits may comprise instructions for performing the assay and methods for interpreting and analyzing the data resulting from performing the assay. In a specific embodiment, the kits comprise instructions for predicting whether a hematological cancer in a patient is clinically sensitive to a compound. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own suitable container.

In certain embodiments, a nucleic acid microarray kit comprises materials and reagents necessary for measuring the expression levels of 1, 2, 3, 4, 5, 6, 7, 8, 9, 10, 15, 20, 25, 30, 35, 40, 45, 50, or more of the genes of the biomarkers provided herein, or a combination thereof, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than those of the biomarkers provided herein. In other embodiments, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not of the biomarkers provided herein. In another embodiment, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, or any combination thereof, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, or 500-1000 genes that are not of the biomarkers provided herein.

For quantitative PCR, the kits generally comprise pre-selected primers specific for particular nucleic acid sequences. The quantitative PCR kits may also comprise enzymes suitable for amplifying nucleic acids (e.g., polymerases such as Taq polymerase), deoxynucleotides, and buffers needed for amplification reaction. The quantitative PCR kits may also comprise probes specific for the nucleic acid sequences associated with or indicative of a condition. The probes may or may not be labeled with a fluorophore. The probes may or may not be labeled with a quencher molecule. In some embodiments, the quantitative PCR kits also comprise components suitable for reverse-transcribing RNA, including enzymes (e.g., reverse transcriptases such as AMV, MMLV, and the like) and primers for reverse transcription along with deoxynucleotides and buffers needed for reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the reaction and methods for interpreting and analyzing the data resulting from performing the reaction. In a specific embodiment, the kits contain instructions for predicting whether a patient having or suspected of having multiple myeloma is clinically sensitive to a compound.

For antibody-based kits, the kit can comprise, for example: (1) a first antibody (which may or may not be attached to a solid support) that binds to a peptide, polypeptide or protein of interest; and, optionally, (2) a second, different antibody that binds to either the first antibody or the peptide, polypeptide, or protein, and is conjugated to a detectable label (e.g., a fluorescent label, radioactive isotope, or enzyme). In a specific embodiment, the peptide, polypeptide, or protein of interest is associated with or indicative of a condition (e.g., a disease). The antibody-based kits may also comprise beads for conducting immunoprecipitation. Each component of the antibody-based kits is generally in its own suitable container. Thus, these kits generally comprise distinct containers suitable for each antibody and reagent. Further, the antibody-based kits may comprise instructions for performing the assay and methods for interpreting and analyzing the data resulting from performing the assay. In a specific embodiment, the kits contain instructions for predicting whether a hematological cancer in a patient is clinically sensitive to a compound.

In one embodiment, a kit provided herein comprises a compound provided herein, or an enantiomer, a mixture of enantiomers, tautomer, isotopolog or pharmaceutically acceptable salt thereof. Kits may further comprise additional active agents, including but not limited to those disclosed herein.

Kits provided herein may further comprise devices that are used to administer the active ingredients. Examples of such devices include, but are not limited to, syringes, drip bags, patches, and inhalers.

Kits may further comprise cells or blood for transplantation, as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to, water for injection USP; aqueous vehicles (such as, but not limited to, sodium chloride injection, Ringer's injection, dextrose injection, dextrose and sodium chloride injection, and lactated Ringer's injection); water-miscible vehicles (such as, but not limited to, ethyl alcohol, polyethylene glycol, and polypropylene glycol); and non-aqueous vehicles (such as, but not limited to, corn oil, cottonseed oil, peanut oil, sesame oil, ethyl oleate, isopropyl myristate, and benzyl benzoate).

In certain embodiments of the methods and kits provided herein, solid phase supports are used for purifying proteins, labeling samples, or carrying out the solid phase assays. Examples of solid phases suitable for carrying out the methods disclosed herein include beads, particles, colloids, single surfaces, tubes, multi-well plates, microtiter plates, slides, membranes, gels, and electrodes. When the solid phase is a particulate material (e.g., a bead), it is, in one embodiment, distributed in the wells of multi-well plates to allow for parallel processing of the solid phase supports.

It is noted that any combination of the above-listed embodiments, for example, with respect to one or more reagents, such as, without limitation, nucleic acid primers, solid support, and the like, are also contemplated in relation to any of the various methods and/or kits provided herein.

Certain embodiments of the invention are illustrated by the following non-limiting examples.

6. EXAMPLES

Examples

The examples below are carried out using standard techniques, which are well known and routine to those of skill in the art, except where otherwise described in detail. The examples are intended to be merely illustrative.

Example 1: Synthesis of 4-(4-(4-(((2-(2,6-dioxopiperidin-3-yl)-1-oxoisoindolin-4-yl)oxy)methyl)benzyl)piperazin-1-yl)-3-fluorobenzonitrile (Compound 1)

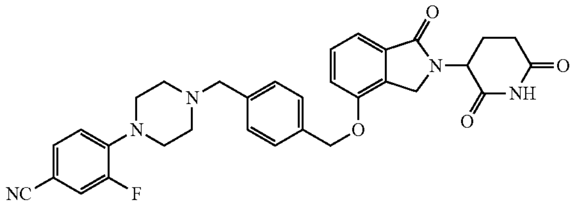 [SMILES: N#Cc1ccc(N2CCN(Cc3ccc(COc4cccc5c4CN(C4CCC(=O)NC4=O)C5=O)cc3)CC2)c(F)c1]

2-Amino-5-methoxy-5-oxopentanoic acid. To a suspension of 2-aminopentanedioic acid (250 g, 1.70 mol) in dry methanol (2.5 L) under nitrogen was added trimethylsilyl chloride (277 g, 2.55 mol) over 30 mins. The resulting clear solution was stirred at room temperature (20° C.) for 30 min. $^1$H NMR showed the starting material was consumed completely. The reaction mixture was used in the next step without further work-up. $^1$H NMR: 400 MHz $CD_3OD$ δ: 4.17-4.15 (m, 1H), 3.71 (s, 3H), 2.70-2.60 (m, 2H), 2.33-2.25 (m, 2H).

2-((tert-Butoxycarbonyl)amino)-5-methoxy-5-oxopentanoic acid. To the above solution was added triethylamine (275 g, 2.72 mol) and di-tert-butyl dicarbonate (447.35 g, 2.05 mol). The reaction mixture was stirred at 25° C. for 2 h. The solution was concentrated to dryness, then water (2.5 L) was added to dissolve the residue. The resulting aqueous phase was washed with ethyl acetate (200 mL), then acidified to pH=3 by HCl (1 N) and extracted with ethyl acetate (1 L×3). The combined organic layers were washed with brine (800 mL), dried over sodium sulfate, filtered and concentrated to offer 2-(tert-butoxycarbonylamino)-5-methoxy-5-oxo-pentanoic acid (250 g 56% yield, two steps) as a white solid. $^1$H NMR: 400 MHz $CD_3OD$ δ: 4.18-4.11 (m, 1H), 3.69 (s, 3H), 2.48-2.43 (m, 2H), 2.21-2.15 (m, 1H), 1.95-1.91 (m, 1H), 1.46 (s, 9H).

Methyl 5-amino-4-(tert-butoxycarbonyl amino)-5-oxo-pentanoate. To a solution of 2-(tert-butoxycarbonylamino)-5-methoxy-5-oxo-pentanoic acid (200 g, 765 mmol) in 1,4-dioxane (1.5 L) were added di-tert-butyl dicarbonate (267 g, 1.22 mol) and pyridine (121 g, 1.53 mol). After the reaction mixture was stirred at 25° C. for 30 min, ammonium carbonate (182 g, 2.30 mol) was added to the mixture and stirred for additional 16 h at 25° C. The organic solvent was removed by rotary evaporation, the residue was acidified by HCl (6 M) to pH=3 and then extracted with ethyl acetate (800 mL×3). The combined organic phase was washed with brine (800 mL), dried over sodium sulfate, and filtered. Volatile organics were removed under reduced pressure to offer methyl 5-amino-4-(tert-butoxycarbonyl amino)-5-oxo-pentanoate (180 g, 90% yield) as a white solid. $^1$H NMR: 400 MHz $CDCl_3$δ: 6.51 (s, 1H), 5.94 (s, 1H), 5.43 (s, 1H), 4.21 (s, 1H), 3.63 (s, 3H), 2.59-2.40 (m, 2H), 2.15-2.11 (m, 1H), 1.94-1.90 (m, 1H), 1.42 (s, 9H).

Methyl 4,5-diamino-5-oxo-pentanoate hydrochloride. A mixture of methyl 5-amino-4-(tert-butoxycarbonylamino)-5-oxo-pentanoate (180 g, 692 mmol) and HCl/ethyl acetate (300 mL, 4 M) was stirred at 25° C. for 12 h. The precipitated solid was collected by vacuum filtration and washed with ethyl acetate (500 mL) to give methyl 4,5-diamino-5-oxo-pentanoate hydrochloride (130 g, 95% yield) as a white solid. $^1$H NMR: 400 MHz $CD_3OD$ δ: 4.00-3.96 (m, 1H), 3.70 (s, 3H), 2.59-2.52 (m, 2H), 2.22-2.13 (m, 2H).

Methyl 3-hydroxy-2-methyl-benzoate. Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) until pH>3. The solid was dried under vacuum at 45° C. to give methyl 3-hydroxy-2-methyl-benzoate (700 g, 80.4% yield) as a gray solid.

Methyl 3-[tert-butyl(dimethyl)silyl]oxy-2-methyl-benzoate. Two batches (240 g each) were run in parallel. To a solution of methyl 3-hydroxy-2-methyl-benzoate (240 g, 1.44 mol) in N,N-dimethylformamide (1.40 L) was added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred and the organic phase was separated. The combined organic phase (two batches combined) was washed with water (1700 mL×3) and concentrated to ~1500 mL (KF<0.05%). The product was stored as an isopropyl acetate solution which was used in the next step without further purification.

Methyl 2-(bromomethyl)-3-[tert-butyl(dimethyl)silyl]oxy-benzoate. Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) was removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl(dimethyl)silyl]oxy-benzoate (920 g, 95.5% yield) as dark orange oil. $^1$H NMR: 400 MHz DMSO-$d_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

Methyl 5-amino-4-[4-[tert-butyl)(dimethyl)silyl]oxy-1-oxo-isoindolin-2-yl]-5-oxo-pentanoate. To a stirred solution of methyl 4,5-diamino-5-oxo-pentanoate hydrochloride (74.5 g, 379 mmol) in acetonitrile (2.50 L) was added methyl 2-(bromomethyl)-3-[tert-butyl(dimethyl)silyl] oxy-benzoate (125 g, 348 mmol). To the suspension was added diisopropylethylamine (89.9 g, 696 mmol) through an addition funnel over 10 min and then the mixture was stirred at 60° C. for 16 h. The reaction mixture was diluted with ethyl acetate (1.0 L), washed with HCl (1N, 1.0 L), sodium bicarbonate (sat. 1.0 L) and brine (1.0 L) successively. The organic layer was concentrated to give crude methyl 5-amino-4-[4-[tert-butyl(dimethyl)silyl]oxy-1-oxo-isoindolin-2-yl]-5-oxo-pentanoate (108 g, crude) as a light yellow solid. LCMS: m/z 407.3 [M+1]$^+$.

Methyl 5-amino-4-(4-hydroxy-1-oxo-isoindolin-2-yl)-5-oxo-pentanoate. To a stirred cold solution of methyl 5-amino-4-[4-[tert-butyl(dimethyl)silyl]oxy-1-oxo-isoindolin-2-yl]-5-oxo-pentanoate (108 g, 266 mmol) in N,N-dimethylformamide (350 mL) was added potassium carbonate (14.7 g, 106 mmol) in water (40 mL) in portions over 5 min. The resulting reaction mixture was stirred at 15° C. for 15 h. The reaction mixture was cooled in an ice bath, and HCl (12 M, 15 mL) was added slowly at 0-5° C. Acetonitrile (200 mL) was added to the mixture and precipitate solid formed. The suspension was stirred at room temperature for 10 min and filtered. The filter cake was washed with ethyl acetate (200 mL×5) to give product (55 g). The filtrate was concentrated under high vacuum to give a crude product (100 g) which was dissolved in dichloromethane (1.0 L) and allowed to stand at 15° C. for 16 h. White solid was formed which was filtered to give 5 g of product. The solids were combined to give methyl 5-amino-4-(4-hydroxy-1-oxo-isoindolin-2-yl)-5-oxo-pentanoate (60 g, 77% yield) as a white solid. $^1$H NMR: 400 MHz DMSO-$d_6$ δ: 7.58 (s, 1H), 7.31 (t, J=8.0 Hz, 1H), 7.19-7.14 (m, 2H), 7.01 (d, J=7.6 Hz, 1H), 4.75-4.71 (m, 1H), 4.50 (d, J=17.6 Hz, 1H), 4.32 (d, J=17.6 Hz, 1H), 3.51 (s, 3H), 2.29-2.18 (m, 3H), 2.09-1.99 (m, 1H).

Methyl 5-amino-4-[4-[[4-(bromomethyl)phenyl]methoxy]-1-oxo-isoindolin-2-yl]-5-oxo-pentanoate. Two reactions (25 g, 85.5 mmol) were run in parallel. A mixture of 1,4-bis(bromomethyl)benzene (67.7 g, 257 mmol), potassium carbonate (11.8 g, 85.5 mmol) and methyl 5-amino-4-(4-hydroxy-1-oxo-isoindolin-2-yl)-5-oxo-pentanoate (25 g, 85.5 mmol) in acetonitrile (1 L) was stirred at 60° C. for 16 h. The two batches were combined and the mixture was cooled to 15° C. and filtered. The filtrate was concentrated and purified by silica gel column chromatography (eluted by 50% petroleum ether in ethyl acetate to 100% ethyl acetate) to afford methyl 5-amino-4-[4-[[4-(bromomethyl)phenyl]methoxy]-1-oxo-isoindolin-2-yl]-5-oxo-pentanoate (52 g, 63% yield) as a white solid. $^1$H NMR: 400 MHz DMSO-$d_6$ δ: 7.59 (s, 1H), 7.50-7.44 (m, 5H), 7.32-7.28 (m, 2H), 7.19 (s, 1H), 5.26 (s, 2H), 4.79-4.71 (m, 3H), 4.55 (d, J=17.6 Hz, 1H), 4.43 (d, J=17.6 Hz, 1H), 3.52 (s, 3H), 2.30-2.19 (m, 3H), 2.10-2.08 (m, 1H).

3-[4-[[4-(Bromomethyl)phenyl]methoxy]-1-oxo-isoindolin-2-yl]piperidine-2,6-dione. Two reactions (28.5 g, 60.0 mmol) were run in parallel. Methyl 5-amino-4-[4-[[4-(bromomethyl)phenyl]methoxy]-1-oxo-isoindolin-2-yl]-5-oxo-pentanoate (28.5 g, 60.0 mmol) was dissolved in tetrahydrofuran (720 mL) and the solution was cooled in dry ice/acetone bath to −70° C. While stirring, potassium tert-butoxide (7.4 g, 66.0 mmol) was added in one portion to the clear solution. The reaction mixture turned to pale yellow and stirring was continued for additional 2 h at −70° C. A cooled solution of HCl (1N, 260 mL) was rapidly transferred to the reaction mixture while maintaining temperature at −70° C. The mixture immediately turned milky white and the dry ice/acetone bath was removed. The mixture was concentrated to remove most of the tetrahydrofuran. Upon concentration of the reaction mixture, a white solid precipitated. The white slurry was diluted with water (500 mL) and then filtered. The filter cake was washed with water (500 mL) and dried in vacuum oven at 40° C. for 12 hr, then washed with ethyl acetate (500 mL). The batches were combined to give 3-[4-[[4-(bromomethyl)phenyl]methoxy]-1-oxo-isoindolin-2-yl]piperidine-2,6-dione (49.85 g, 93%) as a light yellow solid. $^1$H NMR: 400 MHz DMSO-$d_6$ δ: 10.95 (s, 1H), 7.51-7.41 (m., 5H), 7.35-7.28 (m, 2H), 5.23 (s, 2H), 5.12-5.07 (m, 1H), 4.70 (s, 2H), 4.41 (d, J=17.6 Hz, 1H), 4.25 (d, J=17.6 Hz, 1H), 2.90-2.84 (m, 1H), 2.58-2.53 (m, 1H), 2.44-2.41 (m, 1H), 1.98-1.95 (m, 1H).

4-(4-(4-(((2-(2,6-Dioxopiperidin-3-yl)-1-oxoisoindolin-4-yl)oxy)methyl)benzyl)piperazin-1-yl)-3-fluorobenzonitrile. 3-(4-((4-(bromomethyl)benzyl)oxy)-1-oxoisoindolin-2-yl)piperidine-2,6-dione (5.0 g, 11.28 mmol) was placed in a flask with 3-fluoro-4-(piperazin-1-yl)benzonitrile (2.315 g, 11.28 mmol), diisopropylethylamine (5.91 ml, 33.8 mmol), and acetonitrile (100 ml). The reaction mixture was stirred at 40° C. for 18 h. Volatile organics were removed under reduced pressure and purification by standard methods provided 4-(4-(4-(((2-(2,6-dioxopiperidin-3-yl)-1-oxoisoindolin-4-yl)oxy)methyl)benzyl)piperazin-1-yl)-3-fluorobenzonitrile. $^1$H NMR (400 MHz, DMSO-$d_6$) δ 10.97 (s, 1H), 7.68 (dd, J=1.96, 13.45 Hz, 1H), 7.56 (dd, J=1.77, 8.38 Hz, 1H), 7.43-7.52 (m, 3H), 7.30-7.38 (m, 4H), 7.11 (t, J=8.80 Hz, 1H), 5.24 (s, 2H), 5.11 (dd, J=5.14, 13.33 Hz, 1H), 4.37-4.46 (m, 1H), 4.22-4.30 (m, 1H), 3.54 (s, 2H), 3.12-3.23 (m, 4H), 2.84-2.98 (m, 1H), 2.52-2.62 (m, 5H), 2.36-2.48 (m, 1H), 1.92-2.04 (m, 1H). MS (ESI) m/z 568.2 [M+1]$^+$. Anal. Calcd for $C_{32}H_{30}FN_5O_4$: C, 67.71; H, 5.33; N, 12.34. Found: C, 67.50; H, 5.44; N, 12.34.

Example 2: Synthesis of (S)-4-(4-(4-(((2-(2,6-dioxopiperidin-3-yl)-1-oxoisoindolin-4-yl)oxy)methyl)benzyl)piperazin-1-yl)-3-fluorobenzonitrile (Compound 2)

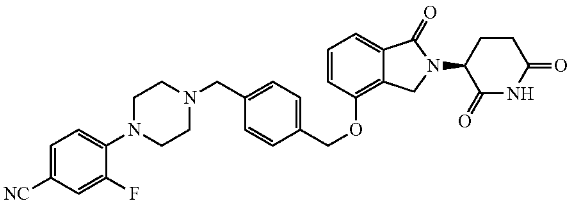 [SMILES: N#Cc1ccc(N2CCN(Cc3ccc(COc4cccc5c4CN([C@H]4CCC(=O)NC4=O)C5=O)cc3)CC2)c(F)c1]

tert-Butyl (4S)-5-amino-4-(benzyloxycarbonylamino)-5-oxo-pentanoate. To a solution of (2S)-2-(benzyloxycarbonylamino)-5-tert-butoxy-5-oxo-pentanoic acid (150 g, 445 mmol) in 1,4-dioxane (1.50 L) was added di-tert-butyl dicarbonate (155 g, 711 mmol), pyridine (70.3 g, 889 mmol) and ammonium bicarbonate (105 g, 1.33 mol). The reaction mixture was stirred at 18° C. for 16 h and then concentrated. The residue was dissolved in ethyl acetate (5.0 L) and water (5.0 L), the organic layer was separated and washed with HCl (3.0 mL, 1 N), saturated sodium bicarbonate (3.0 L), brine (3.0 L), dried over anhydrous sodium sulfate, filtered and concentrated to give crude tert-butyl (4S)-5-amino-4-(benzyloxycarbonylamino)-5-oxo-pentanoate (450 g, crude) as a white solid, which was used in the next step without further purification. $^1$H NMR 400 MHz DMSO-$d_6$ δ: 7.35-7.30 (m, 5H), 7.02 (s, 1H), 5.01 (d, J=3.2 Hz, 1H), 3.93-3.90 (m, 1H), 2.20 (t, J=8.0 Hz, 2H), 1.88-1.84 (m, 1H), 1.72-1.69 (m, 1H), 1.35 (s, 9H).

tert-Butyl (4S)-4,5-diamino-5-oxo-pentanoate. To a solution of tert-butyl (4S)-5-amino-4-(benzyloxycarbonylamino)-5-oxo-pentanoate (112 g, 333 mmol) in methanol (1.0 L) was added 10% palladium on carbon (15 g) under nitrogen. The suspension was degassed under vacuum and purged with hydrogen several times. The mixture was stirred under hydrogen gas (40 psi) at 30° C. for 16 h. The reaction mixture was filtered and the filtrate was concentrated to give crude tert-butyl (4S)-4,5-diamino-5-oxo-pentanoate as a colorless oil. $^1$H NMR 400 MHz DMSO-$d_6$ δ: 7.30 (s, 1H), 6.95 (s, 1H), 3.10-3.07 (m, 1H), 2.27-2.23 (m, 2H), 1.69-1.78 (m, 1H), 1.59-1.55 (m, 1H), 1.38 (s, 9H).

Methyl 3-hydroxy-2-methyl-benzoate. Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) until pH>3. The solid was dried under vacuum at 45° C. to give methyl 3-hydroxy-2-methyl-benzoate (700 g, 80.4% yield) as a gray solid. $^1$H NMR: 400 MHz DMSO-$d_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl)(dimethyl)silyl]oxy-2-methyl-benzoate. Two batches (240 g each) were run in parallel. To a solution of methyl 3-hydroxy-2-methyl-benzoate (240 g, 1.44 mol) in N,N-dimethylformamide (1.40 L) were added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred followed by separation of the organic phase. The combined organics (two batches combined) were washed with water (1700 mL×3) and concentrated to 1500 mL (KF<0.05%). The product was stored as an isopropyl acetate solution which was used in the next step without further purification.

Methyl 2-(bromomethyl)-3-[tert-butyl)(dimethyl)silyl]oxy-benzoate. Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) were removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl(dimethyl)silyl]oxy-benzoate (920 g, 95.5% yield) as dark orange oil. $^1$H NMR: 400 MHz DMSO-$d_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

tert-Butyl (4S)-5-amino-4-[4-[tert-butyl)(dimethyl)silyl]oxy-1-oxo-isoindolin-2-yl]-5-oxo-pentanoate. To a solution of tert-butyl (4S)-4,5-diamino-5-oxo-pentanoate (130 g, 643 mmol) in acetonitrile (4.0 L) was added methyl 2-(bromomethyl)-3-[tert-butyl(dimethyl)silyl]oxy-benzoate (210 g, 584 mmol) and diisopropylethylamine (113 g, 877 mmol). The reaction mixture was stirred at 50° C. for 16 h. The reaction mixture was concentrated to remove most of the acetonitrile, the residue was dissolved in methyl tert-butyl ether (2.0 L) and water (1.5 L), the organic layer was washed with saturated monopotassium phosphate (1.0 L×2), brine (1.0 L), dried over anhydrous sodium sulfate, filtered and concentrated to give crude tert-butyl (4S)-5-amino-4-[4-[tert-butyl(dimethyl)silyl]oxy-1-oxo-isoindolin-2-yl]-5-oxo-pentanoate (524 g), which was used into next step without further purification.

tert-Butyl (4S)-5-amino-4-(4-hydroxy-1-oxo-isoindolin-2-yl)-5-oxo-pentanoate. To a solution of tert-butyl (4S)-5-amino-4-[4-[tert-butyl(dimethyl)silyl]oxy-1-oxo-isoindolin-2-yl]-5-oxo-pentanoate (275 g, 613 mmol,) in methanol (2.0 L) was added tetrabutylammonium fluoride trihydrate (38.7 g, 123 mmol). The mixture was stirred at 18° C. for 16 h. The reaction mixture was concentrated to remove most of the methanol, the residue was dissolved in dichloromethane/water (3 L/2 L), the organic layer was washed with brine (1.0 L), dried over anhydrous sodium sulfate, filtered, and concentrated to give crude product which was purified by silica gel column to give product (260 g). Product was added into acetonitrile (750 mL) and the mixture was stirred at 60° C. for 2 h, cooled to 18° C., and stirred for another 2 h. The solid was filtered and the cake was dried to give tert-butyl (4S)-5-amino-4-(4-hydroxy-1-oxo-isoindolin-2-yl)-5-oxo-pentanoate (248 g, 60.5% yield) as a gray solid. $^1$H NMR 400 MHz DMSO-$d_6$ δ: 10.00 (s, 1H), 7.54 (s, 1H), 7.29 (t, J=7.6 Hz, 1H), 7.14 (d, J=4.8 Hz, 2H), 4.72-4.68 (m, 1H), 4.49-4.28 (m, 2H), 2.17-1.97 (m, 4H), 1.31 (s, 9H).

4-(4-(4-(Chloromethyl)benzyl)piperazin-1-yl)-3-fluorobenzonitrile. 1,4-Bis(chloromethyl)benzene (51.2 g, 292 mmol) was placed in a flask with acetonitrile (195 mL) and N,N-dimethylformamide (195 mL). The reaction mixture was stirred at ambient temperature until all the solids dissolved. Diisopropylamine (51.1 mL, 292 mmol) was then added along with 3-Fluoro-4-(piperazin-1-yl)benzonitrile (20 g, 97 mmol). The reaction was heated to 60° C. for 1 h. The acetonitrile was removed under reduced pressure. The remaining mixture was partitioned between ethyl acetate (1.0 L), water (700 mL), and brine (300 mL). The organic layer was separated and the aqueous layer was extracted with ethyl acetate twice. Volatile organics were combined and removed under reduced pressure. The solid was dissolved in minimal dichloromethane and purified on silica gel column (0-100% ethyl acetate in hexanes over 3 L). Fractions containing desired product were combined and volatile organics were removed under reduced pressure. The residue was dissolved in minimal dichloromethane and purified a second time on silica gel column (10% isocratic ethyl acetate in hexanes over 800 mL followed by 20-80% ethyl acetate in hexanes over 4 L). Fractions containing desired product were combined and volatile organics were removed under reduced pressure to afford 4-(4-(4-(chloromethyl)benzyl)piperazin-1-yl)-3-fluorobenzonitrile (22.7 g, 66.0 mmol, 67.7% yield) as an off-white solid. $^1$H NMR (400 MHz, $CDCl_3$) δ ppm 7.33-7.39 (m, 5H) 7.29 (d, J=1.96 Hz, 1H) 7.25 (d, J=1.96 Hz, 1H) 6.91 (t, J=8.56 Hz, 1H) 4.60 (s, 2H) 3.58 (s, 2H) 3.19-3.27 (m, 4H) 2.58-2.66 (m, 4H). MS (ESI) m/z 344.2 $[M+1]^+$.

(S)-tert-Butyl 5-amino-4-(4-((4-((4-(4-cyano-2-fluorophenyl)piperazin-1-yl)methyl)benzyl)oxy)-1-oxoisoindolin-2-yl)-5-oxopentanoate. (S)-tert-Butyl 5-amino-4-(4-hydroxy-1-oxoisoindolin-2-yl)-5-oxopentanoate (22.05 g, 65.9 mmol) was placed in a flask with 4-(4-(4-(chloromethyl)benzyl)piperazin-1-yl)-3-fluorobenzonitrile (22.67 g, 65.9 mmol), potassium carbonate (18.23 g, 132 mmol), and N,N-dimethylformamide (330 mL). The reaction mixture was heated to 45° C. for 16 h. The reaction was diluted with ethyl acetate (50 mL) and filtered. The filtrate was partitioned with ethyl acetate (900 mL) and water (600 mL) and brine (200 mL). The organic layer was isolated and partitioned with water (600 mL). The organic layer was isolated and all organic layers were combined, dried over sodium sulfate, and volatiles were removed under reduced pressure. The residue was treated with 20% ethyl acetate in hexanes and volatiles were removed under reduced pressure to afford (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (44.02 g, 68.6 mmol, 104% yield) as an off-white solid. Yield was slightly over quantitative as some N, N-dimethylformamide remained. $^{1}H$ NMR (400 MHz, $CDCl_3$) δ ppm 7.43-7.49 (m, 2H) 7.40 (s, 4H) 7.36 (dd, J=8.38, 1.28 Hz, 1H) 7.29 (d, J=1.96 Hz, 1H) 7.26 (d, J=1.83 Hz, 1H) 7.11 (dd, J=7.64, 1.16 Hz, 1H) 6.92 (t, J=8.50 Hz, 1H) 6.23 (br s, 1H) 5.24-5.32 (m, 1H) 5.15 (s, 2H) 4.86-4.94 (m, 1H) 4.38-4.55 (m, 2H) 3.61 (s, 2H) 3.18-3.32 (m, 4H) 2.58-2.70 (m, 4H) 2.09-2.47 (m, 4H) 1.43 (s, 8H). MS (ESI) m/z 642.4 $[M+1]^+$.

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile. (S)-tert-Butyl 5-amino-4-(4-((4-((4-(4-cyano-2-fluorophenyl)piperazin-1-yl)methyl)benzyl)oxy)-1-oxoisoindolin-2-yl)-5-oxopentanoate (12.1 g, 18.86 mmol) was placed in a vial with acetonitrile (189 mL) and benzenesulfonic acid (3.96 g, 24.51 mmol). The reaction mixture was placed under vacuum and purged with nitrogen. This was repeated once more and the mixture was then heated to 85° C. overnight under a nitrogen atmosphere. The reaction mixture was poured warm directly into 2 separatory funnels containing dichloromethane (1000 mL) and ethyl acetate (300 mL). To this mixture a saturated solution of sodium bicarbonate (900 mL), water (100 mL), and brine (450 mL) was added. The organic layer was isolated and the aqueous layer was extracted with dichloromethane (800 mL) and ethyl acetate (200 mL). The combined organic layers were dried over anhydrous magnesium sulfate, and concentrated. Purification by standard methods provided the title compound. $^{1}H$ NMR (400 MHz, DMSO-$d_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 $[M+1]^+$.

Example 3: Compound 1, Compound 2, and Compound 3 have Potent Antiproliferative Activity in Multiple Myeloma Cells The relative effectiveness of Compound 2 and Compound 3 to promote the destruction of Aiolos protein by the $CRL4^{CRBN}$ E3 ubiquitin ligase was investigated in DF15 myeloma cells at different time points (45 minutes, 90 minutes, and 3 hours). DF15 cells expressing Enhanced ProLabel (ePL)-tagged Aiolos were incubated with Compound 2 or Compound 3 for 45 minutes, 90 minutes, or 3 hours. Cell extracts were then generated and the amount of Aiolos ePL protein was determined by ePL luminescence assay. Values shown in Table 1 correspond to data presented in FIG. 1 for Aiolos content vs. concentration. The results demonstrated that a time-dependent and concentration-dependent loss of Aiolos was induced by both enantiomers (FIG. 1).

TABLE 1

Compounds 2 and 3 Promoted Aiolos Degradation

| Compound | Degradation of Aiolos $IC_{50}$ (μM) 45 minutes | 90 minutes | 3 hours |
|---|---|---|---|
| Compound 2 | >0.1 (27% inhibition at 0.001 μM) | 0.00036 | 0.000031 |
| Compound 3 | >0.1 (13% inhibition at 0.001 μM) | 0.0059 | 0.00045 |

Collectively, the experiments indicated that Compounds 2 and Compound 3 degrade Aiolos in a time-dependent and concentration-dependent manner. The data also demonstrate that Aiolos degradation is an effective biomarker for monitoring the efficacy of these compounds.

Figure 2:
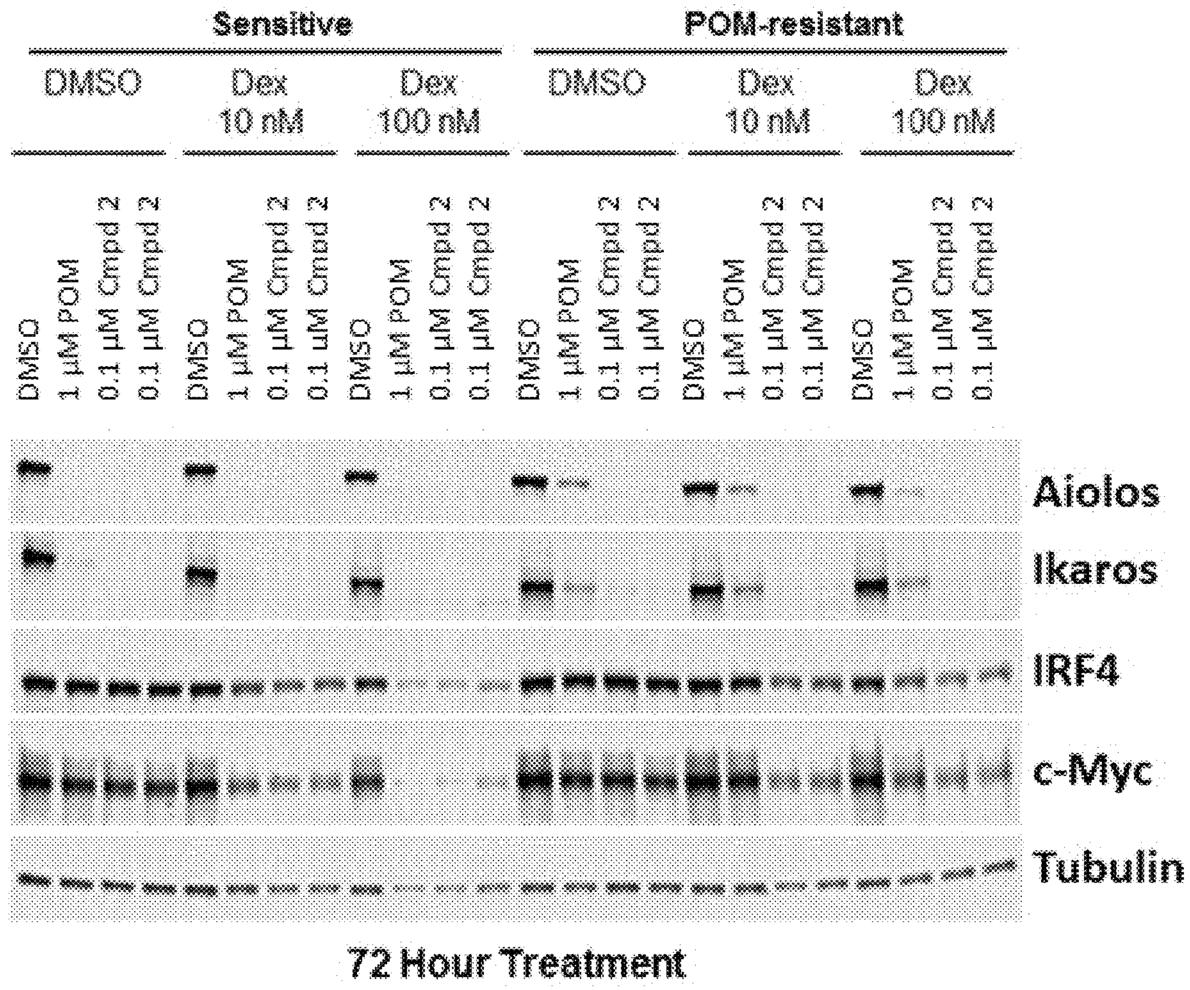
Figure 3:
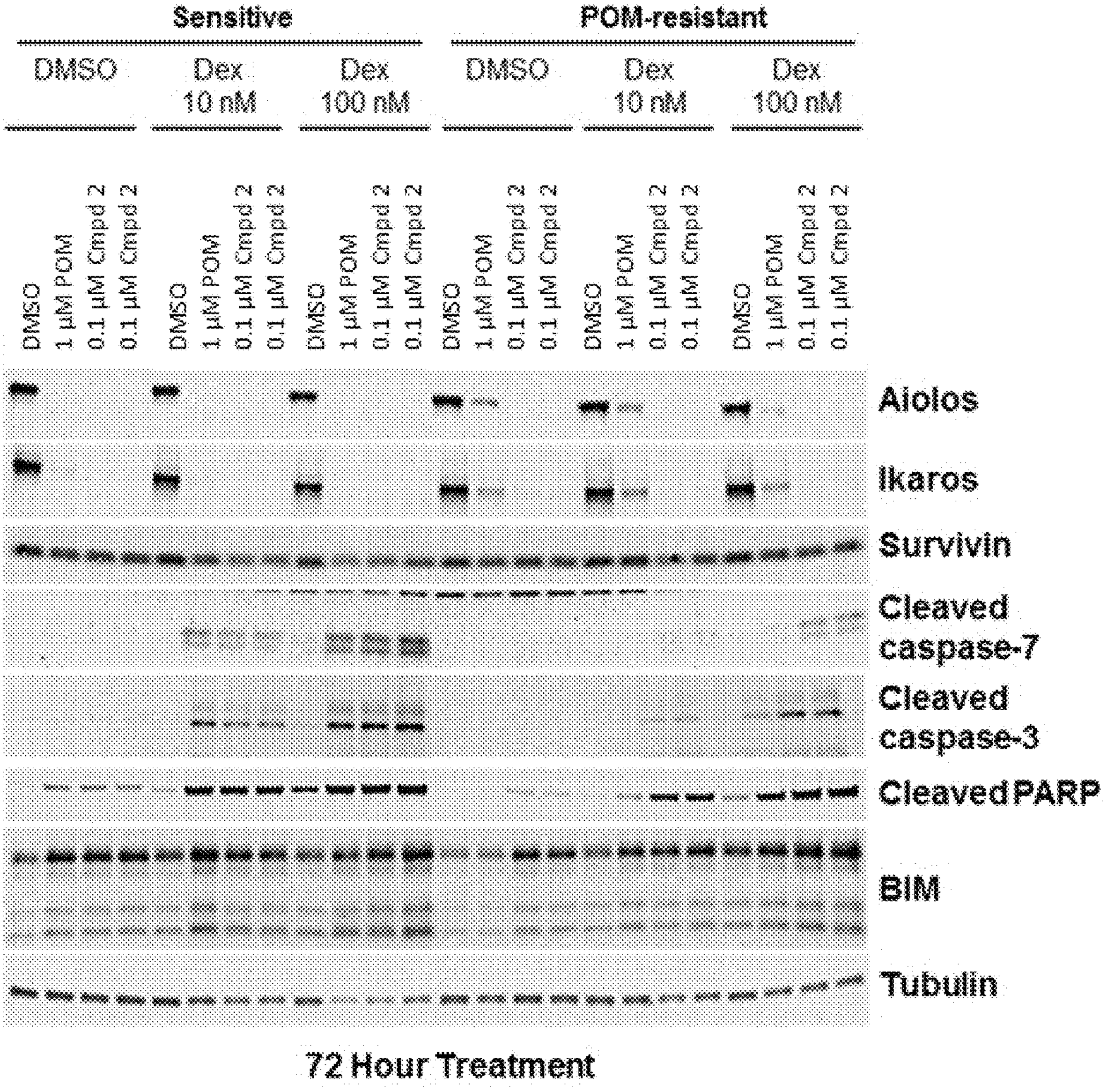

Example 4: Compound 2 Induced Apoptosis and Downregulation of Factors Essential for Tumor Survival, and Synergized with Dexamethasone To determine whether Compound 2 synergizes with dexamethasone, the effect of adding dexamethasone on the loss of known $CRL4^{CRBN}$ E3 ubiquitin ligase substrates, Aiolos, Ikaros, and ZFP91, was examined using pomalidomide-sensitive (OPM2) or resistant (OPM2-P1) myeloma cells. Dexamethasone alone or in combination with Compound 2 led to the degradation of Aiolos, and Ikaros in OPM2 and OPM2-P1 cells after 72 hours of treatment (FIG. 2). Importantly, a greater loss of downstream effector proteins (c-Myc and IRF4) was evident with the addition of 10 or 100 nM dexamethasone to Compound 2 (FIG. 2). In addition, increased induction of apoptotic markers (Bcl-2 interacting mediator [BIM], cleaved caspase-3, cleaved caspase-7, and cleaved poly [adenosine diphosphate ribose] polymerase [PARP]) was observed at 72 hours, as measured by Western blot (FIG. 3).

Similarly, a five-day incubation of OPM2 myeloma cells with Compound 2 alone significantly decreased the expression level of Aiolos and Ikaros, as well as ZFP91 (FIG. 4). Ikaros and Aiolos degradation was followed by reduction in the levels of two additional and highly critical transcription factors, c-Myc and IRF4 (FIG. 4). The loss or reduction of these factors was associated with an increase of the cyclin-dependent kinase inhibitor p21 and induction of apoptosis, as measured by cleaved caspase-3 (FIG. 4). The results suggest that Compound 2 elicits its antitumor activity via eliminating the expression of key multiple myeloma survival factors, including IRF4 and c-Myc.

Taken together, these results indicate that Aiolos, Ikaros, ZFP91, c-Myc, and IRF4, as well as apoptotic markers, such as Bcl-2 interacting mediator (BIM), cleaved caspase-3, cleaved caspase-7, and cleaved poly (adenosine diphosphate ribose) polymerase (PARP), and p21 can serve as biomarkers for monitoring the efficacy of treatment with Compound 2.

Example 5: Cereblon and Ikaros Degradation are Required for the Antiproliferative Activity of Compound 2

Figure 5A:
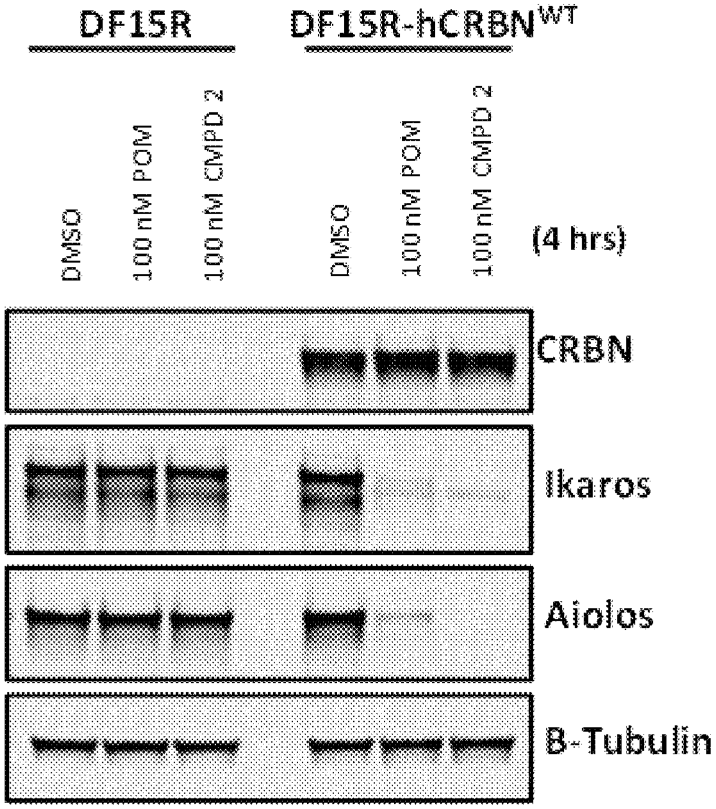

To determine whether cereblon could serve as a biomarker for predicting response to Compound 2, the myeloma cell line DF15R was treated with Compound 2. The DF15R cell line is a multiple myeloma cell line that has developed resistance to lenalidomide and pomalidomide by continuous administration of pomalidomide (up to 100 and lacks detectable levels of CRBN protein. Treatment of this cell line with Compound 2 did not show any degradation of Ikaros or Aiolos (FIG. 5A). Reintroduction of CRBN protein into the DF15R cells reactivated the Compound 2-induced degradation of Ikaros and Aiolos (FIG. 5A). These results indicate that CRBN is important in mediating the response to Compound 2. Thus, CRBN levels can serve as a biomarker to assess the potential response to Compound 2.

Compound 2 was shown to downregulate Ikaros, Aiolos, and ZFP91 (FIG. 4), and CRBN was found to be required for degradation of Ikaros and Aiolos (FIG. 5A). To determine whether the degradation of Ikaros, Aiolos, or ZFP91 was responsible for the effects on c-Myc, IRF4, and p21 or on the apoptosis induced by Compound 2, stabilized mutants of all three proteins were generated and overexpressed one at a time in OPM2 cells (FIG. 5B).

Figure 5B:
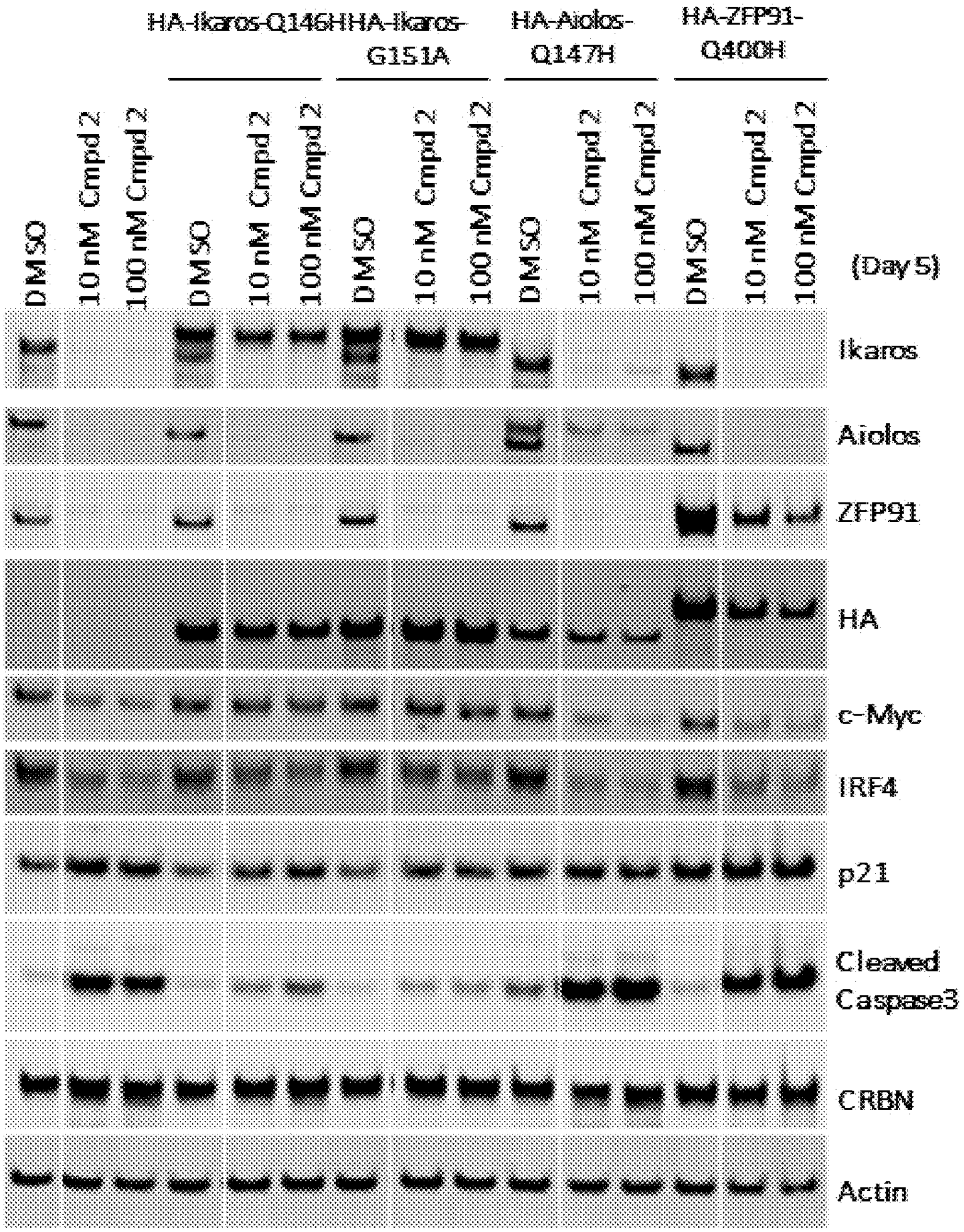

The successful overexpression of the stabilized Ikaros mutants, Ikaros-Q146H or Ikaros-G151A, prevented degradation of Ikaros and abrogated the Compound 2-induced effects on c-Myc, IRF4, p21, and cleaved caspase-3 (FIG. 5B). However, a stabilizing mutation in ZFP91 (Q400H) was not able to abrogate the effect of Compound 2, despite the mutation being able to effectively protect the protein from degradation in the presence of Compound 2 (FIG. 5B).

The effect of the stabilizing mutations on cell proliferation was also measured. Consistent with the effects on the downstream proteins, overexpression of the stabilized Ikaros mutants, Ikaros-Q146H or Ikaros-G151A, abrogated the anti-proliferative effects of Compound 2 (Table 2). Specifically, the concentration at which cells had their proliferation inhibited by 50% upon treatment with Compound 2 increased more than 200 fold (>100 nM) in the cells overexpressing stabilized Ikaros mutants, relative to the parental cells (0.488 nM) (Table 2). There was no apparent downstream effect of stabilizing ZFP91 or reduction in sensitivity to the antiproliferative activity of Compound 2 (FIG. 5B and Table 2). The potential contributions of Aiolos degradation to the inhibition of MM cell growth by Compound 2 could not be confirmed in cells overexpressing the Aiolos mutant, due to the less efficient stabilization of Aiolos to degradation in comparison with Ikaros in this particular assay.

Taken together, these results further demonstrate that Ikaros degradation is required for the activity of Compound 2, and indicate that Ikaros is an important biomarker for the activity of Compound 2.

TABLE 2

Inhibition of Proliferation of OPM2 Cells

| Compound | Inhibition of Proliferation of OPM2 Cells $IC_{50}$ (nM) | | | | | | |
|---|---|---|---|---|---|---|---|
| | Parental | Ikaros | Ikaros-Q146H | Ikaros-G151A | Aiolos | Aiolos Q147H | ZFP91-Q400H |
| Compound 2 | 0.08 | 0.13 | >100 | >100 | 0.08 | 0.06 | 0.08 |
| Pomalidomide | 64 | 91 | >100 | >100 | 89 | 56 | 73 |
| Lenalidomide | >100 | >100 | >100 | >100 | >100 | >100 | >100 |

Figures 6A, 6B:
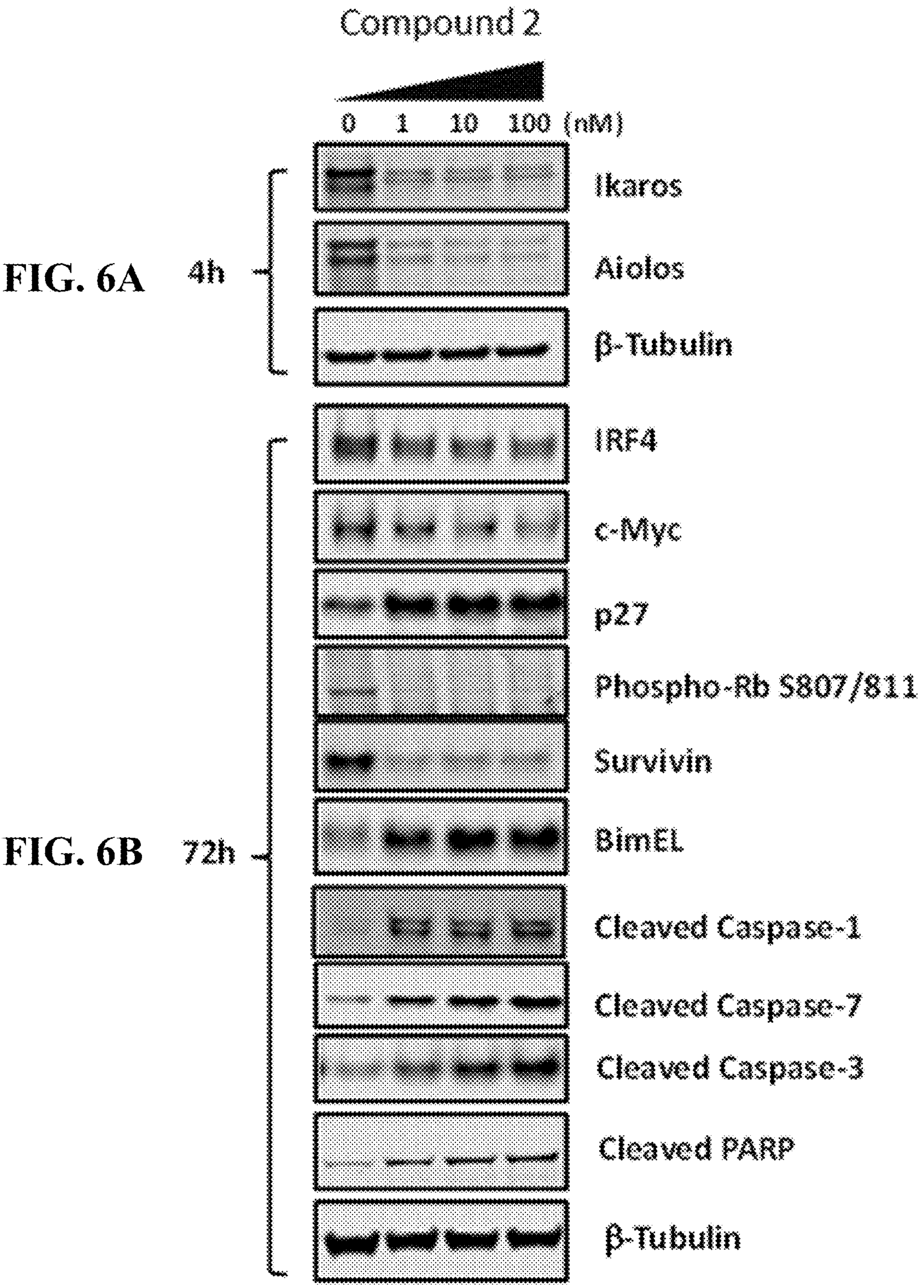

Example 6: Compound 2-Induced Degradation of Ikaros and Aiolos Correlated with G1 Cell Cycle Arrest and Apoptosis in Multiple Myeloma Cells To evaluate the functional response of multiple myeloma cells to treatment with Compound 2, the myeloma cell line H929-1051, which is resistant to lenalidomide, was treated with Compound 2 for 4 hours (FIG. 6A) or 72 hours (FIG. 6B). Incubation with concentrations as low as 1 nM of Compound 2 promoted the robust degradation of Ikaros and Aiolos within 4 hours (FIG. 6A).

Figure 10:
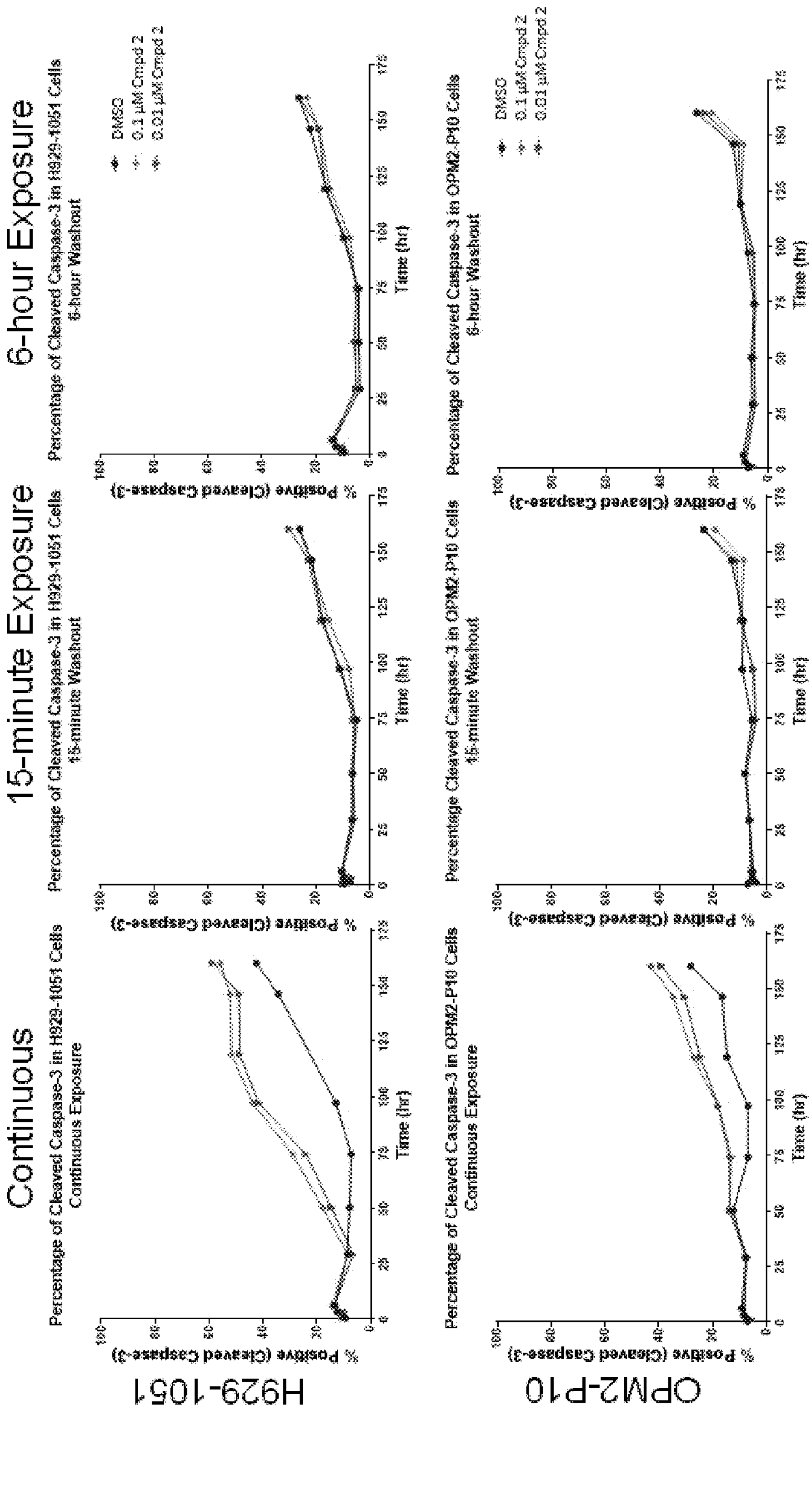

In agreement, after 72 hours of treatment with Compound 2 there was an appreciable decrease in the phosphorylation of pRB1, and an increase in the levels of the CDK inhibitor p27 in the H929-1051 cells (FIG. 6B). These events were accompanied by a decrease in the level of survivin, a dramatic increase in the level of the proapoptotic protein Bim extra-long isoform (BimEL), and cleavage of Caspase-1, Caspase-7, Caspase-3, and PARP (FIG. 6B). The results demonstrate that the antitumor activity of Compound 2 in lenalidomide- and/or pomalidomide-resistant cells is due to the degradation of Ikaros and Aiolos, leading to cell cycle arrest and apoptosis. Furthermore, the nearly complete and sustained degradation of Aiolos and Ikaros demonstrated the in vitro efficacy of Compound 2, even in cells that were resistant to treatment with lenalidomide and pomalidomide (FIG. 10). These results demonstrate that Compound 2 induces cell cycle arrest and apoptosis, and that detection of Ikaros, Aiolos, IRF4, c-Myc, p27, phospho-Rb, BimEL, cleaved-Caspase-1, -Caspase-7, -Caspase-3, and -PARP can all serve as biomarkers for treatment with Compound 2.

Figure 7A:
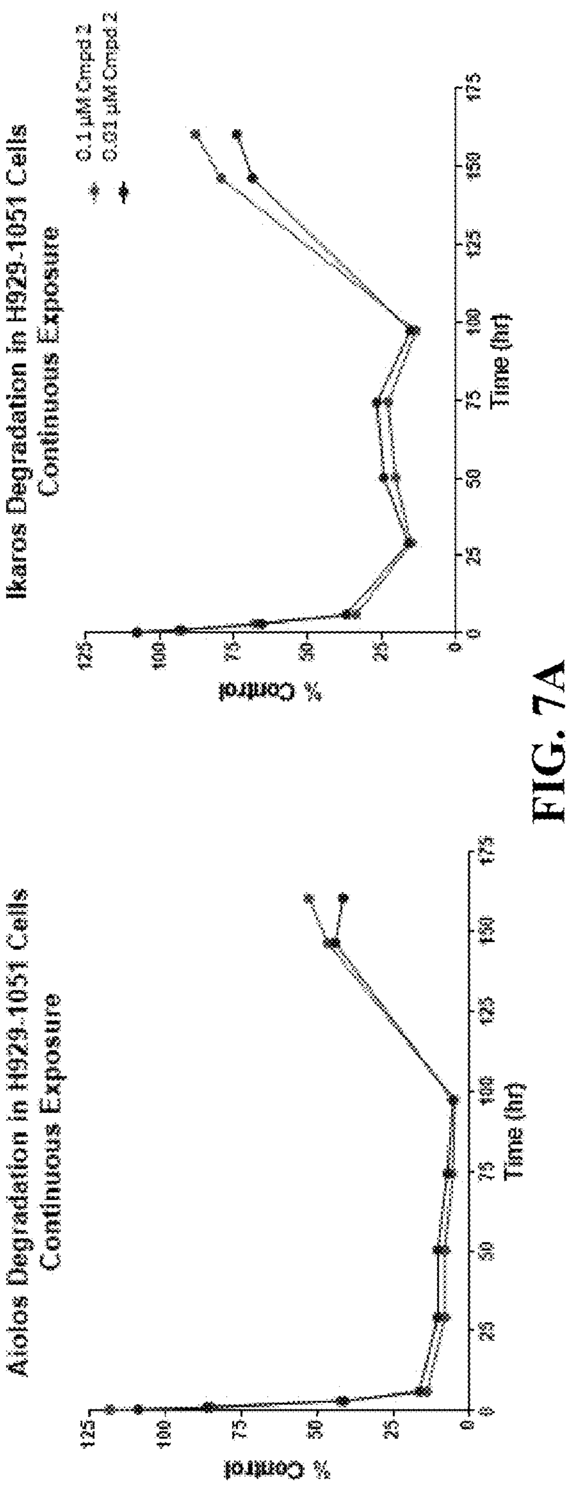
Figure 7B:
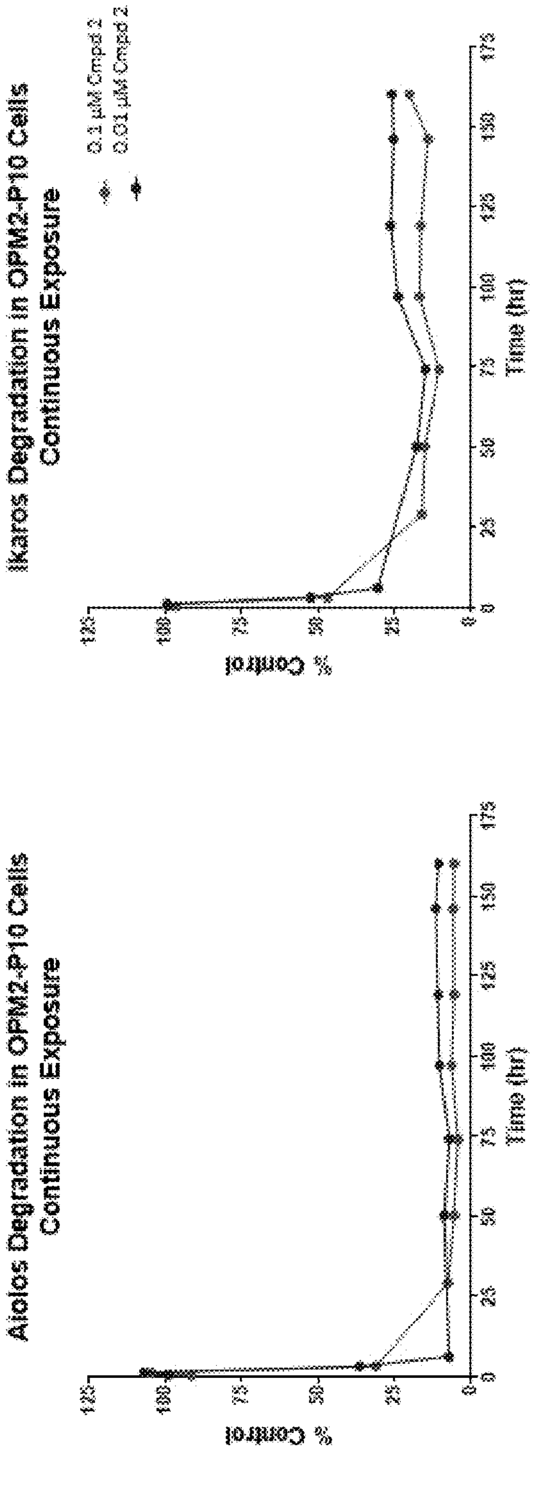

Example 7: Compound 2 Induced Degradation of Aiolos and Ikaros, and Increased Apoptosis in Myeloma Cell Lines The effects of continuous exposure of Compound 2 on the degradation and re-expression of Aiolos and Ikaros, and the induction of apoptosis were measured in the multiple myeloma cell lines H929-1051 and OPM2-P10, which are resistant to lenalidomide and pomalidomide, respectively. The cell lines were treated with a single continuous exposure to Compound 2, with no washout, and the levels of Aiolos and Ikaros were measured by flow cytometry. After treatment there was greater than 70% degradation of Aiolos and Ikaros within 3 to 6 hours, depending on the cell line (FIG. 7A and FIG. 7B). The depletion of substrates was sustained for up to 70 hours in H929-1051 cells or up to 100 hours in OPM2-P10 cells (FIG. 7A and FIG. 7B). Increasing the concentration 10-fold to 0.1 μM produced little to no additional degradation (FIG. 7A and FIG. 7B).

In H929-1051 cells, the degradation of Aiolos lasted for 75 to 100 hours, whereas the degradation of Ikaros levels was prolonged for a shorter period of time (FIG. 7A and FIG. 7B). The degradation of both proteins was sustained for more than 150 hours in the OPM2-P10 cells (FIG. 7A and FIG. 7B).

Figure 8:
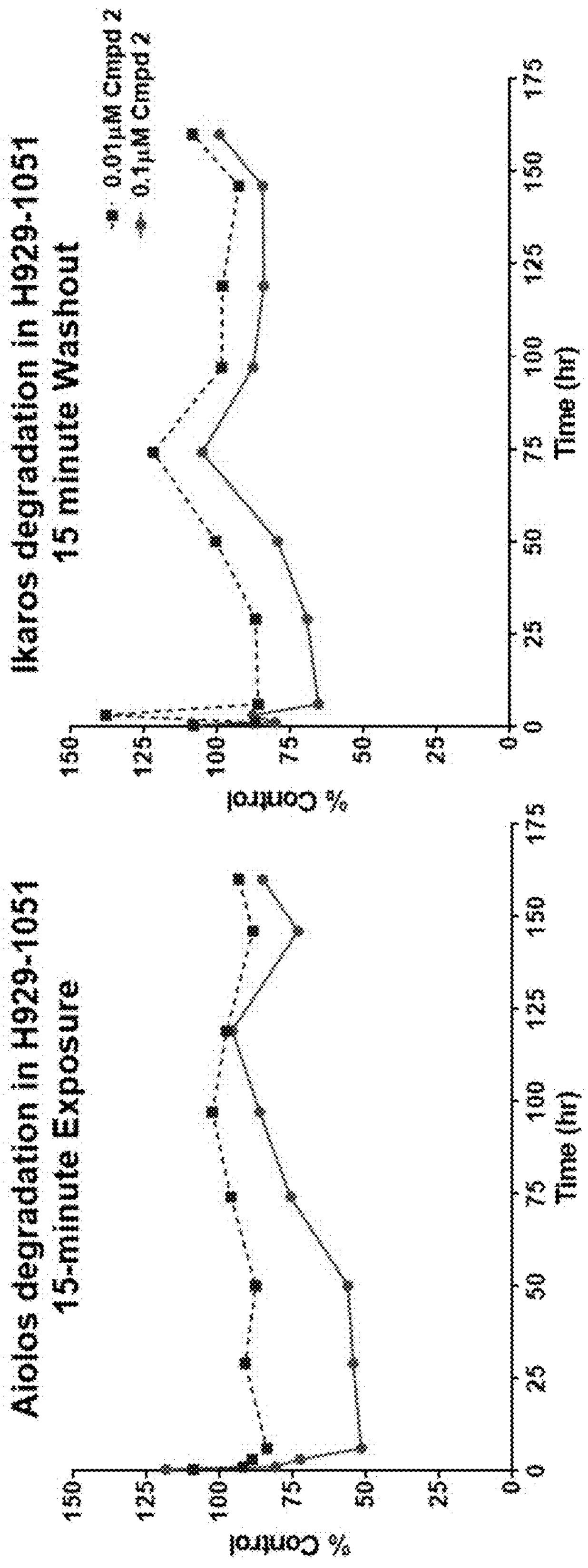

The effect of transient exposures of H929-1051 cells to Compound 2 on the degradation of Aiolos and Ikaros was also evaluated. A short transient exposure of 15 minutes at 0.1 μM Compound 2 induced Aiolos and Ikaros degradation (FIG. 8). Although the extent of degradation (25% to 50%) was not complete, a prolonged pharmacodynamic (PD) effect was seen that lasted between 25 and 50 hours post-exposure (FIG. 8).

Figure 9:
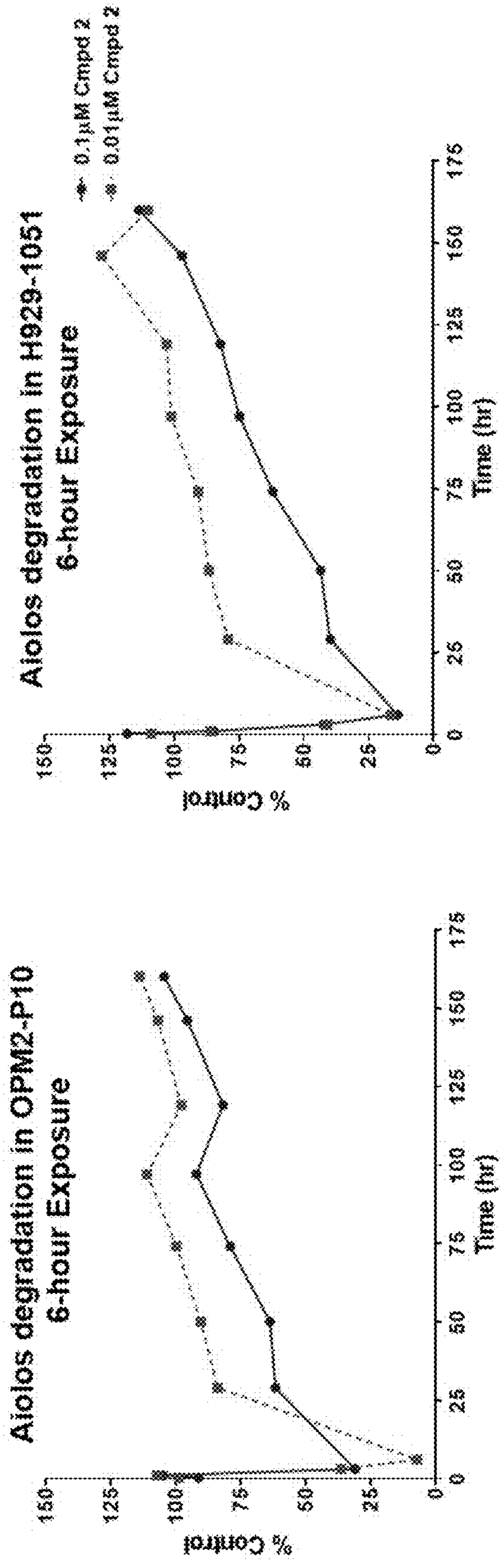

To further understand the kinetics of Compound 2 exposure and Aiolos and Ikaros degradation, a longer exposure of 6 hours to Compound 2 (0.01 and 0.1 μM), followed by washout was investigated. Treatment with Compound 2 produced greater than 70% degradation of Aiolos and Ikaros (FIG. 9). The washout of Compound 2 after a single 6-hour exposure resulted in a rapid recovery from degradation for both proteins (FIG. 9). Greater than 75% substrate recovery was seen by 25 hours in cells exposed to 0.01 μM Compound 2 and within 75 to 100 hours in cultures exposed to 0.1 μM Compound 2 (FIG. 9).

The effect of Aiolos and Ikaros degradation on induction of apoptosis was also evaluated. The nearly complete and prolonged substrate suppression observed upon continuous exposure of Compound 2 coincided with apoptosis induction in MM cells (FIG. 10). A continuous single exposure to 0.01 and 0.1 μM Compound 2 led to induction of apoptosis in H929-1051 and OPM2-P10 cells (within 50 to 75 hours) (FIG. 10). However, the 15 minute or 6 hour transient exposure to Compound 2 precluded the induction of apoptosis (FIG. 10).

Taken together, these observations show that both the magnitude and duration of Aiolos and Ikaros loss are important mediators of apoptosis induction in the MM cell models tested. Further, these data demonstrate the use of Aiolos and Ikaros, as well as apoptosis markers, such as cleaved-Caspase-3, are biomarkers for the response to Compound 2, and also suggest that these biomarkers could be useful for determining or adjusting the dosage of Compound 1, Compound 2, or Compound 3.

Example 8: Compound 2 Inhibited Proliferation of Multiple Myeloma Cell Lines with Acquired Resistance with Low CRBN Compound 2 activity was tested in myeloma cells that have acquired resistance to lenalidomide or pomalidomide due to continued exposure to either compound and, in the process, have acquired downregulated cereblon levels (Table 2). Cells were treated for 5 days and then assessed using an ATP determination assay (CellTiter-Glo). The percentage of control was calculated by subtracting the background and normalizing to the DMSO control (100% of control). The relative percentage of cereblon in cell lines with acquired resistance to lenalidomide or pomalidomide was determined by Western Blot and is presented in Table 3, relative to the CRBN levels in the parental cell lines as 100%.

Figure 11B:
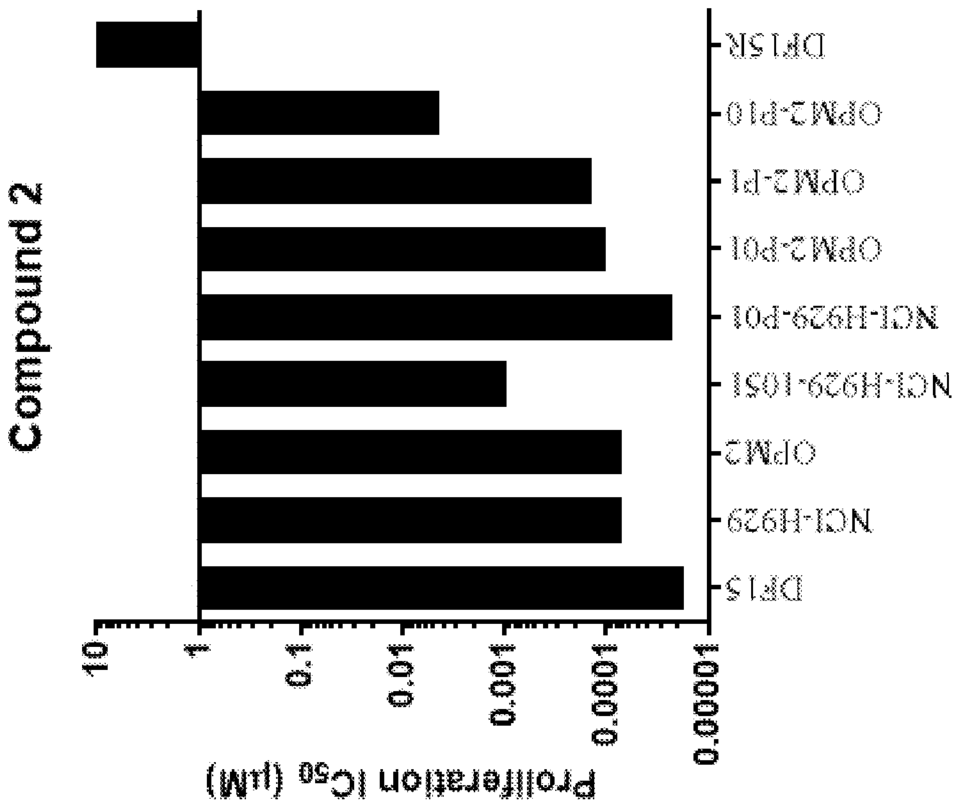
Figure 11A:
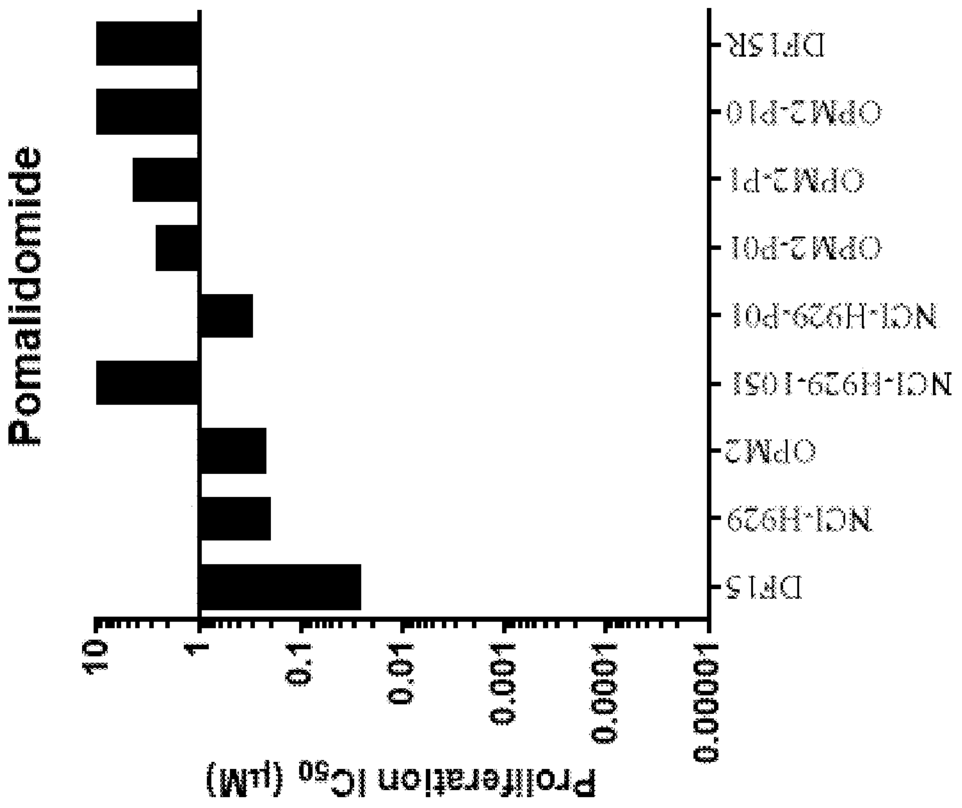

FIG. 11 shows the $IC_{50}$ of the concentration response curves comparing the activity of Compound 2 and pomalidomide in the parental lines (DF15, NCI-H929 and OPM2), a lenalidomide-resistant cell line (NCI-H929-1051), or five pomalidomide-resistant cell lines (NCI-H929-P01, OPM2-P01, OPM2-P1, OPM2-P10 and DF15R).

TABLE 3

Cereblon Protein Expression Levels in Drug Sensitive and Drug Resistant Multiple Myeloma Cell Lines

| Cell Line | Resistance | Cereblon (%) (Normalized to Parental Line) |
|---|---|---|
| DF15 | N/A | 100 |
| DF15R | 100 μM Pom | 14* |
| NCI-H929 | N/A | 100 |
| NCI-H929-1051 | 10 μM Len | 50 |
| NCI-H929-P01 | 100 nM Pom | 35 |
| OPM2 | N/A | 100 |
| OPM2-P01 | 100 nM Pom | 61 |
| OPM2-P1 | 1 μM Pom | 33 |
| OPM2-P10 | 10 μM Pom | 31 |

N/A = not applicable;
Pom = pomalidomide;
*background level, not actual CRBN, which is absent in this cell line Comparison of the cell lines made resistant to pomalidomide or lenalidomide demonstrated that CRBN protein levels were lower than the sensitive, parental cell lines (Table 3). Proliferation was assessed using the CellTitre-Glo® assay. The results of the study show that the cell lines were sensitive to Compound 2, even in multiple models of acquired resistance where CRBN levels were low, as determined by the quantitative assessment of ATP levels present in the media after 5 days (FIG. 11). However, Compound 2 showed little anti-proliferative activity on the DF15R cell line, which lack CRBN expression (FIG. 11 and FIG. 5A).

Taken together these data shows that Compound 2 has very potent anti-multiple myeloma activity in models of acquired resistance with low, but detectable, levels of CRBN. Thus, detectable levels of CRBN can be a biomarker for predicting a patient's responsiveness to Compound 2.

Example 9: Compound 2 Alone, and in Combination with Dexamethasone, Induced Apoptosis in Lenalidomide-Resistant Multiple Myeloma Dexamethasone was assessed for its ability to induce apoptosis as a single agent or in combination with Compound 2. Induction of apoptosis was measured using Caspase-Glo in lenalidomide-resistant multiple myeloma cells (H929-1051). Dexamethasone was dispensed at 20 concentrations, using an acoustic dispenser. The plates were sealed and stored at room temperature for the next day. The final concentrations of compounds for the assay were: dexamethasone (0.8 μM to 0.00002 μM), and Compound 2 (0.001, 0.01, or 0.1 μM). Cells were dispensed into the assay plates with a Multidrop dispenser and duplicate plates were made for the assay. Measurement of apoptosis was made at 72 hours post-compound treatment using a Caspase-Glo 3/7 and CellTiter-Glo Assays. The Caspase-Glo 3/7 luminescence was normalized to the CellTiter-Glo luminescence to account for differences in cell number. The fold change of the treated sample was calculated as follows: normalized caspase of treated sample/average of normalized DMSO control.

Figure 12:
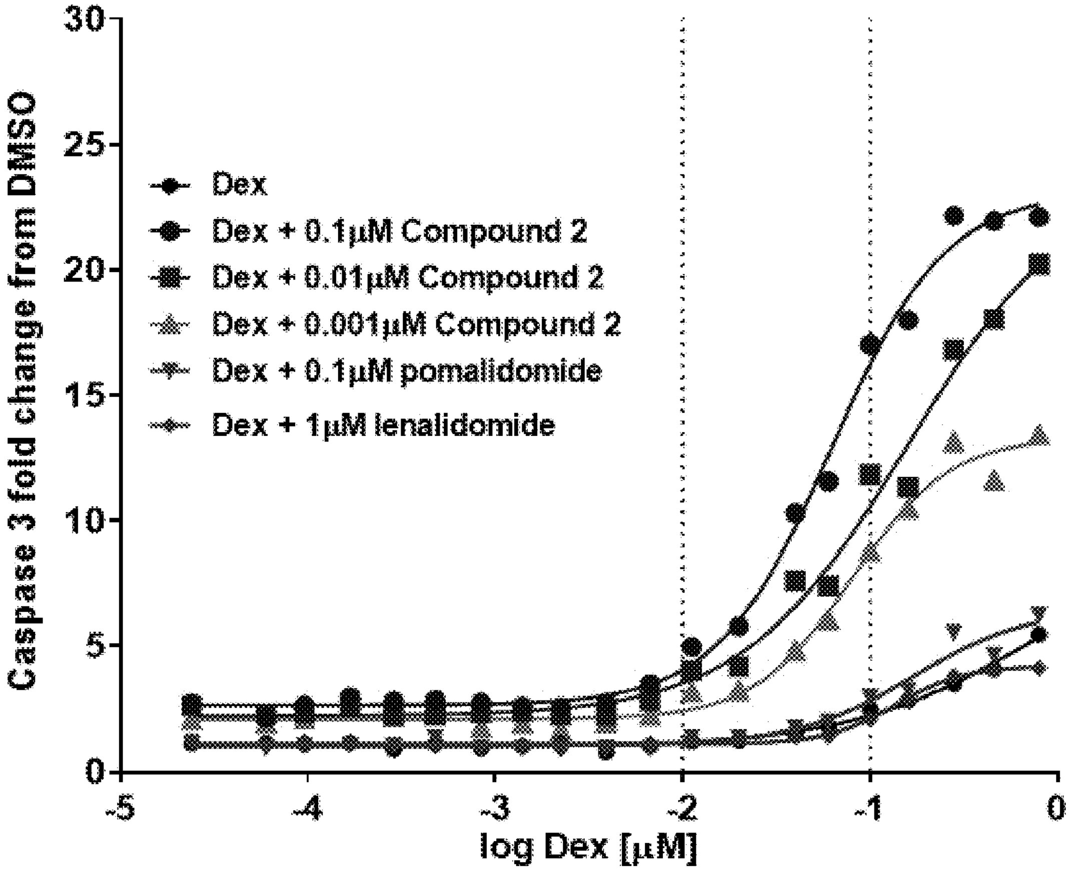

The apoptosis activity of dexamethasone alone or in combination with lenalidomide, pomalidomide, or Compound 2 was measured by Caspase-3 induction. The results indicated that Compound 2 synergized with dexamethasone to reduce cell viability and potentiated the apoptotic ability of dexamethasone in a concentration-dependent manner (FIG. 12). The dose response to treatment with dexamethasone alone resulted in a minor increase in apoptosis, according to Caspase-3 change relative to DMSO treatment (FIG. 12). In contrast, the onset of dexamethasone activity was shifted by 1 log in the presence of Compound 2. Treatment with three different concentrations of Compound 2 potentiated the apoptotic activity of dexamethasone, as measured by Caspase-3 (FIG. 12). Further, even the lowest dose of Compound 2 resulted in a strong induction of apoptosis. As little as 10 nM dexamethasone enhanced the cell killing ability of Compound 2, and low to sub-nanomolar concentrations of Compound 2 potentiated the apoptotic effects of dexamethasone (FIG. 12). This demonstrated the ability of dexamethasone plus Compound 2 to induce apoptosis in lenalidomide-resistant Multiple Myeloma cells, and demonstrates that measurement of Caspase-3 can serve as a biomarker for treatment with Compound 2.

Example 10: Ex Vivo Effect of Compound 2 on Maturation of Myeloid Progenitors to Adult Neutrophils Ex vivo cultures of bone marrow (BM) $CD34^+$ cells from healthy donors (HD) were used to investigate the effect of Compound 2 on neutropenia. Previous data indicated that recovery of mature neutrophil levels to at least 50% of the untreated control level in the assay system utilized in the present study correlates with the absence of induction of, or recovery from, clinically significant neutropenia. Therefore, we monitored the effects of Compound 2 on mature neutrophils.

Figure 13:
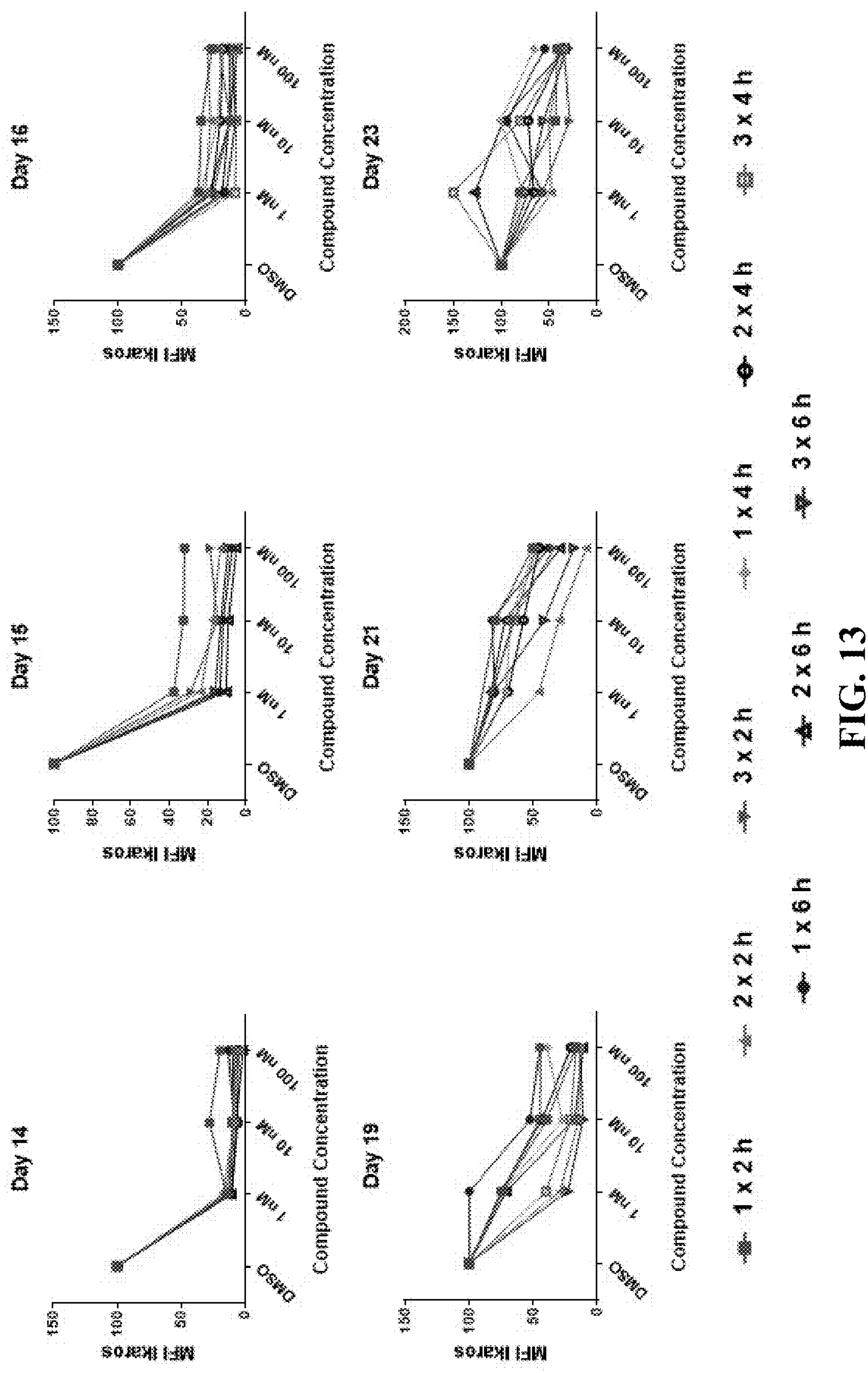

Ikaros protein level was analyzed by flow cytometry after each exposure period, and also at Days 19, 21, and 23 corresponding to 3, 5, and 7 days following the last exposure, respectively. $CD34^+$ cells derived from healthy donor bone marrow were exposed to different concentrations of Compound 2 and different incubation schedules. The percentage of Ikaros content (normalized to the DMSO control) following Compound 2 exposure at concentrations of 1, 10, and 100 nM for 2, 4, and 6 hours on each of 1, 2, or 3 consecutive days starting on Day 14 were measured. At the end of the exposure period, Compound 2 was removed and cells were incubated in the absence of Compound 2 (recovery period). Ikaros was measured by flow cytometry after incubation with Compound 2 (Days 14 to 16) and during recovery on Days 19, 21, and 23. The data were collected for two donors and presented in FIG. 13. Ikaros levels were reduced during Compound 2 exposure and recovered following drug withdrawal in a concentration-dependent manner with no significant differences noted in association with different exposure schedules (FIG. 13). Ikaros levels began returning to normal after at least 3 days following washout, pre-dating full recovery of maturation of late-stage neutrophil precursors. These data suggest that Ikaros degradation in late-stage neutrophil precursors could be an important mediator of neutropenia in recipients of Compound 2. Furthermore, the findings suggest that restoration of Ikaros levels precedes recovery of maturation of neutrophil progenitors, and that successful management of neutropenia in MM patients treated with Compound 2 may be possible with use of appropriate dosing schedules.

Figure 14:
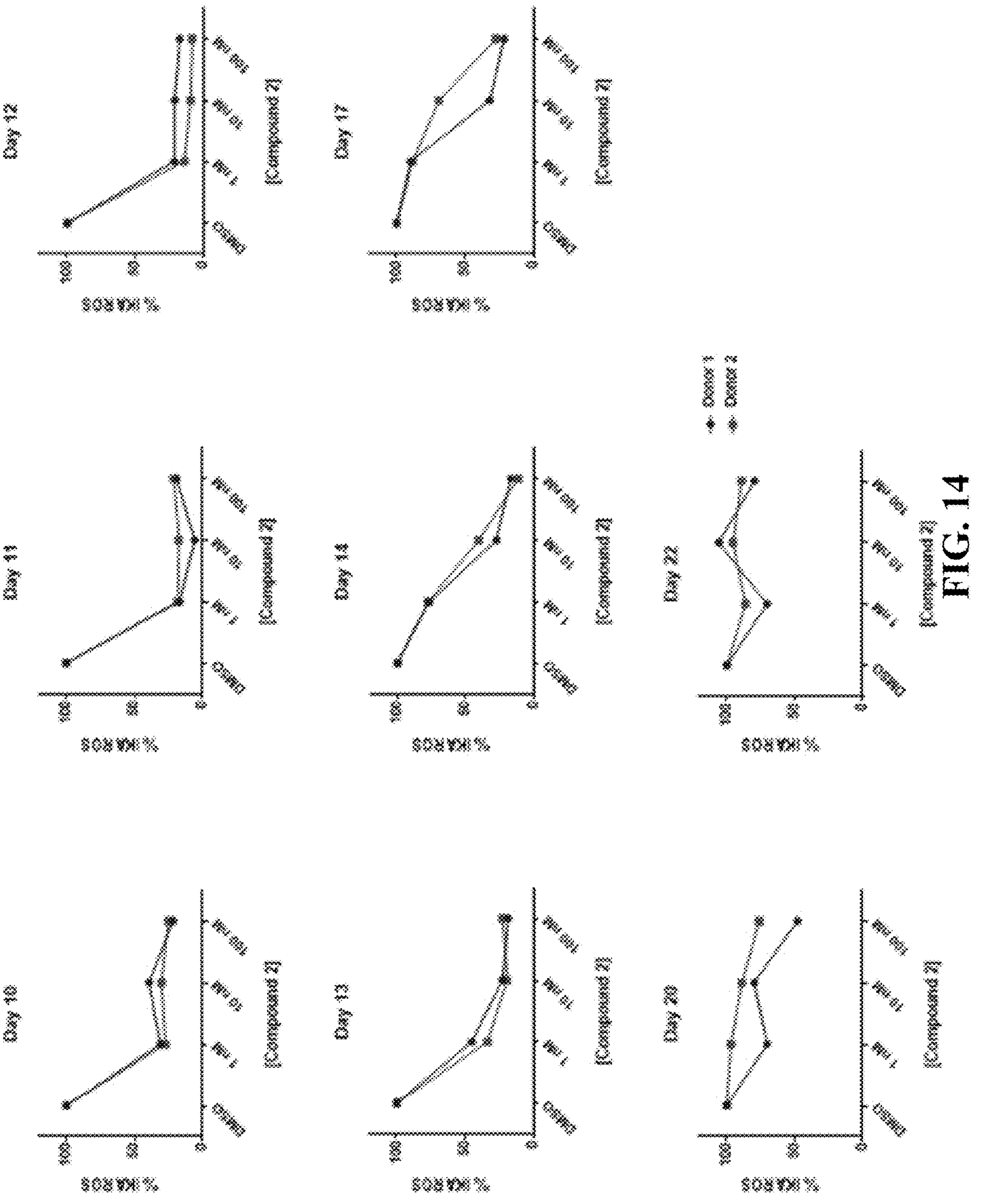
Figure 15:
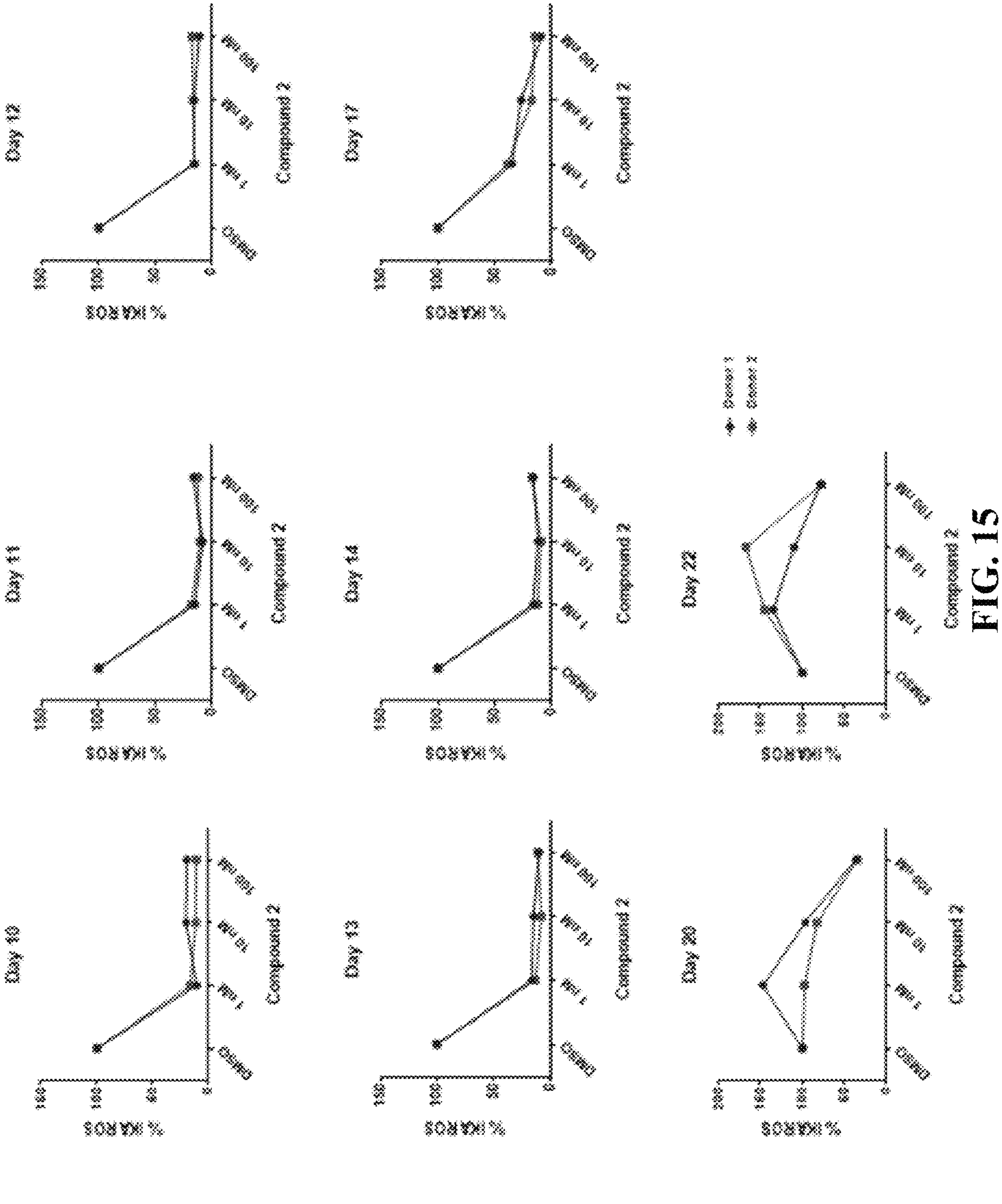
Figure 16A:
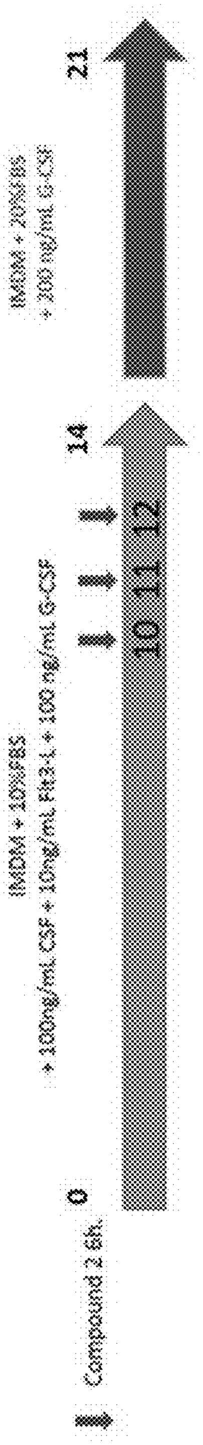
Figure 16B:
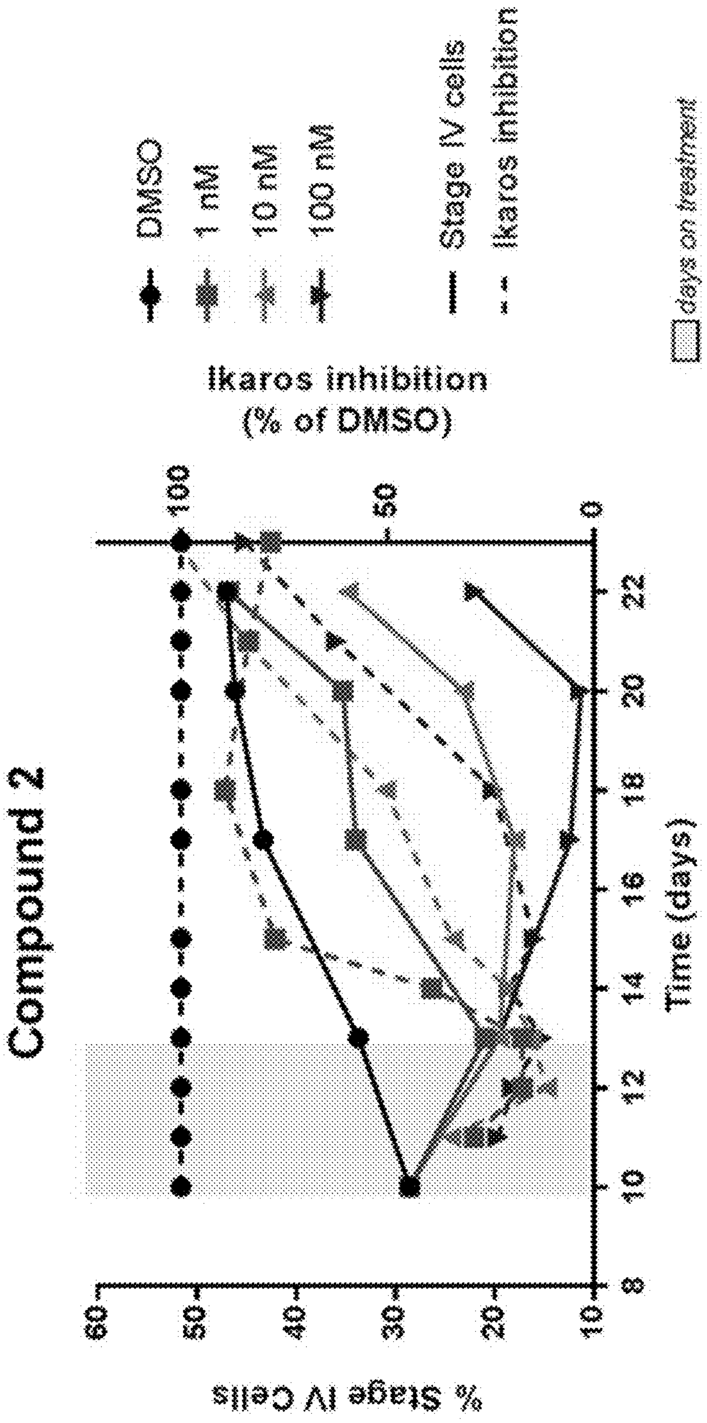

To further explore the role of Ikaros in relationship to the maturation of neutrophil progenitors, Ikaros protein levels were analyzed by flow cytometry after each exposure and every other day following the last exposure to Compound 2. Ikaros was fully degraded after one exposure to Compound 2 at all concentrations and all exposure schedules (FIG. 14 and FIG. 15). After 3 days of exposure to Compound 2, the recovery of Ikaros began in a concentration-dependent manner just 24 hours after drug washout and returned to control levels after 10 days (FIG. 14; FIG. 16B). With 5 days of exposure to Compound 2, recovery of Ikaros started on Day 17, three days after drug washout (FIG. 15). Full recovery to control levels was evident by 6 days after the last exposure at a concentration of 10 nM, whereas greater than 50% recovery was apparent by 8 days following Compound 2 exposures at a concentration of 100 nM (FIG. 15).

The data support the hypothesis that Ikaros degradation induced by Compound 2 is a factor driving the blockade of maturation of neutrophil precursors and that restoration of Ikaros recovery precedes the recovery of mature neutrophils, as illustrated in FIG. 16B. Taken together, the data suggest that induction of and recovery from neutropenia in patients may not be adversely affected by more intensive dosing of Compound 2 (multiple doses per day) as compared with once-daily dosing.

Example 11: Compound 2 Enhanced the Antitumor Activity of Immune Cells from Healthy Human Donors PBMCs isolated from healthy donors were cultured in RPMI 1640 medium with 10% FBS at a density of $1\times10^6$ cells/mL.

K562 cells were kept in log phase, and cell density and viability were monitored by trypan blue exclusion using the Vi-CELL® XR cell viability analyzer (Beckman Coulter, Brea, CA).

Freshly isolated human PBMCs were cultured with recombinant IL-2 at concentration of 20 units/mL for 72 hours. Peripheral blood mononuclear cells were then spun down and re-suspended in fresh RPMI complete medium to $2\times10^6$ cells/mL. Cells were then treated with DMSO or Compound 2 at the indicated concentrations and incubated for an additional 72 hours. The PBMCs were then washed twice in fresh RPMI complete medium prior to coculture. K562 cells were re-suspended to a cell density of $1\times10^6$ cells/mL and stained with 1 μM CellTrace CFSE according to manufacturer's instructions. The labeled K562 cells were then seeded into a 96-well round bottom plate at $1\times10^5$ cells/well. Peripheral blood mononuclear cells were then transferred into the same 96-well plate at a 1:15 ratio, in triplicate and incubated at 37° C. for 4 hours. Specific target cell lysis by PBMC mediated apoptosis was measured using Annexin V-fluorescein isothiocyanate (FITC) and propidium iodide (PI) according to manufacturer's instructions and samples were run on the FACS Array scan. Non-labeled K562 cells, CellTrace CFSE-labeled K562 cells, and Annexin V-FITC- and PI labeled untreated K562 cells were included in each assay as controls. All myeloma cell lines were kept in log phase, and cell density and viability were monitored by trypan blue exclusion using the Vi-CELL XR cell viability analyzer. Ninety-six-well dishes were pre-coated with anti-CD3 antibody (OKT3, 3 μg/mL) and incubated at 4° C. overnight before the start of the experiment. Frozen PBMC donors, were thawed at 37° C. for 2 minutes in RPMI medium with 10% FBS and cell counts and viability were measured on the Vi-CELL® (Beckman Coulter). Peripheral blood mononuclear cells were washed and diluted to $1\times10^6$ cells/mL and dispensed to the compound-treated plates in a total volume of 200 μL. Cells were incubated with compounds for 2 hours before being transferred onto anti-CD3-coated plates and incubated for an additional 72 hours at 37° C. After 72 hours, the PBMCs were centrifuged, and cells were washed twice in RPMI medium+10% FBS. Untreated MM cell lines (H929 and H929-1051) were labeled with CellTrace CFSE according to manufacturer's instructions and re-suspended at a total concentration of $0.1\times10^6$ cells/mL into a U bottom 96-well plate in a total volume of 100 μL. Peripheral blood mononuclear cells were counted and added to the MM cells at a target: effector (T:E) ratio of 1:5. After 24 hours coculture, specific target cell lysis by PBMC induced apoptosis was measured using Annexin V-AF647 and 7-AAD according to manufacturer's instructions and samples were run on the Attune NxT Cytometer (Thermo Fisher).

Ninety-six-well dishes were pre-coated with anti-CD3 antibody (OKT3, 3 μg/mL) and incubated at 4° C. overnight before the start of the experiment. Frozen PBMC donor cells were thawed at 37° C. for 2 minutes in RPMI medium with 10% FBS and cell counts and viability were measured on the Vi-CELL analyzer. Peripheral blood mononuclear cells were washed and diluted to $1\times10^6$ cells/mL and dispensed into the compound-treated plates in a total volume of 200 μL. Cells were incubated with Compound 2 for 2 hours before being transferred onto anti-CD3-coated plates and incubated for an additional 72 hours. At the same time, MM cell lines (NCI-H929, H929-1051, OPM2, OPM2-P10) were diluted to a final concentration of $0.1\times10^6$ cells/mL and labeled with CellTrace CFSE according to manufacturer's instructions. Multiple myeloma cell lines were then dispensed into compound-treated plates at a total volume of 200 μL and incubated for 72 hours. After 72 hours, the PBMCs and MM cells were counted and transferred into a U-bottom 96-well plate at a final T:E ratio of 1:5. After 24 hours coculture, specific target cell lysis by PBMC mediated apoptosis was measured using Annexin V-AF647 and 7-AAD according to manufacturer's instructions and samples were run on the Attune NxT Cytometer.

Figure 17A:
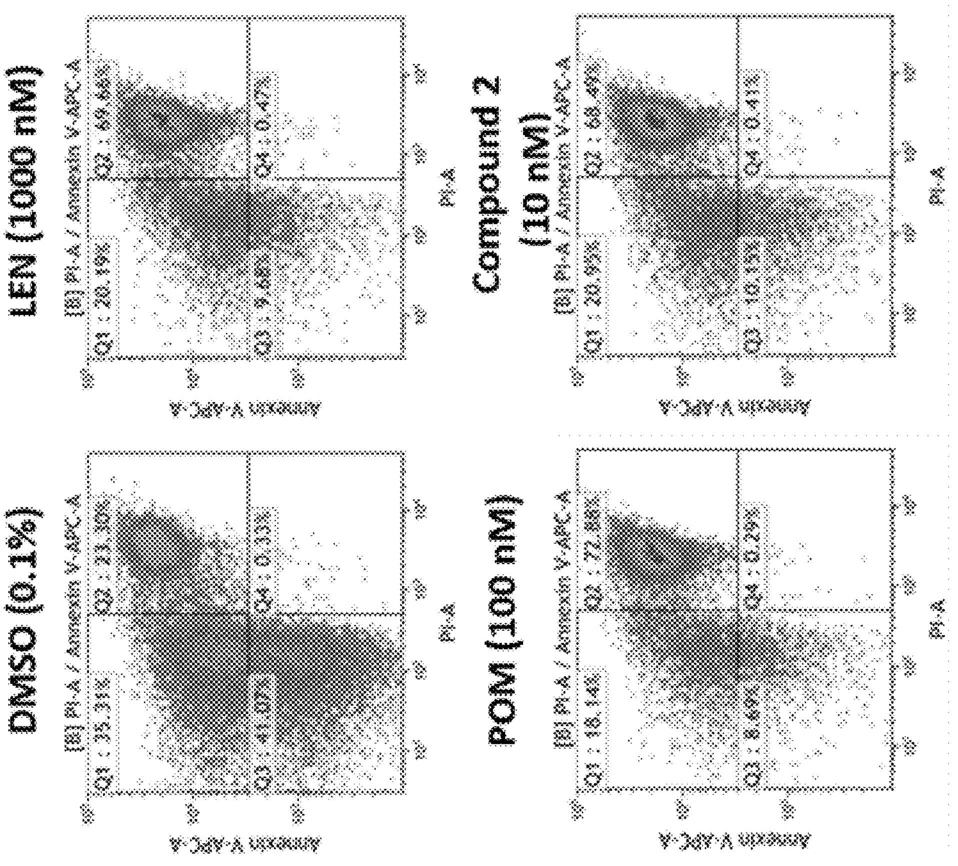
Figure 17B:
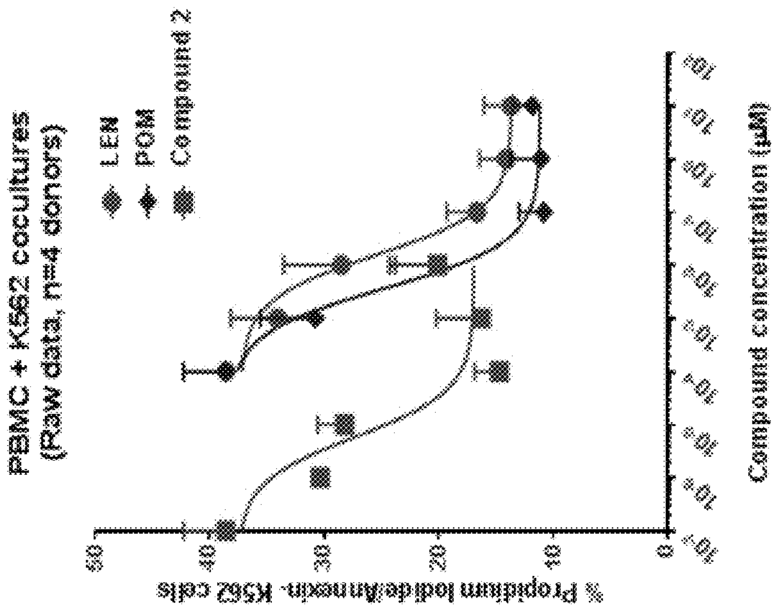

The coculture model was used to determine the direct effects of Compound 2 on the anti-tumor activity of PBMCs taken from healthy donors. Compound 2 treatment of IL-2-activated PBMCs induced the killing of untreated K562 cells in a concentration-dependent manner (FIG. 17A and FIG. 17B). Compound 2-treated PBMCs ($IC_{50}$=5.9 pM) potently achieved 50% direct K562 cell killing.

Figure 18A:
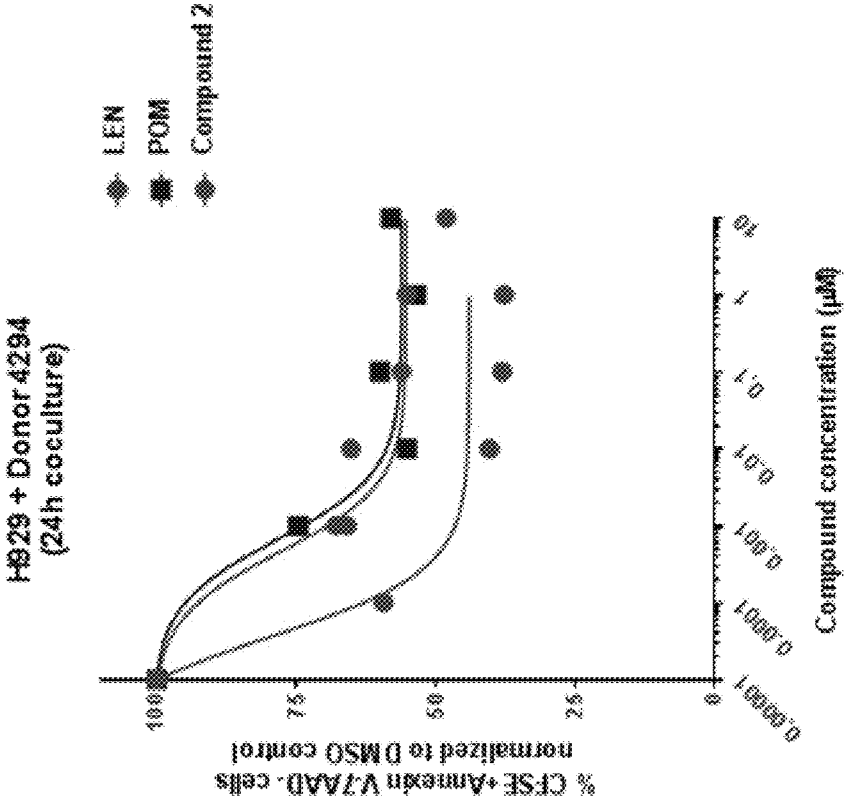
Figure 18B:
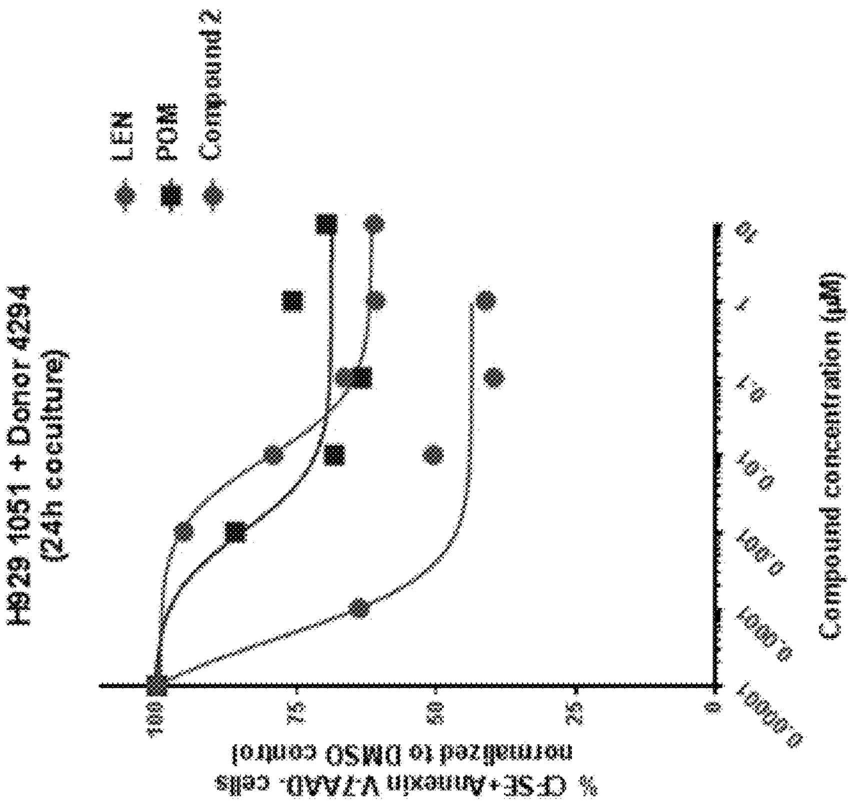

The effects of Compound 2 on the anti-MM cell activity of PBMCs incubated with Compound 2 were examined further in cell lines displaying the resistance phenotype in order to compare with the response in sensitive cells. In a different co-culture model, PBMC donor cells were pre-treated with Compound 2 for 2 hours before being cultured on anti-CD3 antibody-coated plates for 72 hours. The anti-CD3 antibody-activated PBMCs treated with Compound 2 demonstrated a concentration-dependent increase in the tumor cell lysis of untreated lenalidomide-sensitive (NCI-H929; $IC_{50}$=0.005 μM) and lenalidomide-resistant (H929-1051; $IC_{50}$=0.0002 μM) MM cell lines to a similar degree (FIG. 18A and FIG. 18B). A similar level of tumor cell killing by PBMC mediated apoptosis was seen against the lenalidomide-sensitive and lenalidomide-resistant co-cultured tumor cells, showing that the PBMCs were primed to induce apoptosis in tumor cells independent of their resistance phenotype.

Figure 19A:
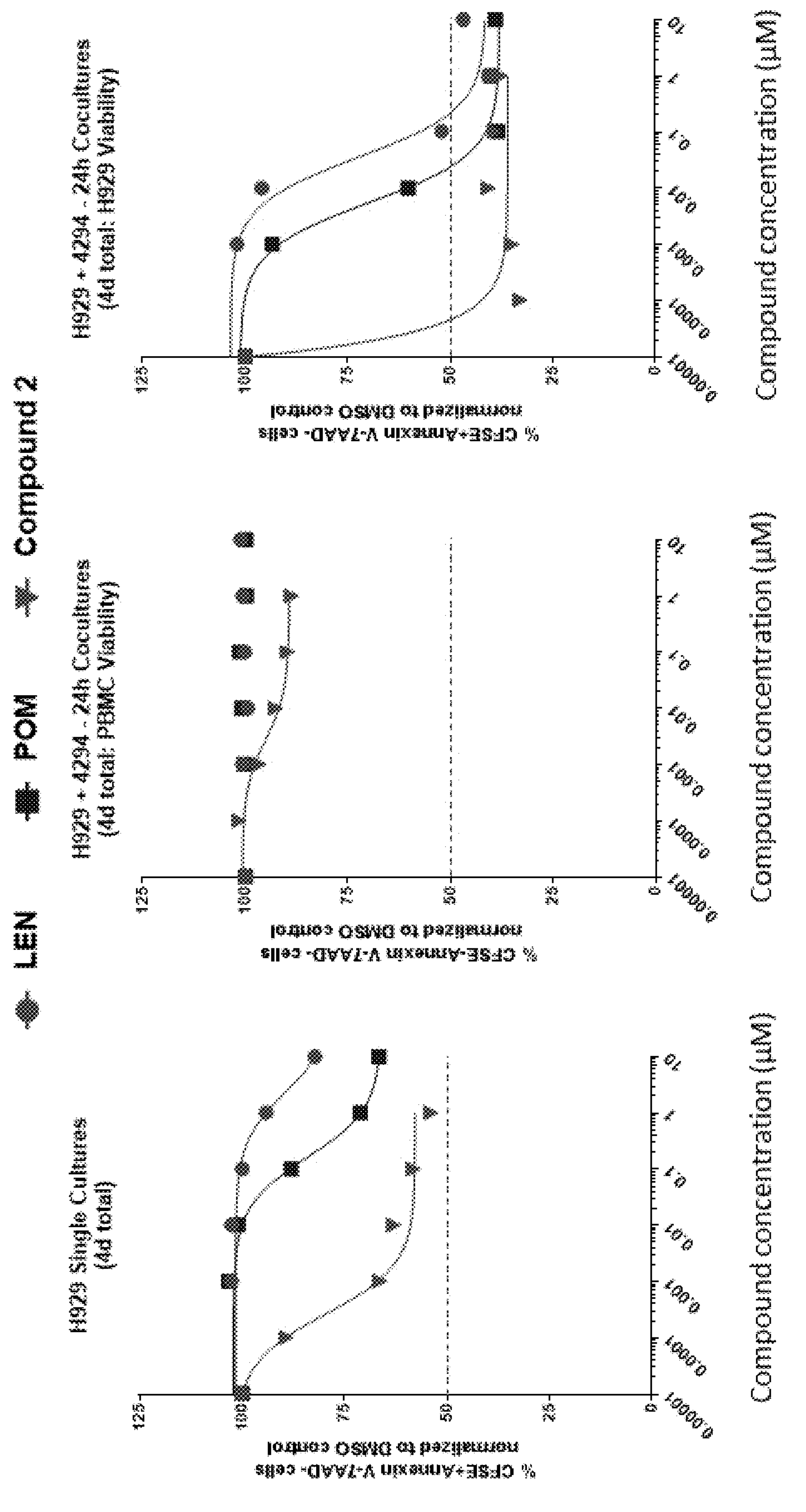
Figure 19B:
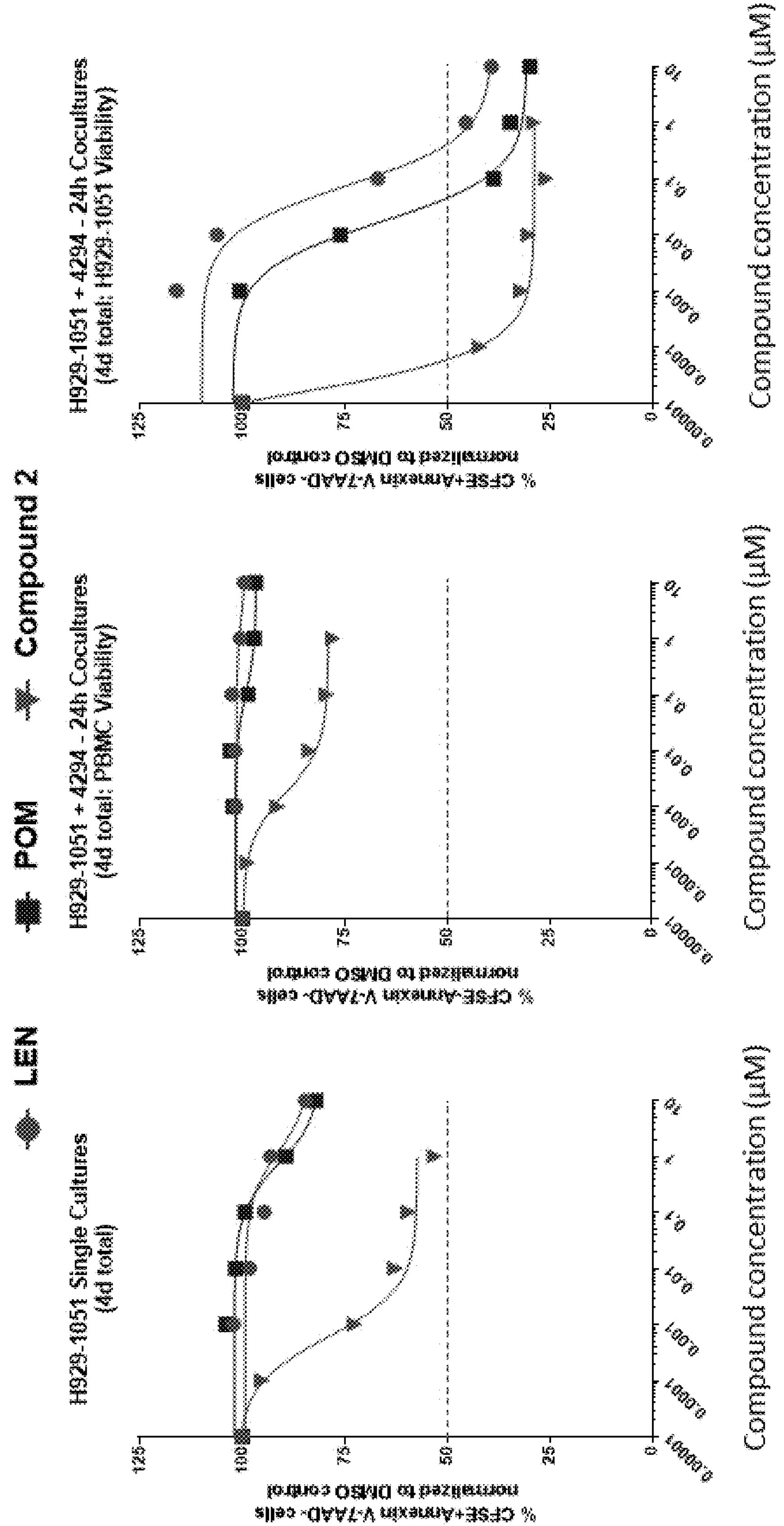
Figure 19C:
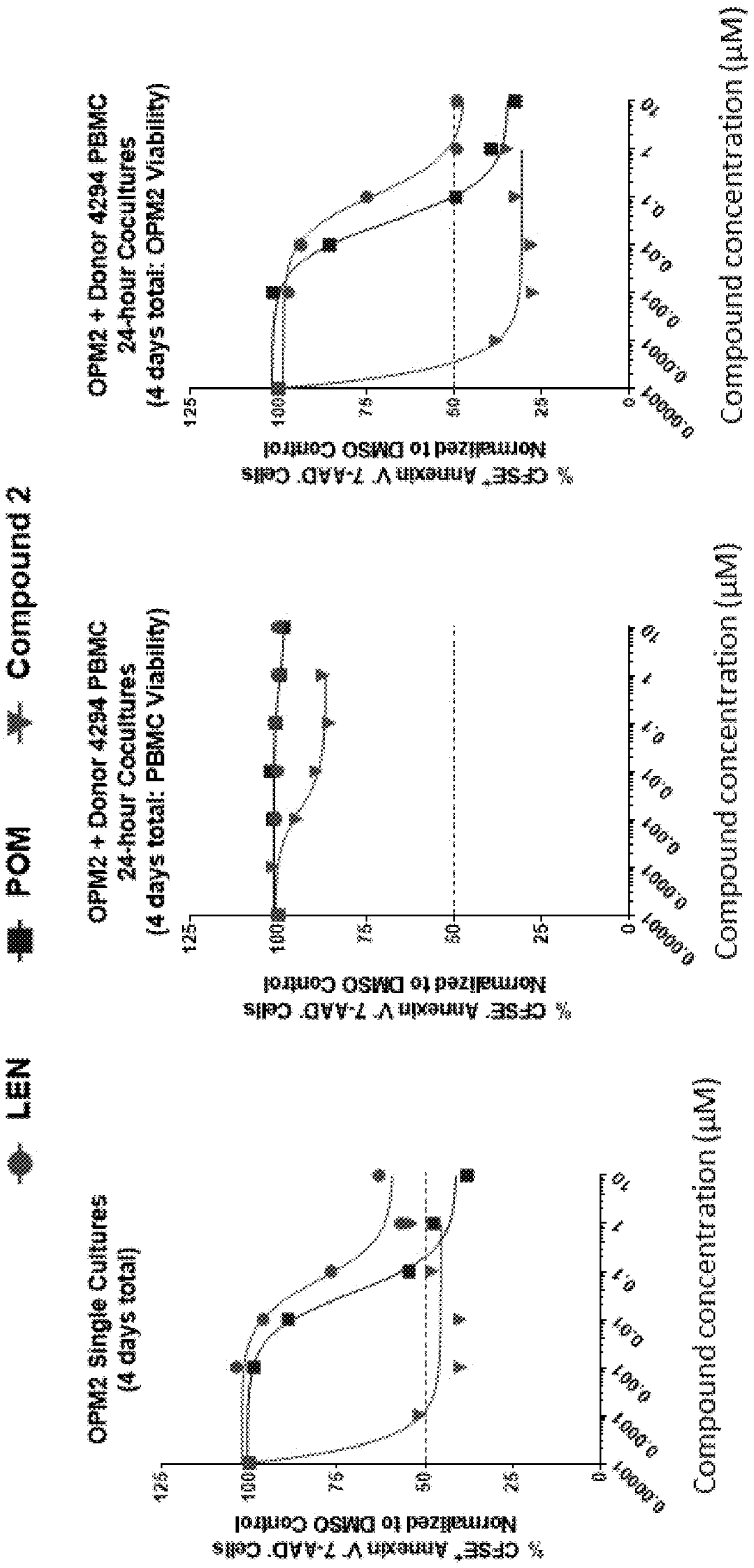
Figure 19D:
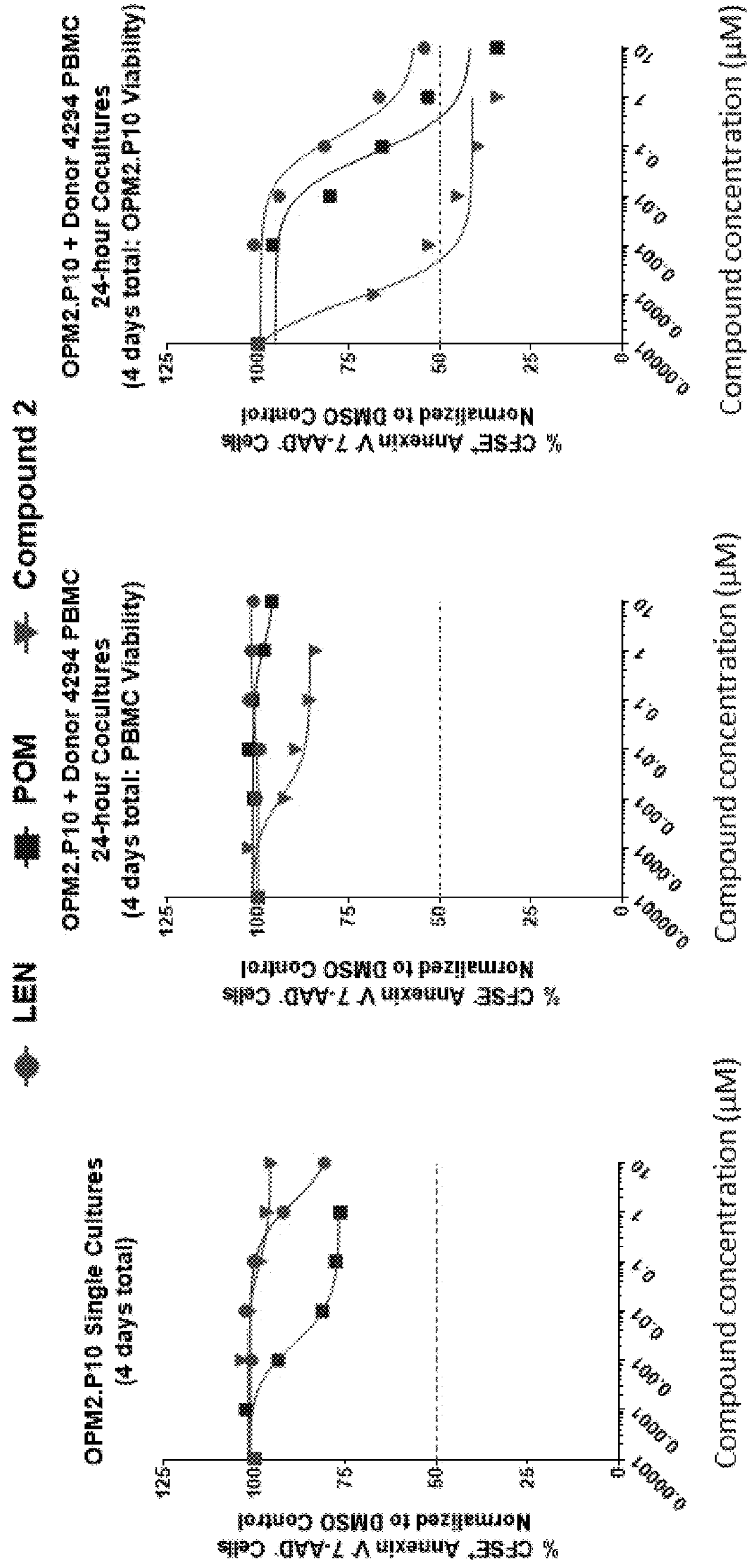

Because preincubation of immune cells with Compound 2 enhanced the targeting and lysing of MM cells, the effect of preincubation of MM cells with Compound 2 on their susceptibility to immune-mediated killing was also explored (FIG. 19A-FIG. 19D). Four MM cell lines and anti-CD3 antibody-activated PBMCs were separately preincubated with Compound 2 for 72 hours. When anti-CD3 antibody-activated PBMCs and MM lines were both pretreated with Compound 2, followed by co-culture, the effects on the PBMC-induced MM cell lysis were enhanced both in the potency and magnitude of the killing response. Comparing the $IC_{50}$ values from single MM cell cultures versus the immune and tumor cell co-cultures, Compound 2 enhanced the killing of the NCI-H929 cells by ~7000-fold, and it enhanced the killing of the H929-1051 cells by ~6000-fold (FIG. 19A and FIG. 19B).

Compound 2-treated PBMCs potently induced the tumor lysis of untreated K562 and MM cell lines. Moreover, tumor cell killing was greatly enhanced if both PBMCs and MM cell lines were pretreated with Compound 2, indicating that in addition to its potent cell autonomous effects, Compound 2 may also enhance the immunogenicity of MM cell lines. Collectively, the results indicate the combination of the potent cell-autonomous and immunogenic effects on MM cells, as well as its immunomodulatory properties.

Example 12: Compound 2 Activated Effector Lymphocytes and Cytokines

Figure 20:
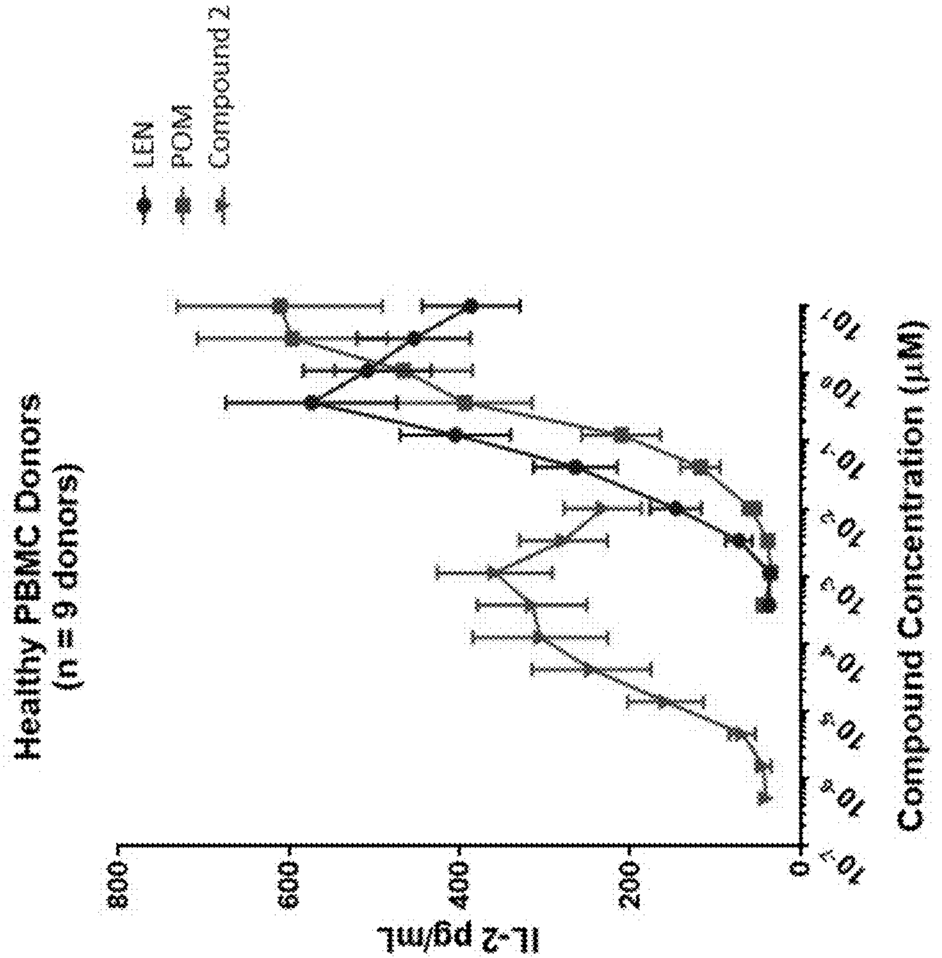
Figure 21C:
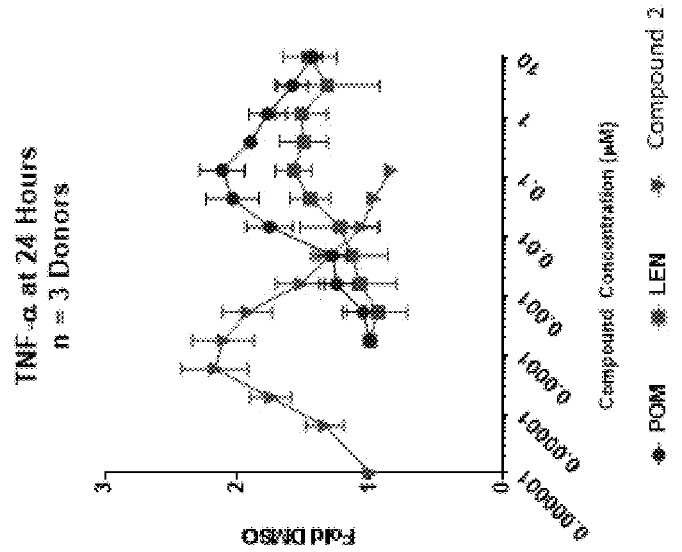
Figure 21B:
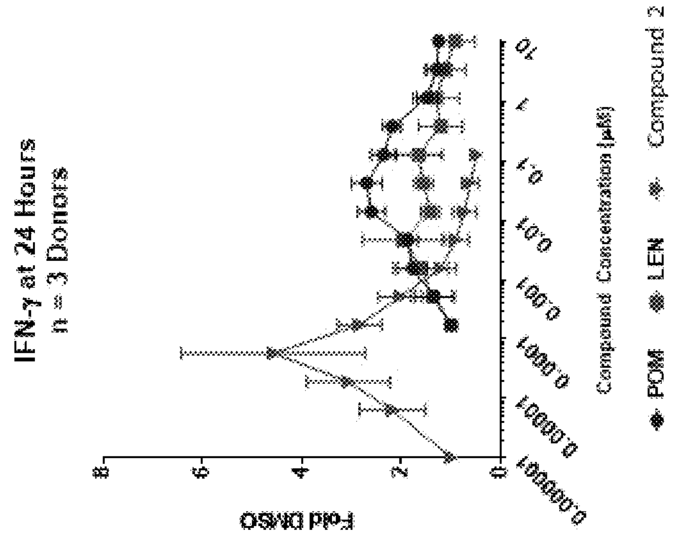
Figure 21A:
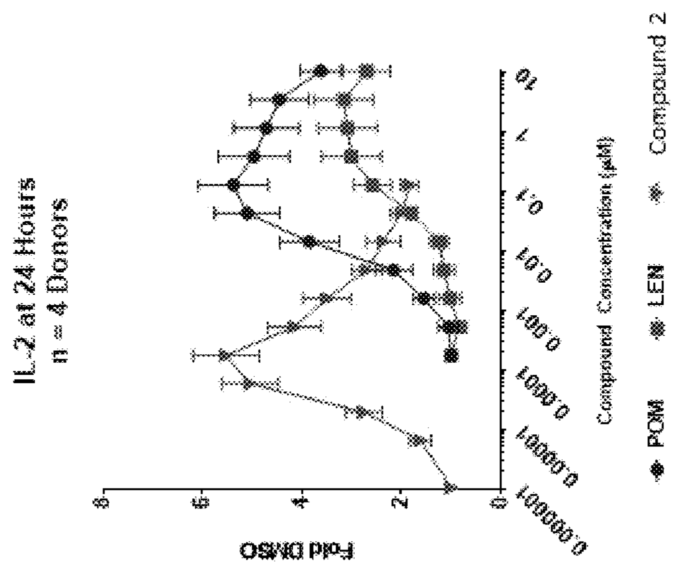

The immunomodulatory activity of Compound 2 on T cell receptor (TCR)-activated healthy PBMCs was assessed. In a panel of cells from nine healthy PBMC donors, incubation with Compound 2 in the presence of anti-CD3 antibody stimulation for 72 hours induced IL-2 secretion with a mean half-maximal effective concentration ($EC_{50}$) of 14 pM (FIG. 20). This increased in cytokine secretion was evident as early as 24 hours after introduction of Compound 2 with the peak of the effector cytokine production induced by Compound 2 being 5.5-fold for IL-2, 4.5-fold for interferon gamma (IFN-γ), and 2-fold for tumor necrosis factor alpha (TNF-α) above the vehicle control (FIG. 21A-FIG. 21C, respectively). These data demonstrate that Compound 2 can activate T cells, and stimulate their secretion of cytokines, such as TNF-α, IFN-γ, and IL-2. Furthermore, these data show that these cytokines can serve as biomarkers for activated T-cells, in response to Compound 2.

Example 13: Compound 2 Induced Substrate Degradation in T Cells

Figure 22C:
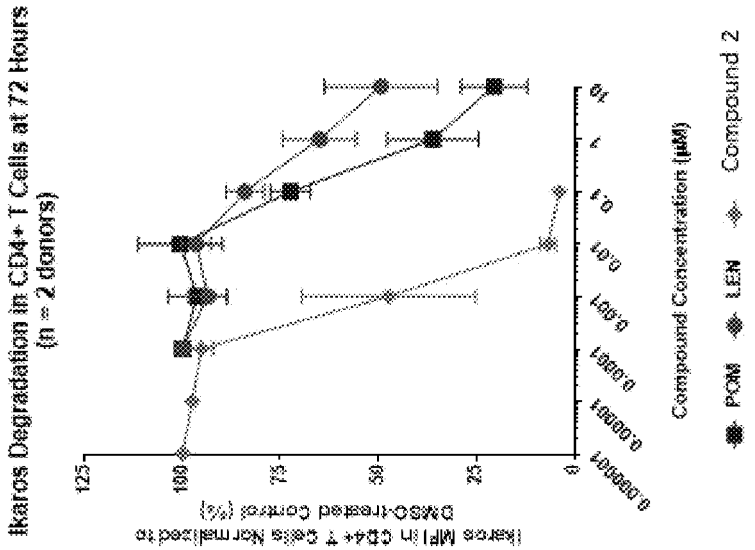
Figure 22B:
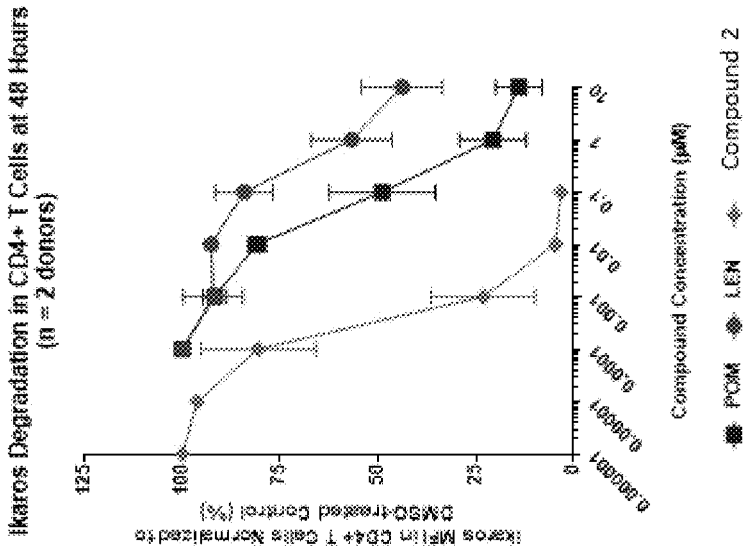
Figure 22A:
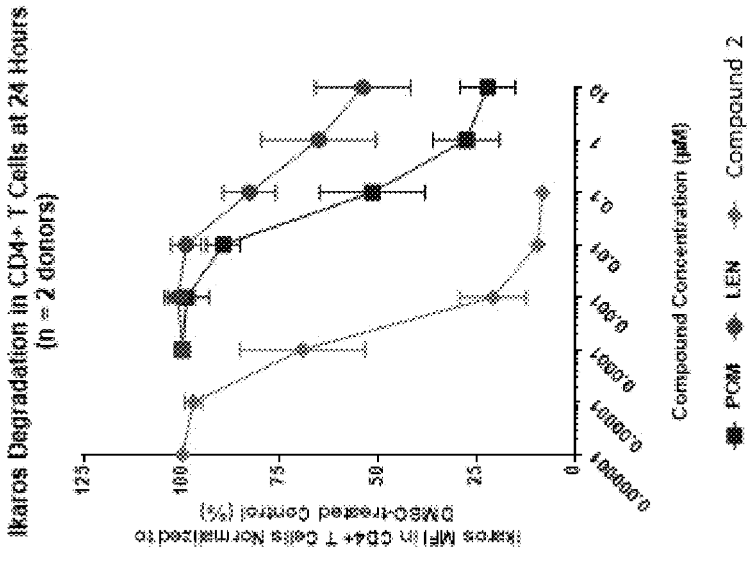

The effects of Compound 2 on the degradation of Ikaros in CD4+ and CD8+ T cells over a 72 hour time course were investigated. The ability of Compound 2 to induce effector cytokine release correlated with degradation of Ikaros in CD4+ T cells, a known transcriptional repressor of IL-2 (FIG. 22A-FIG. 22C). In CD4+ T cells, after 24-hours, treatment with Compound 2 demonstrated robust Ikaros degradation (24-hour $IC_{50}$=0.0003 μM) (FIG. 22A). In the CD8+ T cell population, the potency was also observed, with Compound 2 displaying a 24-hour $IC_{50}$ of 0.0005 μM (data not shown). The ability of Compound 2 to degrade Ikaros was also observed at the 48 and 72 hour time point in both CD4+(FIG. 22B and FIG. 22C) and CD8+ (data not shown) T cell populations. These data demonstrate that Compound 2 degrades Ikaros in T-cells, which correlates with induction of effector cytokine release. Thus, Ikaros and Aiolos can serve as biomarkers of T-cell activation.

Figure 23A:
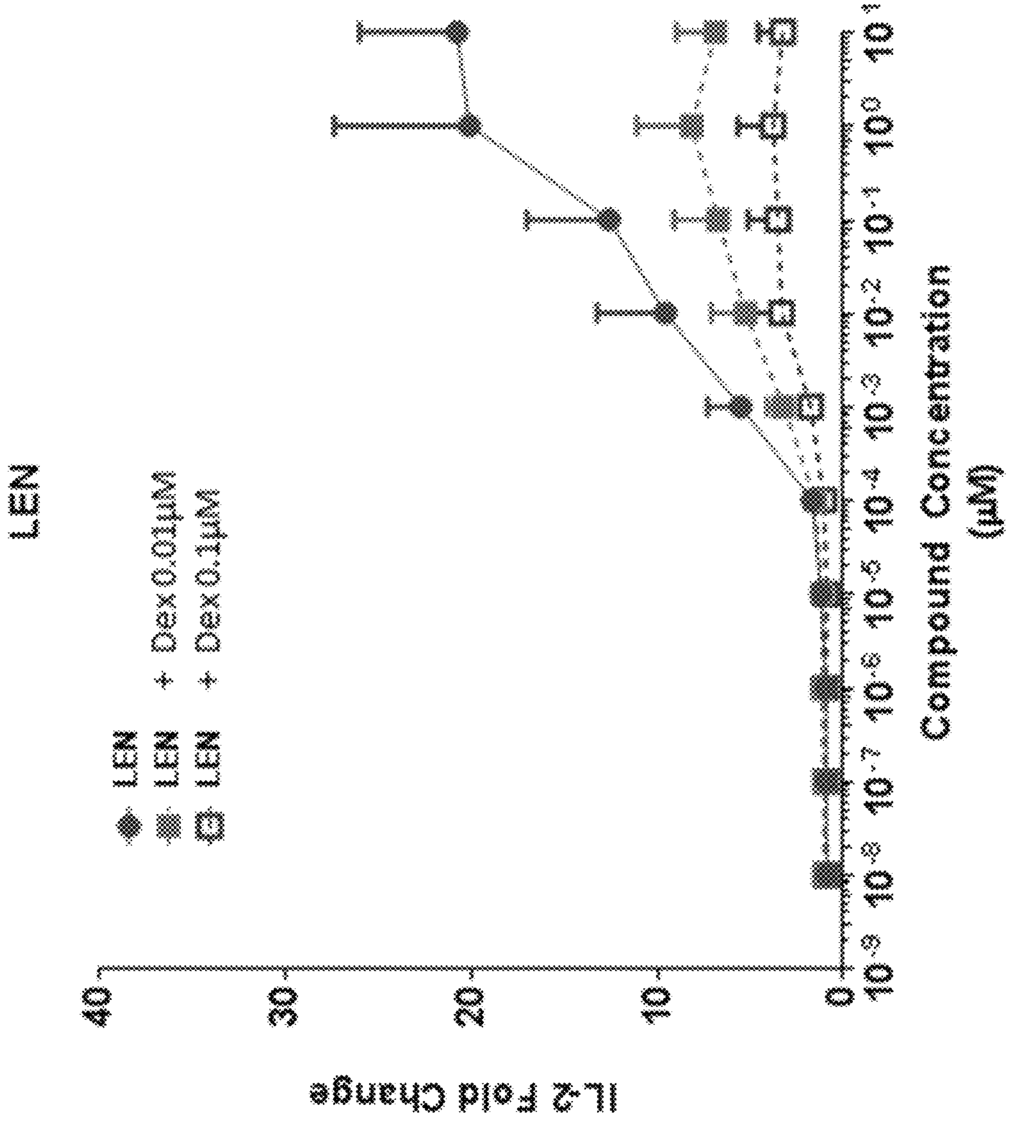
Figure 23B:
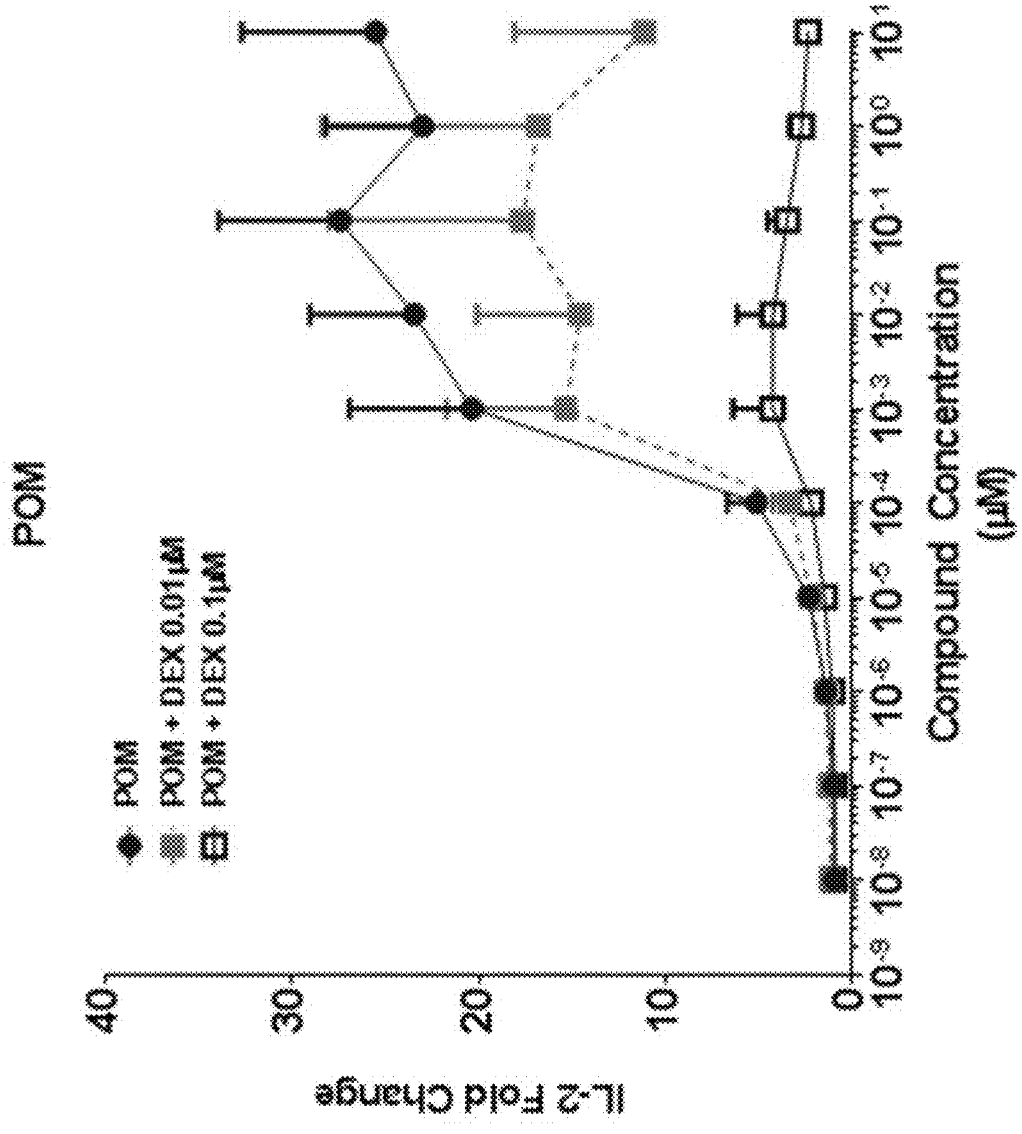
Figure 23C:
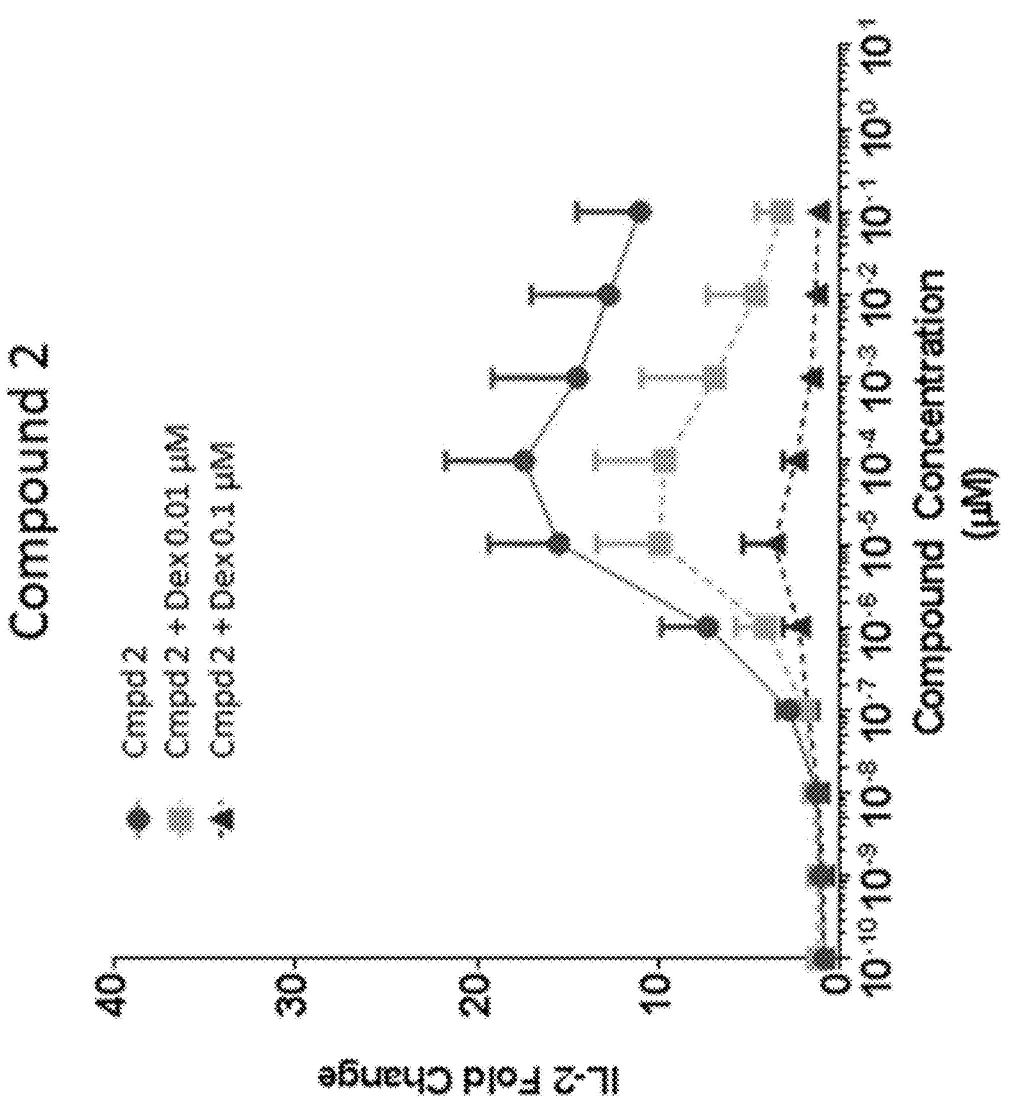

Example 14: Effect of Compound 2 in Combination with Dexamethasone on Immunomodulation/Interleukin-2 Induction The effect of Compound 2 in combination with different concentrations of dexamethasone on the ability of PBMCs to produce IL-2 was explored. Peripheral blood mononuclear cells from 4 healthy donors were preincubated with Compound 2 for 2 hours prior to being stimulated with anti-CD3 antibody coated beads for a further 72 hours. When used in combination with 10 nM dexamethasone, Compound 2 was still able to induce IL-2 to a level at least 10-fold above the vehicle control, with the peak response achieved at 0.01 nM Compound 2 (FIG. 23C). However, the combination of Compound 2 with higher dexamethasone concentrations (100 nM), showed little induction of IL-2 above baseline.

Taken together, these data indicate that the immunomodulatory activity of Compound 2 was maintained in the presence of low levels (10 nM) of dexamethasone, where dramatic synergy in MM cell autonomous killing was observed with Compound 2.

Example 15: Pharmacodynamics, Efficacy, and Predictive Assessments Using Biomarkers The pharmacodynamics (PD), efficacy, and predictive endpoints can be assessed by analyzing various biomarkers in a patient's blood, and bone marrow. Biomarkers to be assessed include Aiolos and Ikaros degradation; cytokine profile upon ex vivo stimulation; phenotypic analysis of immune cells (e.g. T-cells); expression levels of CRBN, Aiolos, Ikaros, tumor infiltrating lymphocytes (TILs), c-Myc, IRF4, c-Caspase3; cytogenics, mutations, and TCR clonality; soluble BCMA, free light chain (FLC), and circulating tumor cells (CTCs).

A bone marrow aspiration (BMA) is taken from a patient prior to treatment, during treatment, and upon termination of the study. Approximately 6 mLs of BMA are taken, and 1 mL of fixed BMA clot at the clinical site are used for immunohistochemistry (IHC) to evaluate the expression levels of CRBN, Aiolos, Ikaros, ZFP91, c-Myc, IRF4, c-Caspase-3, as well as TILs, as biomarkers. The remaining BMA is then subjected to $CD138^+$ selection to isolate the myeloma cells and $CD138^-$ and $CD138^+$ fractions are collected. A portion of the $CD138^+$ cells is used for fluorescent in situ hybridization (FISH). The remaining $CD138^+$ cells are prioritized into aliquots for RNA and DNA isolation and analysis, additional FISH analysis, and viably frozen $CD138^+$ cells. Bone marrow mononuclear cells (BMMNCs) are isolated from the $CD138^-$ fraction by ficoll density gradient centrifugation. The $CD138^-$ BMMNCs are prioritized into aliquots for RNA and DNA isolation and analysis, viably frozen $CD138^-$ cells immune profiling, and frozen cell pellet for TCR clonality.

The whole blood of patients is also analyzed. Peripheral blood mononuclear cells (PBMCs), and/or serum/plasma are isolated from the samples. Whole blood is also used directly for analysis of some biomarkers.

Analysis of whole blood may be used to determine T-cell activation as a biomarker. Blood is drawn at screening and during treatment for all schedules. Blood is drawn into a TruCulture tube containing anti-CD3 antibody to stimulate the T-cells. The tube is incubated at 37° C. for 42±4 hr. The media is separated from the cells and frozen at −70° C. Samples are analyzed for T-cell activation using a custom cytokine panel (Myriad RBM, Inc.), that includes cytokines indicative of T-cell activation, such as interferon gamma (IFNγ), tumor necrosis factor alpha (TNFα), and interleukin-2 (IL-2).

Serum is isolated from the whole blood, and soluble BCMA (sBCMA) is measured by ELISA as a biomarker before and during treatment on all cycles and schedules. In addition, serum free light chain (sFLC) is measured as a biomarker in the same serum samples as sBCMA. The FreeLite test will be used to measure the ratio between the kappa light chain and the lambda light chain (k/l ratio).

PBMCs isolated from whole blood are analyzed for protein expression of the biomarkers Aiolos and Ikaros by FACS and/or ELISA. The PBMC isolation for measuring the expression levels of these biomarkers is performed for patients that are enrolled in all schedules on days 1, during treatment, as well as at the end of the study.

In addition, biomarker analysis of the PBMCs includes immunophenotyping after collecting whole blood samples before and during treatment. Immune modulation is assessed by FACS assays for T-cell subsets (CD3, CD4, CD8, Treg, Teff, Tmem), B cells, and NK cells.

Finally, the amount of circulating tumor cells (CTCs) present in the peripheral blood is quantified as a biomarker. CTC are identified and analyzed by FACS assays used for minimal residual disease (MRD) assessments. For all schedules, the CTCs are measured in the blood on days 1, and during treatment.

The biomarkers are used to determine the combination activity of Compound 2 with low dose dexamethasone and to evaluate the Compound 2 dosing schedules. In addition, the efficacy of Compound 2 in combination with dexamethasone relative to other cereblon modulators compounds is assessed according to the biomarkers. Collectively, the evaluation of these biomarkers can instruct patient selection, schedule guidance, predict response to therapy, and/or determine the efficacy of treatment.

Example 16: Use of Biomarkers to Alter Treatment Schedule for Relapsed and Refractory Multiple Myeloma Biomarkers provided herein can be used to determine whether treatment should be altered, such as extending the schedule or shortening the schedule. Assessment of Aiolos/Ikaros repression, and T-cell activation and proliferation are able to guide treatment schedule.

To determine whether the optimal dose has been achieved, blood is collected during treatment, PBMCs are isolated, and Aiolos/Ikaros repression is measured by FACS. In one scenario, the amount of Aiolos/Ikaros recovery above assay background is <15%. In addition, IHC shows that the correlation of Aiolos/Ikaros repression in the bone marrow across multiple dose levels supports that the bone marrow Aiolos suppression is also within 15% of the assay floor. Further, there is little to no further PD response compared to the next lowest dose level, suggesting that the PD effects are saturated. The measurement of T-cell activation and proliferation are determined by evaluating the increase in soluble CD25 in the serum/plasma, as well as the increase in Ki67 in CD8+ and CD4+ cells. Results indicating that the T-cell activation and proliferation plateau with dose, and that there is no loss of Teff populations indicate that the optimal dosage has been achieved. The absence of grade 3 or higher neutropenia also demonstrates that the PD is optimized and indicates that the schedule can be extended instead of increasing the dose. Under this scenario, the biomarkers indicate that the optimal biological dose has been achieved and the schedule can continue without alteration.

Alternatively, the biomarker data may indicate the schedule requires altering. In a different scenario, the results upon treatment with the dosing schedule can indicate that the protein expression level of the biomarkers Aiolos/Ikaros recovered is more than 15% above background during treatment in PBMC and/or BM. In addition, an absence of a plateau for suppressing the expression of the biomarker Aiolos in PBMC and/or BM in escalating doses can be observed. Further, evaluation of T-cell activation and proliferation as a biomarker may indicate that the T-cell activation is not maximized. This suggests that the PD effects have not been optimized at the treatment schedule MTD. The addition of unacceptable neutropenia, and an incomplete or absent recovery in ANC during treatment indicate that the rest window that is provided with the treatment schedule is insufficient to allow sufficient neutrophil maturation recovery. Therefore, the schedule can be shortened to increase the recovery window and resume dose escalation. Collectively, these two scenarios demonstrate that biomarkers can instruct in the scheduling of patient treatment with a cereblon modulator for multiple myeloma.

Example 17: Use of Biomarkers for Patient Selection and as Predictive Markers for Treating Relapsed and Refractory Multiple Myeloma with Cereblon Modulators Biomarkers can also be used to define patient selection, and to predict response or resistance to treatment of relapsed/refractory multiple myeloma with the cereblon modulator such as Compound 2, or an enantiomer, a mixture of enantiomers, a tautomer, or a pharmaceutically acceptable salt.

Bone marrow samples are collected prior to treatment for screening purposes during treatment, and upon termination of the study. Approximately 6 mLs of BMA are taken, and CD138 fractionation can be performed. Further, ex vivo drug testing can be performed on the primary samples. The ex vivo data can be integrated with the clinical data that is collected from the CD138 populations. Collectively, the data that is collected from the biomarkers can serve to define patient selection for treatment with the compounds.

Example 18: A Phase 1 Multicenter, Open-Label Study to Assess the Safety, Pharmacokinetics and Preliminary Efficacy of Compound 2 in Combination with Dexamethasone in Subjects with Relapsed and Refractory Multiple Myeloma Indication: Relapsed and refractory multiple myeloma (RRMM).

Primary Objectives:

To assess the pharmacokinetics (PK), safety/tolerability and define the maximally tolerated dose (MTD)/recommended Part 2 dose (RP2D) of Compound 2 in combination with dexamethasone in conjunction with a minimum of two Compound 2 dosing schedules.

Secondary Objectives:

To assess the preliminary efficacy of Compound 2 in combination with dexamethasone.

Study Design

This is an open-label, multi-center, international, Phase 1 study to assess the safety, PK/PD and preliminary efficacy of Compound 2 in combination with dexamethasone in subjects with RRMM. RRMM patient previously treated with at least 3 prior regimens including lenalidomide or pomalidomide, a proteasome inhibitor and an anti-CD38 antibody will be eligible.

The study will be conducted in two parts: Part 1 will assess the PK/PD and safety of escalating doses of Compound 2 with concurrent, standard dose dexamethasone and determine the MTD/RP2D for the combination when administered according to a minimum of two different dosing schedules. Part 2 will consist of a single-arm expansion cohort(s) of Compound 2 at the RP2D plus dexamethasone for one or more dosing schedules. In addition to safety, PK and PD assessments, all subjects will undergo monthly response assessments per International Myeloma Working Group (IMWG) Uniform Response Criteria (Rajkumar et al., *Blood,* 2011, 117(18):4691-5; Kumar et al., *Lancet Oncol.,* 2016, 17(8):e328-e346) and may continue study treatment until disease progression, intolerable toxicity or physician or subject decision to discontinue study treatment.

The study will be conducted in compliance with the International Council on Harmonisation (ICH) Technical Requirements for Registration of Pharmaceuticals for Human Use/Good Clinical Practice (GCP) and applicable regulatory requirements.

Part 1 (Dose Escalation)

Cohorts of subjects with RRMM will receive escalating doses of Compound 2 plus a fixed dose of dexamethasone (40 mg/dose; 20 mg/dose in subjects≥75 yrs) in order to assess its safety, the MTD/RP2D and PK/PD profiles. A minimum of two different dosing schedules will be assessed in Part 1, the first consisting of 10 consecutive days of once daily (QD) dosing followed by 4 days of no treatment×2 each 28 day cycle (referred to as the 20/28 schedule). The second schedule will consist of twice daily (BID) dosing for 3 consecutive days followed by 11 days of no study treatment×2 each cycle (referred to as the 6/28 schedule). The initial dose cohorts will receive 0.1 mg/day Compound 2 QD on the 20/28 schedule and 0.2 mg BID on the 6/28 schedule. Switching between dosing schedules will not be allowed. Additional dosing schedules involving daily (QD) or twice daily (BID) doses of Compound 2 dosing followed by days of no treatment×2 per 28 day cycle (e.g., 5 days QD or BID of dosing followed by 9 days of no treatment×2 per 28 day cycle, or 7 days QD or BID of dosing followed by 7 days of no treatment×2 per 28 day cycle, and 21 days of daily dosing followed by 7 days of no treatment per 28 day cycle) may be explored following review of the safety and PK/PD results in association with the 20/28 and 6/28 schedules initially and subsequent tested schedules.

For all dosing schedules, Cycle 1, Days 1-28 will constitute the dose-limiting toxicity (DLT) assessment period for purposes of MTD determination. Subjects will be evaluable for DLT if they receive the prescribed dose of Compound 2 on at least 16 of the 20 dose days on the 20/28 schedule and at least 5 of the 6 dose days (10 doses) on the 6/28 schedule (or at least 80% of the prescribed dose on the alternative schedules) in Cycle 1 or experience a DLT. Non-DLT evaluable subjects will be replaced.

In each schedule, cohorts of three or more subjects will receive Compound 2 at doses that will increase in 100% increments in successive cohorts until the occurrence of two, Grade 2 treatment-emergent adverse events that cannot be clearly and incontrovertibly attributed to extraneous causes. Thereafter, dose increments not to exceed 50% will ensue until the occurrence of a first DLT. A Bayesian dose escalation methodology using logistic regression will be utilized after the occurrence of a first DLT in any dosing schedule, with the assigned dose of Compound 2, number of doses per day (QD vs BID) and number of consecutive dose days for each schedule as covariates.

Intra-subject dose escalation will not be allowed during the DLT assessment period, however, in Cycle 2 and beyond, subjects who are tolerating their assigned dose of Compound 2 may escalate to the highest dose level shown to be adequately tolerated by at least one cohort of subjects within the assigned dosing schedule.

Part 2 (Cohort Expansion)

Upon completion of Part 1, a single-arm, expansion study of Compound 2 plus dexamethasone will be conducted in 20 subjects per one or more dosing schedule(s) to further assess its safety, PD and efficacy at the RP2D and schedule.

Study Population

Subjects≥18 yrs of age with RRMM who are refractory to their last line of treatment, previously treated with at least 3 prior regimens including lenalidomide or pomalidomide, a proteasome inhibitor and an anti-CD38 antibody, have an Eastern Cooperative Oncology Group Performance Status (ECOG PS) 0-2, measurable disease, and adequate bone marrow, renal and cardiac function may enroll. Subjects with a history of allogeneic transplantation, non- or oligosecretory MM, plasma cell leukemia or primary refractory MM (i.e., no history of at least a minor response to a prior treatment regimen) are excluded.

Number of Subjects

Approximately 120 subjects with RRMM from North America and Europe will enroll. Approximately 80 subjects will be allocated to one of two dosing schedules (either QD or BID) to determine the MTD/RP2D with concurrent dexamethasone for each schedule in Part 1. Twenty subjects per dosing schedule (n=40 in total) will enroll in Part 2 to receive Compound 2 at the MTD/RP2D with dexamethasone.

Estimates of the number of subjects enrolled to Part 1 are based on the following assumptions: 40 subjects for each dosing schedule including a minimum of 9 subjects treated at the MTD/RP2D for each schedule. Estimates of the number of subjects enrolled to Part 2 assumes 20 subjects per dosing schedule. These estimates may be modified based on the actual number of cohorts, subjects per cohort enrolled to each dosing schedule (Part 1) and whether additional dosing schedules are assessed in Part 2.

Inclusion Criteria

Subjects must satisfy the following criteria to be enrolled in the study:

Subject is ≥18 years of age at the time of signing the informed consent form (ICF).

Subject must understand and voluntarily sign an ICF prior to any study-related assessments/procedures being conducted.

Subject is willing and able to adhere to the study visit schedule and other protocol requirements.

Eastern Cooperative Oncology Group (ECOG) performance status score of 0, 1 or 2.

Subjects must have a documented diagnosis of MM and measurable disease at enrollment. Measurable disease is defined as: (a) M-protein quantities≥0.5 g/dL by sPEP; or (b) ≥200 mg/24 hour urine collection by uPEP; or (c) Serum FLC levels>100 mg/L involved light chain and an abnormal kappa/lambda (κ/λ) ratio in subjects without measurable serum or urine M-protein; or (d) for subjects with immunoglobulin class A (IgA), myeloma whose disease can only be reliably measured by quantitative immunoglobulin measurement, a serum IgA level≥0.50 g/dL.

All subjects must have: (a) received at least 3 prior anti-myeloma regimens including at least 2 consecutive cycles of lenalidomide, pomalidomide, a proteasome inhibitor, a glucocorticoid and a CD38 antibody (note: induction with or without bone marrow transplant and with or without maintenance therapy is considered one regimen); (b) documented disease progression on or within 60 days from the last dose of their last myeloma therapy; (c) in addition to criteria above (a and b), subjects enrolled in Part 2 must have disease refractory to an immunomodulatory agent (lenalidomide and/or pomalidomide), a glucocorticoid, a proteasome inhibitor, and a CD38 antibody. Refractory is defined as disease that is nonresponsive on therapy (failure to achieve minimal response or development of progressive disease), or progresses within 60 days of last dose.

Subjects must have the following laboratory values: (a) Absolute neutrophil count (ANC)≥$1.25\times10^9$/L without growth factor support for ≥7 days (≥14 days for pegfilgrastim). ANC of ≥$1.00\times10^9$/L is permitted for the dose expansion cohorts (Part 2); (b) Hemoglobin (Hgb)≥8 g/dL; (c) Platelets (plt)≥$75\times10^9$/L without transfusion for ≥7 days; (d) Corrected serum calcium≤13.5 mg/dL (≤3.4 mmol/L); (e) 24-hr creatinine clearance (CrCl)≥45 mL/min; (f) AST/SGOT and ALT/SGPT≤3.0× upper limit of normal (ULN); (g) Serum bilirubin≤1.5×ULN or <3.0 mg/dL for subjects with documented Gilbert's syndrome; (h) Uric acid≤7.5 mg/dL (446 μmol/L); (i) PT/INR<1.5×ULN and partial thromboplastin time (PTT)<1.5×ULN, (for subjects not receiving therapeutic anticoagulation). Note: Subjects receiving therapy for a thromboembolic event that occurred >3 months prior to enrollment are eligible as long as they are on a stable regimen of anticoagulation with warfarin, low-molecular weight heparin or other approved therapeutic anticoagulation or antiplatelet regimen.

Females of childbearing potential (FCBP) must: (a) Have two negative pregnancy tests as verified by the Investigator prior to starting study therapy. She must agree to ongoing pregnancy testing during the course of the study, and after discontinuation of Compound 2. This applies even if the subject practices true abstinence from heterosexual contact; (b) Either commit to true abstinence from heterosexual contact (which must be reviewed on a monthly basis and source documented) or agree to use, and be able to comply with, two reliable forms of contraception and provided to the subject at the time of informed consent, without interruption, 28 days prior to starting Compound 2, during the study therapy (including during dose interruptions), and for 28 days after discontinuation of study therapy. Note: A female of childbearing potential (FCBP) is a female who: 1) has achieved menarche at some point and, 2) has not undergone a hysterectomy or bilateral oophorectomy, or 3) has not been naturally postmenopausal (amenorrhea following cancer therapy does not rule out childbearing potential) for at least 24 consecutive months (i.e., has had menses at any time in the preceding 24 consecutive months).

Male subjects must: Practice true abstinence (which must be reviewed on a monthly basis) or agree to use of a condom during sexual contact with a pregnant female or a female of childbearing potential while participating in the study (even during dose interruptions) and for at least 3 months following Compound 2 discontinuation provided to the subject at the time of informed consent, even if he has undergone a successful vasectomy. True abstinence is acceptable when this is in line with the preferred and usual lifestyle of the subject. Periodic abstinence (e.g., calendar, ovulation, symptothermal, post-ovulation methods) and coitus interruptus (withdrawal) are not acceptable methods of contraception.

Males must agree to refrain from donating sperm while on Compound 2 for 90 days after its discontinuation. Females must agree to refrain from donating ova while on Compound 2 for 28 days after its discontinuation.

All subjects must agree to refrain from donating blood while on Compound 2 and for 28 days after its discontinuation.

Exclusion Criteria

The presence of any of the following will exclude a subject from enrollment:

Subject has a significant medical condition, laboratory abnormality, or psychiatric illness that would prevent the subject from participating in the study.

Subject has any condition including the presence of laboratory abnormalities, which places the subject at unacceptable risk if he/she were to participate in the study.

Subject has any condition that confounds the ability to interpret data from the study.

Subject has non- or oligosecretory multiple myeloma.

Subject has refractory primary multiple myeloma (i.e., no history of at least a minor response to a prior treatment regimen).

Subject has plasma cell leukemia or active leptomeningeal myelomatosis.

Subject has documented, systemic light chain amyloidosis or Polyneuropathy, Organomegaly, Endocrinopathy, Monoclonal gammopathy, and Skin changes (POEMS) Syndrome.

Subject has immunoglobulin class M (IgM) myeloma.

Subject has a history of allogeneic bone marrow transplantation.

Subject is undergoing dialysis.

Subjects with peripheral neuropathy≥Grade 2.

Subjects with gastrointestinal disease that may significantly alter the absorption of Compound 2.

Subject has impaired cardiac function or clinically significant cardiac disease, including any of the following: (a) LVEF<45% as determined by ECHO or MUGA scan at Screening; (b) Complete left bundle branch, bifascicular block or other clinically significant abnormal electrocardiographic (ECG) finding at Screening; (c) A prolongation of QT interval on Screening ECG as defined by repeated demonstration of a QTc interval≥480 milliseconds (ms) using Fredericia's QT correction formula; a history of or current risk factors for Torsades de Pointe (e.g., heart failure, hypokalemia, or a family history of Long QT Syndrome); and concurrent administration of medications that prolong the QT/QTc interval; (d) Congestive heart failure (New York Heart Association Class III or IV); (e) Myocardial infarction≤6 months prior to starting Compound 2; (f) Unstable or poorly controlled angina pectoris, including the Prinzmetal variant of angina pectoris.

Concurrent Administration of Strong CYP3A Modulators.

Subject had prior systemic myeloma treatment with an investigational agent (e.g., anti-PD-1, anti-PD-L1)≤5 half-lives prior to starting Compound 2; subject had prior exposure to approved myeloma therapies (including therapeutic monoclonal antibodies such as anti-CD38 or anti-SLAM-7) ≤5 half-lives or within 4 weeks prior to starting Compound 2 whichever is shorter.

Subject had major surgery≤2 weeks prior to starting Compound 2. Note: Subjects must have recovered from any clinically significant effects of recent surgery.

Subject is a pregnant or nursing female, or intends to become pregnant or donate ova during participation in the study.

Subject has known human immunodeficiency virus (HIV) infection.

Subject has known active chronic hepatitis B or C virus (HBV/HCV) infection.

Subject has a history of concurrent second cancer requiring ongoing systemic treatment.

Subjects has a history of prior malignancy other than MM, except if the subject has been free of disease for ≥3 years OR the subject had one of the following noninvasive malignancies treated with curative intent without known recurrence: (a) Basal or squamous cell carcinoma of the skin; (b) Carcinoma in situ of the cervix or breast; (c) Stage 1 bladder cancer; (d) Incidental histological findings of localized prostate cancer such as tumor stage 1a or 1b (T1a or T1b) using the Tumor/Node/Metastasis (TNM) classification of malignant tumors OR prostate cancer that has been treated with curative intent.

Subject has a history of anaphylaxis to thalidomide, lenalidomide, pomalidomide or dexamethasone.

Subject has known or suspected hypersensitivity to the excipients (excipients include silica dimethyl silylate, anhydrous colloidal silicon dioxide, mannitol, fumaric acid and stearic acid) contained in the formulation of Compound 2 or dexamethasone.

Subject has undergone either of the following within 14 days of initiating Compound 2: (a) Plasmapheresis; (b) Radiation therapy other than local therapy for symptomatic relief of MM associated bone lesions.

Subject has received immunosuppressive medication within 14 days prior to the first dose of Compound 2. The following are exceptions to this criterion: (a) Intranasal, inhaled, topical or local corticosteroid injections (e.g., intra-articular injection); (b) Systemic corticosteroids at doses that do not exceed 10 mg/day of prednisone or the equivalent; (c) Steroids as premedication for hypersensitivity reactions (e.g., computed tomography [CT] scan premedication).

Subject is unable or unwilling to undergo protocol required venous thromboembolism (VTE) prophylaxis.

Length of Study

The average per subject duration of study participation is expected to be approximately 6 months. Full enrollment is expected to take approximately 21 months to complete (18 months for Part 1 and 3 months for Part 2). Completion of active treatment and post-treatment follow-up is expected to take an additional 6 to 12 months. The entire study is expected to continue for approximately 33 months.

The End of Trial is defined as either the date of the last visit of the last subject to complete the post-treatment follow-up, or the date of receipt of the last data point from the last subject that is required for primary, secondary and/or exploratory analysis, as pre-specified in the protocol, whichever is the later date.

Study Treatments

Compound 2 will be administered orally either QD for subjects enrolled to the 20/28 schedule (or alternative QD schedules), or BID for subjects enrolled to the 6/28 schedule (or alternative BID schedules). For subjects enrolled to the QD dosing schedule, Compound 2 must be administered in the morning with at least 240 mL (milliliter) of water after an overnight fast lasting at least 6 hours. Subjects must refrain from food or other medication intake for at least 2 hours after each morning dose. Subjects enrolled to the BID schedule will follow the aforementioned instructions as outlined for the QD schedule for the first dose of each dose day. The second dose must be administered 12±2 hours after the morning dose, at least 4 hours after and 2 hours before food intake.

For both dosing schedules, dexamethasone can be administered with Compound 2 in the fasted state or at least 2 hours after Compound 2 with food (except on PK assessment days when both must be given at the same time).

Overview of Key Efficacy Assessments

The primary efficacy variable is the best overall response rate (ORR) defined as the percent of subjects whose best response is ≥PR as determined by IMWG Uniform Response Criteria (Rajkumar et al., *Blood,* 2011, 117(18):

4691-5; Kumar et al., *Lancet Oncol.,* 2016, 17(8):e328-e346). Subjects will undergo response assessments monthly. Myeloma response will be determined by the study site investigator based on laboratory investigations (serum protein electrophoresis [sPEP], urine protein electrophoresis [uPEP], immunofixation electrophoresis [IFE], serum free light chain [sFLC] levels, quantitative immunoglobulin A [IgA], bone marrow for plasma cell quantitation, as appropriate) assessed in a central reference laboratory and/or locally, (i.e., corrected serum calcium, computed tomography [CT], positron emission tomography/computed scan [PET/CT] or magnetic resonance imaging [MRI] for plasmacytoma evaluation and/or CT, PET/CT, MRI or skeletal survey for bone lesion evaluation). Additional efficacy variables include time to response, duration of response and progression-free survival.

All safety subjects with a valid baseline and at least one post-baseline response assessment will be included in the efficacy analyses. If treatment is discontinued for reasons other than disease progression, subjects will be requested to continue response assessments according to the specified assessment schedule until progression, withdrawal of consent, death or initiation of new systemic anti-myeloma therapy, whichever is earliest.

Overview of Key Safety Assessments

The safety variables for this study include treatment-emergent adverse events (TEAEs) and changes from baseline in physical findings/vital signs, selected laboratory analytes, and 12-lead electrocardiograms (ECGs). Additional safety metrics include the extent of exposure to study treatment (both Compound 2 and dexamethasone), assessments of concomitant medication use, and pregnancy testing for females of child bearing potential (FCBP).

Overview of Pharmacokinetic Assessments

PK profiles (initial dose and steady state) will be evaluated for Compound 2, its R-enantiomer (Compound 3) and dexamethasone. Exposure-response analyses may be conducted, as appropriate, to assist in identification of the Compound 2 RP2D.

Overview of Pharmacodynamic Assessments

Biomarkers will be assessed in blood and bone marrow at baseline and at specified time points while on study treatment. Changes from baseline in the levels of Aiolos and Ikaros in peripheral blood mononuclear cells (PBMCs) and myeloma cells in bone marrow, peripheral blood and bone marrow immune phenotypes and levels of proinflammatory cytokines (e.g., interleukin-2 [IL-2], interferon-gamma [IFN-γ]) as a function of dose and schedule will be assessed. Longitudinal quantitation of sFLC levels and soluble B-cell maturation antigen (sBCMA) as well as circulating tumor cells will be performed as means to assess early treatment effects. Changes from baseline in the expression of cereblon and downstream markers (e.g., c-Myc, IRF-4) as well as gene expression in myeloma cells will be evaluated as means to identify potential markers of response and resistance to Compound 2 plus dexamethasone. Finally, MRD detection will be performed in subjects who undergo bone marrow evaluation for confirmation of a complete response (CR).

Point estimates and 2-sided 95% confidence intervals of Overall Response Rates (ORRs) will be reported. Additional efficacy variables include duration of response, time to response and progression-free survival (PFS). Efficacy outcomes will be summarized using frequency tabulations for categorical variables, or descriptive statistics for time to event variables. Efficacy analyses will be reported for both the Safety and Efficacy Evaluable (SE) Populations, with results from the EE Population considered primary.

Interim Results of Pharmacodynamic Analysis.

Figure 24A:
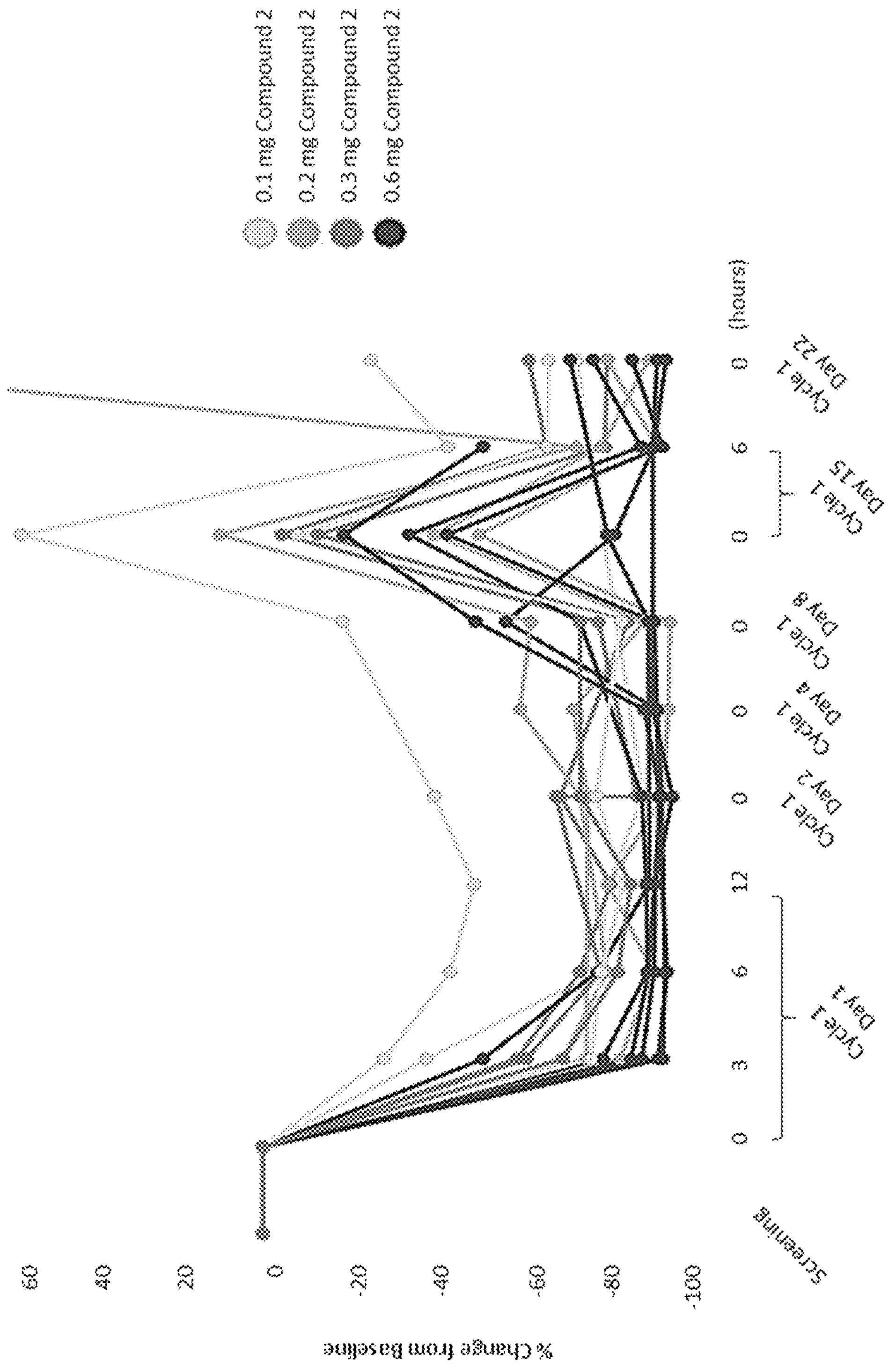
FIG. 24A and FIG. 24B illustrate that Compound 2 induces Aiolos degradation in CD3+ T cells from peripheral blood of relapsed/refractory multiple myeloma patients after (FIG. 24A) the once daily (QD) 1-10, 15-24/28 schedule, or (FIG. 24B) the twice daily (BID) 1-3, 15-17/28 schedule.
Figure 24B:
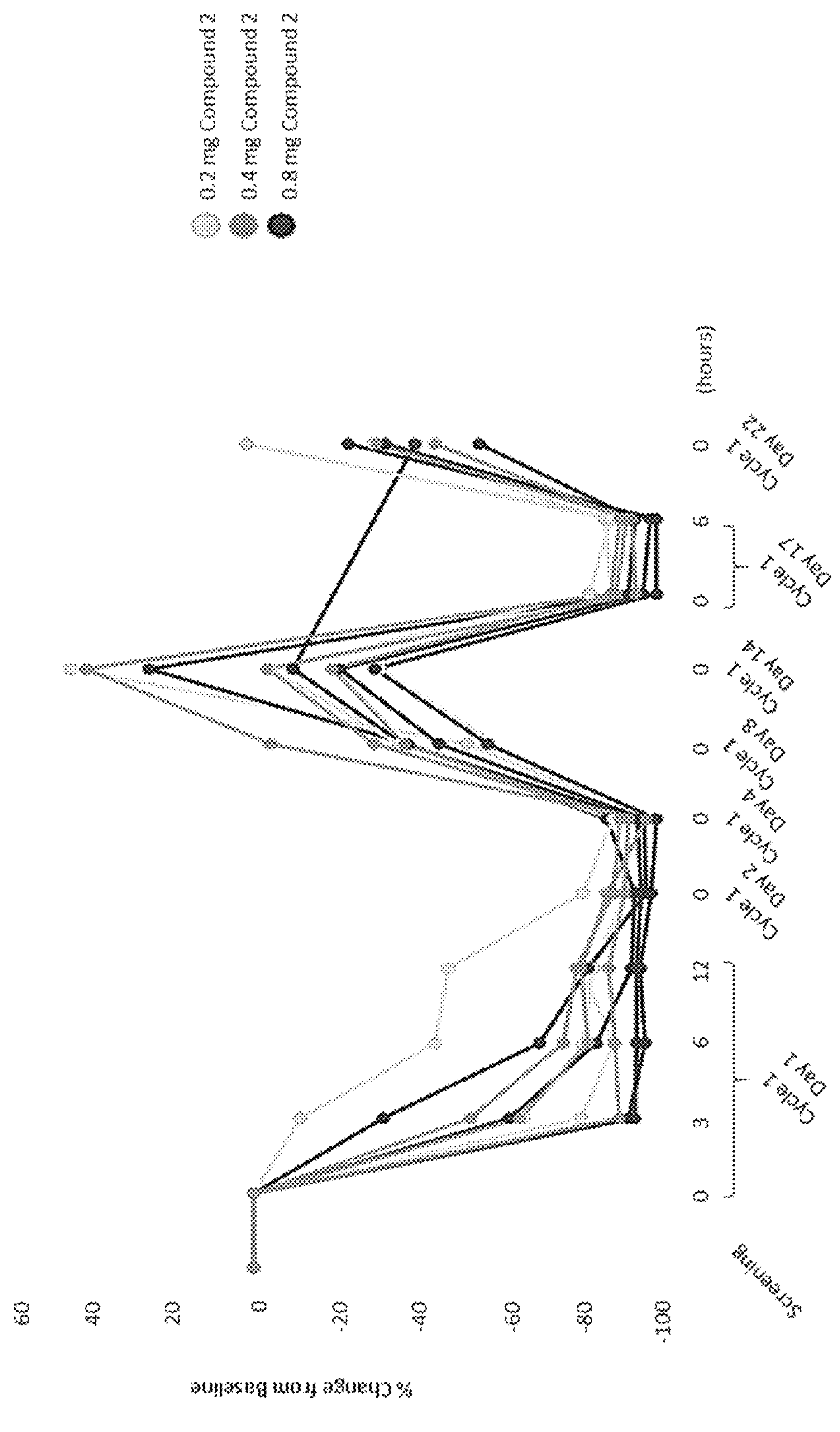

Aiolos expression was measured by flow cytometry in CD3+ T cells before and during Compound 2 treatment in two different dosing schedules (QD administration on days 1 to 10 and days 15 to 24 of a 28 day cycle, and BID administration on days 1 to 3 and days 15 to 17 of a 28 day cycle). As shown in FIG. 24A and FIG. 24B, Aiolos degradation was dose dependent and recovered during compound dosing interruptions on both schedules.

Figure 25A:
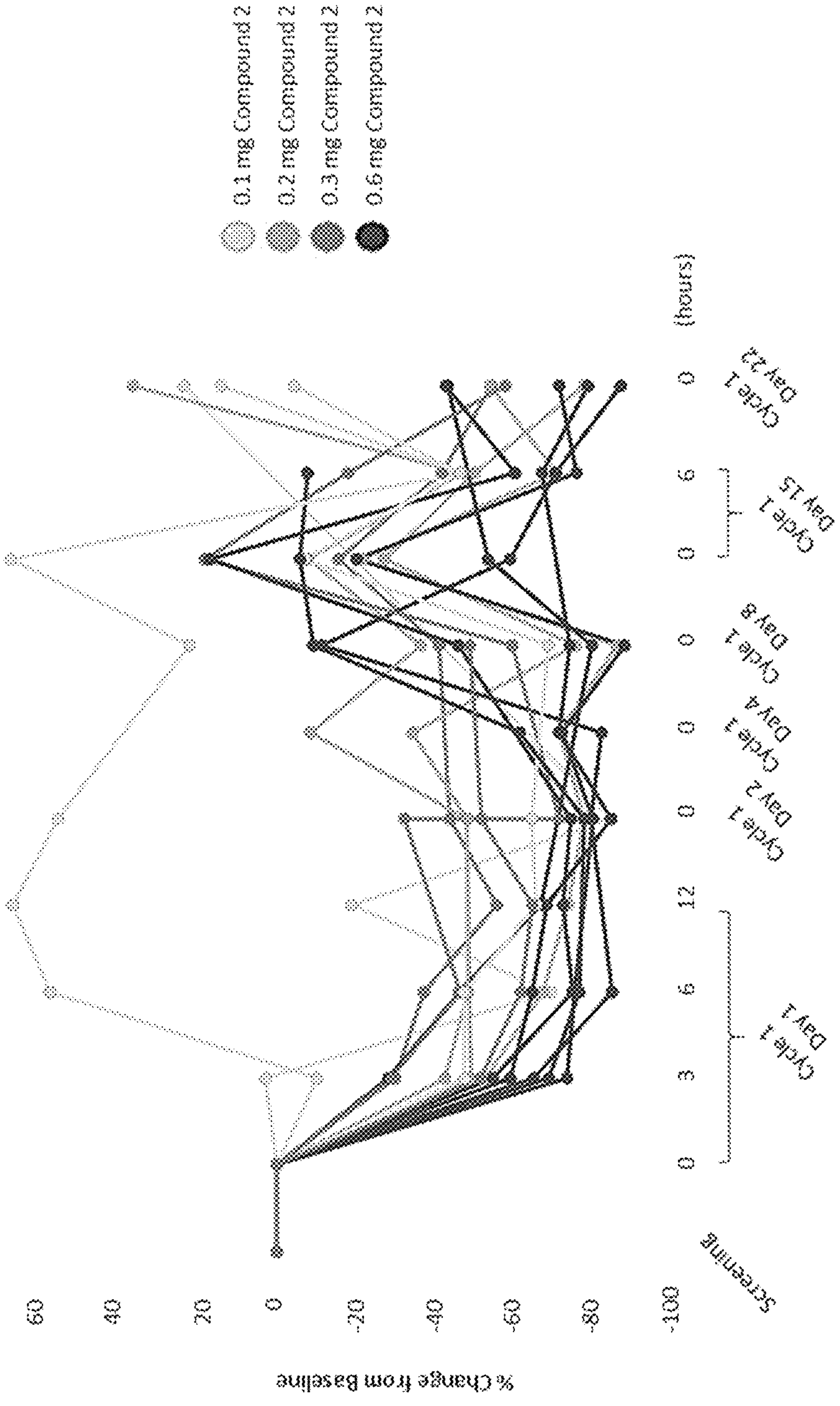
FIG. 25A and FIG. 25B illustrate that Compound 2 induced Ikaros degradation in CD3+ T cells from peripheral blood of relapsed/refractory multiple myeloma patients after (FIG. 25A) the once daily (QD) 1-10, 15-24/28 schedule, or (FIG. 25B) the twice daily (BID) 1-3, 15-17/28 schedule.
Figure 25B:
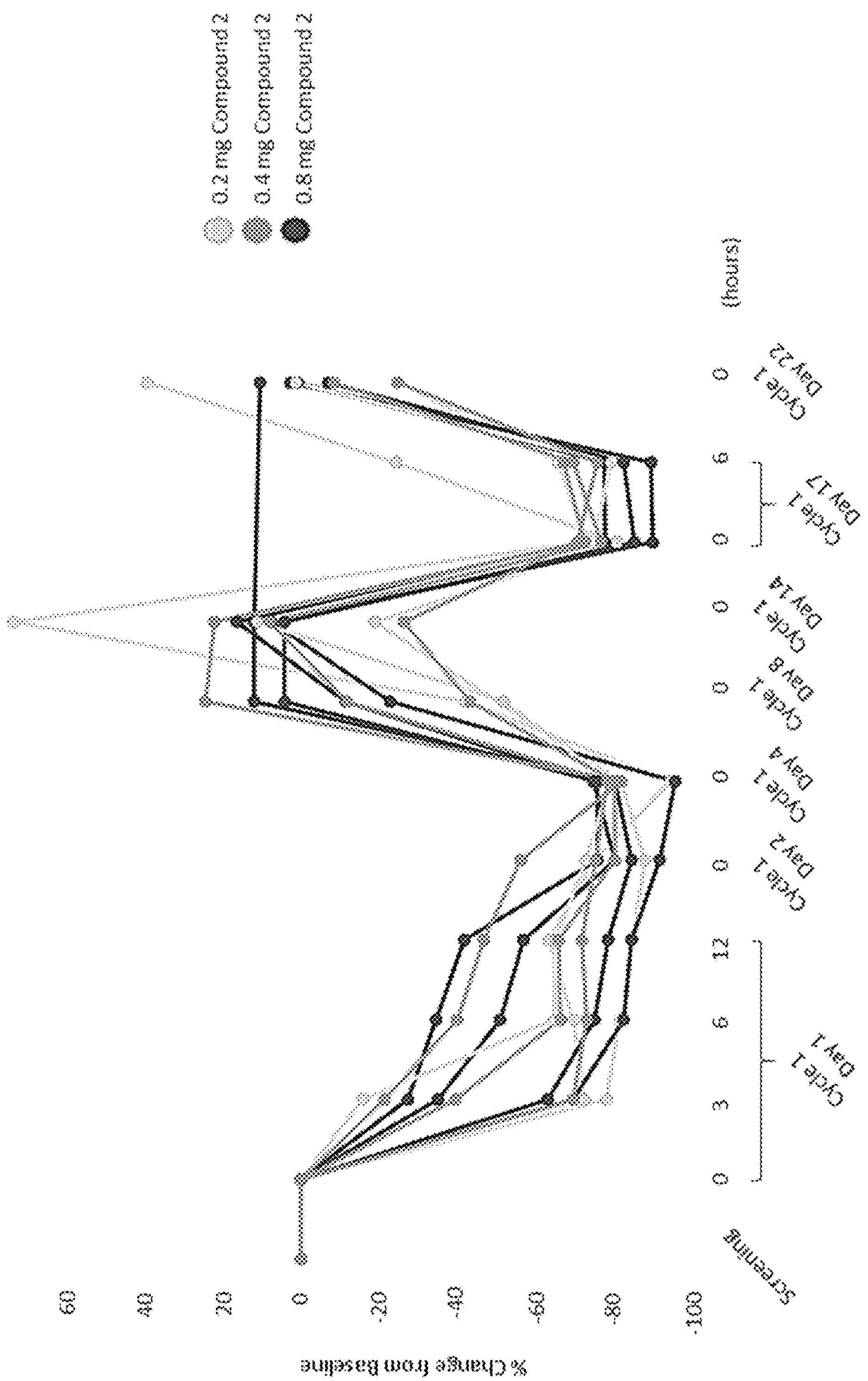
Figure 26A:
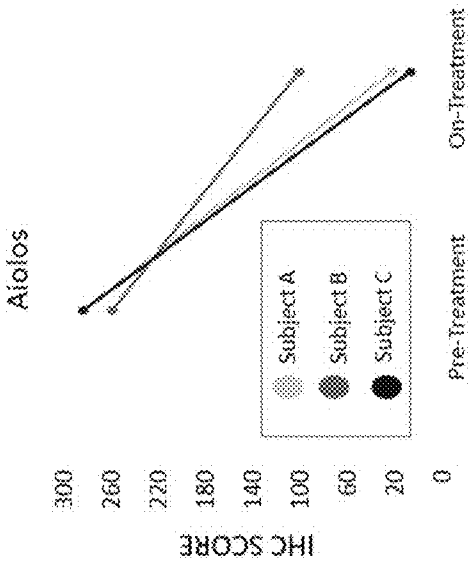
FIG. 26A-FIG. 26E illustrate that the effect of Compound 2 on biomarker expression in CD138+ plasma cells from relapsed/refractory multiple myeloma patients.
Figure 26B:
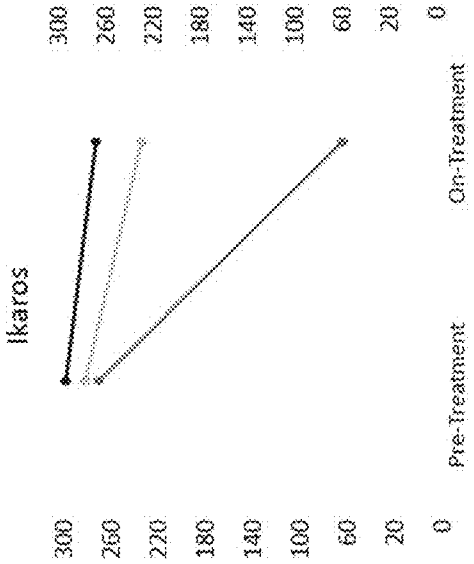
Figure 26C:
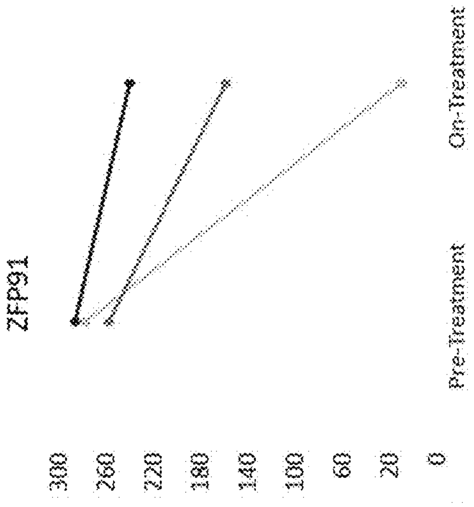
Figure 26D:
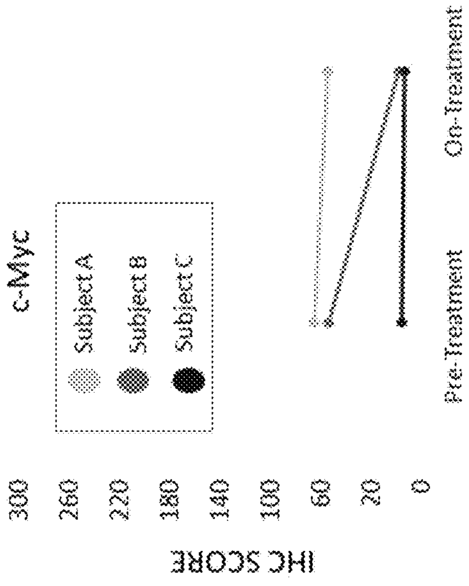
Figure 26E:
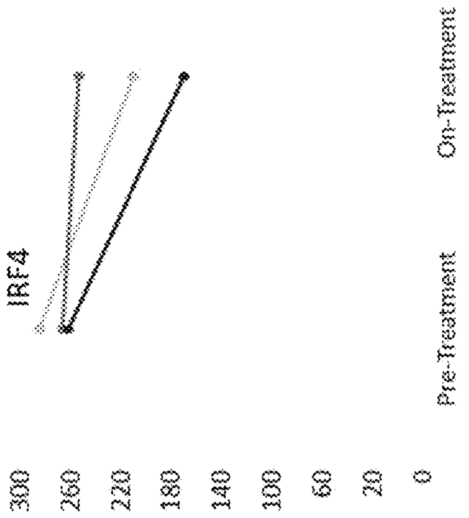

Ikaros expression was measured by flow cytometry in CD3+ T cells before and during Compound 2 treatment in two different dosing schedules (QD administration on days 1 to 10 and days 15 to 24 of a 28 day cycle, and BID administration on days 1 to 3 and days 15 to 17 of a 28 day cycle). As shown in FIG. 25A and FIG. 25B, Ikaros degradation was dose dependent and recovered during compound dosing interruptions on both schedules.

Bone marrow aspirate samples were taken before and during Compound 2 treatment (Cycle 1). Clots were made from each sample and processed into formalin fixed paraffin embedded blocks. Immunohistochemistry (IHC) assays were used to evaluate the biomarker expression. IHC scores were determined based on percent and intensity of positive staining. As shown in FIG. 26A-FIG. 26E, Compound 2 induced degradation of Aiolos, Ikaros, and ZFP91 in the tumor compartment. Down regulation of Aiolos and Ikaros resulted in decreased expression of c-Myc and IRF4, which lead to apoptosis of tumor cells and can be used to indicate response to treatment with Compound 2.

Figure 27:
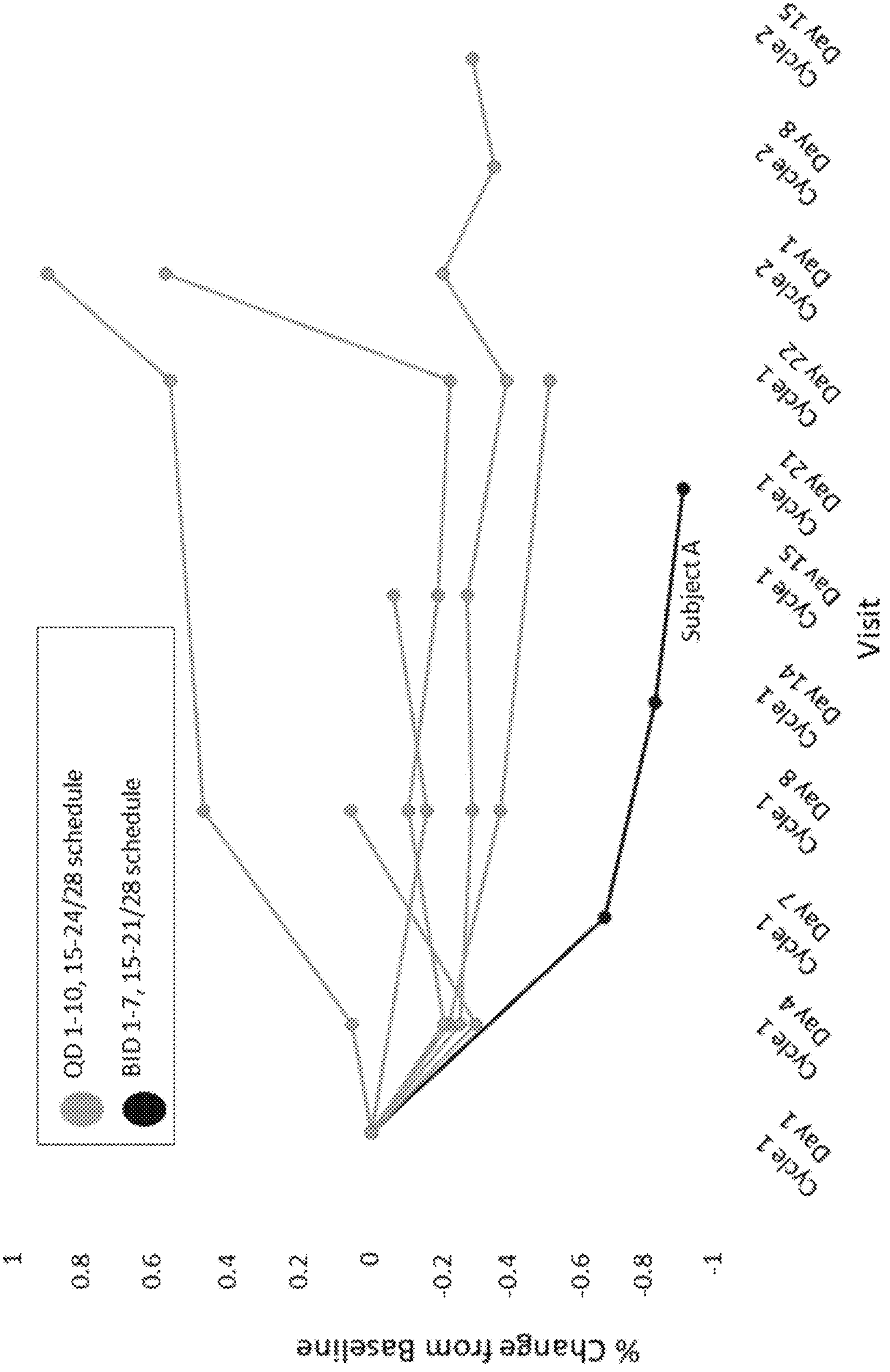
FIG. 27 illustrates the effect of Compound 2 on soluble BCMA (sBCMA) expression in relapsed/refractory multiple myeloma patients.

Serum samples were taken before and during Compound 2 treatment at specified time points. The expression of sBCMA was measured by an ELISA assay. As shown in FIG. 27, the sBCMA signal decreased with Compound 2 treatment. Samples from one subject showed >80% decrease in sBCMA from baseline and the subject had a favorable response to treatment (vert good partial response; VGPR). The extent of decrease and duration of the effect may predict response to treatment with Compound 2.

Figure 28:
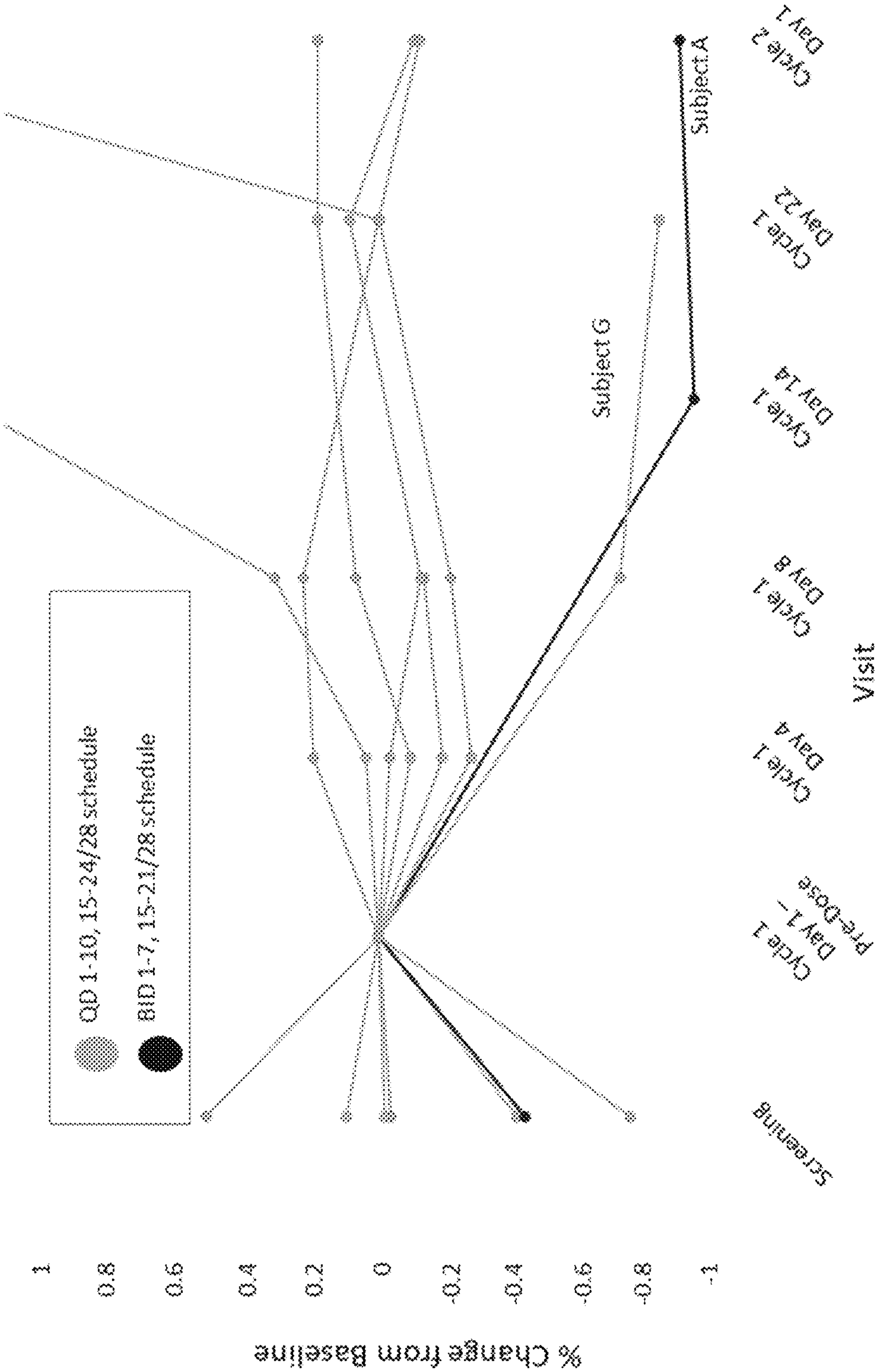
FIG. 28 illustrates the effect of Compound 2 on serum free light chain (sFLC) in relapsed/refractory multiple myeloma patients.

Serum samples were taken before and during Compound 2 treatment at specified time points. Serum free light chain (sFLC) can be used as an efficacy measurement in multiple myeloma. The short half-life of sFLC provides an opportunity to follow the dynamic effect of compound treatment on disease burden. As shown in FIG. 28, the sFLC signal decreased with Compound 2 treatment indicating killing of tumor cells. Two subjects showed >80% decrease in sFLC during the first cycle of treatment and had a favorable response to treatment (PR and VGPR, respectively). The extent of decrease from baseline and duration of the effect may predict response to treatment with Compound 2.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of determining or adjusting a dosage for treating a subject having multiple myeloma with a treatment compound comprising:

(a) administering a dosage of the treatment compound to the subject;

(b) obtaining one or more samples from the subject at different time points; and (c) determining the level of a biomarker in the one or more samples, and thereby determining if the dosage is appropriate or needs an adjustment;

wherein the treatment compound is a compound of Compound 1:

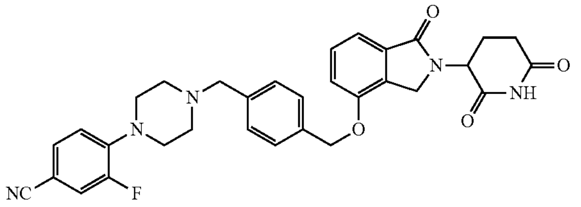 [SMILES: N#Cc1ccc(N2CCN(Cc3ccc(COc4cccc5c4CN(C4CCC(=O)NC4=O)C5=O)cc3)CC2)c(F)c1]

or an enantiomer, mixture of enantiomers, tautomer, isotopolog, or pharmaceutically acceptable salt thereof;

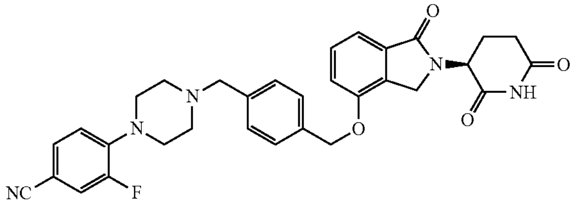 [SMILES: N#Cc1ccc(N2CCN(Cc3ccc(COc4cccc5c4CN([C@H]4CCC(=O)NC4=O)C5=O)cc3)CC2)c(F)c1]

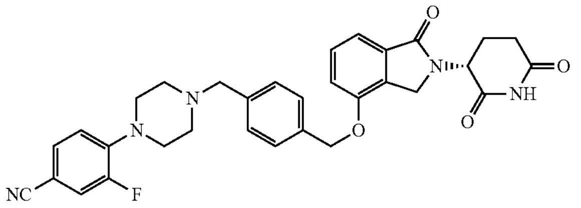 [SMILES: N#Cc1ccc(N2CCN(Cc3ccc(COc4cccc5c4CN([C@@H]4CCC(=O)NC4=O)C5=O)cc3)CC2)c(F)c1]

wherein the biomarker is IKZF1, and/or IKZF3.

2. The method of claim 1, wherein adjusting the dosage comprises:

(a) increasing a dose of the treatment compound; or (b) increasing administration frequency of the treatment compound.

3. The method of claim 1, wherein the biomarker is IKZF1.

4. The method of claim 1, wherein the biomarker is IKZF3.

5. The method of claim 1, wherein the level of the biomarker is measured by (a) determining a protein level of the biomarker;

(b) determining a mRNA level of the biomarker;

(c) determining a cDNA level of the biomarker; or (d) RNA-sequencing (RNA-seq).

6. The method of claim 5, wherein obtaining the protein level of the biomarker comprises contacting proteins within the sample with a first antibody that immunospecifically binds to the biomarker protein.

7. A method of determining or adjusting a dosage for treating a subject having multiple myeloma with a treatment compound comprising:

(a) administering a dosage of the treatment compound to the subject;

(b) obtaining one or more samples from the subject at different time points; and (c) determining the level of a biomarker in the one or more samples, and thereby determining if the dosage is appropriate or needs an adjustment;

wherein the treatment compound is a compound of Compound 2:

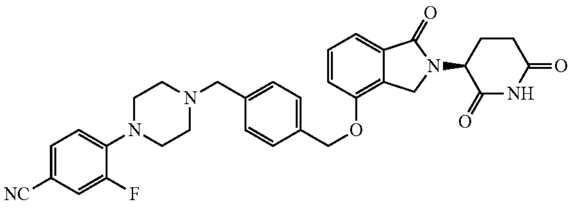 [SMILES: N#Cc1ccc(N2CCN(Cc3ccc(COc4cccc5c4CN([C@H]4CCC(=O)NC4=O)C5=O)cc3)CC2)c(F)c1]

or a tautomer, isotopolog, or pharmaceutically acceptable salt thereof;

wherein the biomarker is IKZF1, and/or IKZF3.

8. The method of claim 7, wherein adjusting the dosage comprises:

(a) increasing a dose of the treatment compound; or (b) increasing administration frequency of the treatment compound.

9. The method of claim 7, wherein the biomarker is IKZF1.

10. The method of claim 7, wherein the biomarker is IKZF3.

11. The method of claim 7, wherein the level of the biomarker is measured by (a) determining a protein level of the biomarker;

(b) determining a mRNA level of the biomarker;

(c) determining a cDNA level of the biomarker; or (d) RNA-sequencing (RNA-seq).

12. The method of claim 11, wherein obtaining the protein level of the biomarker comprises contacting proteins within the sample with a first antibody that immunospecifically binds to the biomarker protein.

13. A method of determining or adjusting a dosage for treating a subject having multiple myeloma with a treatment compound comprising:

(a) administering a dosage of the treatment compound to the subject;

(b) obtaining one or more samples from the subject at different time points; and (c) determining the level of a biomarker in the one or more samples, and thereby determining if the dosage is appropriate or needs an adjustment;

wherein the treatment compound is a compound of Compound 3:

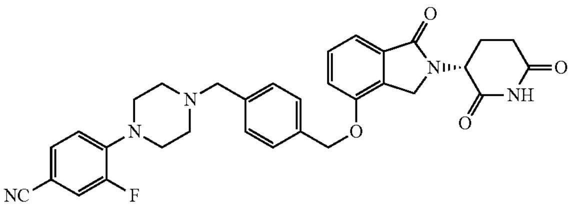 [SMILES: N#Cc1ccc(N2CCN(Cc3ccc(COc4cccc5c4CN([C@@H]4CCC(=O)NC4=O)C5=O)cc3)CC2)c(F)c1]

or a tautomer, isotopolog, or pharmaceutically acceptable salt thereof;

wherein the biomarker is IKZF1, and/or IKZF3.

14. The method of claim 13, wherein adjusting the dosage comprises:

(a) increasing a dose of the treatment compound; or (b) increasing administration frequency of the treatment compound.

15. The method of claim 13, wherein the biomarker is IKZF1.

16. The method of claim 13, wherein the biomarker is IKZF3.

17. The method of claim 13, wherein the level of the biomarker is measured by (a) determining a protein level of the biomarker;

(b) determining a mRNA level of the biomarker;

(c) determining a cDNA level of the biomarker; or (d) RNA-sequencing (RNA-seq).

18. The method of claim 17, wherein obtaining the protein level of the biomarker comprises contacting proteins within the sample with a first antibody that immunospecifically binds to the biomarker protein.

* * * * *